US012616734B2

(12) United States Patent
Jeon et al.

(10) Patent No.: US 12,616,734 B2
(45) Date of Patent: May 5, 2026

(54) CHIMERIC ANTIGEN RECEPTOR SPECIFICALLY BINDING TO CD 300C ANTIGEN OR RECEPTOR THEREOF

(71) Applicant: CentricsBio, Inc., Seoul (KR)

(72) Inventors: Jaewon Jeon, Suwon-si (KR); Sunwha Kim, Seoul (KR); Suin Lee, Guri-si (KR)

(73) Assignee: CENTRICSBIO, INC., Seoul (KR)

( * ) Notice: Subject to any disclaimer, the term of this patent is extended or adjusted under 35 U.S.C. 154(b) by 4 days.

(21) Appl. No.: 17/826,954

(22) Filed: May 27, 2022

(65) Prior Publication Data

US 2022/0305082 A1 Sep. 29, 2022

Related U.S. Application Data

(63) Continuation of application No. PCT/KR2022/007384, filed on May 24, 2022, and a continuation-in-part of application No. PCT/KR2020/017230, filed on Nov. 30, 2020.

(30) Foreign Application Priority Data

| | | |
|---|---|---|
| Nov. 28, 2019 | (KR) | 10-2019-0155027 |
| Nov. 27, 2020 | (KR) | 10-2020-0162200 |
| May 24, 2021 | (KR) | 10-2021-0066547 |

(51) Int. Cl.

| | |
|---|---|
| *A61K 38/17* | (2006.01) |
| *A61K 35/15* | (2025.01) |
| *A61K 35/17* | (2025.01) |
| *A61K 39/00* | (2006.01) |
| *A61K 40/11* | (2025.01) |
| *A61K 40/31* | (2025.01) |
| *A61K 40/42* | (2025.01) |
| *A61K 45/06* | (2006.01) |
| *A61P 35/00* | (2006.01) |
| *C07K 14/725* | (2006.01) |
| *C07K 16/28* | (2006.01) |

(52) U.S. Cl.
CPC .......... *A61K 38/1774* (2013.01); *A61K 35/15* (2013.01); *A61K 35/17* (2013.01); *A61K 39/0011* (2013.01); *A61K 40/11* (2025.01); *A61K 40/31* (2025.01); *A61K 40/4202* (2025.01); *A61K 45/06* (2013.01); *A61P 35/00* (2018.01); *C07K 14/7051* (2013.01); *C07K 16/2803* (2013.01); *A61K 2039/627* (2013.01); *C07K 2317/565* (2013.01); *C07K 2319/02* (2013.01); *C07K 2319/03* (2013.01)

(58) Field of Classification Search
None
See application file for complete search history.

(56) References Cited

U.S. PATENT DOCUMENTS

| | | |
|---|---|---|
| 2016/0194631 A1 | 7/2016 | Yuan et al. |
| 2017/0326179 A1 | 11/2017 | Mukherjee |
| 2017/0335281 A1 | 11/2017 | Loew et al. |
| 2018/0334490 A1 | 11/2018 | Brogdon |

FOREIGN PATENT DOCUMENTS

| | | |
|---|---|---|
| JP | 2017-506636 A | 3/2017 |
| JP | 2017-513818 A | 6/2017 |
| JP | 2018-531260 A | 10/2018 |
| JP | 7578869 B2 | 11/2024 |
| KR | 10-2016-0138404 A | 12/2016 |
| KR | 10-2019-0072639 A | 6/2019 |
| KR | 10-2019-0136949 A | 12/2019 |
| WO | 2018/094460 A1 | 5/2018 |
| WO | 2019/231188 A1 | 12/2019 |
| WO | 2020/014097 A1 | 1/2020 |
| WO | 2020/065406 A2 | 4/2020 |
| WO | 2021/107726 A1 | 6/2021 |

OTHER PUBLICATIONS

American Cancer Society (ACS). Cancer Risk and Prevention Webpage. Saved Mar. 21, 2025. (Year: 2025).*
Herold et al. Determinants of the assembly and function of antibody variable domains. Nature Scientific Reports, 7:12276, Sep. 25, 2017. (Year: 2017).*
Office Action issued Dec. 3, 2024 in Japanese Application No. 2023-573158.
C. Cui, et al., "A CD300c-Fc Fusion Protein Inhibits T Cell Immunity", Frontiers in Immunology, Nov. 2018, Article 2657, pp. 1-14, vol. 9.
International Search Report issued Mar. 2, 2021 in International Application No. PCT/KR2020/016264.
(Continued)

*Primary Examiner* — Julie Wu

*Assistant Examiner* — Amy M. Chattin

(74) *Attorney, Agent, or Firm* — pH IP Law

(57) ABSTRACT

A chimeric antigen receptor that specifically binds to a CD300c antigen or a receptor thereof, immune cells expressing the same, and uses thereof are disclosed. The chimeric antigen receptor that specifically binds to a CD300c antigen or a receptor thereof is able to specifically recognize cancer cells expressing the CD300c antigen or the CD300c receptor so that growth, metastasis, development, and the like of cancer can be suppressed in a direct and effective manner. Thus, it is expected that the chimeric antigen receptor can be effectively used as an immunotherapeutic agent for various cancers.

18 Claims, 58 Drawing Sheets

Specification includes a Sequence Listing.

(56) References Cited

OTHER PUBLICATIONS

M. Dimitrova, et al., "CD300c is uniquely expressed on CD56$^{bright}$ Natural Killer Cells and differs from CD300a upon ligand recognition", Scientific Reports, 2016, pp. 1-12, vol. 6, Article No. 23942.

V. R. Simhadri, et al., "CD300c is an Activating Receptor Expressed on Human Monocytes", Journal of Innate Immunity, 2013, pp. 389-400, vol. 5.

Written Opinion of the International Searching Authority issued Mar. 2, 2021 in International Application No. PCT/KR2020/016264.

Lankry et al., "The interaction between CD300a and phosphatidylserine inhibits tumor cell killing by NK cells", Eur. J. Immunol., 2013, vol. 43, pp. 2151-2161 (12 pages total).

Du et al., "CD300A inhibits tumor cell growth by downregulating AKT phosphorylation in human glioblastoma multiforme", Int J Clin Exp Pathol, Jul. 15, 2018, Vo. 11, No. 7, pp. 3471-3478 (9 pages total).

International Search Report issued Mar. 16, 2021 in International Application No. PCT/KR2020/017230.

Written Opinion of the International Searching Authority issued Mar. 16, 2021 in International Application No. PCT/KR2020/017230.

"PE anti-human CD300c Antibody", BioLegend, Jul. 6, 2015 (2 pages total).

Takahashi, et al. "Human CD300C Delivers an Fc Receptor-γ-dependent Activating Signal in Mast Cells and Monocytes and Differs from CD300A in Ligand Recognition", Journal of Biological Chemistry, Mar. 15, 2013, vol. 288, No. 11, pp. 7662-7675 (14 pages).

Extended European Search Report dated May 9, 2025 in Application No. 22811626.5.

Japanese Office Action dated May 27, 2025 in Application No. 2023-573158.

* cited by examiner

[FIG. 1a]

CDR1, CDR2 and CDR3 are underlined and appear sequentially (1aa)  SEQ ID NO: 301

CK1 Heavy Chain (DNA sequence):

GAAGTGCAGCTGCTGGAAAGTGGAGGTGGACTGGTGCAGCCTGGCGGCAGCCTGCGCCTGAGCTGTGCCGC
CAGCGGATTCACCTTCAGCCGCTATGCCATGACCTGGGTTCGCCAAGCACCTGGCAAAGGCCTGGAATGGGT
GAGCAGCATGAGCGGCACCGGCGGCACCACCTATTATGCCGATAGCGTGAAAGGTCGCTTTACCATCAGCCG
CGATAACAGCAAAAACACCCTGTATCTGCAGATGAACAGCCTGCGCGCCGAGGACACCGCAGTCTACTACTG
TGCCCGCGGCGCCTATGGCTTTGATCATTGGGGACAAGGTACTCTGGTGACCGTGAGCAGC (1ab)  SEQ ID NO: 302

CK1 Light Chain (DNA sequence):

GAAATCGTGCTGACCCAGAGCCCTGGCACCCTGAGCCTGAGCCCTGGCGAACGCGCAACACTGTCATGCCG
CGCCAGCCAGAGCATCGGCAACTATCTGAACTGGTATCAGCAGAAACCAGGTCAGGCTCCACGTCTGCTGAT
CTATGATGCCAGCAACCTGGAAACCGGCATCCCTGATCGCTTCTCAGGATCTGGAAGCGGTACCGATTTTACC
CTGACCATCAGCCGCCTGGAACCTGAGGACTTTGCCGTGTATTATTGTCAGCAGAGTAGCGCCATCCCTTATAC
CTTCGGTCAGGGCACTAAAGTGGAAATCAAA (1ac)  SEQ ID NO: 303

CK1 Heavy Chain (Amino acid sequence):

EVQLLESGGGLVQPGGSLRLSCAASGFTFSRYAMTWVRQAPGKGLEWVSSMSGTGGTTYYADSVKGRFTISRD
NSKNTLYLQMNSLRAEDTAVYYCARGAYGFDHWGQGTLVTVSS (1ad)  SEQ ID NO: 304

CK1 Light Chain (Amino acid sequence):

EIVLTQSPGTLSLSPGERATLSCRASQSIGNYLNWYQQKPGQAPRLLIYDASNLETGIPDRFSGSGSGTDFTLTISRL
EPEDFAVYYCQQSSAIPYTFGQGTKVEIK

[FIG. 1b]

CDR1, CDR2, and CDR3 are underlined and appear sequentially (1ba)   SEQ ID NO: 305

CK2 Heavy Chain (DNA sequence):

GAAGTGCAGCTGCTGGAAAGTGGAGGTGGACTGGTGCAGCCTGGCGGCAGCCTGCGCCTGAGCTGTGCCGC
CAGCGGATTCACCTTCAGCAGCTATGGCATGCATTGGGTTCGCCAAGCACCTGGCAAAGGCCTGGAATGGGT
GAGCGCCATCAGCGGCAGCGGCACCAGCATCTATTATGCCGATAGCGTGAAAGGCCGCTTTACCATCAGCCG
CGATAACAGCAAAAACACCCTGTATCTGCAGATGAACAGCCTGCGCGCCGAGGACACCGCAGTCTACTACTG
TGCCCGCGGCGGCACCGCCTTTGATTATTGGGGACAAGGTACTCTGGTGACCGTGAGCAGC (1bb)   SEQ ID NO: 306

CK2 Light Chain (DNA sequence):

GAAATCGTGCTGACCCAGAGCCCTGGCACCCTGAGCCTGAGCCCTGGCGAACGCGCAACACTGTCATGCCG
CGCCAGCCAGAGATCAGACAACTATCTGGCCTGGTATCAGCAGAAACCAGGTCAGGCTCCACGTCTGCTGAT
CTATGATGCCAGCAACCGCGCCACCGGCATCCCTGATCGCTTCTCAGGATCTGGAAGCGGTACCGATTTTACC
CTGACCATCAGCCGCCTGGAACCTGAGGACTTTGCCGTGTATTATTGTCAGCAGAGCTATAGCACCCCTTTTAC
CTTCGGTCAGGGCACTAAAGTGGAAACCAAA (1bc)   SEQ ID NO: 307

CK2 Heavy Chain (Amino acid sequence):

EVQLLESGGGLVQPGGSLRLSCAASGFTFSSYGMHWVRQAPGKGLEWVSAISGSSTSIYYADSVKGRFTISRDNS
KNTLYLQMNSLRAEDTAVYYCARGGTAFDYWGQGTLVTVSS (1bd)   SEQ ID NO: 308

CK2 Light Chain (Amino acid sequence):

EIVLTQSPGTLSLSPGERATLSCRASQRSDNYLAWYQQKPGQAPRLLIYDASNRATGIPDRFSGSGSGTDFTLTISR
LEPEDFAVYYCQQSYSTPFTFGQGTKVETK

[FIG. 1c]

CDR1, CDR2, and CDR3 are underlined and appear sequentially (1ca)  SEQ ID NO: 309

CK3 Heavy Chain (DNA sequence):

CGAGTGCAGCTGCTGGAAAGTGGAGGTGGACTGGTGCAGCCTGGCGGCAGCCTGCGCCTGAGCTGTGCCGC

CAGCGGATTCACCTTCAGCAGCTATGCCATCAGCTGGGTTCGCCAAGCACCTGGCAAAGGCCTGGAATGGGT

GAGCGCCACCAGCGGCAGCGGCCGCGCCACCTATTATGCCGATAGCGTGAAAGGCCGCTTTACCATCAGCCG

CGATAACAGCAAAAACACCCTGTATCTGCAGATGAACAGCCTGCGCGCCGAGGACACCGCAGTCTACTACTG

TGCGCGCGATACCTGGTGGGAAGGCTATTTTGATCTGTGGGGACAAGGTACTCTGGTGACCGTGAGCAGC (1cb)  SEQ ID NO: 310

CK3 Light Chain (DNA sequence):

GAAATCGTGCTGACCCAGAGCCCTGGCACCCTGAGCCTGAGCCCTGGCGAACGCGCAACACTGTCATGCCA

GGCCAGCCATATCAGCACCCATCTGAACTGGTATCAGCAGAAACCAGGTCAGGCTCCACGTCTGCTGATCTAT

GGCGCCAGCAGCCGCGCCACCGGCATCCCTGATCGCTTCTCAGGATCTGGAAGCGGTACCGATTTTACCCTG

ACCATCAGCCGCCTGGAACCTGAGGACTTTGCCGTGTATTATTGTCAGCAGTATAACACCTATCCTCCTACCTTC

GGTCAGGGCACTAAAGTGGAAATCAAA (1cc)  SEQ ID NO: 311

CK3 Heavy Chain (Amino acid sequence):

RVQLLESGGGLVQPGGSLRLSCAASGFTFSSYAISWVRQAPGKGLEWVSATSGSGRATYYADSVKGRFTISRDNS

KNTLYLQMNSLRAEDTAVYYCARDTWWEGYFDLWGQGTLVTVSS (1cd)  SEQ ID NO: 312

CK3 Light Chain (Amino acid sequence):

EIVLTQSPGTLSLSPGERATLSCQASHISTHLNWYQQKPGQAPRLLIYGASSRATGIPDRFSGSGSGTDFTLTISRLE

PEDFAVYYCQQYNTYPPTFGQGTKVEIK

[FIG. 1d]

CDR1, CDR2, and CDR3 are underlined and appear sequentially (1da) SEQ ID NO: 313

CL4 Heavy Chain (DNA sequence):

CGAGTGCAGCTGCTGGAAAGTGGAGGTGGACTGGTGCAGCCTGGCGGCAGCCTGCGCCTGAGCTGTGCCGC
CAGCGGATTCACCTTCGGCAGCAACTATATGAGCTGGGTTCGCCAAGCACCTGGCAAAGGCCTGGAATGGGT
GAGCACCATCAGCGGCAGCGGCACCAGCACCTATTATGCCGATAGCTTGAAAGGCCGCTTTACCATCAGCCG
CGATAACAGCAAAAACACCCTGTATCTGCAGATGAACAGCCTGCGCGCCGAGGACACCGCAGTCTACTACTG
TGCCCGCGGCATGTGGGGCATGGATGTGTGGGGACAAGGTACTCTGGTGACCGTGAGCAGC (1db) SEQ ID NO: 314

CL4 Light Chain (DNA sequence):

CAGAGCGTGCTGACCCAGCCTCCTAGCGCCTCCGGTACACCAGGACAGCGCGTGACTATTAGCTGTACCGGC
AAACATCGGCACACCGTGAACTGGTACCAGCTACTGCCTGGAACTGCACCTAAGCTGCTGATCTATCTGGATA
GCGAACGCCCTAGCGGCGTACCTGATCGCTTTAGCGGTAGCAAATCAGGCACCAGCGCCAGCCTGGCCATCA
GCGGCCTTCGCTCCGAAGATGAAGCCGATTATTATTGTCAGAGCTATGATAGCAGCAGCGTGGTGTTTGGTGG
CGGTACCAAGCTGACCGTGCTG (1dc) SEQ ID NO: 315

CL4 Heavy Chain (Amino acid sequence):

RVQLLESGGGLVQPGGSLRLSCAASGFTFGSNYMSWVRQAPGKGLEWVSTISGSGTSTYYADSLKGRFTISRDN
SKNTLYLQMNSLRAEDTAVYYCARGMWGMDVWGQGTLVTVSS (1dd) SEQ ID NO: 316

CL4 Light Chain (Amino acid sequence):

QSVLTQPPSASGTPGQRVTISCTGKHRHTVNWYQLLPGTAPKLLIYLDSERPSGVPDRFSGSKSGTSASLAISGLR
SEDEADYYCQSYDSSSVVFGGGTKLTVL

[FIG. 1e]

CDR1, CDR2, and CDR3 are underlined and appear sequentially (1ea)  SEQ ID NO: 317

CL5 Heavy Chain (DNA sequence):

CGAGTGCAGCTGCTGGAAAGTGGAGGTGGACTGGTGCAGCCTGGCGGCAGCCTGCGCCTGAGCTGTGCCGC
CAGCGGATTCACCTTCAGCAGCTATGCCATGCATTGGGTTCGCCAAGCACCTGGCAAAGGCCTGGAATGGGT
GAGCAGCATCAGCGGCGGCGGCTATGGCACCTATTATGCCGATAGCGTGAAAGGCCGCTTTACCATCAGCCG
CGATAACAGCAAAAACACCCTGTATCTGCAGATGAACAGCCTGCGCGCCGAGGACACCGCAGTCTACTACTG
TGCCCGCAGCACCGTGTGGGCCTTTGATATCTGGGGACAAGGTACTCTGGTGACCGTGAGCAGC (1eb)  SEQ ID NO: 318

CL5 Light Chain (DNA sequence):

CAGAGCGTGCTGACCCAGCCTCCTAGCGCCTCCGGTACACCAGGACAGCGCGTGACTATTAGCTGTAGCGGC
AACAACATCGGCAGCAAAAGCGTGCATTGGTACCAGCAACTGCCTGGAACTGCACCTAAGCTGCTGATCTAT
GATGTGAGCAAACGCCCTAGCGAGCGTCCTGATCGCTTTAGCGGTAGCAAATCAGGCACCAGCGCCAGTCTG
GCCATCAGCGACCTTCGCTCCGAAGATGAAGCCGATTATTATTGTCAGAGCTTTGATAGCAGCGGCACCTGGA
TCTTTGGTGGCGGTACCAAGCTGACCGTGCTG (1ec)  SEQ ID NO: 319

CL5 Heavy Chain (Amino acid sequence):

RVQLLESGGGLVQPGGSLRLSCAASGFTFSSYAMHWVRQAPGKGLEWVSSISGGGYGTYYADSVKGRFTISRDN
SKNTLYLQMNSLRAEDTAVYYCARSTVWAFDIWGQGTLVTVSS (1ed)  SEQ ID NO: 320

CL5 Light Chain (Amino acid sequence):

QSVLTQPPSASGTPGQRVTISCSGNNIGSKSVHWYQQLPGTAPKLLIYDVSKRPSERPDRFSGSKSGTSASLAISD
LRSEDEADYYCQSFDSSGTWIFGGGTKLTVL

[FIG. 1f]

CDR1, CDR2, and CDR3 are underlined and appear sequentially (1fa)    SEQ ID NO: 321

CL6 Heavy Chain (DNA sequence):

GAGGTGCAGCTGTTGGAGTCTGGTGGAGGCTTGGTACAGCCTGGAGGTTCTCTTCGCCTCTCCTGTGCAGCCT
CCGGATTCACTTTCAGCAGCTACGGTATGCATTGGGTCAGACAGGCACCAGGTAAGGGACTGGAGTGGGTCT
CTGCAATTAGCGGTAGCGGTGGTAGCACTTACTACGCAGACAGCGTGAAGGGTCGCTTCACCATCTCACGCG
ACAACTCCAAGAACACCCTGTACCTGCAGATGAACAGCCTTCGCGCAGAGGACACTGCCGTGTATTACTGCG
CAGTCAGTGGTGCAGGTCGTGGTTTCTTCGACTACTGGGGACAAGGTACTCTGGTCACTGTCTCCTCA (1fb)    SEQ ID NO: 322

CL6 Light Chain (DNA sequence):

CAGTCTGTGCTGACTCAGCCACCTTCAGCATCTGGTACTCCAGGTCAGCGCGTCACCATCAGCTGCAGCGGTA
GCAGCAGCAACATTGGTAGCAACTACGTGTACTGGTATCAGCAACTCCCAGGCACCGCTCCTAAGCTCCTGAT
TTACGAGGACAACAAGCGTCCTAGTGGTGTGCCTGATCGCTTTTCTGGGTCCAAGTCTGGCACCTCAGCCTCT
CTGGCTATCAGTGGACTTCGCTCCGAGGACGAGGCTGACTATTACTGCAGCAGCTACACTAGCAGCAGCACT
GTGATCTTCGGCGGTGGGACCAAACTGACCGTCCTA (1fc)    SEQ ID NO: 323

CL6 Heavy Chain (Amino acid sequence):

EVQLLESGGGLVQPGGSLRLSCAASGFTFSSYGMHWVRQAPGKGLEWVSAISGSGGSTYYADSVKGRFTISRDN
SKNTLYLQMNSLRAEDTAVYYCAVSGAGRGFFDYWGQGTLVTVSS (1fd)    SEQ ID NO: 324

CL6 Light Chain (Amino acid sequence):

QSVLTQPPSASGTPGQRVTISCSGSSSNIGSNYVYWYQQLPGTAPKLLIYEDNKRPSGVPDRFSGSKSGTSASLAI
SGLRSEDEADYYCSSYTSSSTVIFGGGTKLTVL

[FIG. 1g]

CDR1, CDR2, and CDR3 are underlined and appear sequentially (1ga)  SEQ ID NO: 325

CL7 Heavy Chain (DNA sequence):

GAGGTGCAGCTGTTGGAGTCTGGTGGAGGCTTGGTACAGCCTGGAGGTTCTCTTCGCCTCTCCTGTGCAGCCT
CCGGGATTCACTTTCAGCCGCTACGCAATGAGCTGGGTCAGACAGGCACCAGGTAAGGGACTGGAGTGGGTC
TCTGCAATTAGCGGGTAGCGGTGGTAGCACTTACTACGCAGACAGCGTGAAGGGTCGCTTCACCATCTCACGC
GACAACTCCAAGAACACCCTGTACCTGCAGATGAACAGCCTTCGCGCAGAGGACACTGCCGTGTATTACTGC
GCACGTAGCAGCCAGGGTATCTTCGACATCTGGGGACAAGGTACTCTGGTCACTGTCTCCTCA (1gb)  SEQ ID NO: 326

CL7 Light Chain (DNA sequence):

CAGTCTGTGCTGACTCAGCCACCTTCAGCATCTGGTACTCCAGGTCAGCGCGTCACCATCAGCTGCAGTGGTA
ACAATATCGGTACTAGACGCGTGCATTGGTATCAGCAACTCCCAGACACCGCTCCTAAGCTCCTGATTTACAGT
AAGAACAACCGTCCTAGTGGTGTGCCTGATCGCTTTTCTGGGTCCAAGTCTGGCACCTCAGCCTCTCTGGCTAT
CAGTGGACTTCGCTCCGAGGACGAGGCTGACTATTACTGCGCAGCATGGGACGACAGCCTGAGCGGTCCTGT
GTTCGGCGGTGGGACCAAACTGACCGTCCTA (1gc)  SEQ ID NO: 327

CL7 Heavy Chain (Amino acid sequence):

EVQLLESGGGLVQPGGSLRLSCAASGFTFSRYAMSWVRQAPGKGLEWVSAISGSGGSTYYADSVKGRFTISRDN
SKNTLYLQMNSLRAEDTAVYYCARSSQGIFDIWGQGTLVTVSS (1gd)  SEQ ID NO: 328

CL7 Light Chain (Amino acid sequence):

QSVLTQPPSASGTPGQRVTISCSGNNIGTRRVHWYQQLPDTAPKLLIYSKNNRPSGVPDRFSGSKSGTSASLAIS
GLRSEDEADYYCAAWDDSLSGPVFGGGTKLTVL

[FIG. 1h]

CDR1, CDR2, and CDR3 are underlined and appear sequentially (1ha)    SEQ ID NO: 329

CL8 Heavy Chain (DNA sequence):

GAGGTGCAGCTGTTGGAGTCTGGTGGAGGCTTGGTACAGCCTGGAGGTTCTCTTCGCCTCTCCTGTGCAGCCT
CCGGATTCACTTTCAGCAGCTACGCAATGAGCTGGGTCAGACAGGCACCAGGTAAGGGACTGGAGTGGGTC
TCTGCAATTAGCGGTAGCGGTGGTAGCACTTACTACGCAGACAGCGTGAAGGGTCGCTTCACCATCTCACGCA
ACAACTCCAAGAACACCCTGTACCTGCAGATGAACAGCCTTCGCGCAGAGGACACTGCCGTGTATTACTGCG
CACGTAGCGGTCGTTACGCAGACTTGACATCTGGGGGACAAGGTACTCTGGTCACTGTCTCCTCA (1hb)    SEQ ID NO: 330

CL8 Light Chain (DNA sequence):

CAGTCTGTGCTGACTCAGCCACCTTCAGCATCTGGTACTCCAGGTCAGCGCGTCACCATCAGCTGCAGCGGTA
GCAACAGCAACATCGGTAACAACTACGTGAGCTGGTATCAGCAACTCCCAGACACCCCTCCTAAGCTCCTGAT
TTACGACAACAACAAGCGTCCTAGTGGTGTGCCTGATCGCTTTTCTGGGTCCAAGTCTGGCACCTCAGCCTCTC
TGGCTATCAGTGGACTTCGCTCCGAGGACGAGGCTGACTATTACTGCAGCAGCTACACTAGCAGCAGCACTG
TGATGTTCGGCGGTGGGACCAAACTGACCGTCCTA (1hc)    SEQ ID NO: 331

CL8 Heavy Chain (Amino acid sequence):

EVQLLESGGGLVQPGGSLRLSCAASGFTFSSYAMSWVRQAPGKGLEWVSAISGSGGSTYYADSVKGRFTISRNN
SKNTLYLQMNSLRAEDTAVYYCARSGRYADLTSGGQGTLVTVSS (1hd)    SEQ ID NO: 332

CL8 Light Chain (Amino acid sequence):

QSVLTQPPSASGTPGQRVTISCSGSNSNIGNNYVSWYQQLPDTPPKLLIYDNNKRPSGVPDRFSGSKSGTSASL
AISGLRSEDEADYYCSSYTSSSTVMFGGGTKLTVL

[FIG. 1i]

CDR1, CDR2, and CDR3 are underlined and appear sequentially (1ia)     SEQ ID NO: 333

CL9 Heavy Chain (DNA sequence):

GAGGTGCAGCTGTTGGAGTCTGGTGGAGGCTTGGTACAGCCTGGAGGTTCTCTTCGCCTCTCCTGTGCAGCCT
CCGGATTCACTTTCAGCAGCTACTACTGGAGCTGGGTCAGACAGGCACCAGGTAAGGGACTGGAGTGGGTC
TCTGCAATTAGCGGTAGCGGTGGTAGCACTTACTACGCAGACAGCGTGAAGGGTCGCTTCACCATCTCACGC
GACAACTCCAAGAACACCCTGTACCTGCAGATGAACAGCCTTCGCGCAGAGGACACTGCCGTGTATTACTGC
GCACGTATCGACGTGTACGGTTTCGACATCTGGGGACAAGGTACTCTGGTCACTGTCTCCTCA (1ib)     SEQ ID NO: 334

CL9 Light Chain (DNA sequence):

CAGTCTGTGCTGACTCAGCCACCTTCAGCATCTGGTACTCCAGGTCAGCGCGTCACCATCAGCTGCAGCGGTA
GCACTAGCAACATCGGTACTAACTACGTGTACTGGTATCAGCAACTCCCAGGCACCGCTCCTAAGCTCCTGATT
TACGACAACAACAACCGTCCTAGTGGTGTGCCTGATCGCTTTTCTGGGTCCAAGTCTGGCACCTCAGCCTCTCT
GGCTATCAGTGGACTTCGCTCCGAGGACGAGGCTGACTATTACTGCCAGACTTGGGACAGCAGCACTGACGT
AGTGTTCGGCGGTGGGACCAAACTGACCGTCCTA (1ic)     SEQ ID NO: 335

CL9 Heavy Chain (Amino acid sequence):

EVQLLESGGGLVQPGGSLRLSCAASGFTFSSYYWSWVRQAPGKGLEWVSAISGSGGSTYYADSVKGRFTISRDN
SKNTLYLQMNSLRAEDTAVYYCARIDVYGFDIWGQGTLVTVSS (1id)     SEQ ID NO: 336

CL9 Light Chain (Amino acid sequence):

QSVLTQPPSASGTPGQRVTISCSGSTSNIGTNYYVWYQQLPGTAPKLLIYDNNNRPSGVPDRFSGSKSGTSASLA
ISGLRSEDEADYYCQTWDSSTDVVFGGGTKLTVL

[FIG. 1j]

CDR1, CDR2, and CDR3 are underlined and appear sequentially (1ja)   SEQ ID NO: 337

CL10 Heavy Chain (DNA sequence):

GAGGTGCAGCTGTTGGAGTCTGGTGGAGGCTTGGTACAGCCTGGAGGTTCTCTTCGCCTCTCCTGTGCAGCCT
CCCGGATTCACTTTCAGCAGCTACGGTATGCATTGGGTCAGACAGGCACCAGGTAAGGGACTGGAGTGGGTCT
CTGCAATTAGCGGTAGCGGTGGTAGCACTTACTACGCAGACAGCGTGAAGGGTCGCTTCACCATCTCACGCG
ACAACTCCAAGAACACCCTGTACCTGCAGATGAACAGCCTTCGCGCAGAGGACACTGCCGTGTATTACTGCG
CAAGCGGTTACGGTCTGATGGACGTGTGGGGACAAGGTACTCTGGTCACTGTCTCCTCA (1jb)   SEQ ID NO: 338

CL10 Light Chain (DNA sequence):

TCTGTGCTGACTCAGCCACCTTCAGCATCTGGTACTCCAGGTCAGCGCGTCACCATCAGCTGCACTCGTAGCA
GCGGTATCATCGCAAGCAACTACGTGCAGTGGTATCAGCAACTCCCAGGCACCGCTCCTAAGCTCCTGATTTA
CCGCAACAACCAGCGCCCTAGTGGTGTGCCTGATCGCTTTTCTGGGTCCAAGTCTGGCACCTCAGCCTCTCTG
GCTATCAGTGGACTTCGCTCCGAGGACGAGGCTGACTATTACTGCAGCAGCTACGCAGGTAACAACAACCTG
GTGTTCGGCGGTGGGACCAAACTGACCGTCCTA (1jc)   SEQ ID NO: 339

CL10 Heavy Chain (Amino acid sequence):

EVQLLESGGGLVQPGGSLRLSCAASGFTFSSYGMHWVRQAPGKGLEWVSAISGSGGSTYYADSVKGRFTISRDN
SKNTLYLQMNSLRAEDTAVYYCASGYGLMDVWGQGTLVTVSS (1jd)   SEQ ID NO: 340

CL10 Light Chain (Amino acid sequence):

QSVLTQPPSASGTPGQRVTISCTRSSGIIASNYVQWYQQLPGTAPKLLIYRNNQRPSGVPDRFSGSKSGTSASLAI
SGLRSEDEADYYCSSYAGNNNLVFGGGTKLTVL

[FIG. 1k]

CDR1, CDR2, and CDR3 are underlined and appear sequentially (1ka)    SEQ ID NO: 341

SK11 Heavy Chain (DNA sequence):

CGAGTGCAGCTGCTGGAAAGTGGAGGTGGACTGGTGCAGCCTGGCGGCAGCCTGCGGCCTGAGCTGTGCCGC
CAGCGGGATTCACCTTCAGCACCTATGGCATGCATTGGGTTCGCCAAGCACCTGGCAAAGGCCTGGAATGGGT
GAGCGCCATCAGCGGCAGCGGCGGCAGCACCTATTATGCCGATAGCGTGAAAGGCCGCTTTACCATCAGCCG
CGATAACAGCAAAAACACCCTGTATCTGCAGATGAACAGCCTGCGCGCCGAGGACACCGCAGTCTACTACTG
TGCCCGCGGCCTGAGCGGCCTTGATTATTGGGGACAAGGTACTCTGGTGACCGTGAGCAGC (1kb)    SEQ ID NO: 342

SK11 Light Chain (DNA sequence):

GAAATCGTGCTGACCCAGAGCCCTGGCACCCTGAGCCTGAGCCCTGGCGAACGCGCCAACACTGTCATGCCG
CTCCAGCCAGGGCATCACCAACTATCTGGCCTGGTATCAGCAGAAACCAGGTCAGGCTCCACGTCTGCTGATC
TATGATGCCAGCAACCGCGCCACCGGCATCCCTGATCGCTTCTCAGGATCTGGAAGCGGTACCGATTTTACCC
TGACCATCAGCCGCCTGGAACCTGAGGACTTTGCCGTGTATTATTGTCAGCAGAGCTATAGCACCCCTCTGACC
TTCGGTCAGGGCACTAAAGTGGAAATCAAA (1kc)    SEQ ID NO: 343

SK11 Heavy Chain (Amino acid sequence):

RVQLLESGGGLVQPGGSLRLSCAASGFTFSTYGMHWVRQAPGKGLEWVSAISGSGGSTYYADSVKGRFTISRDN
SKNTLYLQMNSLRAEDTAVYYCARGLSGLDYWGQGTLVTVSS (1kd)    SEQ ID NO: 344

SK11 Light Chain (Amino acid sequence):

EIVLTQSPGTLSLSPGERATLSCRSSQGITNYLAWYQQKPGQAPRLLIYDASNRATGIPDRFSGSGSGTDFTLTISRL
EPEDFAVYYCQQSYSTPLTFGQGTKVEIK

[FIG. 1I]

CDR1, CDR2, and CDR3 are underlined and appear sequentially (1Ia)    SEQ ID NO: 345

SK12 Heavy Chain (DNA sequence):

CGAGTGCAGCTGCTGGAAAGTGGAGGTGGACTGGTGCAGCCTGGCCGGCAGCCTGCGCCTGAGCTGTGCCGC
CAGCGGATTCACCTTCAGCAGCTATGCCATGCATTGGGTTCGCCAAGCACCTGGCAAAGGCCTGGAATGGGT
GAGCGCCATCAGCGGCAGCGGCGGCGATACCTATCATGCCGATAGCGTGAAAGGCCGCTTTACCATCAGCCG
CGATAACAGCAAAAACACCCTGTATCTGCAGATGAACAGCCTGCGCGCCGAGGACACCGCAGTCTACTACTG
TACCCGCGGCCTGAGCGGCTTTGATTATTGGGGACAAGGTACTCTGGTGACCGTGAGCAGC (1Ib)    SEQ ID NO: 346

SK12 Light Chain (DNA sequence):

GAAATCGTGCTGACCCAGAGCCCTGGCACCCTGAGCCTGAGCCCTGGCGAACGCGCAACACTGTCATGCCG
CGCCAGCCAGAGCATCAGCAGCTATCTGAACTGGTATCAGCAGAAACCAGGTCAGGCTCCACGTCTGCTGAT
CTATGATGCCAGCAACCGCGCCCCTGGCATCCCTGATCGCTTCTCAGGATCTGGAAGCGGGTACCGATTTTACCC
TGACCATCAGCCGCCTGGAACCTGAGGACTTTGCCGTGTATTATTGTCAGCAGAGCTATAGCATCCCTATCACC
TTCGGTCAGGGCACTAAAGTGGAAATCAAA (1Ic)    SEQ ID NO: 347

SK12 Heavy Chain (Amino acid seqeucne):

RVQLLESGGGLVQPGGSLRLSCAASGFTFSSYAMHWVRQAPGKGLEWVSAISGSGGDTYHADSVKGRFTISRD
NSKNTLYLQMNSLRAEDTAVYYCTRGLSGFDYWGQGTLVTVSS (1Id)    SEQ ID NO: 348

SK12 Light Chain (Amino acid seqeucne):

EIVLTQSPGTLSLSPGERATLSCRASQSISSYLNWYQQKPGQAPRLLIYDASNRAPGIPDRFSGSGSGTDFTLTISR
LEPEDFAVYYCQQSYSIPITFGQGTKVEIKFSD

[FIG. 1m]

CDR1, CDR2, and CDR3 are underlined and appear sequentially (1ma)   SEQ ID NO: 349

SK13 Heavy Chain (DNA sequence):

CGAGTGCAGCTGCTGGAAAGTGGAGGTGGACTGGTGCAGCCTGGCGGCAGCCTGCGCCTGAGCTGTGCCGC
CAGCGGATTCACCTTCAGCGATTATGCCATGAGCTGGGTTCGCCAAGCACCTGGCAAAGGCCTGGAATGGGT
GAGCAGCATCAGCAGCAGCAGCAGCTATATCTACTATACCGATAGCGTGAAAGGCCGCTTTACCATCAGCCGC
GATAACAGCAAAAACACCCTGTATCTGCAGATGAACAGCCTGCGCGCCGAGGACACCGCAGTCTACTACTGT
GCCCGCGGCGGCTATGGCTTTGATTATTGGGGACAAGGTACCCTGGTGACCGTGAGCAGC (1mb)   SEQ ID NO: 350

SK13 Light Chain (DNA sequence):

GAAATCGTGCTGACCCAGAGCCCCTGGCACCCTGAGCCTGAGCCCTGGCGAACGCGCAACACTGTCATGCCG
CGCCAGCCAGAGCATCAGCAGCTATCTGAACTGGTATCAGCAGAAACCAGGTCAGGCTCCACGTCTGCTGAT
CTATAGCGCCAGCAGCCGCCCACAGGGCATCCCCGATCGCTTCTCAGGATCTGGAAGCGGTACCGATTTTACC
CTGACCATCAGCCGCCTGGAACCTGAGGACTTTGCCGTGTATTATTGTCAGCAGTATGATGATCTGCCTTTTACC
TTCGGTCAGGGCACTAAAGTGGAAATCAAA (1mc)   SEQ ID NO: 351

SK13 Heavy Chain (Amino acid sequence):

RVQLLESGGGLVQPGGSLRLSCAASGFTFSDYAMSWVRQAPGKGLEWVSSISSSSSYIYYTDSVKGRFTISRDNS
KNTLYLQMNSLRAEDTAVYYCARGGYGFDYWGQGTLVTVSS (1md)   SEQ ID NO: 352

SK13 Light Chain (Amino acid sequence):

EIVLTQSPGTLSLSPGERATLSCRASQSISSYLNWYQQKPGQAPRLLIYSASSRPQGIPDRFSGSGSGTDFTLTISRL
EPEDFAVYYCQQYDDLPFTFGQGTKVEIK

[FIG. 1n]

CDR1, CDR2, and CDR3 are underlined and appear sequentially (1na) SEQ ID NO: 353

SK14 Heavy Chain (DNA sequence):

GAAGTGCAGCTGCTGGAAAGTGGAGGTGGACTGGTGCAGCCTGGCGGCAGCCTGCGCCTGAGCTGTGCCGC
CAGCGGATTCACCTTCAGCAACTTTGCGATCGCCTGGGTTCGCCAAGCACCTGGCAAAGGCCTGGAATGGGT
GAGCGCCATCAGCGGCCGCGGCACCAGCACCTATTATGCCGATAGCGTGAAAGGCCGCTTTACCATCAGCCG
CGATAACAGCAAAAACACCCTGTATCTGCAGATGAACAGCCTGCGCGCCGAGGACACCGCAGTCTACTACTG
TGCCCGCGGCGTGAGCGGCTTTGATAGCTGGGGACAAGGTACTCTGGTGACCGTGAGCA (1nb) SEQ ID NO: 354

SK14 Light Chain (DNA sequence):

GAAATCGTGCTGACCCAGAGCCCTGGCACCCTGAGCCTGAGCCCTGGCGAACGCGCAACACTGTCATGCCG
CGCCAGCCAGAGCATCAGCAGCCATCTGGCCTGGTATCAGCAGAAACCAGGTCAGGCTCCACGTCTGCTGAT
CTATGATACCAGCAACCGCGCCACCGGCATCCCTGATCGCTTCTCAGGATCTGGGAGCGGGTACCGATTTTACC
CTGACCATCAGCCGCCTGGAACCTGAGGACTTTGCCGTGTACTATTGTCAGCAGAGCTATAGCACCCCTTTTAC
CTTCGGTCAGGGCACTAAAGTGGAAATCAAA (1nc) SEQ ID NO: 355

SK14 Heavy Chain (Amino acid sequence):

EVQLLESGGGLVQPGGSLRLSCAASGFTFSNFAIAWVRQAPGKGLEWVSAISGRGTSTYYADSVKGRFTISRDNS
KNTLYLQMNSLRAEDTAVYYCARGVSGFDSWGQGTLVTVSS (1nd) SEQ ID NO: 356

SK14 Light Chain (Amino acid sequence):

EIVLTQSPGTLSLSPGERATLSCRASQSISSHLAWYQQKPGQAPRLLIYDTSNRATGIPDRFSGSGSGTDFTLTISRL
EPEDFAVYYCQQSYSTPFTFGQGTKVEIK

[FIG. 1o]

CDR1, CDR2, and CDR3 are underlined and appear sequentially (1oa)  SEQ ID NO: 357

SK15 Heavy Chain (DNA sequence):

CGAGTGCAGCTGCTGGAAAGTGGAGGTGGACTGGTGCAGCCTGGCGGCAGCCTGCGCCTGAGCTGTGCCGC
CAGCGGATTCACCTTCAGCAGCTATGCCATGCATTGGGTTCGCCAAGCACCTGGCAAAGGCCTGGAATGGGT
GAGCGCCATCAACGGCAGCGGCGGCAGCACCTATTATGCCGATAGCGTGAAAGGCCGCTTTACCATCAGCCG
CGATAACAGCAAAAACACCCTGTATCTGCAGACGAACAGCCTGCGCGCCGAGGACACCGCAGTCTACTACTG
TGCCCGCGGCCTGCAGGGCTTTGATTATTGGGGACAAGGTACTCTGGTGACCGTGAGCAGCA (1ob)  SEQ ID NO: 358

SK15 Light Chain (DNA sequence):

GAAATCGTGCTGACCCAGAGCCCTGGCACCCTGAGCCTGAGCCCTGGCGAACGCGCAACACTGTCATGCCA
GGCCAGCCAGGATATCACCAACTATCTGAACTGGTATCAGCAGAAACCAGGTCAGGCTCCACGTCTGCTGATC
TATGATGCCAGCAGCCTGGAAACCGGCATCCCTGATCGTTTCTCAGGATCTGGAAGCGGTACCGATTTTACCCT
GACCATCAGCCGCCTGGAACCTGAGGACTTTGCCGTGTATTATTGTCAGCAGAGCTATAGCACCCCTATCACCT
TCGGTCAGGGCACTAAAGTGGAAATCAAA (1oc)  SEQ ID NO: 359

SK15 Heavy Chain (Amino acid sequence):

RVQLLESGGGLVQPGGSLRLSCAASGFTFSSYAMHWVRQAPGKGLEWVSAINGSGGSTYYADSVKGRFTISRD
NSKNTLYLQTNSLRAEDTAVYYCARGLQGFDYWGQGTLVTVSS (1od)  SEQ ID NO: 360

SK15 Light Chain (Amino acid sequence):

EIVLTQSPGTLSLSPGERATLSCQASQDITNYLNWYQQKPGQAPRLLIYDASSLETGIPDRFSGSGSGTDFTLTISRL
EPEDFAVYYCQQSYSTPITFGQGTKVEIK

[FIG. 1p]

CDR1, CDR2, and CDR3 are underlined and appear sequentially (1pa) SEQ ID NO: 361

SK16 Heavy Chain (DNA sequence):

CGAGTGCAGCTGCTGGAAAGTGGAGGTGGACTGGTGCAGCCTGGCGGCAGCCTGCGCCTGAGCTGTGCCGC
CAGCGGATTCACCTTCAGCAGCTATGCCATGAGCTGGGTTCGCCAAGCACCTGGCAAAGGCCTGGAATGGGT
GAGCGCCATCAACGGCAGCGGCGGCAGCACCCTGTATGCCGATAGCGTGAAAGGCCGCTTTACCATCAGCCC
GCGATAACAGCAAAAACACCCTGTATCTGCAGATGAACAGCCTGCGCGCCGAGGACACCGCAGTCTACTACT
GTGCCCGCGGCGTGAGCGGCTTTGATAGCTGGGGACAAGGTACTCTGGTGACCGTGAGCAGCG (1pb) SEQ ID NO: 362

SK16 Light Chain (DNA sequence):

GAAATCGTGCTGACCCAGAGCCCTGGCACCCTGAGCCTGAGCCCTGGCGAACGCGCAACACTGTCATGCCG
CATCAGCCAGAGCATCAGCAGCTATCTGAACTGGTATCAGCAGAAACCAGGTCAGGCTCCACGTCTGCTGATC
TATGATGCCAGCCTGCGCGCCACCGGCATCCCTGATCGCTTCTCAGGATCTGGAAGCGGTACCGATTTTACCCT
GACCATCAGCCGCCTGGAACCTGAGGACTTTGCCGTGTATTATTGTCAGCAGAGCTATAAAACCCCTATCACCT
TCGGTCAGGGCACTAAAGTGGAAATCAAA (1pc) SEQ ID NO: 363

SK16 Heavy Chain (Amino acid sequence):

RVQLLESGGGLVQPGGSLRLSCAASGFTFSSYAMSWVRQAPGKGLEWVSAINGSGGSTLYADSVKGRFTISRDN
SKNTLYLQMNSLRAEDTAVYYCARGVSGFDSWGQGTLVTVSS (1pd) SEQ ID NO: 364

SK16 Light Chain (Amino acid sequence):

EIVLTQSPGTLSLSPGERATLSCRISQSISSYLNWYQQKPGQAPRLLIYDASLRATGIPDRFSGSGSGTDFTLTISRLE
PEDFAVYYCQQSYKTPITFGQGTKVEIK

[FIG. 1q]

CDR1, CDR2, and CDR3 are underlined and appear sequentially (1qa)   SEQ ID NO: 365

SK17 Heavy Chain (DNA sequence):

GAAGTGCAGCTGCTGGAAAGTGGAGGTGGACTGGTGCAGCCTGGCGGCAGCCTGCGCCTGAGCTGTGCCGC
CAGCGGATTCACCTTCAGCAGCTATTATTGGAGCTGGGTTCGCCAAGCACCTGGCAAAGGCCTGGAATGGGT
GAGCACCATCACCGGCAGCGGCGGCAGCACCGATTATGCCAACAGCGTGAAAGGCCGCTTTACCATCAGCC
GCGATAACAGCAAAAACACCCTGTATCTGCAGATGAACAGCCTGCGCGCCGAGGACACCGCAGTCTACTACT
GTGCCACCGGCGGCGGCATCTTTGACTATTGGGGACAAGGTACTCTGGTGACCGTGAGCAGCG (1qb)   SEQ ID NO: 366

SK17 Light Chain (DNA sequence):

GAAATCGTGCTGACCCAGAGCCCTGGCACCCTGAGCCTGAGCCCTGGCGAACGCGCAACACTGTCATGCCA
GGCCAGCCAGACCATCAGCAACTATCTGAACTGGTATCAGCAGAAACCAGGTCAGGCTCCACGTCTGCTGAT
CTATGATGCCAGCAACCGCGCCACCGGCATCCCTGATCGCTTCTCAGGATCTGGAAGCGGTACCGATTTTACC
CTGACCATCAGCCGCCTGGAACCTGAGGACTTTGCCGTGTATTATTGTCAGCAGTACAACAGCTATCCTCCTAG
CTTCGGTCAGGGCACTAAAGTGGAAATCAAA (1qc)   SEQ ID NO: 367

SK17 Heavy Chain (Amino acid sequence):

EVQLLESGGGLVQPGGSLRLSCAASGFTFSSYYWSWVRQAPGKGLEWVSTITGSGGSTDYANSVKGRFTISRDN
SKNTLYLQMNSLRAEDTAVYYCATGGGIFDYWGQGTLVTVSS (1qd)   SEQ ID NO: 368

SK17 Light Chain (Amino acid sequence):

EIVLTQSPGTLSLSPGERATLSCQASQTISNYLNWYQQKPGQAPRLLIYDASNRATGIPDRFSGSGSGTDFTLTISRL
EPEDFAVYYCQQYNSYPPSFGQGTKVEIK

[FIG. 1r]

CDR1, CDR2, and CDR3 are underlined and appear sequentially (1ra)  SEQ ID NO: 369

SL18 Heavy Chain (DNA sequence):

CGAGTGCAGCTGCTGGAAAGTGGAGGTGGACTGGTGCAGCCTGGCGGCAGCCTGCGCCTGAGCTGTGCCGC
CAGCGGATTCACCTTCAGCGATTATCATATGCATTGGGTTCGCCAAGCACCTGGCAAAGGCCTGGAATGGGTG
AGCACCATCAGCAGCAGCGGCGGCTATACCTATTATGCCGAAAGCGTGAAAAGCCGCTTTACCATCAGCCGC
GATAACAGCAAAAACACCCTGTATCTGCAGATGAACAGCCTGCGCGCCGAGGACACCGCAGTCTACTACTGT
GCCCGATCGATACGCCTGCCTCTGGATTATTGGGGACAAGGTACTCTGGTGACCGTGAGCAGCA (1rb)  SEQ ID NO: 370

SL18 Light Chain (DNA sequence):

CAGAGCGTGCTGACCCAGCCTCCTAGCGCCTCCGGTACACCAGGACAGCGCGTGACTATTAGCTGTAGCGGC
AACAACATCGGCAGCAAAGGCGTGCATTGGTATCAGCAACTGCCTGGAACTGCACCTAAGCTGCTGATCTAT
GAAGATAGCAAACGCCCTAGCGGCGTGCGTGATCGCTTTAGCGGTAGCAAATCAGGCACCAGCGCCAGCCT
GGCCATCAGCGGCCTTCGCTCCGAAGATGAAGCCGATTATTATTGTCAGAGCTATGATAGCACCAAAGGCGTG
GTGTTTGGTGGCGGTACCAAGCTGACCGTGCTG (1rc)  SEQ ID NO: 371

SL18 Heavy Chain (Amino acid sequence):

RVQLLESGGGLVQPGGSLRLSCAASGFTFSDYHMHWVRQAPGKGLEWVSTISSSGGYTYYAESVKSRFTISRDN
SKNTLYLQMNSLRAEDTAVYYCARSIRLPLDYWGQGTLVTVSS (1rd)  SEQ ID NO: 372

SL18 Light Chain (Amino acid sequence):

QSVLTQPPSASGTPGQRVTISCSGNNIGSKGVHWYQQLPGTAPKLLIYEDSKRPSGVRDRFSGSKSGTSASLAISG
LRSEDEADYYCQSYDSTKGVVFGGGTKLTVL

[FIG. 1s]

CDR1, CDR2, and CDR3 are underlined and appear sequentially (1sa) SEQ ID NO: 373

CB301_H3L1_A10 Heavy Chain (DNA sequence):

GAGGTGCAGCTGTTGGAGTCTGGTGGAGGCTTGGTACAGTCTGGAGGTTCTCTTCGCCTCTCCTGTGCAGCCT
CCGGATTCACTTTCAGCAGCTACGGTATGCATTGGGTCAGACAGGCACCAGGTAAGGGACTGGAGTGGGTCT
CTGCAATTAGCGGTAGCGGTGGTAGCACTTACTACGCAGACAGCGTGAAGGGTCGCTTCACCATCTCACGCG
ACAACTCCAAGAACACCCTGTACCTGCAGATGAACAGCCTTCGCGCAGAGGACACTGCCGTGTATTACTGCG
TGCGTGGTTACGGTGCAATGGACGTGTGGGGACAAGGTACTCTGGTCACTGTCTCCTCA (1sb) SEQ ID NO: 374

CB301_H3L1_A10 Light Chain (DNA sequence):

CAGTCTGTGCTGACTCAGCCACCTTCAGCATCTGGTACTCCAGGTCAGCGCGTCACCATCAGCTGCACTCGTA
GCAGCGGGTAGCATCGCAAGCAACTACGTGCAGTGGTATCAGCAACTCCCAGGCACCGCTCCTAAGCTCCTGA
TTTACCGCAACAACCAGCGCCCCTAGTGGTGTGCCTGATCGCTTTTCTGGGTCCAAGTCTGGCACCTCAGCCTC
TCTGGCTATCAGTGGACTTCGCTCCGAGGACGAGGCTGACTATTACTGCAGCAGCTACACTACTAGCAGCACT
CTGGTGTTCGGCGGTGGGACCAAACTGACCGTCCTA (1sc) SEQ ID NO: 375

CB301_H3L1_A10 Heavy Chain (Amino acid sequence):

EVQLLESGGGLVQSGGSLRLSCAASGFTFSSYGMHWVRQAPGKGLEWVSAISGSGGSTYYADSVKGRFTISRDN
SKNTLYLQMNSLRAEDTAVYYCVRGYGAMDVWGQGTLVTVSS (1sd) SEQ ID NO: 376

CB301_H3L1_A10 Light Chain (Amino acid sequence):

QSVLTQPPSASGTPGQRVTISCTRSSGSIASNYVQWYQQLPGTAPKLLIYRNNQRPSGVPDRFSGSKSGTSASLA
ISGLRSEDEADYYCSSYTTSSTLVFSGGTKLTVL

[FIG. 1t]

CDR1, CDR2, and CDR3 are underlined and appear sequentially (1ta)    SEQ ID NO: 377

CB301_H3L1_A12 Heavy Chain (DNA sequence):

GAGGTGCAGCTGTTGGAGTCTGGTGGAGGCTTGGTACAGCCTGGAGGTTCTCTTCGCCTCTCCTGTGCAGCCT
CCGGATTCACTTTCAGCAGCTACGCAATGCATTGGGTCAGACAGGCACCAGGTAAGGGACTGGAGTGGGTCT
CTGCAATTAGCGGTAGCGGTGGTAGCACTTACTACGCAGACAGCGTGAAGGGTCGCTTCACCATCTCACGCG
ACAACTCCAAGAACACCCTGTACCTGCAGATGAACAGCCTTCGCGCAAAGGACACTGCCGTGTATTACTGCG
CAAGCGGCTACGGTCTGATGGACGTATGGGGACAAGGTACTCTGGTCACTGTCTCCTCA (1tb)    SEQ ID NO: 378

CB301_H3L1_A12 Light Chain (DNA sequence):

CAGTCTGTGCTGACTCAGCCACCTTCAGCATCTGGTACTCCAGGTCAGCGCGTCACCATCAGCTGCACTGGTA
CTAGCAGCGACGTGGGTAACTACAACCTGGTGAGCTGGTATCAGCAACTCCCAGGCACCGCTCCTAAGCTCCT
GATTTACAGCAACAACCAGCGGCCCTAGTGGTGTGCCTGATCGCTTTTCTGGGTCCAAGTCTGGCACCTCAGCC
TCTCTGGCTATCAGTGGACTTCGCTCCGAGGACGAGGCTGACTATTACTGCAGCAGCTACACTGGTAGCAACG
CTCTGTTGTTCGGCGGTGGGACCAAACTGACCGTCCTA (1tc)    SEQ ID NO: 379

CB301_H3L1_A12 Heavy Chain (Amino acid sequence):

EVQLLESGGGLVQPGGSLRLSCAASGFTFSSYAMHWVRQAPGKGLEWVSAISGSGGSTYYADSVKGRFTISRDN
SKNTLYLQMNSLRAKDTAVYYCASGYGLMDVWGQGTLVTVSS (1td)    SEQ ID NO: 380

CB301_H3L1_A12 Light Chain (Amino acid sequence):

QSVLTQPPSASGTPGQRVTISCTGTSSDVGNYNLVSWYQQLPGTAPKLLIYSNNQRPSGVPDRFSGSKSGTSASL
AISGLRSEDEADYYCSSYTGSNALLFGGGTKLTVL

[FIG. 1u]

CDR1, CDR2, and CDR3 are underlined and appear sequentially (1ua)     SEQ ID NO: 381

CB301_H3L1_E6 Heavy Chain (DNA sequence):

GAGGTGCAGCTGTTGGAGTCTGGTGGAGGCTTGGTACAGCCTGGAGGTTCTCTTCGCCTCTCCTGTGCAGCCT
CCGGATTCACTTTCAGCAGCTACGCAATGAGCTGGGTCAGACAGGCACCAGGTAAGGGACTGGAGTGGGTC
TCTGCAATTAGCGGTAGCGGTGGTAGCACTTACTACGCAGACAGCGTGAAGGGTCGCCTTCACCATCTCACGC
GACAACTCCAAGAACACCCTGTACCTGCAGATGAACAGCCTTCGCGCAGAGGACACTGCCGTGTATTACTGC
GCACGCTGGCATTACAGCTTCGACTACTGGGGACAAGGTACTCTGGTCACTGTCTCCTCA (1ub)     SEQ ID NO: 382

CB301_H3L1_E6 Light Chain (DNA sequence):

CAGTCTGTGCTGACTCAGCCACCTTCAGCATCTGGTACTCCAGGTCAGCGCGTCACCATCAGCTGCCGTGGTA
ACAACATCGGTAGCAAGCGTGTGCATTGGTATCAGCAACTCCCAGGCACCGCTCCTAAGCTCCTGATTTACAG
CTACAACCACCGTCCTAGCGGTGTGCCTGATCGCTTTTCTGGGTCCAAGTCTGGCACCTCAGCCTCTCTGGCTA
TCACTGGACTTCGCTCCGAGGACGAAGCTGACTATTACTGCAACACTTGGGACGACAGCCTGGAGGGTCCTG
TGTTCGGCGGTGGGACCAAACTGACCGTCCTA (1uc)     SEQ ID NO: 383

CB301_H3L1_E6 Heavy Chain (Amino acid sequence):

EVQLLESGGGLVQPGGSLRLSCAASGFTFSSYAMSWVRQAPGKGLEWVSAISGSGGSTYYADSVKGRFTISRDN
SKNTLYLQMNSLRAEDTAVYYCARWHYSFDYWGQGTLVTVSS (1ud)     SEQ ID NO: 384

CB301_H3L1_E6 Light Chain (Amino acid sequence):

QSVLTQPPSASGTPGQRVTISCRGNNIGSKRVHWYQQLPGTAPKLLIYSYNHRPSGVPDRFSGSKSGTSASLAIT
GLRSEDEADYYCNTWDDSLEGPVFGGGTKLTVL

[FIG. 1v]

CDR1, CDR2, and CDR3 are underlined and appear sequentially (1va)    SEQ ID NO: 385

CB301_H3L1_F4 Heavy Chain (DNA sequence):

GAGGTGCAGCTGTTGGAGTCTGGTGGAGGCTTGGTACAGCCTGGAGGTTCTCTTCGCCTCTCCTGTGCAGCCT
CCGGATTCACTTTCAGCGGCTACGCAATGAGCTGGGTCAGACAGGCACCAGGTAAGGGACTGGAGTGGGTC
TCTGCAATTAGCGGTAGCGGTGGTAGCACTTACTACGCAGACAGCGTGAAGGGTCGCTTCACCATCTCACGC
GACAACTCCAAGAACACCCTGTACCTGCAGATGAACAGCCTTCGCGCAGAGGACACTGCCGTGTATTACTGC
GCACGTAGTCCTAGCGGTCTGTTCGACTACTGGGGACAAGGTACTCTGGTCACTGTCTCCTCAG (1vb)    SEQ ID NO: 386

CB301_H3L1_F4 Light Chain (DNA sequence):

CAGTCTGTGCTGACTCAGCCACCTTCAGCATCTGGTACTCCAGGTCAGCGCGTCACCATCAGCTGCGGTGGTA
ACAACATCGGTAGCAAGCGTGTGCATTGGTATCAGCAACTCCCAGGCACCGCTCCTAAGCTCCTGATTTACAA
CACTAGCAACAAGCATAGCGGTGTGCCTGATCGCTTTTCTGGGTCCAAGTCTGGCACCTCAGCCTCTCTGGCT
ATCAGTGGACTTCGCTCCGAGGACGAGGCTGACTATTACTGCAGCAGCTACCTACAGCAGCACTCTCTGTTCG
GCGGTGGGACCAAACTAACCGTCCTA (1vc)    SEQ ID NO: 387

CB301_H3L1_F4 Heavy Chain (Amino acid sequence):

EVQLLESGGGLVQPGGSLRLSCAASGFTFSGYAMSWVRQAPGKGLEWVSAISGSGGSTYYADSVKGRFTISRDN
SKNTLYLQMNSLRAEDTAVYYCARSPSGLFDYWGQGTLVTVSS (1vd)    SEQ ID NO: 388

CB301_H3L1_F4 Light Chain (Amino acid sequence):

QSVLTQPPSASGTPGQRVTISCGGNNIGSKRVHWYQQLPGTAPKLLIYNTSNKHSGVPDRFSGSKSGTSASLAIS
GLRSEDEADYYCSSYLQQHSLFGGGTKLTVL

[FIG. 1w]

CDR1, CDR2, and CDR3 are underlined and appear sequentially (1wa)  SEQ ID NO: 389

C8301_H3L1_G11 Heavy Chain (DNA sequence):

GAGGTGCAGCTGTTGGAGTCTGGTGGAGGCTTGGTACAGCCTGGAGGTTCCTCTTCCGCCTCCTCCTGTGCAG
CCTCCGGATTCACTTTCAGCAGCTACGCAATGAGCTGGGTCAGACAGGCACCAGGTAAGGGACTGGAGTGG
GTCTCTGCAATTAGCGGTAGCGGTGGTAGCACTTACTACGCAGACAGCGTGAAGGGTCGCTTCACCATCTCAC
GCGACAACTCCAAGAACACCCTGTACCTGCAGATGAACAGCCTTCGCGCAGAGGACACTGCCGTGTATTACT
GCACACGTTTCGTGGGTGCAATCGGTGCATTCGACTACTGGGGACAAGGTACTCTGGTCACTGTCTCCTCA (1wb)  SEQ ID NO: 390

C8301_H3L1_G11 Light Chain (DNA sequence):

CAGTCTGTGCTGACTCAGCCACCTTCAGCATCTGGTACTCCAGGTCAGCGCGTCACCATCAGCTGCAGTGGTA
ACAACATCGGTAGCCGTAGCGTGCATTGGTATCAGCAACTCCCAGGCACCGCTCCTAAGCTCCTGATTTACCG
CAACAACCAGCGCCCTAGTGGTGTGCCTGATCGCTTTTCTGGGTCCAAGTCTGGCACCTCAGCCTCTCTGGCT
ATCAGTGGACTTCGCTCCGAGGACGAGGCTGACTATTACTGCGCAGCATGGGACGACAGCCTGAGCGGTCCT
GTGTTCGGCGGTGGGACCAAACTGACCGTCCTA (1wc)  SEQ ID NO: 391

C8301_H3L1_G11 Heavy Chain (Amino acid sequence):

EVQLLESGGGLVQPGGSSSASSCAASGFTFSSYAMSWVRQAPGKGLEWVSAISGSGGSTYYADSVKGRFTISRD
NSKNTLYLQMNSLRAEDTAVYYCTRFVGAIGAFDYWGQGTLVTVSS (1wd)  SEQ ID NO: 392

C8301_H3L1_G11 Light Chain (Amino acid sequence):

QSVLTQPPSASGTPGQRVTISCSGNNIGSRSVHWYQQLPGTAPKLLIYRNNQRPSGVPDRFSGSKSGTSASLAIS
GLRSEDEADYYCAAWDDSLSGPVFGGGTKLTVL

[FIG. 1x]

CDR1, CDR2, and CDR3 are underlined and appear sequentially (1xa)    SEQ ID NO: 393

CB301_OPALTL_BS heavy Chain (DNA sequence):

GAGGTGCAGCTGTTGGAGTCTGGTGGAGGCTTGGTACAGCCTGGAGGTTCTCTTCGCCTCTCCTGTGCAGCCT
CCGGATTCACTTTCAGCCATTACGCAATGAGCTGGGTCAGACAGGCACCAGGTAAGGGACTGGAGTGGGTCT
CTGCAATTAGCGGTAGCGGTGGTAGCACTTACTACGCAGACAGCGTGAAGGGTCGCTTCACCATCTCACGCG
ACAACTCCAAGAACACCCTGTACCTGCAGATGAACAGCCTTCGCGCCAGAGGACACTGCCGTGTATTACTGCG
CACGTGGTTGGGACAGCCCTACTCTGACATACTTCGACAGCTGGGGACAAGGTACTCTGGTCACTGTCTCCTC
A (1xb)    SEQ ID NO: 394

CB301_OPALTL_BS Light Chain (DNA sequence):

CAGTCTGTGCTGACTCAGCCACCTTCAGCATCTGGTACTCCAGGTCAGCGCGTCACCATCAGCTGCAGCGGTA
CTAGCAGCAACATCGGTAACAACGACGTGAGCTGGTATCAGCAACTCCCAGGCACCGCTCCTAAGCTCCTGAT
TTACCAGGACACTAAGCGTCCTAGCGGTGTGCCTGATCGCTTTTCTGGGTCCAAGTCTGGCACCTCAGCCTCT
CTGGCTATCAGTGGACTTCGCTCCGAGGACGAGGCTGACTATTACTGCGCAGCATGGGACGACAGCCTGAGC
GGTCCTGTGTTCGGCGGTGGGACCAAACTGACCGTCCTA (1xc)    SEQ ID NO: 395

CB301_OPALTL_BS heavy Chain (Amino acid sequence):

EVQLLESGGGLVQPGGSLRLSCAASGFTFSHYAMSWVRQAPGKGLEWVSAISGSGGSTYYADSVKGRFTISRDN
SKNTLYLQMNSLRAEDTAVYYCARGWDSPTLTYFDSWGQGTLVTVSS (1xd)    SEQ ID NO: 396

CB301_OPALTL_BS Light Chain (Amino acid sequence):

QSVLTQPPSASGTPGQRVTISCSGTSSNIGNNDVSWYQQLPGTAPKLLIYQDTKRPSGVPDRFSGSKSGTSASLA
ISGLRSEDEADYYCAAWDDSLSGPVFGGGTKLTVL

[FIG. 1y]

CDR1, CDR2, and CDR3 are underlined and appear sequentially (1ya)  SEQ ID NO: 397

C8301_OPALTL_E6 Heavy Chain (DNA sequence):

GAGGTGCAGCTGTTGGAGTCTGGTGGAGGCTTGGTACAGCCTGGAGGTTCTCTTCGCCTCTCCTGTGCAGCCT
CCGGATTCACTTTCAGCAGCTACGGTATGCATTGGGTCAGACAGGCACCAGGTAAGGGACTGGAGTGGGTCT
CTGCAATCAGCGGTAGCGGTGGTTACACTTACTACGCAGACAGCGTGAAGGGTCGCTTCACCATCTCACGCG
ACAACTCCAAGAACACCCTGTACCTGCAGATGAACAGCCTTCGCGCAGAGGACACTGCCGTGTATTACTGCG
CACGCTGGCATTACAGCTTCGACTACTGGGGACAAGGTACTCTGGTCACTGTCTCCTCA (1yb)  SEQ ID NO: 398

C8301_OPALTL_E6 Light Chain (DNA sequence):

CAGTCTGTGCTGACTCAGCCACCTTCAGCATCTGGTACTCCAGGTCAGCGCGTCACCATCAGCTGCAGCGGTA
GCAGCAGCAACATCGGTAACAACTACGTGAGCTGGTATCAGCAACTCCCAGGCACCGCTCCTAAGCTCCTGA
TTTACCGCAACAACCAGCGCCCTAGTGGTGTGCCTGATCGCTTTTCTGGGGTCCAAGTCTGGCACCTCAGCCTCT
CTGGCTATCAGTGGACTTCGCTCCGAGGACGAGGCTGACTATTACTGCCAGAGCTACGACAACAGCAACGTG
CTGTTCGGCGGTGGGACCAAACTGACCGTCCTA (1yc)  SEQ ID NO: 399

C8301_OPALTL_E6 Heavy Chain (Amino acid sequence):

EVQLLESGGGLVQPGGSLRLSCAASGFTFSSYGMHWVRQAPGKGLEWVSAISGSGGYTYYADSVKGRFTISRDN
SKNTLYLQMNSLRAEDTAVYYCARWHYSFDYWGQGTLVTVSS (1yd)  SEQ ID NO: 400

C8301_OPALTL_E6 Light Chain (Amino acid sequence):

QSVLTQPPSASGTPGQRVTISCSGSSSNIGNNYVSWYQQLPGTAPKLLIYRNNQRPSGVPDRFSGSKSGTSASLA
ISGLRSEDEADYYCQSYDNSNVLFGGGTKLTVL

[FIG. 2]
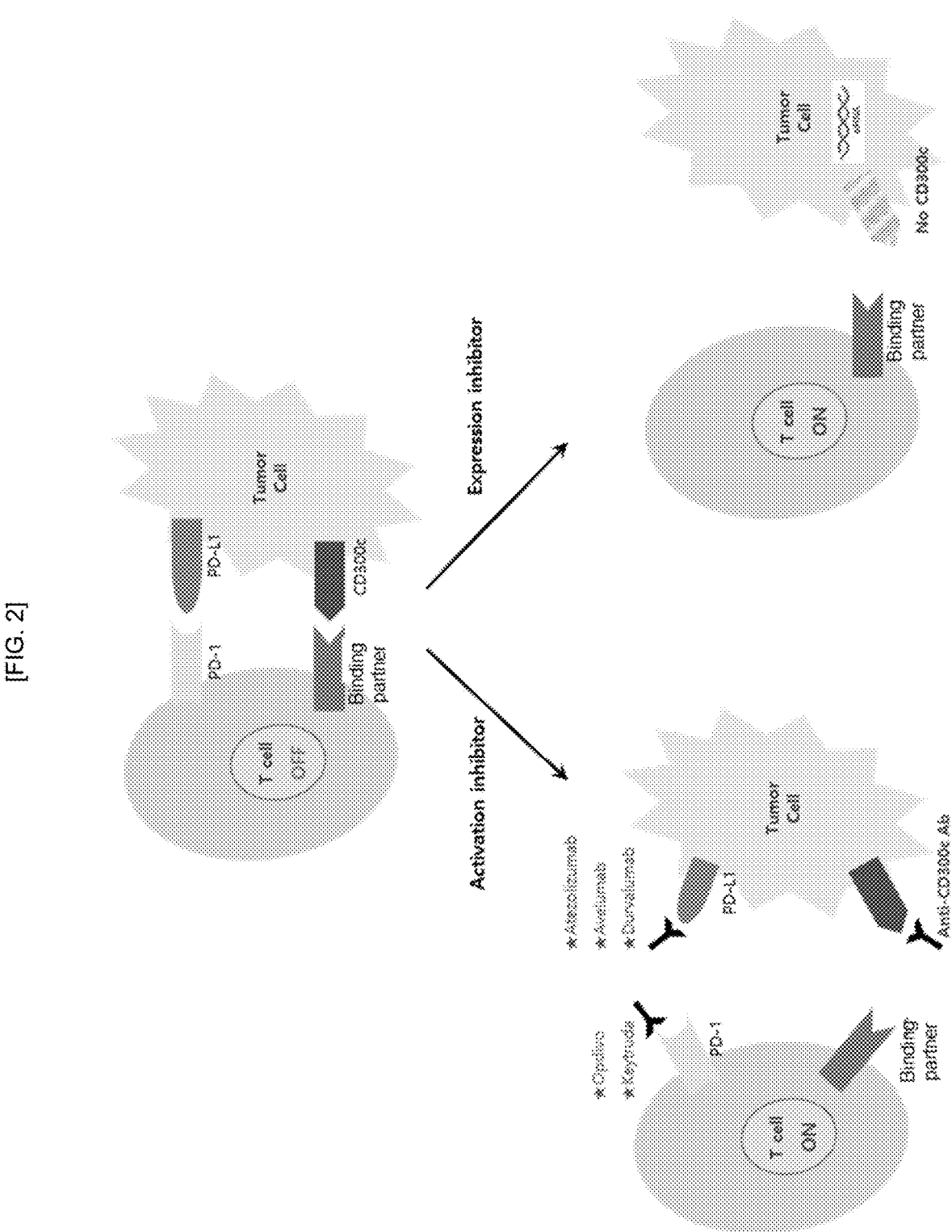

[FIG. 3]
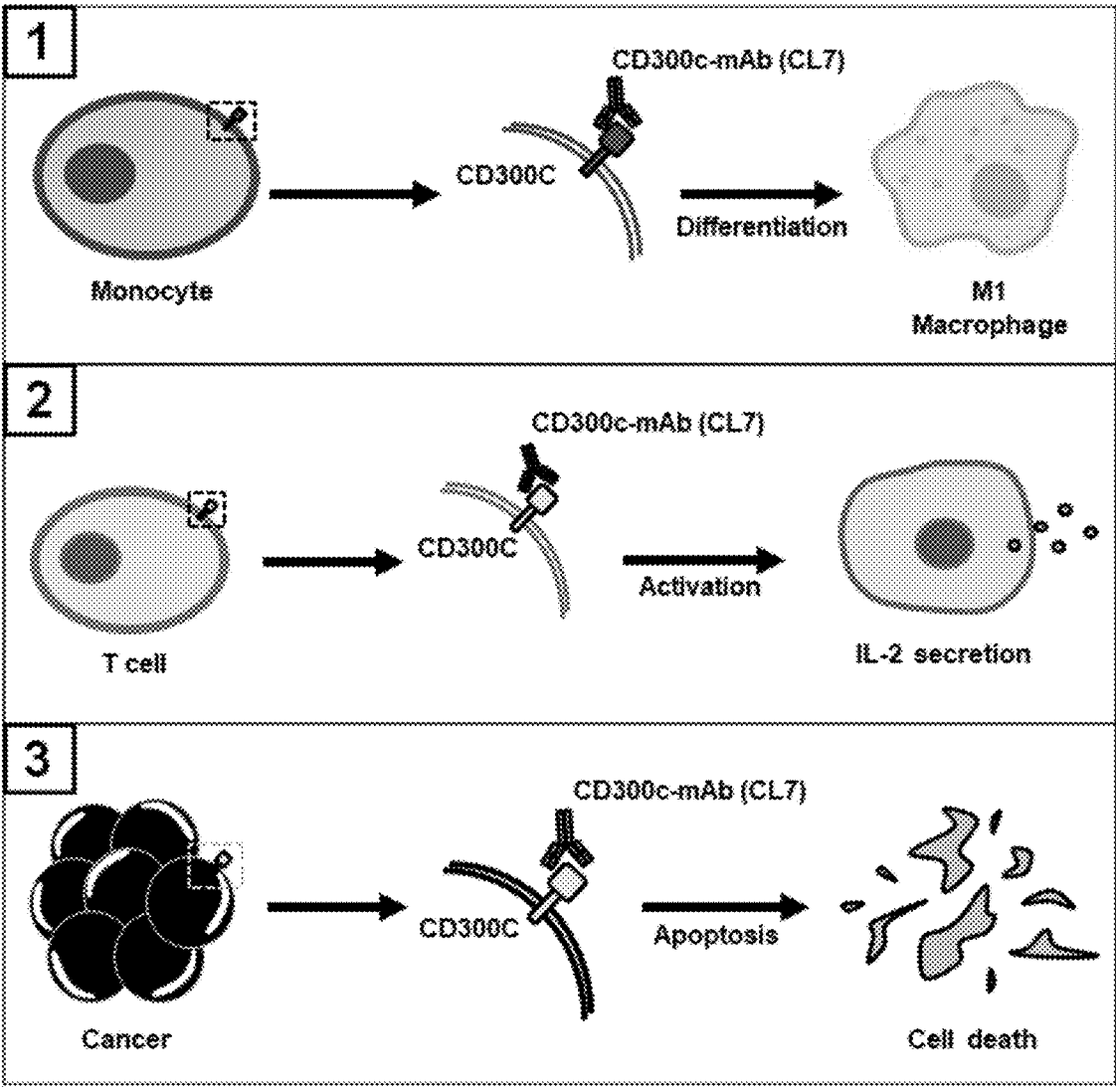

[FIG. 4]
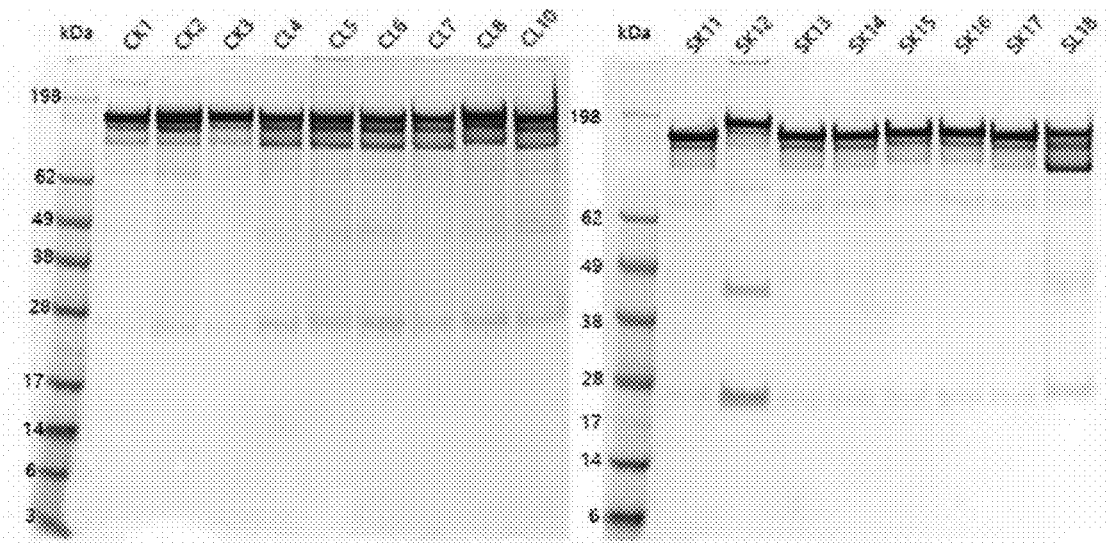
[FIG. 5]
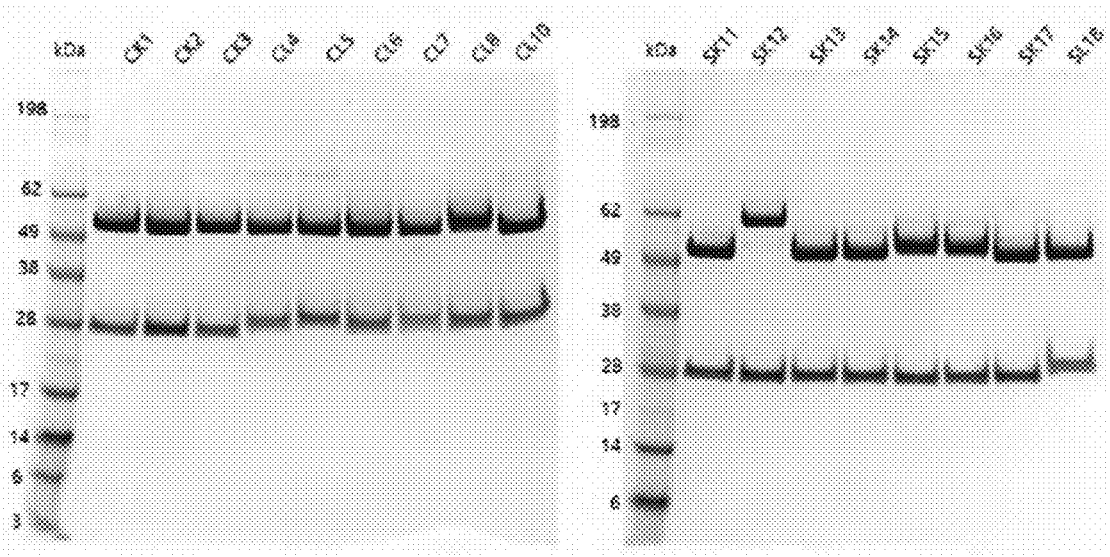

[FIG. 6]
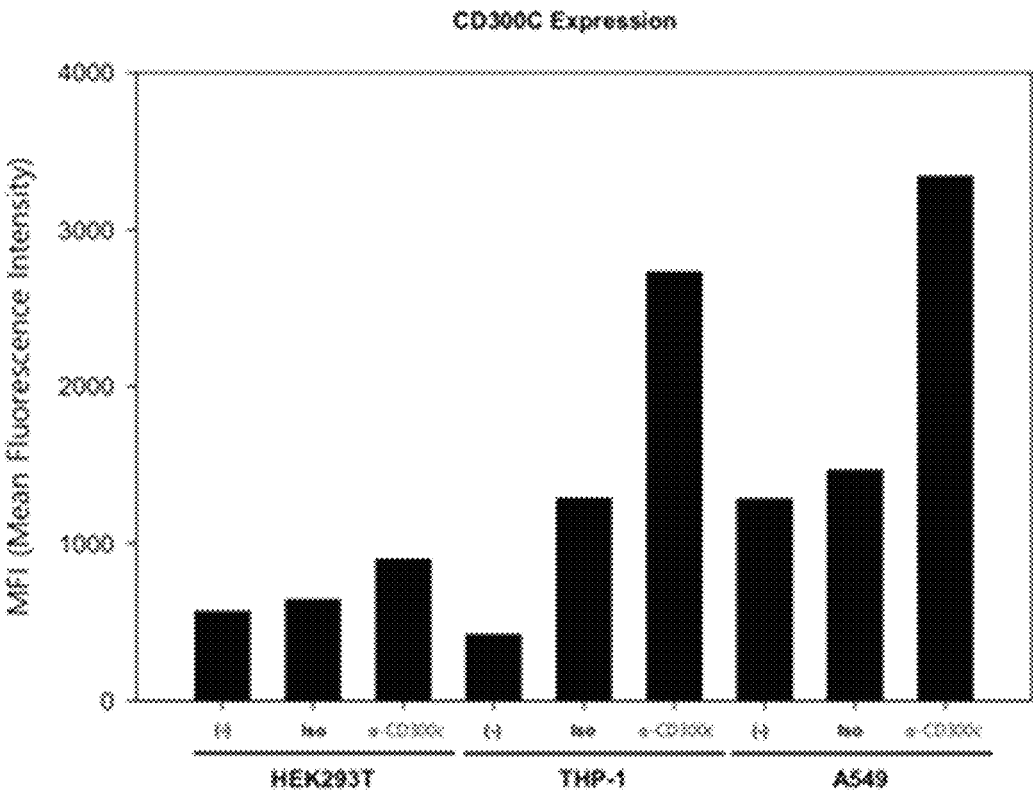

[FIG. 7]
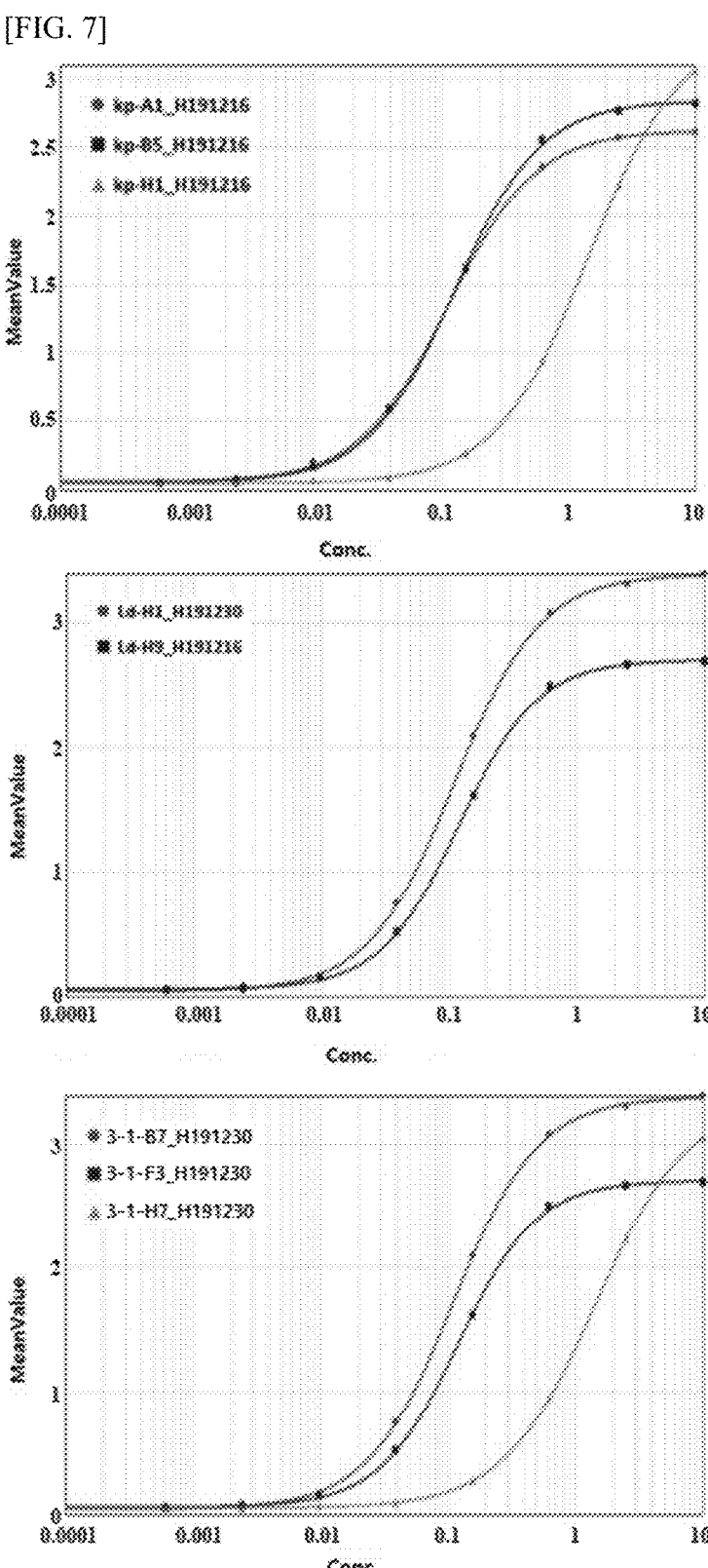

[FIG. 8]
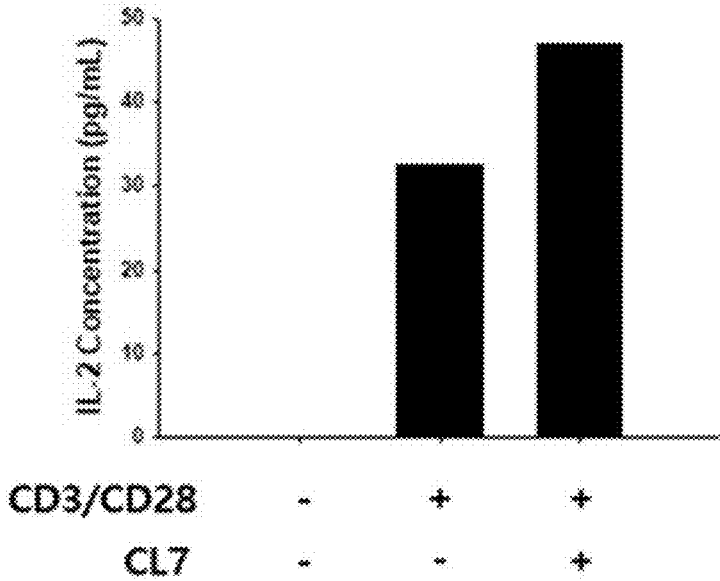
[FIG. 9]
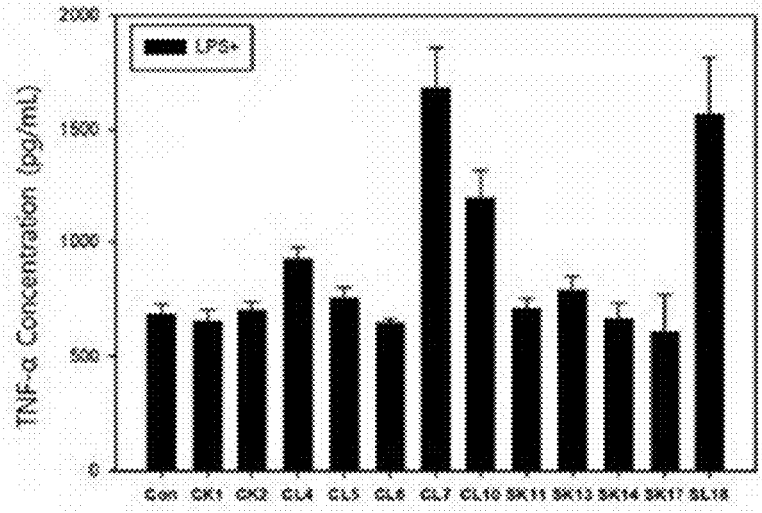

[FIG. 10]
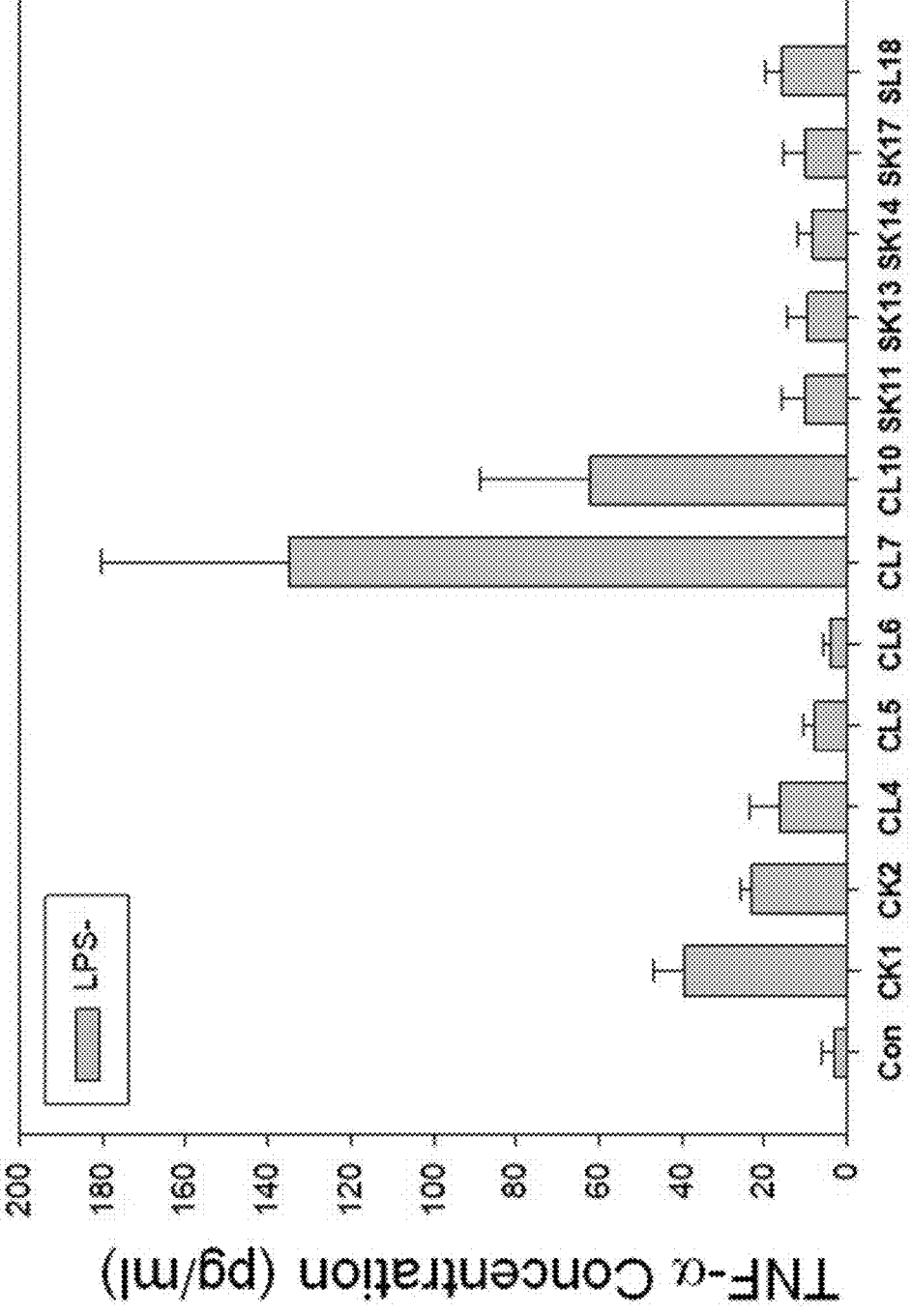

[FIG. 11]
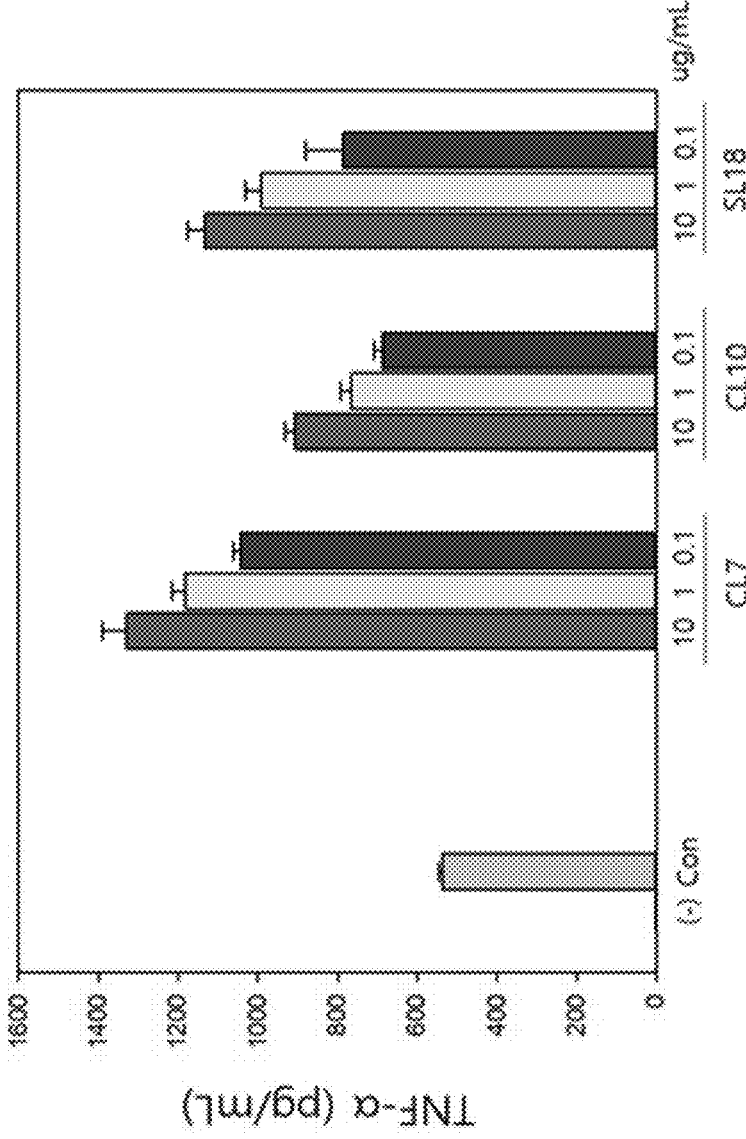

[FIG. 12]
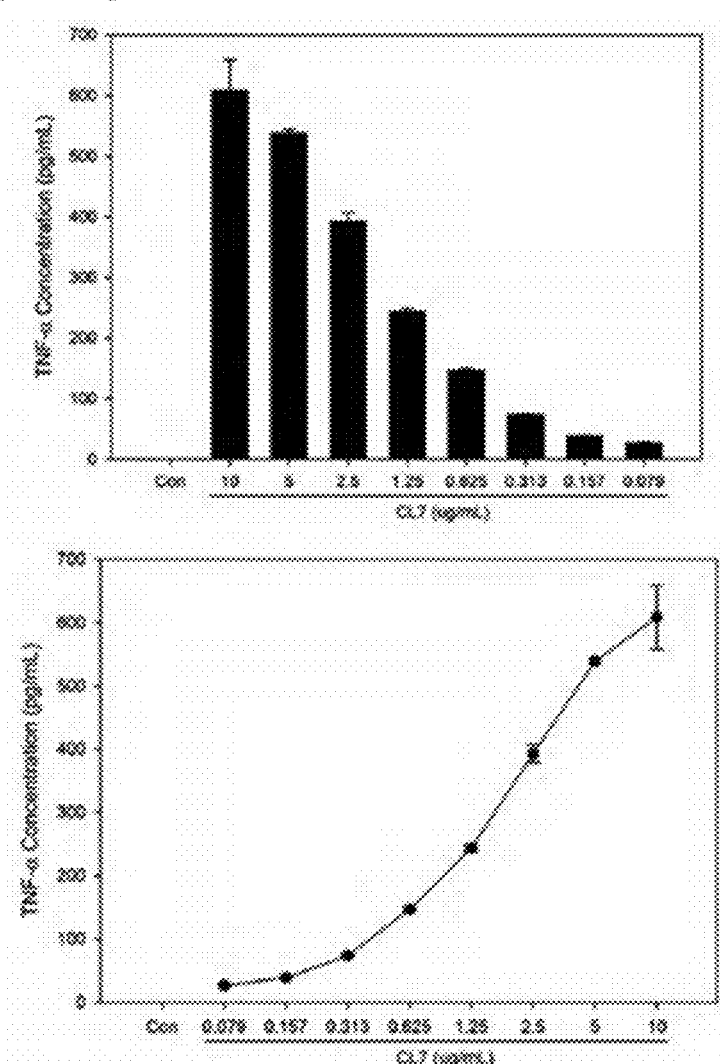
[FIG. 13]
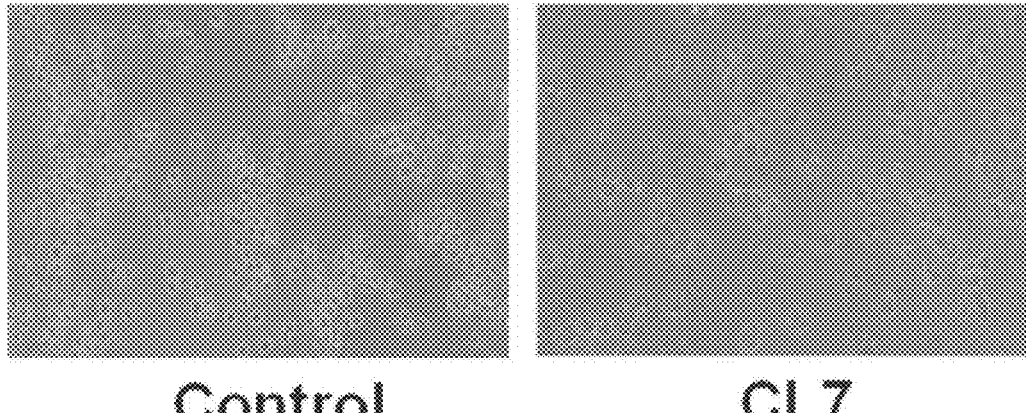

[FIG. 14]
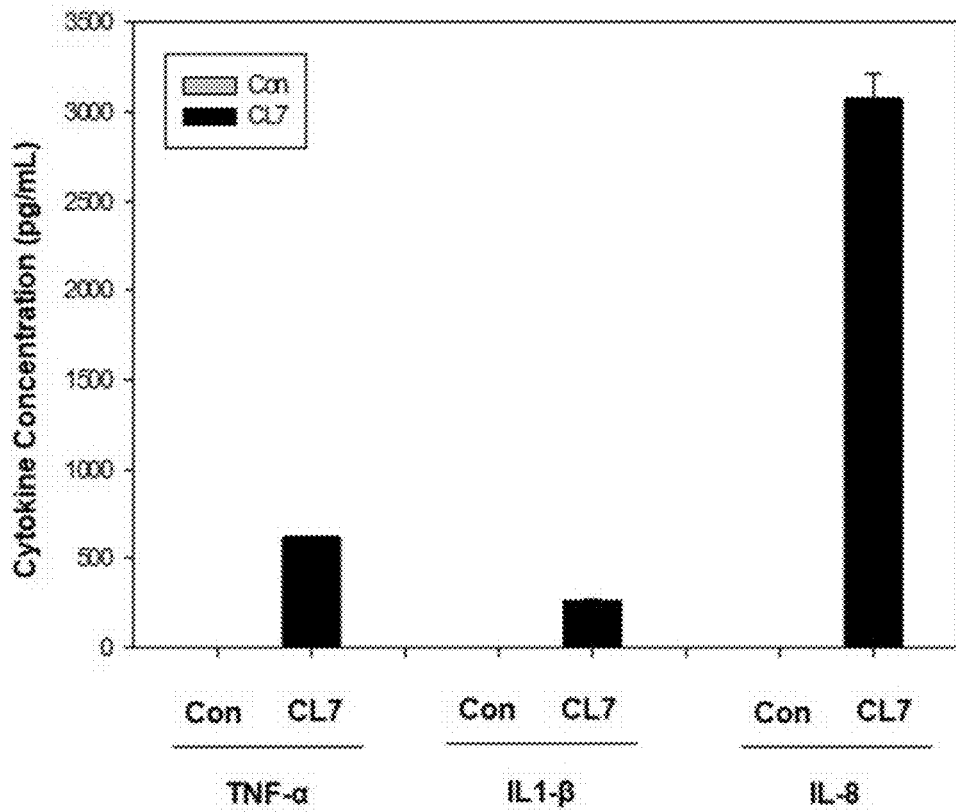

[FIG. 15]
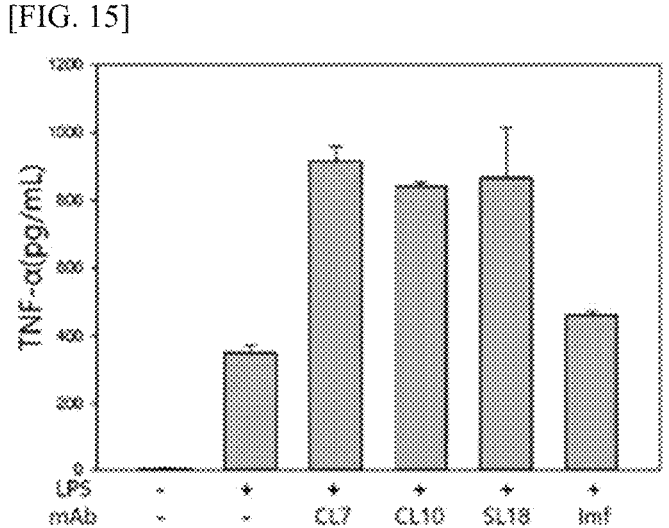
[FIG. 16]
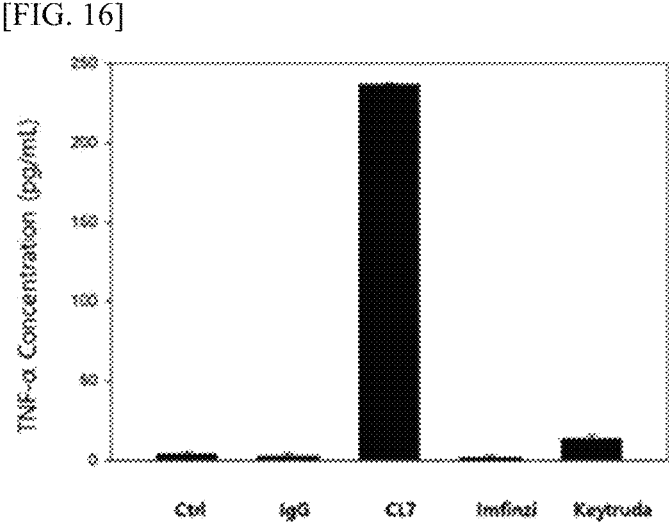

[FIG. 17]
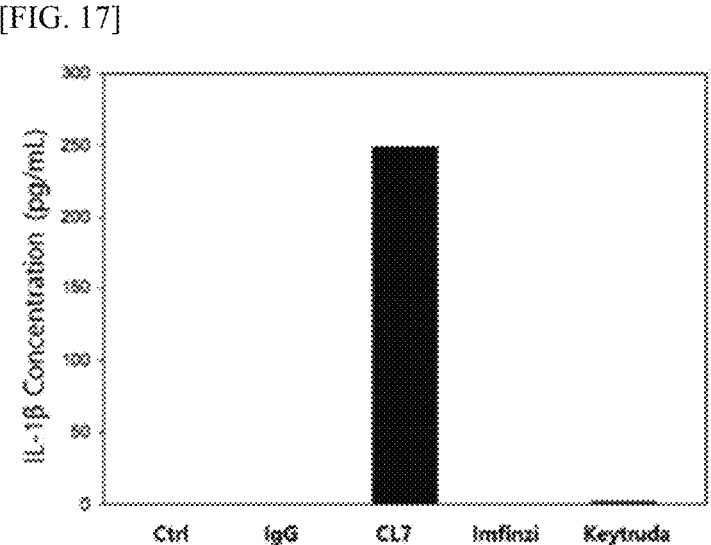
[FIG. 18]
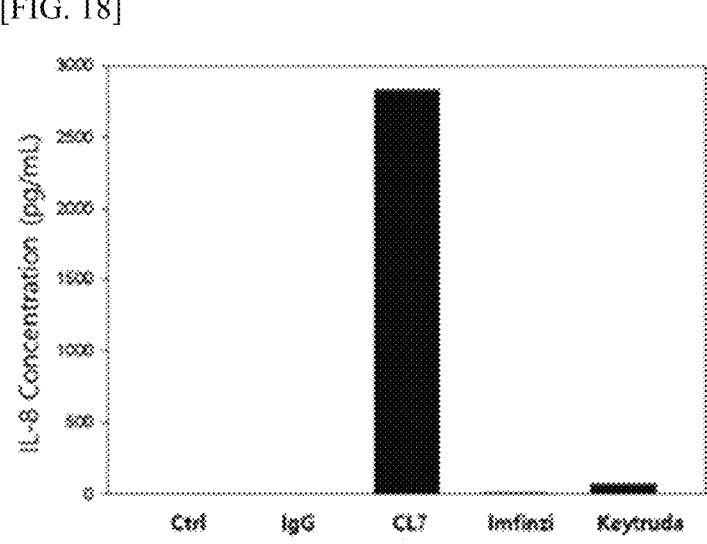

[FIG. 19]
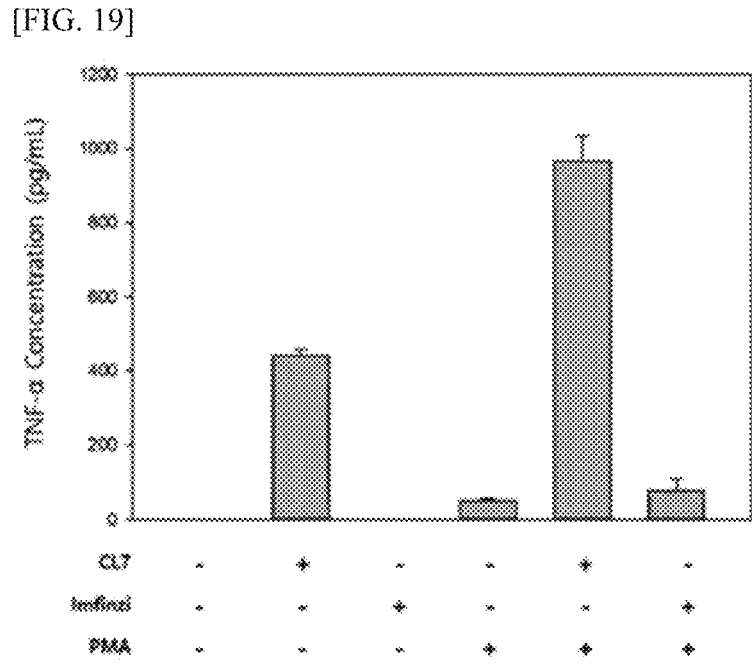
[FIG. 20]
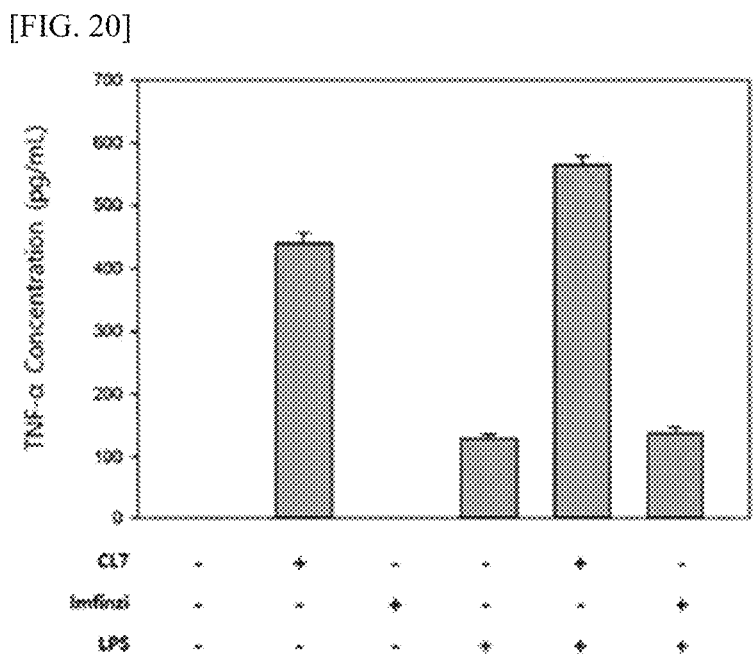

[FIG. 21]
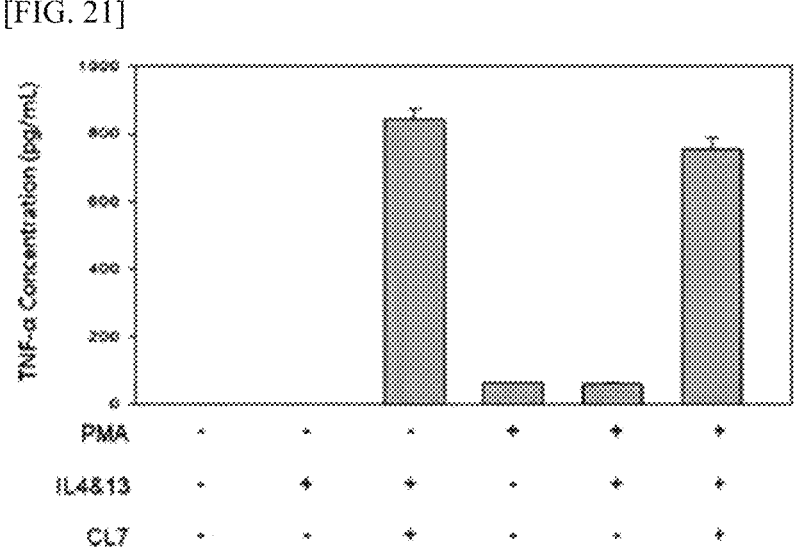
[FIG. 22]
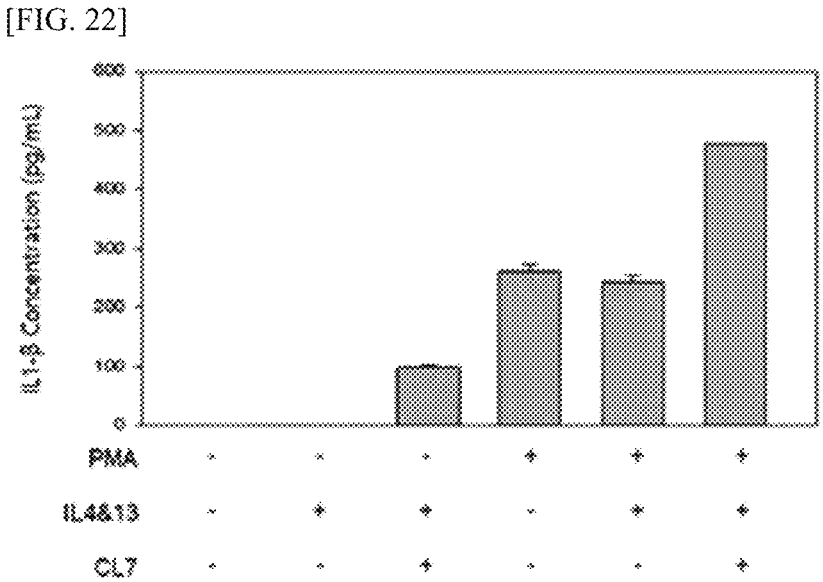

[FIG. 23]
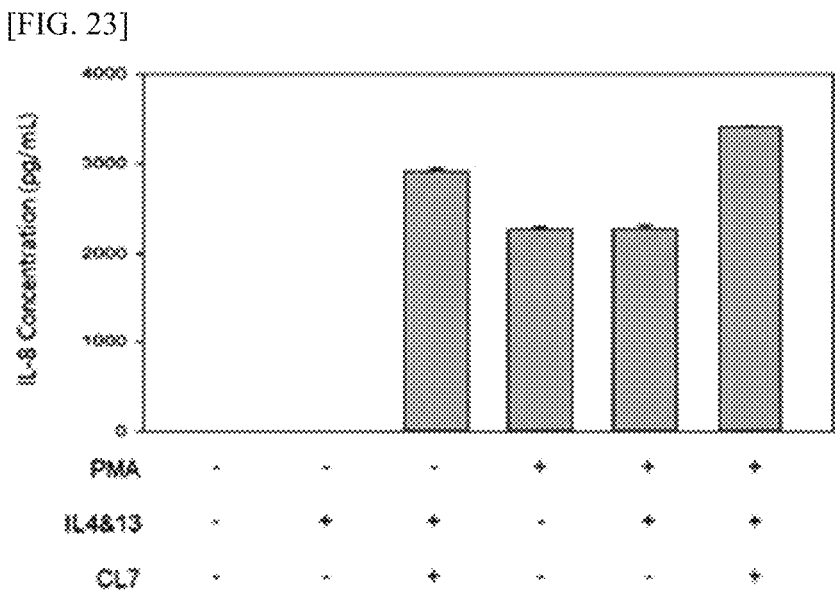
[FIG. 24]
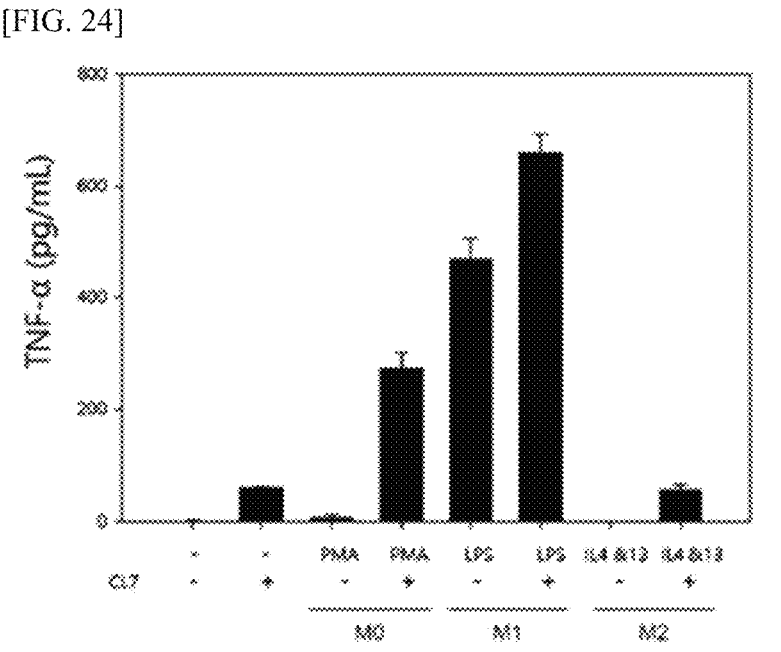

[FIG. 25]
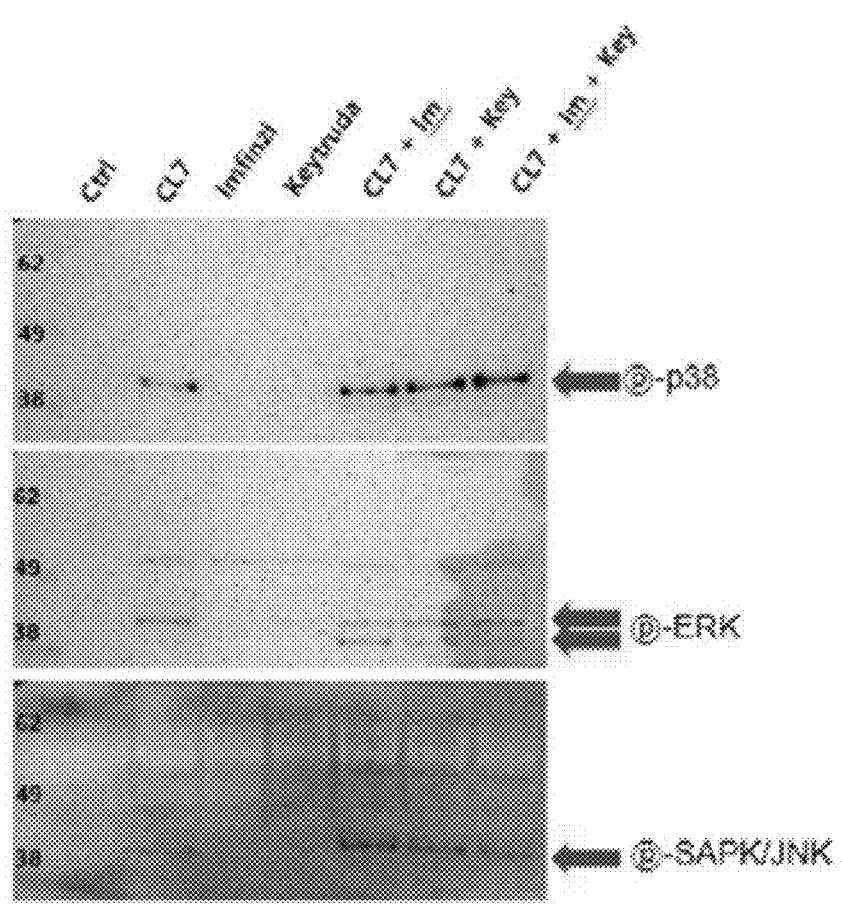

[FIG. 26]
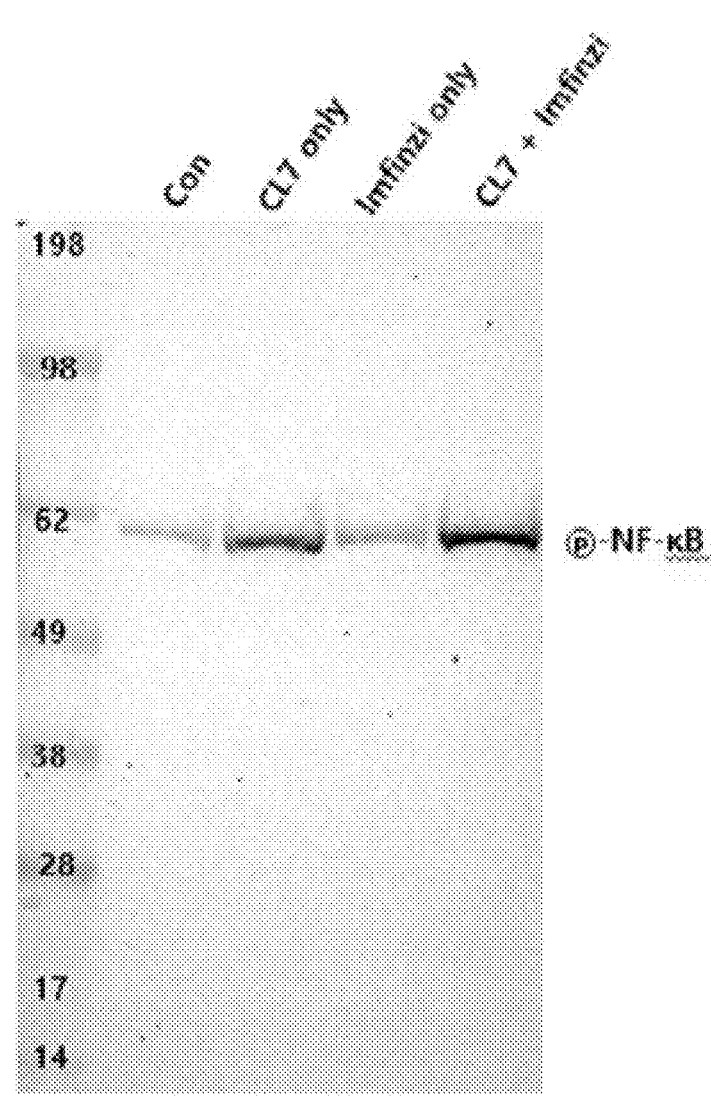

[FIG. 27]
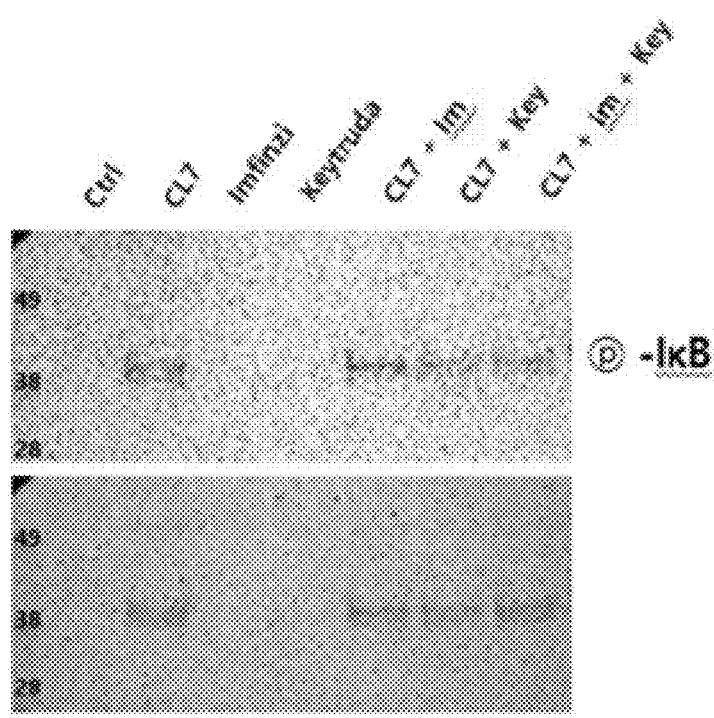

[FIG. 28]
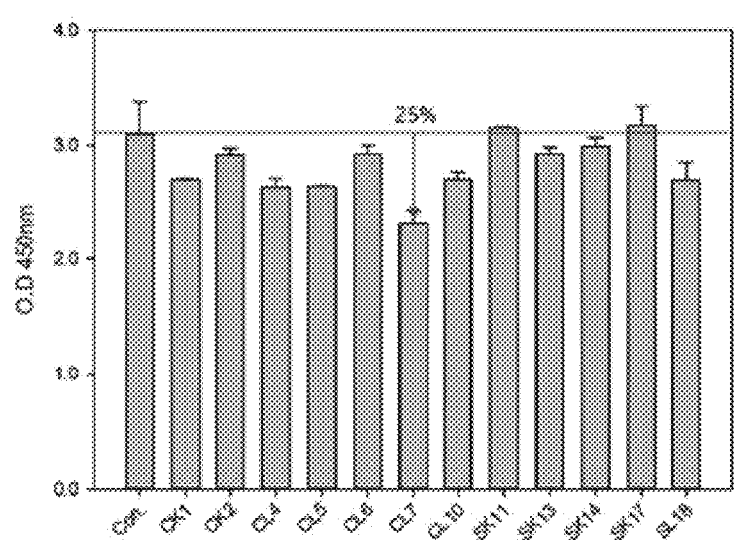
[FIG. 29]
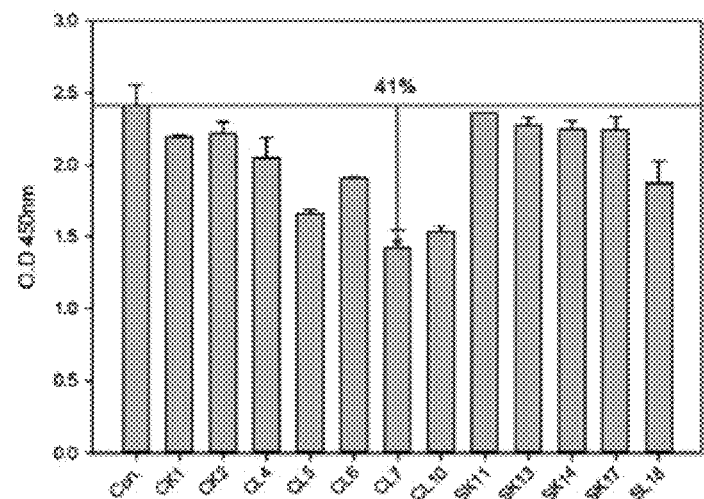

[FIG. 30]
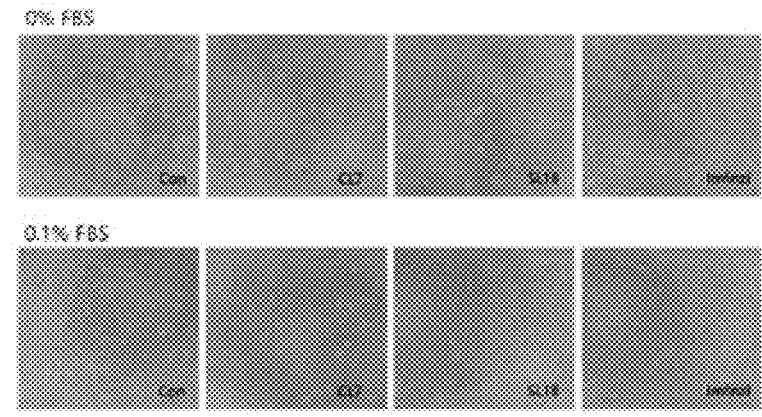
[FIG. 31]
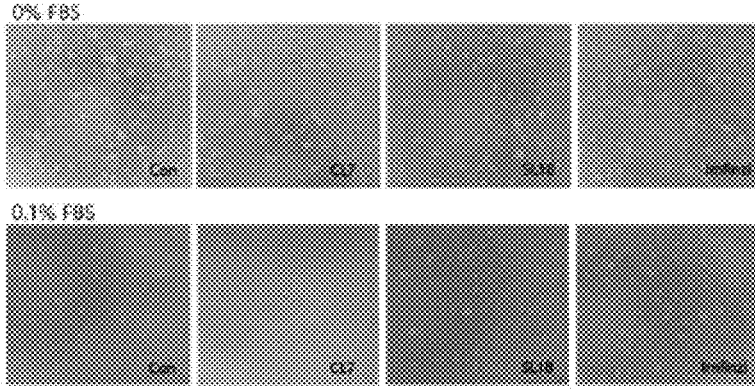

[FIG. 32]
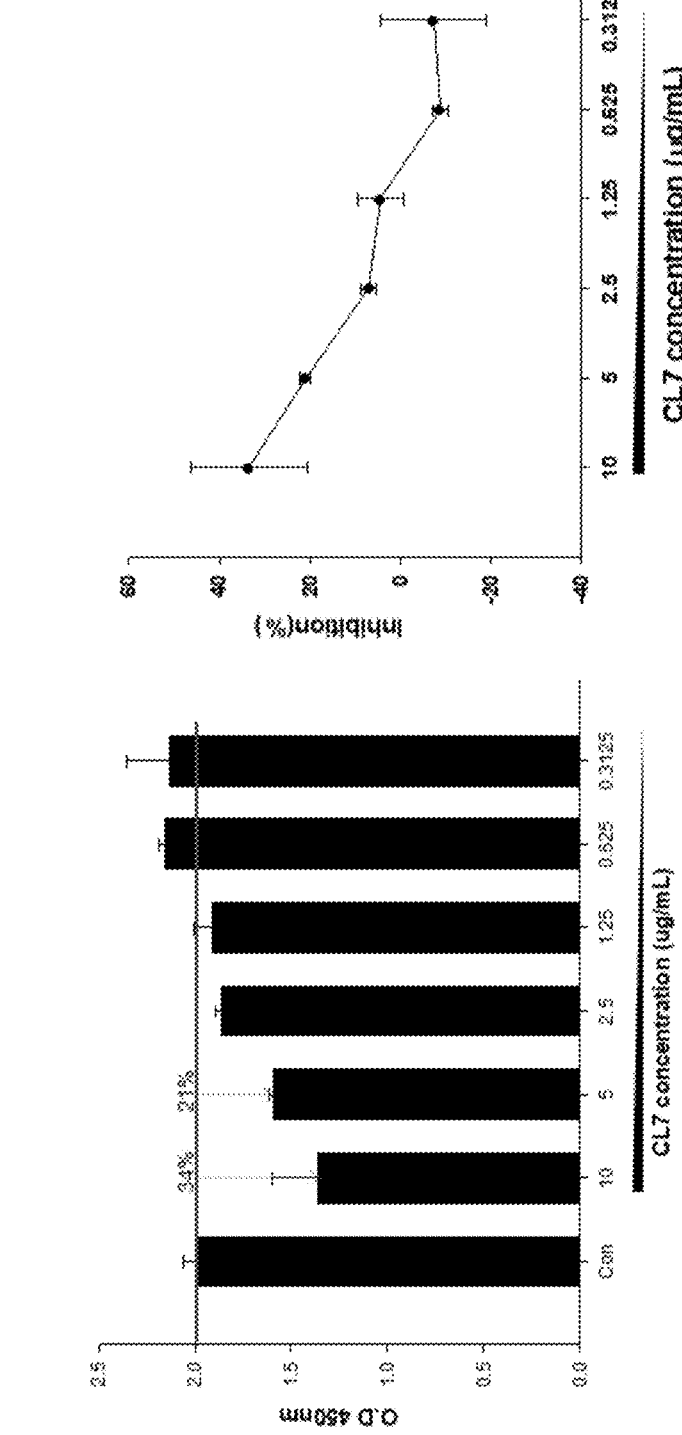

[FIG. 33]
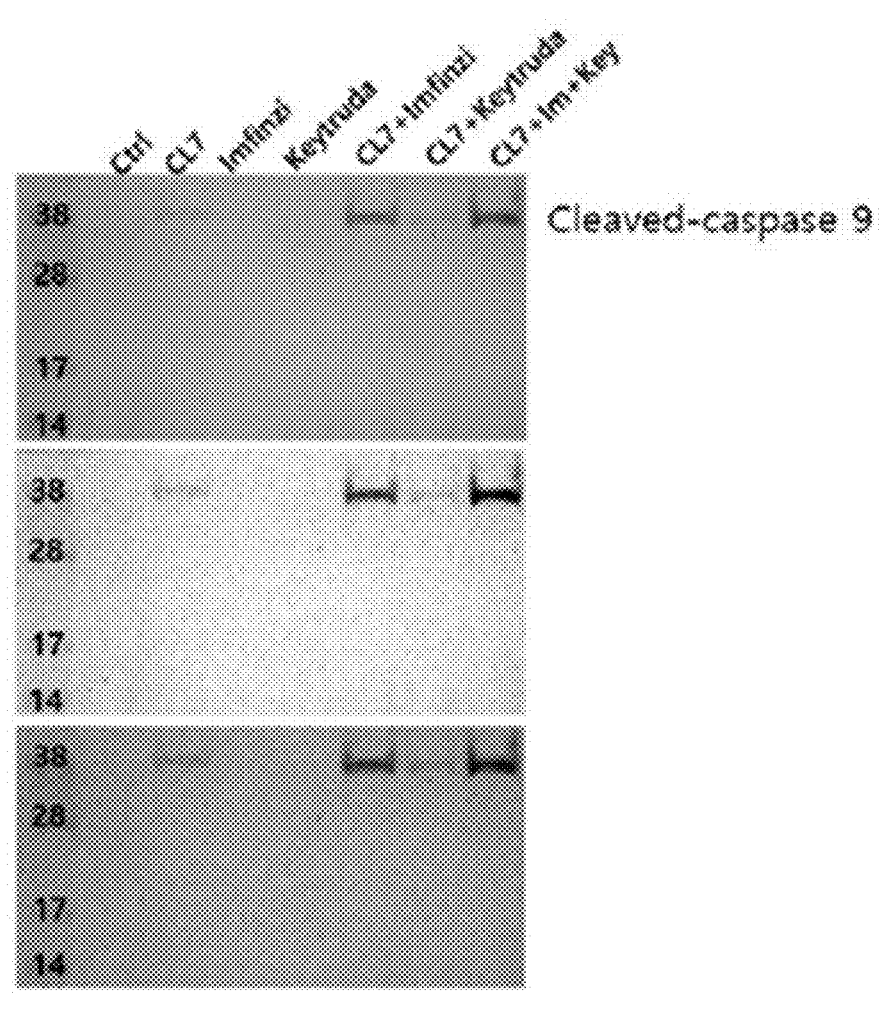

[FIG. 34]
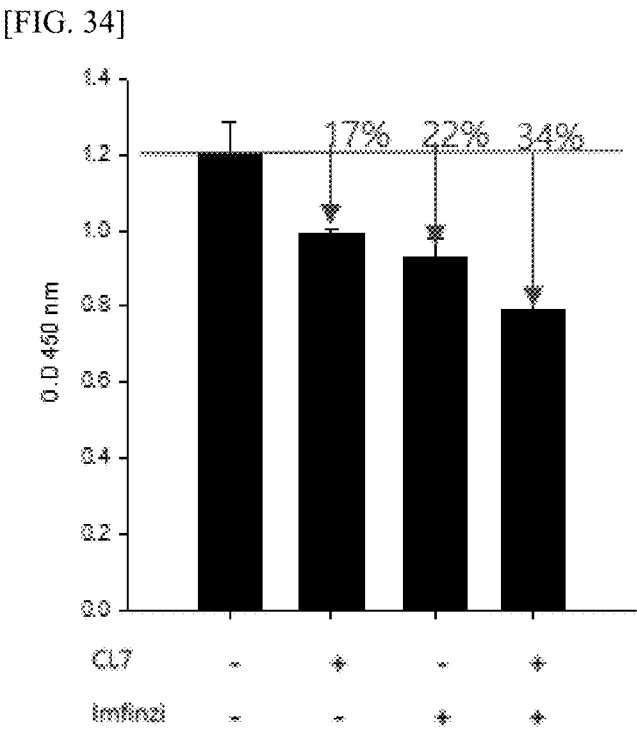

[FIG. 35]
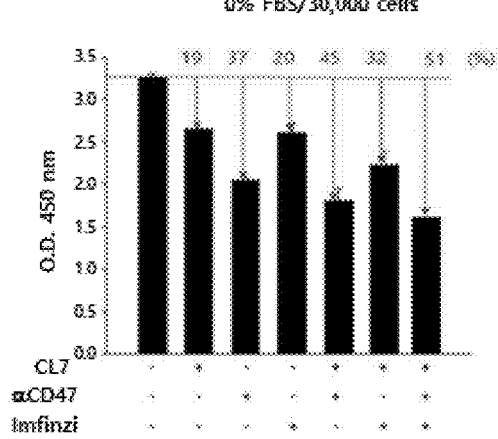
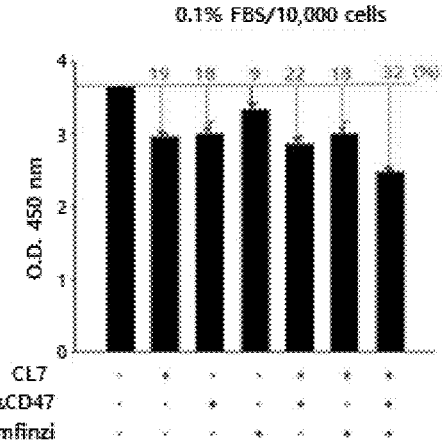
[FIG. 36]
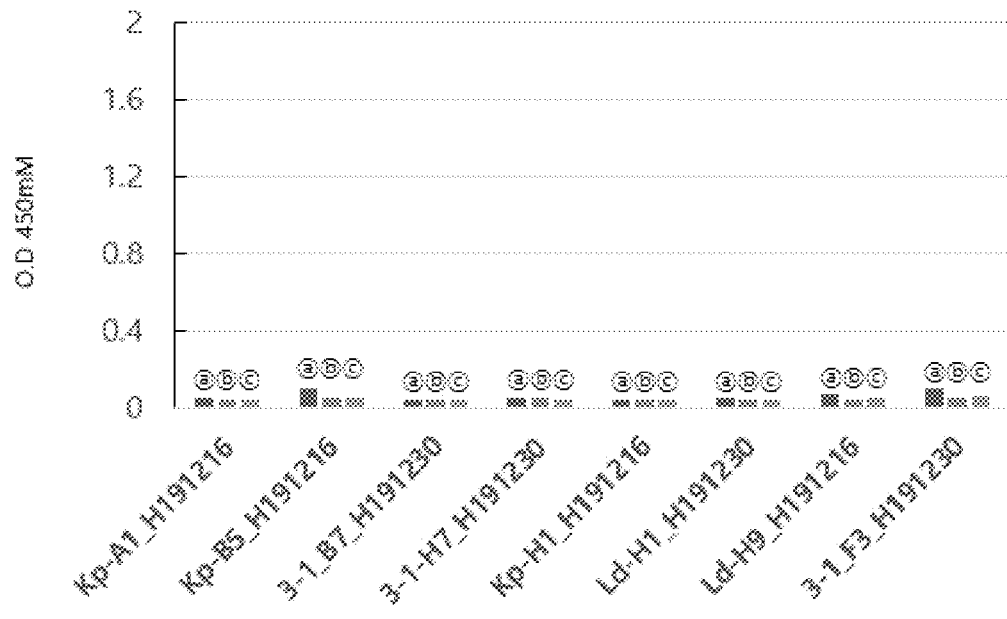

[FIG. 37]
[FIG. 38]
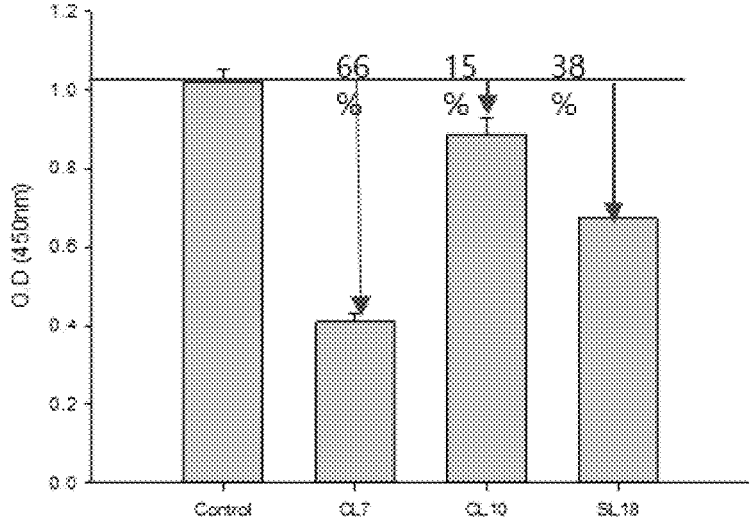

[FIG. 39]
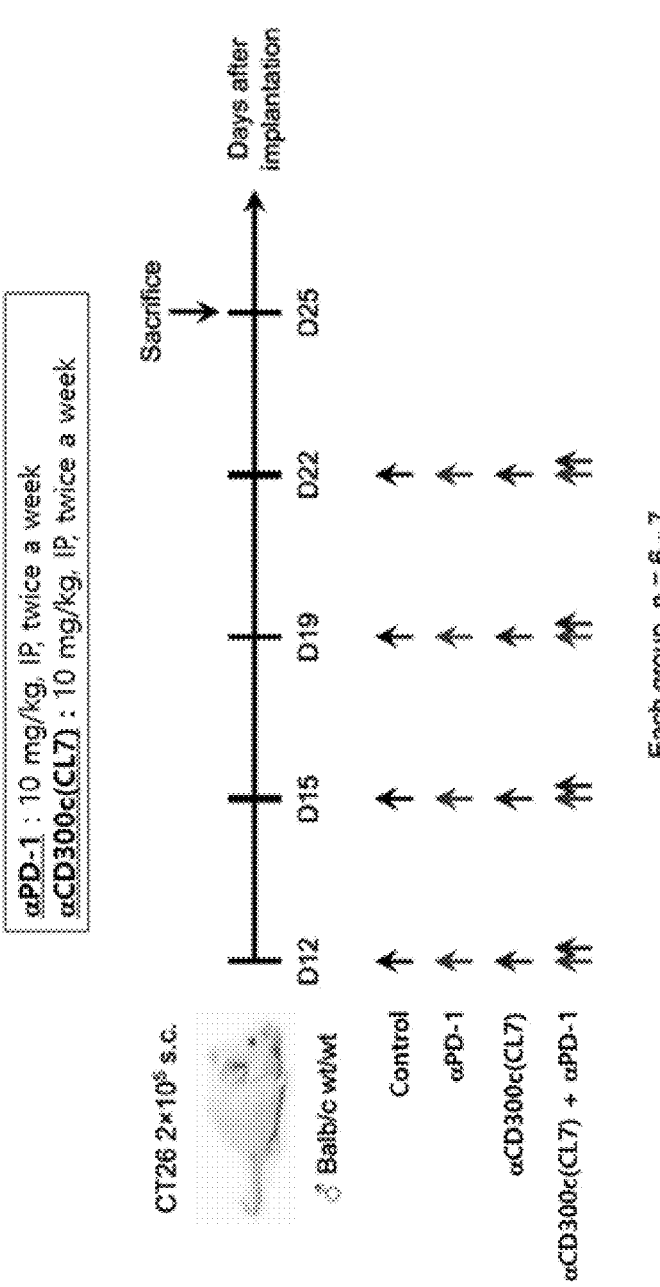

[FIG. 40]
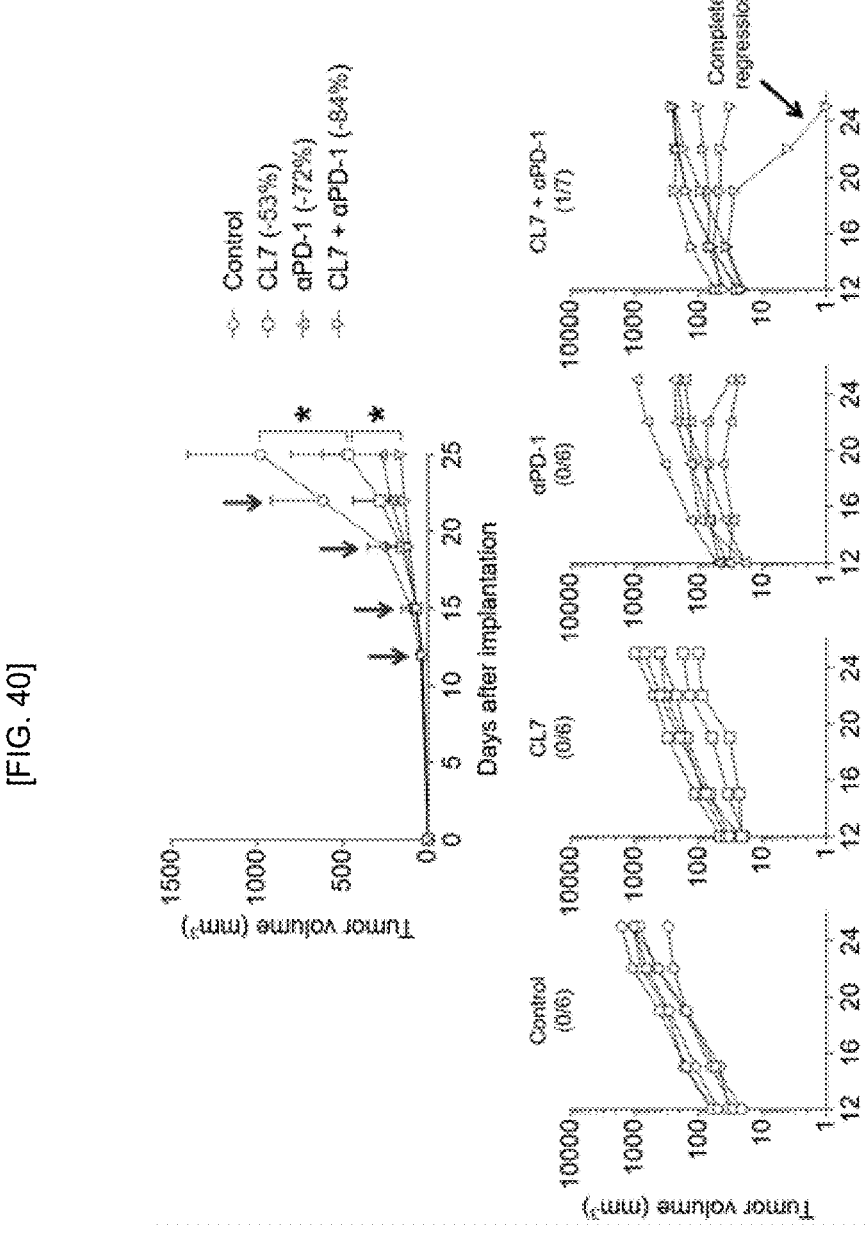

[FIG. 41]

Scale bars, 50 μm

[FIG. 42]
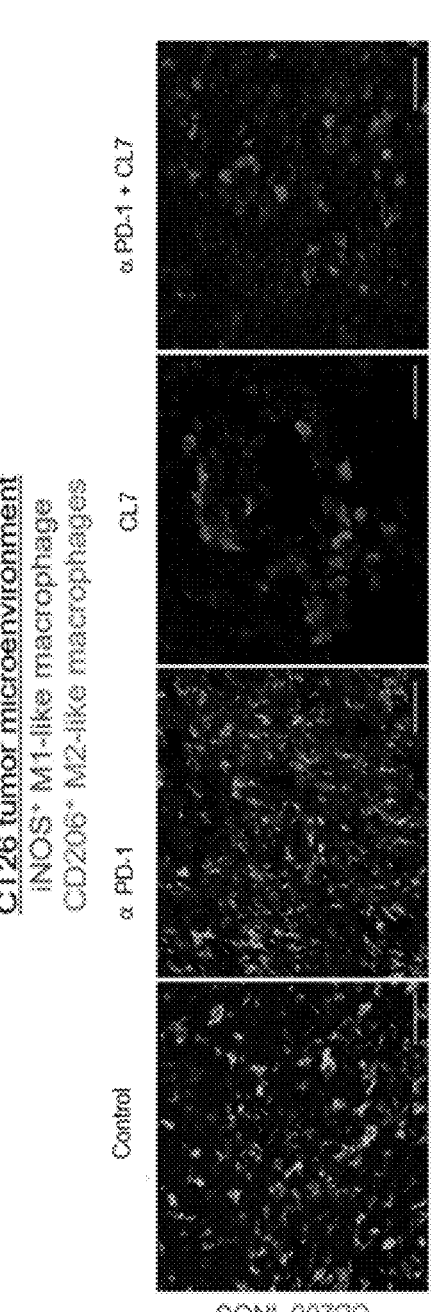

[FIG. 43]
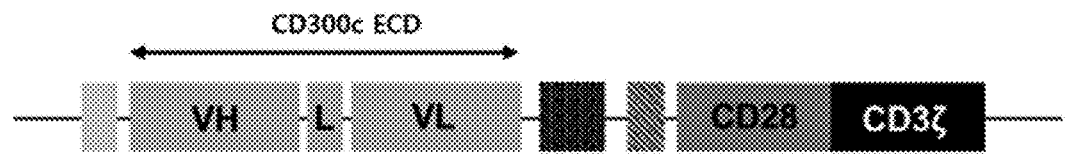
Anti-CD300c scFv or
CD300c ECD
VH  L  VL  CD28  CD3ζ
Intracellular domain
: CD8a signal peptide
: CD8a hinge
: CD28 TM

[FIG. 44]
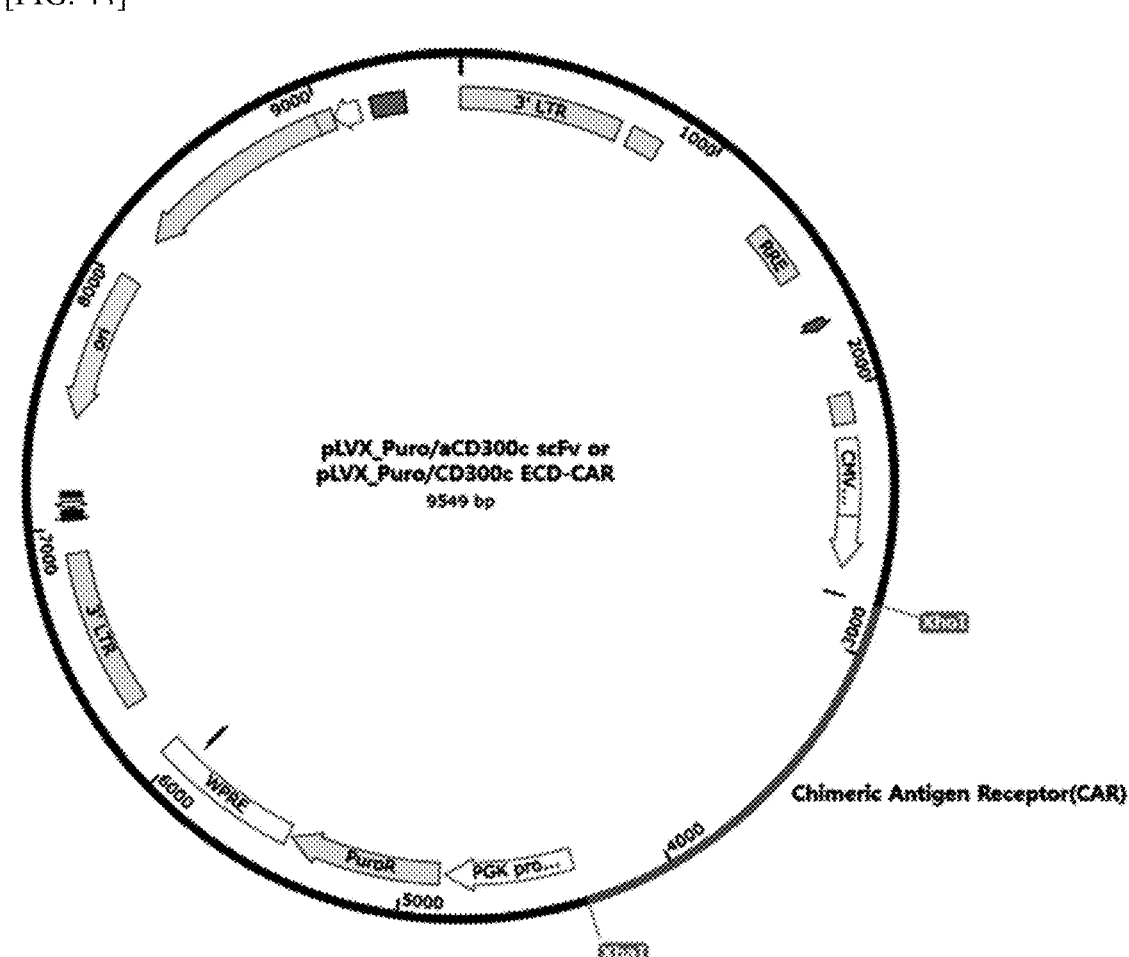

[FIG. 45]
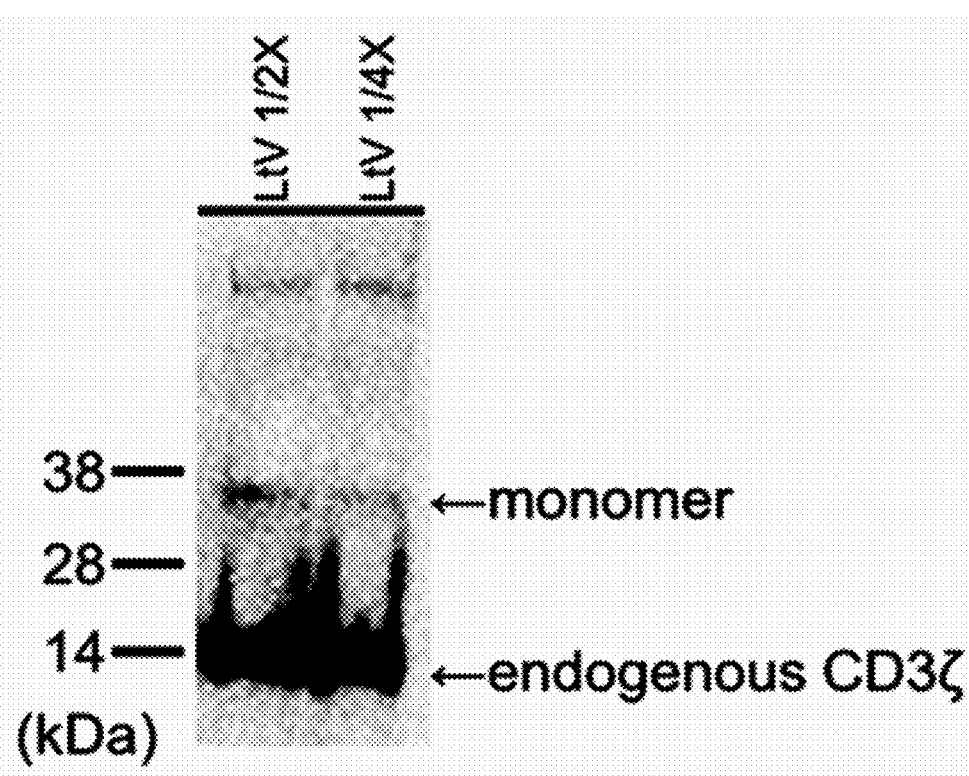

[FIG. 46]
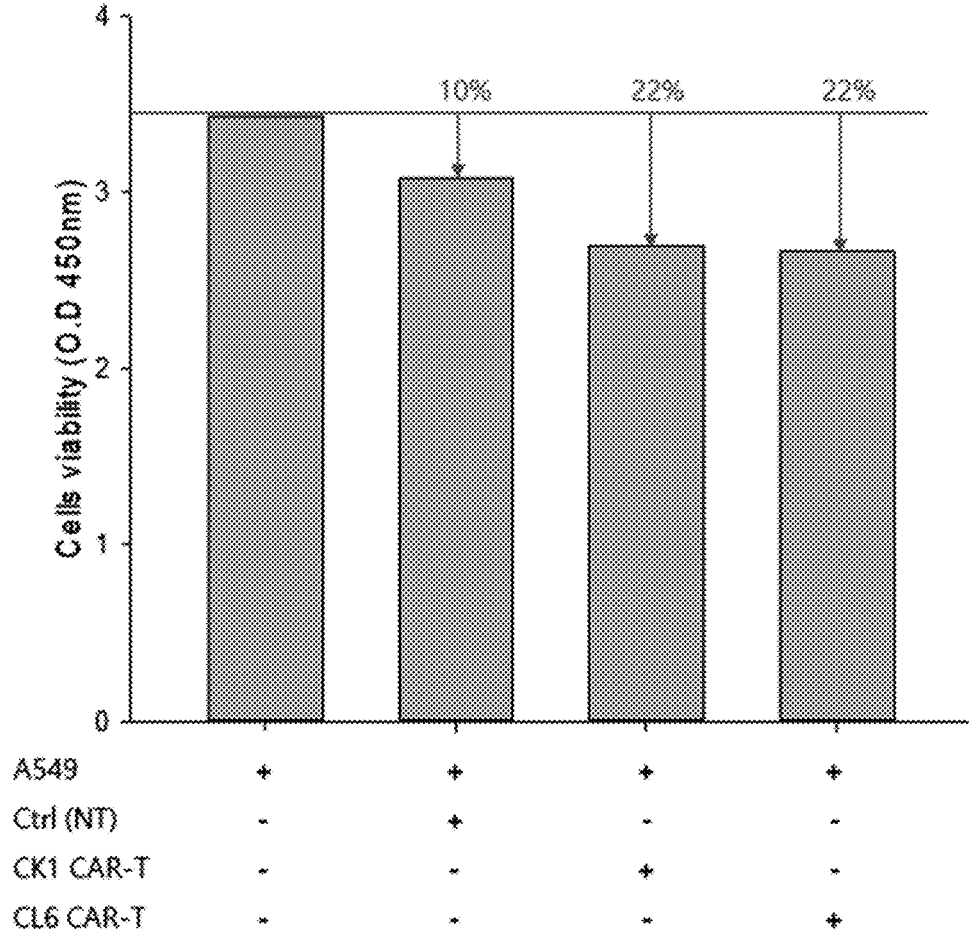

SEQUENCE LISTING

```
<160> NUMBER OF SEQ ID NOS: 448

<210> SEQ ID NO 1
<211> LENGTH: 30
<212> TYPE: DNA
<213> ORGANISM: Artificial Sequence
<220> FEATURE:
<223> OTHER INFORMATION: CK1 Heavy Chain CDR1

<400> SEQUENCE: 1
ttcagccgct atgccatgac ctgggttcgc                                     30
```

-continued

```
<210> SEQ ID NO 2
<211> LENGTH: 45
<212> TYPE: DNA
<213> ORGANISM: Artificial Sequence
<220> FEATURE:
<223> OTHER INFORMATION: CK1 Heavy Chain CDR2

<400> SEQUENCE: 2
agcagcatga gcggcaccgg cggcaccacc tattatgccg atagc                45

<210> SEQ ID NO 3
<211> LENGTH: 36
<212> TYPE: DNA
<213> ORGANISM: Artificial Sequence
<220> FEATURE:
<223> OTHER INFORMATION: CK1 Heavy Chain CDR3

<400> SEQUENCE: 3
tactgtgccc gcggcgccta tggctttgat cattgg                          36

<210> SEQ ID NO 4
<211> LENGTH: 41
<212> TYPE: DNA
<213> ORGANISM: Artificial Sequence
<220> FEATURE:
<223> OTHER INFORMATION: CK1 Light Chain CDR1

<400> SEQUENCE: 4
tgccgcgcca gccagagcat cggcaactat ctgaactggt a                    41

<210> SEQ ID NO 5
<211> LENGTH: 36
<212> TYPE: DNA
<213> ORGANISM: Artificial Sequence
<220> FEATURE:
<223> OTHER INFORMATION: CK1 Light Chain CDR2

<400> SEQUENCE: 5
ctgatctatg atgccagcaa cctggaaacc ggcatc                          36

<210> SEQ ID NO 6
<211> LENGTH: 45
<212> TYPE: DNA
<213> ORGANISM: Artificial Sequence
<220> FEATURE:
<223> OTHER INFORMATION: CK1 Light Chain CDR3

<400> SEQUENCE: 6
tattattgtc agcagagtag cgccatccct tataccttcg gtcag                45

<210> SEQ ID NO 7
<211> LENGTH: 12
<212> TYPE: PRT
<213> ORGANISM: Artificial Sequence
<220> FEATURE:
<223> OTHER INFORMATION: CK1 Heavy Chain CDR1

<400> SEQUENCE: 7

Phe Thr Phe Ser Arg Tyr Ala Met Thr Trp Val Arg
1               5                   10

<210> SEQ ID NO 8
<211> LENGTH: 13
<212> TYPE: PRT
<213> ORGANISM: Artificial Sequence
<220> FEATURE:
```

-continued

<223> OTHER INFORMATION: CK1 Heavy Chain CDR2

<400> SEQUENCE: 8

Ser Met Ser Gly Thr Gly Gly Thr Thr Tyr Tyr Ala Asp
1               5                   10

<210> SEQ ID NO 9
<211> LENGTH: 12
<212> TYPE: PRT
<213> ORGANISM: Artificial Sequence
<220> FEATURE:
<223> OTHER INFORMATION: CK1 Heavy Chain CDR3

<400> SEQUENCE: 9

Tyr Cys Ala Arg Gly Ala Tyr Gly Phe Asp His Trp
1               5                   10

<210> SEQ ID NO 10
<211> LENGTH: 13
<212> TYPE: PRT
<213> ORGANISM: Artificial Sequence
<220> FEATURE:
<223> OTHER INFORMATION: CK1 Light Chain CDR1

<400> SEQUENCE: 10

Cys Arg Ala Ser Gln Ser Ile Gly Asn Tyr Leu Asn Trp
1               5                   10

<210> SEQ ID NO 11
<211> LENGTH: 10
<212> TYPE: PRT
<213> ORGANISM: Artificial Sequence
<220> FEATURE:
<223> OTHER INFORMATION: CK1 Light Chain CDR2

<400> SEQUENCE: 11

Asp Ala Ser Asn Leu Glu Thr Gly Ile Pro
1               5                   10

<210> SEQ ID NO 12
<211> LENGTH: 12
<212> TYPE: PRT
<213> ORGANISM: Artificial Sequence
<220> FEATURE:
<223> OTHER INFORMATION: CK1 Light Chain CDR3

<400> SEQUENCE: 12

Tyr Cys Gln Gln Ser Ser Ala Ile Pro Tyr Thr Phe
1               5                   10

<210> SEQ ID NO 13
<211> LENGTH: 30
<212> TYPE: DNA
<213> ORGANISM: Artificial Sequence
<220> FEATURE:
<223> OTHER INFORMATION: CK2 Heavy Chain CDR1

<400> SEQUENCE: 13
ttcagcagct atggcatgca ttgggttcgc                                    30

<210> SEQ ID NO 14
<211> LENGTH: 45
<212> TYPE: DNA
<213> ORGANISM: Artificial Sequence
<220> FEATURE:
<223> OTHER INFORMATION: CK2 Heavy Chain CDR2

-continued

<400> SEQUENCE: 14
agcgccatca gcggcagcgg caccagcatc tattatgccg atagc                         45

<210> SEQ ID NO 15
<211> LENGTH: 36
<212> TYPE: DNA
<213> ORGANISM: Artificial Sequence
<220> FEATURE:
<223> OTHER INFORMATION: CK2 Heavy Chain CDR3

<400> SEQUENCE: 15
tactgtgccc gcggcggcac cgcctttgat tattgg                                   36

<210> SEQ ID NO 16
<211> LENGTH: 39
<212> TYPE: DNA
<213> ORGANISM: Artificial Sequence
<220> FEATURE:
<223> OTHER INFORMATION: CK2 Light Chain CDR1

<400> SEQUENCE: 16
tgccgcgcca gccagagatc agacaactat ctggcctgg                                39

<210> SEQ ID NO 17
<211> LENGTH: 36
<212> TYPE: DNA
<213> ORGANISM: Artificial Sequence
<220> FEATURE:
<223> OTHER INFORMATION: CK2 Light Chain CDR2

<400> SEQUENCE: 17
ctgatctatg atgccagcaa ccgcgccacc ggcatc                                   36

<210> SEQ ID NO 18
<211> LENGTH: 45
<212> TYPE: DNA
<213> ORGANISM: Artificial Sequence
<220> FEATURE:
<223> OTHER INFORMATION: CK2 Light Chain CDR3

<400> SEQUENCE: 18
tattattgtc agcagagcta tagcaccccct tttaccttcg gtcag                        45

<210> SEQ ID NO 19
<211> LENGTH: 12
<212> TYPE: PRT
<213> ORGANISM: Artificial Sequence
<220> FEATURE:
<223> OTHER INFORMATION: CK2 Heavy Chain CDR1

<400> SEQUENCE: 19

Phe Thr Phe Ser Ser Tyr Gly Met His Trp Val Arg
1               5                   10

<210> SEQ ID NO 20
<211> LENGTH: 13
<212> TYPE: PRT
<213> ORGANISM: Artificial Sequence
<220> FEATURE:
<223> OTHER INFORMATION: CK2 Heavy Chain CDR2

<400> SEQUENCE: 20

Ala Ile Ser Gly Ser Gly Thr Ser Ile Tyr Tyr Ala Asp
1               5                   10

```
<210> SEQ ID NO 21
<211> LENGTH: 12
<212> TYPE: PRT
<213> ORGANISM: Artificial Sequence
<220> FEATURE:
<223> OTHER INFORMATION: CK2 Heavy Chain CDR3

<400> SEQUENCE: 21

Tyr Cys Ala Arg Gly Gly Thr Ala Phe Asp Tyr Trp
1               5                   10

<210> SEQ ID NO 22
<211> LENGTH: 13
<212> TYPE: PRT
<213> ORGANISM: Artificial Sequence
<220> FEATURE:
<223> OTHER INFORMATION: CK2 Light Chain CDR1

<400> SEQUENCE: 22

Cys Arg Ala Ser Gln Arg Ser Asp Asn Tyr Leu Ala Trp
1               5                   10

<210> SEQ ID NO 23
<211> LENGTH: 10
<212> TYPE: PRT
<213> ORGANISM: Artificial Sequence
<220> FEATURE:
<223> OTHER INFORMATION: CK2 Light Chain CDR2

<400> SEQUENCE: 23

Asp Ala Ser Asn Arg Ala Thr Gly Ile Pro
1               5                   10

<210> SEQ ID NO 24
<211> LENGTH: 12
<212> TYPE: PRT
<213> ORGANISM: Artificial Sequence
<220> FEATURE:
<223> OTHER INFORMATION: CK2 Light Chain CDR3

<400> SEQUENCE: 24

Tyr Cys Gln Gln Ser Tyr Ser Thr Pro Phe Thr Phe
1               5                   10

<210> SEQ ID NO 25
<211> LENGTH: 30
<212> TYPE: DNA
<213> ORGANISM: Artificial Sequence
<220> FEATURE:
<223> OTHER INFORMATION: CK3 Heavy Chain CDR1

<400> SEQUENCE: 25
ttcagcagct atgccatcag ctgggttcgc                                      30

<210> SEQ ID NO 26
<211> LENGTH: 45
<212> TYPE: DNA
<213> ORGANISM: Artificial Sequence
<220> FEATURE:
<223> OTHER INFORMATION: CK3 Heavy Chain CDR2

<400> SEQUENCE: 26
agcgccacca gcggcagcgg ccgcgccacc tattatgccg atagc                     45

<210> SEQ ID NO 27
<211> LENGTH: 45
<212> TYPE: DNA
```

<213> ORGANISM: Artificial Sequence
<220> FEATURE:
<223> OTHER INFORMATION: CK3 Heavy Chain CDR3

<400> SEQUENCE: 27
tactgtgcgc gcgatacctg gtgggaaggc tattttgatc tgtgg                45

<210> SEQ ID NO 28
<211> LENGTH: 36
<212> TYPE: DNA
<213> ORGANISM: Artificial Sequence
<220> FEATURE:
<223> OTHER INFORMATION: CK3 Light Chain CDR1

<400> SEQUENCE: 28
tgccaggcca gccatatcag cacccatctg aactgg                36

<210> SEQ ID NO 29
<211> LENGTH: 36
<212> TYPE: DNA
<213> ORGANISM: Artificial Sequence
<220> FEATURE:
<223> OTHER INFORMATION: CK3 Light Chain CDR2

<400> SEQUENCE: 29
ctgatctatg gcgccagcag ccgcgccacc ggcatc                36

<210> SEQ ID NO 30
<211> LENGTH: 45
<212> TYPE: DNA
<213> ORGANISM: Artificial Sequence
<220> FEATURE:
<223> OTHER INFORMATION: CK3 Light Chain CDR3

<400> SEQUENCE: 30
tattattgtc agcagtataa cacctatcct cctaccttcg gtcag                45

<210> SEQ ID NO 31
<211> LENGTH: 12
<212> TYPE: PRT
<213> ORGANISM: Artificial Sequence
<220> FEATURE:
<223> OTHER INFORMATION: CK3 Heavy Chain CDR1

<400> SEQUENCE: 31

Phe Thr Phe Ser Ser Tyr Ala Ile Ser Trp Val Arg
1               5                   10

<210> SEQ ID NO 32
<211> LENGTH: 13
<212> TYPE: PRT
<213> ORGANISM: Artificial Sequence
<220> FEATURE:
<223> OTHER INFORMATION: CK3 Heavy Chain CDR2

<400> SEQUENCE: 32

Ala Thr Ser Gly Ser Gly Arg Ala Thr Tyr Tyr Ala Asp
1               5                   10

<210> SEQ ID NO 33
<211> LENGTH: 15
<212> TYPE: PRT
<213> ORGANISM: Artificial Sequence
<220> FEATURE:
<223> OTHER INFORMATION: CK3 Heavy Chain CDR3

<400> SEQUENCE: 33

Tyr Cys Ala Arg Asp Thr Trp Trp Glu Gly Tyr Phe Asp Leu Trp
1               5                   10                  15

<210> SEQ ID NO 34
<211> LENGTH: 12
<212> TYPE: PRT
<213> ORGANISM: Artificial Sequence
<220> FEATURE:
<223> OTHER INFORMATION: CK3 Light Chain CDR1

<400> SEQUENCE: 34

Cys Gln Ala Ser His Ile Ser Thr His Leu Asn Trp
1               5                   10

<210> SEQ ID NO 35
<211> LENGTH: 10
<212> TYPE: PRT
<213> ORGANISM: Artificial Sequence
<220> FEATURE:
<223> OTHER INFORMATION: CK3 Light Chain CDR2

<400> SEQUENCE: 35

Gly Ala Ser Ser Arg Ala Thr Gly Ile Pro
1               5                   10

<210> SEQ ID NO 36
<211> LENGTH: 12
<212> TYPE: PRT
<213> ORGANISM: Artificial Sequence
<220> FEATURE:
<223> OTHER INFORMATION: CK3 Light Chain CDR3

<400> SEQUENCE: 36

Tyr Cys Gln Gln Tyr Asn Thr Tyr Pro Pro Thr Phe
1               5                   10

<210> SEQ ID NO 37
<211> LENGTH: 33
<212> TYPE: DNA
<213> ORGANISM: Artificial Sequence
<220> FEATURE:
<223> OTHER INFORMATION: CL4 Heavy Chain CDR1

<400> SEQUENCE: 37
accttcggca gcaactatat gagctgggtt cgc                                    33

<210> SEQ ID NO 38
<211> LENGTH: 33
<212> TYPE: DNA
<213> ORGANISM: Artificial Sequence
<220> FEATURE:
<223> OTHER INFORMATION: CL4 Heavy Chain CDR2

<400> SEQUENCE: 38
atcagcggca gcggcaccag cacctattat gcc                                    33

<210> SEQ ID NO 39
<211> LENGTH: 27
<212> TYPE: DNA
<213> ORGANISM: Artificial Sequence
<220> FEATURE:
<223> OTHER INFORMATION: CL4 Heavy Chain CDR3

<400> SEQUENCE: 39
cgcggcatgt ggggcatgga tgtgtgg                                           27

-continued

```
<210> SEQ ID NO 40
<211> LENGTH: 27
<212> TYPE: DNA
<213> ORGANISM: Artificial Sequence
<220> FEATURE:
<223> OTHER INFORMATION: CL4 Light Chain CDR1

<400> SEQUENCE: 40
ggcaaacatc ggcacaccgt gaactgg                                          27

<210> SEQ ID NO 41
<211> LENGTH: 30
<212> TYPE: DNA
<213> ORGANISM: Artificial Sequence
<220> FEATURE:
<223> OTHER INFORMATION: CL4 Light Chain CDR2

<400> SEQUENCE: 41
ctggatagcg aacgccctag cggcgtacct                                       30

<210> SEQ ID NO 42
<211> LENGTH: 27
<212> TYPE: DNA
<213> ORGANISM: Artificial Sequence
<220> FEATURE:
<223> OTHER INFORMATION: CL4 Light Chain CDR3

<400> SEQUENCE: 42
tatgatagca gcagcgtggt gtttggt                                          27

<210> SEQ ID NO 43
<211> LENGTH: 12
<212> TYPE: PRT
<213> ORGANISM: Artificial Sequence
<220> FEATURE:
<223> OTHER INFORMATION: CL4 Heavy Chain CDR1

<400> SEQUENCE: 43

Phe Thr Phe Gly Ser Asn Tyr Met Ser Trp Val Arg
1               5                   10

<210> SEQ ID NO 44
<211> LENGTH: 13
<212> TYPE: PRT
<213> ORGANISM: Artificial Sequence
<220> FEATURE:
<223> OTHER INFORMATION: CL4 Heavy Chain CDR2

<400> SEQUENCE: 44

Thr Ile Ser Gly Ser Gly Thr Ser Thr Tyr Tyr Ala Asp
1               5                   10

<210> SEQ ID NO 45
<211> LENGTH: 12
<212> TYPE: PRT
<213> ORGANISM: Artificial Sequence
<220> FEATURE:
<223> OTHER INFORMATION: CL4 Heavy Chain CDR3

<400> SEQUENCE: 45

Tyr Cys Ala Arg Gly Met Trp Gly Met Asp Val Trp
1               5                   10

<210> SEQ ID NO 46
<211> LENGTH: 11
<212> TYPE: PRT
```

-continued

<213> ORGANISM: Artificial Sequence
<220> FEATURE:
<223> OTHER INFORMATION: CL4 Light Chain CDR1

<400> SEQUENCE: 46

Cys Thr Gly Lys His Arg His Thr Val Asn Trp
1               5                   10

<210> SEQ ID NO 47
<211> LENGTH: 10
<212> TYPE: PRT
<213> ORGANISM: Artificial Sequence
<220> FEATURE:
<223> OTHER INFORMATION: CL4 Light Chain CDR2

<400> SEQUENCE: 47

Leu Asp Ser Glu Arg Pro Ser Gly Val Pro
1               5                   10

<210> SEQ ID NO 48
<211> LENGTH: 12
<212> TYPE: PRT
<213> ORGANISM: Artificial Sequence
<220> FEATURE:
<223> OTHER INFORMATION: CL4 Light Chain CDR3

<400> SEQUENCE: 48

Tyr Cys Gln Ser Tyr Asp Ser Ser Ser Val Val Phe
1               5                   10

<210> SEQ ID NO 49
<211> LENGTH: 33
<212> TYPE: DNA
<213> ORGANISM: Artificial Sequence
<220> FEATURE:
<223> OTHER INFORMATION: CL5 Heavy Chain CDR1

<400> SEQUENCE: 49
accttcagca gctatgccat gcattgggtt cgc                               33

<210> SEQ ID NO 50
<211> LENGTH: 33
<212> TYPE: DNA
<213> ORGANISM: Artificial Sequence
<220> FEATURE:
<223> OTHER INFORMATION: CL5 Heavy Chain CDR2

<400> SEQUENCE: 50
atcagcggcg gcggctatgg cacctattat gcc                               33

<210> SEQ ID NO 51
<211> LENGTH: 30
<212> TYPE: DNA
<213> ORGANISM: Artificial Sequence
<220> FEATURE:
<223> OTHER INFORMATION: CL5 Heavy Chain CDR3

<400> SEQUENCE: 51
cgcagcaccg tgtgggcctt tgatatctgg                                   30

<210> SEQ ID NO 52
<211> LENGTH: 30
<212> TYPE: DNA
<213> ORGANISM: Artificial Sequence
<220> FEATURE:
<223> OTHER INFORMATION: CL5 Light Chain CDR1

-continued

```
<400> SEQUENCE: 52
ggcaacaaca tcggcagcaa aagcgtgcat                                        30

<210> SEQ ID NO 53
<211> LENGTH: 30
<212> TYPE: DNA
<213> ORGANISM: Artificial Sequence
<220> FEATURE:
<223> OTHER INFORMATION: CL5 Light Chain CDR2

<400> SEQUENCE: 53
gatgtgagca aacgccctag cgagcgtcct                                        30

<210> SEQ ID NO 54
<211> LENGTH: 30
<212> TYPE: DNA
<213> ORGANISM: Artificial Sequence
<220> FEATURE:
<223> OTHER INFORMATION: CL5 Light Chain CDR3

<400> SEQUENCE: 54
tttgatagca gcggcacctg gatctttggt                                        30

<210> SEQ ID NO 55
<211> LENGTH: 12
<212> TYPE: PRT
<213> ORGANISM: Artificial Sequence
<220> FEATURE:
<223> OTHER INFORMATION: CL5 Heavy Chain CDR1

<400> SEQUENCE: 55

Phe Thr Phe Ser Ser Tyr Ala Met His Trp Val Arg
1               5                   10

<210> SEQ ID NO 56
<211> LENGTH: 13
<212> TYPE: PRT
<213> ORGANISM: Artificial Sequence
<220> FEATURE:
<223> OTHER INFORMATION: CL5 Heavy Chain CDR2

<400> SEQUENCE: 56

Ser Ile Ser Gly Gly Gly Tyr Gly Thr Tyr Tyr Ala Asp
1               5                   10

<210> SEQ ID NO 57
<211> LENGTH: 13
<212> TYPE: PRT
<213> ORGANISM: Artificial Sequence
<220> FEATURE:
<223> OTHER INFORMATION: CL5 Heavy Chain CDR3

<400> SEQUENCE: 57

Tyr Cys Ala Arg Ser Thr Val Trp Ala Phe Asp Ile Trp
1               5                   10

<210> SEQ ID NO 58
<211> LENGTH: 13
<212> TYPE: PRT
<213> ORGANISM: Artificial Sequence
<220> FEATURE:
<223> OTHER INFORMATION: CL5 Light Chain CDR1

<400> SEQUENCE: 58

Cys Ser Gly Asn Asn Ile Gly Ser Lys Ser Val His Trp
1               5                   10
```

-continued

```
<210> SEQ ID NO 59
<211> LENGTH: 11
<212> TYPE: PRT
<213> ORGANISM: Artificial Sequence
<220> FEATURE:
<223> OTHER INFORMATION: CL5 Light Chain CDR2

<400> SEQUENCE: 59

Asp Val Ser Lys Arg Pro Ser Glu Arg Pro Asp
1               5                   10

<210> SEQ ID NO 60
<211> LENGTH: 13
<212> TYPE: PRT
<213> ORGANISM: Artificial Sequence
<220> FEATURE:
<223> OTHER INFORMATION: CL5 Light Chain CDR3

<400> SEQUENCE: 60

Tyr Cys Gln Ser Phe Asp Ser Ser Gly Thr Trp Ile Phe
1               5                   10

<210> SEQ ID NO 61
<211> LENGTH: 27
<212> TYPE: DNA
<213> ORGANISM: Artificial Sequence
<220> FEATURE:
<223> OTHER INFORMATION: CL6 Heavy Chain CDR1

<400> SEQUENCE: 61
agcagctacg gtatgcattg ggtcaga                                    27

<210> SEQ ID NO 62
<211> LENGTH: 39
<212> TYPE: DNA
<213> ORGANISM: Artificial Sequence
<220> FEATURE:
<223> OTHER INFORMATION: CL6 Heavy Chain CDR2

<400> SEQUENCE: 62
gcaattagcg gtagcggtgg tagcacttac tacgcagac                       39

<210> SEQ ID NO 63
<211> LENGTH: 45
<212> TYPE: DNA
<213> ORGANISM: Artificial Sequence
<220> FEATURE:
<223> OTHER INFORMATION: CL6 Heavy Chain CDR3

<400> SEQUENCE: 63
tgcgcagtca gtggtgcagg tcgtggtttc ttcgactact gggga               45

<210> SEQ ID NO 64
<211> LENGTH: 39
<212> TYPE: DNA
<213> ORGANISM: Artificial Sequence
<220> FEATURE:
<223> OTHER INFORMATION: CL6 Light Chain CDR1

<400> SEQUENCE: 64
tgcagcggta gcagcagcaa cattggtagc aactacgtg                       39

<210> SEQ ID NO 65
<211> LENGTH: 24
<212> TYPE: DNA
```

-continued

<213> ORGANISM: Artificial Sequence
<220> FEATURE:
<223> OTHER INFORMATION: CL6 Light Chain CDR2

<400> SEQUENCE: 65
gacaacaagc gtcctagtgg tgtg                                          24

<210> SEQ ID NO 66
<211> LENGTH: 33
<212> TYPE: DNA
<213> ORGANISM: Artificial Sequence
<220> FEATURE:
<223> OTHER INFORMATION: CL6 Light Chain CDR3

<400> SEQUENCE: 66
tgcagcagct acactagcag cagcactgtg atc                                33

<210> SEQ ID NO 67
<211> LENGTH: 12
<212> TYPE: PRT
<213> ORGANISM: Artificial Sequence
<220> FEATURE:
<223> OTHER INFORMATION: CL6 Heavy Chain CDR1

<400> SEQUENCE: 67

Phe Thr Phe Ser Ser Tyr Gly Met His Trp Val Arg
1               5                   10

<210> SEQ ID NO 68
<211> LENGTH: 13
<212> TYPE: PRT
<213> ORGANISM: Artificial Sequence
<220> FEATURE:
<223> OTHER INFORMATION: CL6 Heavy Chain CDR2

<400> SEQUENCE: 68

Ala Ile Ser Gly Ser Gly Gly Ser Thr Tyr Tyr Ala Asp
1               5                   10

<210> SEQ ID NO 69
<211> LENGTH: 15
<212> TYPE: PRT
<213> ORGANISM: Artificial Sequence
<220> FEATURE:
<223> OTHER INFORMATION: CL6 Heavy Chain CDR3

<400> SEQUENCE: 69

Tyr Cys Ala Val Ser Gly Ala Gly Arg Gly Phe Phe Asp Tyr Trp
1               5                   10                  15

<210> SEQ ID NO 70
<211> LENGTH: 15
<212> TYPE: PRT
<213> ORGANISM: Artificial Sequence
<220> FEATURE:
<223> OTHER INFORMATION: CL6 Light Chain CDR1

<400> SEQUENCE: 70

Cys Ser Gly Ser Ser Ser Asn Ile Gly Ser Asn Tyr Val Tyr Trp
1               5                   10                  15

<210> SEQ ID NO 71
<211> LENGTH: 10
<212> TYPE: PRT
<213> ORGANISM: Artificial Sequence
<220> FEATURE:
<223> OTHER INFORMATION: CL6 Light Chain CDR2

<400> SEQUENCE: 71

Glu Asp Asn Lys Arg Pro Ser Gly Val Pro
1               5                   10

<210> SEQ ID NO 72
<211> LENGTH: 13
<212> TYPE: PRT
<213> ORGANISM: Artificial Sequence
<220> FEATURE:
<223> OTHER INFORMATION: CL6 Light Chain CDR3

<400> SEQUENCE: 72

Tyr Cys Ser Ser Tyr Thr Ser Ser Ser Thr Val Ile Phe
1               5                   10

<210> SEQ ID NO 73
<211> LENGTH: 27
<212> TYPE: DNA
<213> ORGANISM: Artificial Sequence
<220> FEATURE:
<223> OTHER INFORMATION: CL7 Heavy Chain CDR1

<400> SEQUENCE: 73
agccgctacg caatgagctg ggtcaga                                        27

<210> SEQ ID NO 74
<211> LENGTH: 39
<212> TYPE: DNA
<213> ORGANISM: Artificial Sequence
<220> FEATURE:
<223> OTHER INFORMATION: CL7 Heavy Chain CDR2

<400> SEQUENCE: 74
gcaattagcg gtagcggtgg tagcacttac tacgcagac                          39

<210> SEQ ID NO 75
<211> LENGTH: 39
<212> TYPE: DNA
<213> ORGANISM: Artificial Sequence
<220> FEATURE:
<223> OTHER INFORMATION: CL7 Heavy Chain CDR3

<400> SEQUENCE: 75
tgcgcacgta gcagccaggg tatcttcgac atctgggga                          39

<210> SEQ ID NO 76
<211> LENGTH: 33
<212> TYPE: DNA
<213> ORGANISM: Artificial Sequence
<220> FEATURE:
<223> OTHER INFORMATION: CL7 Light Chain CDR1

<400> SEQUENCE: 76
tgcagtggta acaatatcgg tactagacgc gtg                                33

<210> SEQ ID NO 77
<211> LENGTH: 24
<212> TYPE: DNA
<213> ORGANISM: Artificial Sequence
<220> FEATURE:
<223> OTHER INFORMATION: CL7 Light Chain CDR2

<400> SEQUENCE: 77
aagaacaacc gtcctagtgg tgtg                                          24

```
<210> SEQ ID NO 78
<211> LENGTH: 39
<212> TYPE: DNA
<213> ORGANISM: Artificial Sequence
<220> FEATURE:
<223> OTHER INFORMATION: CL7 Light Chain CDR3

<400> SEQUENCE: 78
tgcgcagcat gggacgacag cctgagcggt cctgtgttc                              39

<210> SEQ ID NO 79
<211> LENGTH: 12
<212> TYPE: PRT
<213> ORGANISM: Artificial Sequence
<220> FEATURE:
<223> OTHER INFORMATION: CL7 Heavy Chain CDR1

<400> SEQUENCE: 79

Phe Thr Phe Ser Arg Tyr Ala Met Ser Trp Val Arg
1               5                   10

<210> SEQ ID NO 80
<211> LENGTH: 13
<212> TYPE: PRT
<213> ORGANISM: Artificial Sequence
<220> FEATURE:
<223> OTHER INFORMATION: CL7 Heavy Chain CDR2

<400> SEQUENCE: 80

Ala Ile Ser Gly Ser Gly Gly Ser Thr Tyr Tyr Ala Asp
1               5                   10

<210> SEQ ID NO 81
<211> LENGTH: 13
<212> TYPE: PRT
<213> ORGANISM: Artificial Sequence
<220> FEATURE:
<223> OTHER INFORMATION: CL7 Heavy Chain CDR3

<400> SEQUENCE: 81

Tyr Cys Ala Arg Ser Ser Gln Gly Ile Phe Asp Ile Trp
1               5                   10

<210> SEQ ID NO 82
<211> LENGTH: 13
<212> TYPE: PRT
<213> ORGANISM: Artificial Sequence
<220> FEATURE:
<223> OTHER INFORMATION: CL7 Light Chain CDR1

<400> SEQUENCE: 82

Cys Ser Gly Asn Asn Ile Gly Thr Arg Arg Val His Trp
1               5                   10

<210> SEQ ID NO 83
<211> LENGTH: 10
<212> TYPE: PRT
<213> ORGANISM: Artificial Sequence
<220> FEATURE:
<223> OTHER INFORMATION: CL7 Light Chain CDR2

<400> SEQUENCE: 83

Ser Lys Asn Asn Arg Pro Ser Gly Val Pro
1               5                   10

<210> SEQ ID NO 84
```

-continued

```
<211> LENGTH: 14
<212> TYPE: PRT
<213> ORGANISM: Artificial Sequence
<220> FEATURE:
<223> OTHER INFORMATION: CL7 Light Chain CDR3

<400> SEQUENCE: 84

Tyr Cys Ala Ala Trp Asp Asp Ser Leu Ser Gly Pro Val Phe
1               5                   10

<210> SEQ ID NO 85
<211> LENGTH: 27
<212> TYPE: DNA
<213> ORGANISM: Artificial Sequence
<220> FEATURE:
<223> OTHER INFORMATION: CL8 Heavy Chain CDR1

<400> SEQUENCE: 85
agcagctacg caatgagctg ggtcaga                                     27

<210> SEQ ID NO 86
<211> LENGTH: 39
<212> TYPE: DNA
<213> ORGANISM: Artificial Sequence
<220> FEATURE:
<223> OTHER INFORMATION: CL8 Heavy Chain CDR2

<400> SEQUENCE: 86
gcaattagcg gtagcggtgg tagcacttac tacgcagac                        39

<210> SEQ ID NO 87
<211> LENGTH: 42
<212> TYPE: DNA
<213> ORGANISM: Artificial Sequence
<220> FEATURE:
<223> OTHER INFORMATION: CL8 Heavy Chain CDR3

<400> SEQUENCE: 87
tgcgcacgta gcggtcgtta cgcagacttg acatctgggg ga                    42

<210> SEQ ID NO 88
<211> LENGTH: 39
<212> TYPE: DNA
<213> ORGANISM: Artificial Sequence
<220> FEATURE:
<223> OTHER INFORMATION: CL8 Light Chain CDR1

<400> SEQUENCE: 88
tgcagcggta gcaacagcaa catcggtaac aactacgtg                        39

<210> SEQ ID NO 89
<211> LENGTH: 24
<212> TYPE: DNA
<213> ORGANISM: Artificial Sequence
<220> FEATURE:
<223> OTHER INFORMATION: CL8 Light Chain CDR2

<400> SEQUENCE: 89
aacaacaagc gtcctagtgg tgtg                                        24

<210> SEQ ID NO 90
<211> LENGTH: 36
<212> TYPE: DNA
<213> ORGANISM: Artificial Sequence
<220> FEATURE:
<223> OTHER INFORMATION: CL8 Light Chain CDR3
```

-continued

```
<400> SEQUENCE: 90
tgcagcagct acactagcag cagcactgtg atgttc                                    36

<210> SEQ ID NO 91
<211> LENGTH: 12
<212> TYPE: PRT
<213> ORGANISM: Artificial Sequence
<220> FEATURE:
<223> OTHER INFORMATION: CL8 Heavy Chain CDR1

<400> SEQUENCE: 91

Phe Thr Phe Ser Ser Tyr Ala Met Ser Trp Val Arg
1               5                   10

<210> SEQ ID NO 92
<211> LENGTH: 13
<212> TYPE: PRT
<213> ORGANISM: Artificial Sequence
<220> FEATURE:
<223> OTHER INFORMATION: CL8 Heavy Chain CDR2

<400> SEQUENCE: 92

Ala Ile Ser Gly Ser Gly Gly Ser Thr Tyr Tyr Ala Asp
1               5                   10

<210> SEQ ID NO 93
<211> LENGTH: 14
<212> TYPE: PRT
<213> ORGANISM: Artificial Sequence
<220> FEATURE:
<223> OTHER INFORMATION: CL8 Heavy Chain CDR3

<400> SEQUENCE: 93

Tyr Cys Ala Arg Ser Gly Arg Tyr Ala Asp Leu Thr Ser Gly
1               5                   10

<210> SEQ ID NO 94
<211> LENGTH: 15
<212> TYPE: PRT
<213> ORGANISM: Artificial Sequence
<220> FEATURE:
<223> OTHER INFORMATION: CL8 Light Chain CDR1

<400> SEQUENCE: 94

Cys Ser Gly Ser Asn Ser Asn Ile Gly Asn Asn Tyr Val Ser Trp
1               5                   10                  15

<210> SEQ ID NO 95
<211> LENGTH: 10
<212> TYPE: PRT
<213> ORGANISM: Artificial Sequence
<220> FEATURE:
<223> OTHER INFORMATION: CL8 Light Chain CDR2

<400> SEQUENCE: 95

Asp Asn Asn Lys Arg Pro Ser Gly Val Pro
1               5                   10

<210> SEQ ID NO 96
<211> LENGTH: 13
<212> TYPE: PRT
<213> ORGANISM: Artificial Sequence
<220> FEATURE:
<223> OTHER INFORMATION: CL8 Light Chain CDR3

<400> SEQUENCE: 96
```

-continued

```
Tyr Cys Ser Ser Tyr Thr Ser Ser Ser Thr Val Met Phe
1               5                   10
```

<210> SEQ ID NO 97
<211> LENGTH: 27
<212> TYPE: DNA
<213> ORGANISM: Artificial Sequence
<220> FEATURE:
<223> OTHER INFORMATION: CL9 Heavy Chain CDR1

<400> SEQUENCE: 97
agcagctact actggagctg ggtcaga                                       27

<210> SEQ ID NO 98
<211> LENGTH: 39
<212> TYPE: DNA
<213> ORGANISM: Artificial Sequence
<220> FEATURE:
<223> OTHER INFORMATION: CL9 Heavy Chain CDR2

<400> SEQUENCE: 98
gcaattagcg gtagcggtgg tagcacttac tacgcagac                          39

<210> SEQ ID NO 99
<211> LENGTH: 39
<212> TYPE: DNA
<213> ORGANISM: Artificial Sequence
<220> FEATURE:
<223> OTHER INFORMATION: CL9 Heavy Chain CDR3

<400> SEQUENCE: 99
tgcgcacgta tcgacgtgta cggtttcgac atctgggga                          39

<210> SEQ ID NO 100
<211> LENGTH: 39
<212> TYPE: DNA
<213> ORGANISM: Artificial Sequence
<220> FEATURE:
<223> OTHER INFORMATION: CL9 Light Chain CDR1

<400> SEQUENCE: 100
tgcagcggta gcactagcaa catcggtact aactacgtg                          39

<210> SEQ ID NO 101
<211> LENGTH: 24
<212> TYPE: DNA
<213> ORGANISM: Artificial Sequence
<220> FEATURE:
<223> OTHER INFORMATION: CL9 Light Chain CDR2

<400> SEQUENCE: 101
aacaacaacc gtcctagtgg tgtg                                          24

<210> SEQ ID NO 102
<211> LENGTH: 33
<212> TYPE: DNA
<213> ORGANISM: Artificial Sequence
<220> FEATURE:
<223> OTHER INFORMATION: CL9 Light Chain CDR3

<400> SEQUENCE: 102
tgccagactt gggacagcag cactgacgta gtg                                33

<210> SEQ ID NO 103
<211> LENGTH: 12
<212> TYPE: PRT

```
<213> ORGANISM: Artificial Sequence
<220> FEATURE:
<223> OTHER INFORMATION: CL9 Heavy Chain CDR1

<400> SEQUENCE: 103

Phe Thr Phe Ser Ser Tyr Tyr Trp Ser Trp Val Arg
1               5                   10

<210> SEQ ID NO 104
<211> LENGTH: 13
<212> TYPE: PRT
<213> ORGANISM: Artificial Sequence
<220> FEATURE:
<223> OTHER INFORMATION: CL9 Heavy Chain CDR2

<400> SEQUENCE: 104

Ala Ile Ser Gly Ser Gly Gly Ser Thr Tyr Tyr Ala Asp
1               5                   10

<210> SEQ ID NO 105
<211> LENGTH: 13
<212> TYPE: PRT
<213> ORGANISM: Artificial Sequence
<220> FEATURE:
<223> OTHER INFORMATION: CL9 Heavy Chain CDR3

<400> SEQUENCE: 105

Tyr Cys Ala Arg Ile Asp Val Tyr Gly Phe Asp Ile Trp
1               5                   10

<210> SEQ ID NO 106
<211> LENGTH: 15
<212> TYPE: PRT
<213> ORGANISM: Artificial Sequence
<220> FEATURE:
<223> OTHER INFORMATION: CL9 Light Chain CDR1

<400> SEQUENCE: 106

Cys Ser Gly Ser Thr Ser Asn Ile Gly Thr Asn Tyr Val Tyr Trp
1               5                   10                  15

<210> SEQ ID NO 107
<211> LENGTH: 10
<212> TYPE: PRT
<213> ORGANISM: Artificial Sequence
<220> FEATURE:
<223> OTHER INFORMATION: CL9 Light Chain CDR2

<400> SEQUENCE: 107

Asp Asn Asn Asn Arg Pro Ser Gly Val Pro
1               5                   10

<210> SEQ ID NO 108
<211> LENGTH: 13
<212> TYPE: PRT
<213> ORGANISM: Artificial Sequence
<220> FEATURE:
<223> OTHER INFORMATION: CL9 Light Chain CDR3

<400> SEQUENCE: 108

Tyr Cys Gln Thr Trp Asp Ser Ser Thr Asp Val Val Phe
1               5                   10

<210> SEQ ID NO 109
<211> LENGTH: 31
<212> TYPE: DNA
<213> ORGANISM: Artificial Sequence
```

<220> FEATURE:
<223> OTHER INFORMATION: CL10 Heavy Chain CDR1

<400> SEQUENCE: 109
tcagcagcta cggtatgcat tgggtcagac a                                    31

<210> SEQ ID NO 110
<211> LENGTH: 43
<212> TYPE: DNA
<213> ORGANISM: Artificial Sequence
<220> FEATURE:
<223> OTHER INFORMATION: CL10 Heavy Chain CDR2

<400> SEQUENCE: 110
ctgcaattag cggtagcggt ggtagcactt actacgcaga cag                       43

<210> SEQ ID NO 111
<211> LENGTH: 40
<212> TYPE: DNA
<213> ORGANISM: Artificial Sequence
<220> FEATURE:
<223> OTHER INFORMATION: CL10 Heavy Chain CDR3

<400> SEQUENCE: 111
actgcgcaag cggttacggt ctgatggacg tgtggggaca                           40

<210> SEQ ID NO 112
<211> LENGTH: 43
<212> TYPE: DNA
<213> ORGANISM: Artificial Sequence
<220> FEATURE:
<223> OTHER INFORMATION: CL10 Light Chain CDR1

<400> SEQUENCE: 112
gctgcactcg tagcagcggt atcatcgcaa gcaactacgt gca                       43

<210> SEQ ID NO 113
<211> LENGTH: 27
<212> TYPE: DNA
<213> ORGANISM: Artificial Sequence
<220> FEATURE:
<223> OTHER INFORMATION: CL10 Light Chain CDR2

<400> SEQUENCE: 113
cgcaacaacc agcgccctag tggtgtg                                         27

<210> SEQ ID NO 114
<211> LENGTH: 40
<212> TYPE: DNA
<213> ORGANISM: Artificial Sequence
<220> FEATURE:
<223> OTHER INFORMATION: CL10 Light Chain CDR3

<400> SEQUENCE: 114
actgcagcag ctacgcaggt aacaacaacc tggtgttcgg                           40

<210> SEQ ID NO 115
<211> LENGTH: 12
<212> TYPE: PRT
<213> ORGANISM: Artificial Sequence
<220> FEATURE:
<223> OTHER INFORMATION: CL10 Heavy Chain CDR1

<400> SEQUENCE: 115

Phe Thr Phe Ser Ser Tyr Gly Met His Trp Val Arg
1               5                   10

```
<210> SEQ ID NO 116
<211> LENGTH: 13
<212> TYPE: PRT
<213> ORGANISM: Artificial Sequence
<220> FEATURE:
<223> OTHER INFORMATION: CL10 Heavy Chain CDR2

<400> SEQUENCE: 116

Ala Ile Ser Gly Ser Gly Gly Ser Thr Tyr Tyr Ala Asp
1               5                   10

<210> SEQ ID NO 117
<211> LENGTH: 12
<212> TYPE: PRT
<213> ORGANISM: Artificial Sequence
<220> FEATURE:
<223> OTHER INFORMATION: CL10 Heavy Chain CDR3

<400> SEQUENCE: 117

Tyr Cys Ala Ser Gly Tyr Gly Leu Met Asp Val Trp
1               5                   10

<210> SEQ ID NO 118
<211> LENGTH: 15
<212> TYPE: PRT
<213> ORGANISM: Artificial Sequence
<220> FEATURE:
<223> OTHER INFORMATION: CL10 Light Chain CDR1

<400> SEQUENCE: 118

Cys Thr Arg Ser Ser Gly Ile Ile Ala Ser Asn Tyr Val Gln Trp
1               5                   10                  15

<210> SEQ ID NO 119
<211> LENGTH: 10
<212> TYPE: PRT
<213> ORGANISM: Artificial Sequence
<220> FEATURE:
<223> OTHER INFORMATION: CL10 Light Chain CDR2

<400> SEQUENCE: 119

Arg Asn Asn Gln Arg Pro Ser Gly Val Pro
1               5                   10

<210> SEQ ID NO 120
<211> LENGTH: 13
<212> TYPE: PRT
<213> ORGANISM: Artificial Sequence
<220> FEATURE:
<223> OTHER INFORMATION: CL10 Light Chain CDR3

<400> SEQUENCE: 120

Tyr Cys Ser Ser Tyr Ala Gly Asn Asn Asn Leu Val Phe
1               5                   10

<210> SEQ ID NO 121
<211> LENGTH: 30
<212> TYPE: DNA
<213> ORGANISM: Artificial Sequence
<220> FEATURE:
<223> OTHER INFORMATION: SK11 Heavy Chain CDR1

<400> SEQUENCE: 121
ttcagcacct atggcatgca ttgggttcgc                                30
```

-continued

```
<210> SEQ ID NO 122
<211> LENGTH: 42
<212> TYPE: DNA
<213> ORGANISM: Artificial Sequence
<220> FEATURE:
<223> OTHER INFORMATION: SK11 Heavy Chain CDR2

<400> SEQUENCE: 122
agcgccatca gcggcagcgg cggcagcacc tattatgccg at                          42

<210> SEQ ID NO 123
<211> LENGTH: 36
<212> TYPE: DNA
<213> ORGANISM: Artificial Sequence
<220> FEATURE:
<223> OTHER INFORMATION: SK11 Heavy Chain CDR3

<400> SEQUENCE: 123
tactgtgccc gcggcctgag cggccttgat tattgg                                 36

<210> SEQ ID NO 124
<211> LENGTH: 39
<212> TYPE: DNA
<213> ORGANISM: Artificial Sequence
<220> FEATURE:
<223> OTHER INFORMATION: SK11 Light Chain CDR1

<400> SEQUENCE: 124
tgccgctcca gccagggcat caccaactat ctggcctgg                              39

<210> SEQ ID NO 125
<211> LENGTH: 36
<212> TYPE: DNA
<213> ORGANISM: Artificial Sequence
<220> FEATURE:
<223> OTHER INFORMATION: SK11 Light Chain CDR2

<400> SEQUENCE: 125
ctgatctatg atgccagcaa ccgcgccacc ggcatc                                 36

<210> SEQ ID NO 126
<211> LENGTH: 45
<212> TYPE: DNA
<213> ORGANISM: Artificial Sequence
<220> FEATURE:
<223> OTHER INFORMATION: SK11 Light Chain CDR3

<400> SEQUENCE: 126
tattattgtc agcagagcta tagcacccct ctgaccttcg gtcag                       45

<210> SEQ ID NO 127
<211> LENGTH: 12
<212> TYPE: PRT
<213> ORGANISM: Artificial Sequence
<220> FEATURE:
<223> OTHER INFORMATION: SK11 Heavy Chain CDR1

<400> SEQUENCE: 127

Phe Thr Phe Ser Thr Tyr Gly Met His Trp Val Arg
1               5                   10

<210> SEQ ID NO 128
<211> LENGTH: 13
<212> TYPE: PRT
<213> ORGANISM: Artificial Sequence
<220> FEATURE:
<223> OTHER INFORMATION: SK11 Heavy Chain CDR2
```

<400> SEQUENCE: 128

Ala Ile Ser Gly Ser Gly Gly Ser Thr Tyr Tyr Ala Asp
1               5                   10

<210> SEQ ID NO 129
<211> LENGTH: 12
<212> TYPE: PRT
<213> ORGANISM: Artificial Sequence
<220> FEATURE:
<223> OTHER INFORMATION: SK11 Heavy Chain CDR3

<400> SEQUENCE: 129

Tyr Cys Ala Arg Gly Leu Ser Gly Leu Asp Tyr Trp
1               5                   10

<210> SEQ ID NO 130
<211> LENGTH: 13
<212> TYPE: PRT
<213> ORGANISM: Artificial Sequence
<220> FEATURE:
<223> OTHER INFORMATION: SK11 Light Chain CDR1

<400> SEQUENCE: 130

Cys Arg Ser Ser Gln Gly Ile Thr Asn Tyr Leu Ala Trp
1               5                   10

<210> SEQ ID NO 131
<211> LENGTH: 10
<212> TYPE: PRT
<213> ORGANISM: Artificial Sequence
<220> FEATURE:
<223> OTHER INFORMATION: SK11 Light Chain CDR2

<400> SEQUENCE: 131

Asp Ala Ser Asn Arg Ala Thr Gly Ile Pro
1               5                   10

<210> SEQ ID NO 132
<211> LENGTH: 12
<212> TYPE: PRT
<213> ORGANISM: Artificial Sequence
<220> FEATURE:
<223> OTHER INFORMATION: SK11 Light Chain CDR3

<400> SEQUENCE: 132

Tyr Cys Gln Gln Ser Tyr Ser Thr Pro Leu Thr Phe
1               5                   10

<210> SEQ ID NO 133
<211> LENGTH: 34
<212> TYPE: DNA
<213> ORGANISM: Artificial Sequence
<220> FEATURE:
<223> OTHER INFORMATION: SK12 Heavy Chain CDR1

<400> SEQUENCE: 133
ccttcagcag ctatgccatg cattgggttc gcca                          34

<210> SEQ ID NO 134
<211> LENGTH: 49
<212> TYPE: DNA
<213> ORGANISM: Artificial Sequence
<220> FEATURE:
<223> OTHER INFORMATION: SK12 Heavy Chain CDR2

<400> SEQUENCE: 134

-continued tgagcgccat cagcggcagc ggcggcgata cctatcatgc cgatagcgt                       49

<210> SEQ ID NO 135
<211> LENGTH: 40
<212> TYPE: DNA
<213> ORGANISM: Artificial Sequence
<220> FEATURE:
<223> OTHER INFORMATION: SK12 Heavy Chain CDR3

<400> SEQUENCE: 135
actactgtac ccgcggcctg agcggctttg attattgggg                                 40

<210> SEQ ID NO 136
<211> LENGTH: 43
<212> TYPE: DNA
<213> ORGANISM: Artificial Sequence
<220> FEATURE:
<223> OTHER INFORMATION: SK12 Light Chain CDR1

<400> SEQUENCE: 136
catgccgcgc cagccagagc atcagcagct atctgaactg gta                            43

<210> SEQ ID NO 137
<211> LENGTH: 40
<212> TYPE: DNA
<213> ORGANISM: Artificial Sequence
<220> FEATURE:
<223> OTHER INFORMATION: SK12 Light Chain CDR2

<400> SEQUENCE: 137
tgctgatcta tgatgccagc aaccgcgccc ctggcatccc                                 40

<210> SEQ ID NO 138
<211> LENGTH: 49
<212> TYPE: DNA
<213> ORGANISM: Artificial Sequence
<220> FEATURE:
<223> OTHER INFORMATION: SK12 Light Chain CDR3

<400> SEQUENCE: 138
tgtattattg tcagcagagc tatagcatcc ctatcacctt cggtcaggg                        49

<210> SEQ ID NO 139
<211> LENGTH: 12
<212> TYPE: PRT
<213> ORGANISM: Artificial Sequence
<220> FEATURE:
<223> OTHER INFORMATION: SK12 Heavy Chain CDR1

<400> SEQUENCE: 139

Phe Thr Phe Ser Ser Tyr Ala Met His Trp Val Arg
1               5                   10

<210> SEQ ID NO 140
<211> LENGTH: 13
<212> TYPE: PRT
<213> ORGANISM: Artificial Sequence
<220> FEATURE:
<223> OTHER INFORMATION: SK12 Heavy Chain CDR2

<400> SEQUENCE: 140

Ala Ile Ser Gly Ser Gly Gly Asp Thr Tyr His Ala Asp
1               5                   10

<210> SEQ ID NO 141

-continued

```
<211> LENGTH: 12
<212> TYPE: PRT
<213> ORGANISM: Artificial Sequence
<220> FEATURE:
<223> OTHER INFORMATION: SK12 Heavy Chain CDR3

<400> SEQUENCE: 141

Tyr Cys Thr Arg Gly Leu Ser Gly Phe Asp Tyr Trp
1               5                   10

<210> SEQ ID NO 142
<211> LENGTH: 13
<212> TYPE: PRT
<213> ORGANISM: Artificial Sequence
<220> FEATURE:
<223> OTHER INFORMATION: SK12 Light Chain CDR1

<400> SEQUENCE: 142

Cys Arg Ala Ser Gln Ser Ile Ser Ser Tyr Leu Asn Trp
1               5                   10

<210> SEQ ID NO 143
<211> LENGTH: 10
<212> TYPE: PRT
<213> ORGANISM: Artificial Sequence
<220> FEATURE:
<223> OTHER INFORMATION: SK12 Light Chain CDR2

<400> SEQUENCE: 143

Asp Ala Ser Asn Arg Ala Pro Gly Ile Pro
1               5                   10

<210> SEQ ID NO 144
<211> LENGTH: 12
<212> TYPE: PRT
<213> ORGANISM: Artificial Sequence
<220> FEATURE:
<223> OTHER INFORMATION: SK12 Light Chain CDR3

<400> SEQUENCE: 144

Tyr Cys Gln Gln Ser Tyr Ser Ile Pro Ile Thr Phe
1               5                   10

<210> SEQ ID NO 145
<211> LENGTH: 30
<212> TYPE: DNA
<213> ORGANISM: Artificial Sequence
<220> FEATURE:
<223> OTHER INFORMATION: SK13 Heavy Chain CDR1

<400> SEQUENCE: 145
ttcagcgatt atgccatgag ctgggttcgc                                    30

<210> SEQ ID NO 146
<211> LENGTH: 42
<212> TYPE: DNA
<213> ORGANISM: Artificial Sequence
<220> FEATURE:
<223> OTHER INFORMATION: SK13 Heavy Chain CDR2

<400> SEQUENCE: 146
agcatcagca gcagcagcag ctatatctac tataccgata gc                      42

<210> SEQ ID NO 147
<211> LENGTH: 36
<212> TYPE: DNA
<213> ORGANISM: Artificial Sequence
```

<220> FEATURE:
<223> OTHER INFORMATION: SK13 Heavy Chain CDR3

<400> SEQUENCE: 147
tactgtgccc gcggcggcta tggctttgat tattgg                                    36

<210> SEQ ID NO 148
<211> LENGTH: 39
<212> TYPE: DNA
<213> ORGANISM: Artificial Sequence
<220> FEATURE:
<223> OTHER INFORMATION: SK13 Light Chain CDR1

<400> SEQUENCE: 148
tgccgcgcca gccagagcat cagcagctat ctgaactgg                                 39

<210> SEQ ID NO 149
<211> LENGTH: 36
<212> TYPE: DNA
<213> ORGANISM: Artificial Sequence
<220> FEATURE:
<223> OTHER INFORMATION: SK13 Light Chain CDR2

<400> SEQUENCE: 149
ctgatctata gcgccagcag ccgcccacag ggcatc                                    36

<210> SEQ ID NO 150
<211> LENGTH: 45
<212> TYPE: DNA
<213> ORGANISM: Artificial Sequence
<220> FEATURE:
<223> OTHER INFORMATION: SK13 Light Chain CDR3

<400> SEQUENCE: 150
tattattgtc agcagtatga tgatctgcct tttaccttcg gtcag                          45

<210> SEQ ID NO 151
<211> LENGTH: 12
<212> TYPE: PRT
<213> ORGANISM: Artificial Sequence
<220> FEATURE:
<223> OTHER INFORMATION: SK13 Heavy Chain CDR1

<400> SEQUENCE: 151

Phe Thr Phe Ser Asp Tyr Ala Met Ser Trp Val Arg
1               5                   10

<210> SEQ ID NO 152
<211> LENGTH: 13
<212> TYPE: PRT
<213> ORGANISM: Artificial Sequence
<220> FEATURE:
<223> OTHER INFORMATION: SK13 Heavy Chain CDR2

<400> SEQUENCE: 152

Ser Ile Ser Ser Ser Ser Ser Tyr Ile Tyr Tyr Thr Asp
1               5                   10

<210> SEQ ID NO 153
<211> LENGTH: 12
<212> TYPE: PRT
<213> ORGANISM: Artificial Sequence
<220> FEATURE:
<223> OTHER INFORMATION: SK13 Heavy Chain CDR3

<400> SEQUENCE: 153

-continued

```
Tyr Cys Ala Arg Gly Gly Tyr Gly Phe Asp Tyr Trp
1               5                   10

<210> SEQ ID NO 154
<211> LENGTH: 13
<212> TYPE: PRT
<213> ORGANISM: Artificial Sequence
<220> FEATURE:
<223> OTHER INFORMATION: SK13 Light Chain CDR1

<400> SEQUENCE: 154

Cys Arg Ala Ser Gln Ser Ile Ser Ser Tyr Leu Asn Trp
1               5                   10

<210> SEQ ID NO 155
<211> LENGTH: 10
<212> TYPE: PRT
<213> ORGANISM: Artificial Sequence
<220> FEATURE:
<223> OTHER INFORMATION: SK13 Light Chain CDR2

<400> SEQUENCE: 155

Ser Ala Ser Ser Arg Pro Gln Gly Ile Pro
1               5                   10

<210> SEQ ID NO 156
<211> LENGTH: 12
<212> TYPE: PRT
<213> ORGANISM: Artificial Sequence
<220> FEATURE:
<223> OTHER INFORMATION: SK13 Light Chain CDR3

<400> SEQUENCE: 156

Tyr Cys Gln Gln Tyr Asp Asp Leu Pro Phe Thr Phe
1               5                   10

<210> SEQ ID NO 157
<211> LENGTH: 34
<212> TYPE: DNA
<213> ORGANISM: Artificial Sequence
<220> FEATURE:
<223> OTHER INFORMATION: SK14 Heavy Chain CDR1

<400> SEQUENCE: 157
ccttcagcaa ctttgcgatc gcctgggttc gcca                                34

<210> SEQ ID NO 158
<211> LENGTH: 46
<212> TYPE: DNA
<213> ORGANISM: Artificial Sequence
<220> FEATURE:
<223> OTHER INFORMATION: SK14 Heavy Chain CDR2

<400> SEQUENCE: 158
gcgccatcag cggccgcggc accagcacct attatgccga tagcgt                   46

<210> SEQ ID NO 159
<211> LENGTH: 40
<212> TYPE: DNA
<213> ORGANISM: Artificial Sequence
<220> FEATURE:
<223> OTHER INFORMATION: SK14 Heavy Chain CDR3

<400> SEQUENCE: 159
actactgtgc ccgcggcgtg agcggctttg atagctgggg                          40
```

```
<210> SEQ ID NO 160
<211> LENGTH: 43
<212> TYPE: DNA
<213> ORGANISM: Artificial Sequence
<220> FEATURE:
<223> OTHER INFORMATION: SK14 Light Chain CDR1

<400> SEQUENCE: 160
catgccgcgc cagccagagc atcagcagcc atctggcctg gta                          43

<210> SEQ ID NO 161
<211> LENGTH: 40
<212> TYPE: DNA
<213> ORGANISM: Artificial Sequence
<220> FEATURE:
<223> OTHER INFORMATION: SK14 Light Chain CDR2

<400> SEQUENCE: 161
tgctgatcta tgataccagc aaccgcgcca ccggcatccc                              40

<210> SEQ ID NO 162
<211> LENGTH: 49
<212> TYPE: DNA
<213> ORGANISM: Artificial Sequence
<220> FEATURE:
<223> OTHER INFORMATION: SK14 Light Chain CDR3

<400> SEQUENCE: 162
tgtactattg tcagcagagc tatagcaccc cttttacctt cggtcaggg                    49

<210> SEQ ID NO 163
<211> LENGTH: 12
<212> TYPE: PRT
<213> ORGANISM: Artificial Sequence
<220> FEATURE:
<223> OTHER INFORMATION: SK14 Heavy Chain CDR1

<400> SEQUENCE: 163

Phe Thr Phe Ser Asn Phe Ala Ile Ala Trp Val Arg
1               5                   10

<210> SEQ ID NO 164
<211> LENGTH: 13
<212> TYPE: PRT
<213> ORGANISM: Artificial Sequence
<220> FEATURE:
<223> OTHER INFORMATION: SK14 Heavy Chain CDR2

<400> SEQUENCE: 164

Ala Ile Ser Gly Arg Gly Thr Ser Thr Tyr Tyr Ala Asp
1               5                   10

<210> SEQ ID NO 165
<211> LENGTH: 12
<212> TYPE: PRT
<213> ORGANISM: Artificial Sequence
<220> FEATURE:
<223> OTHER INFORMATION: SK14 Heavy Chain CDR3

<400> SEQUENCE: 165

Tyr Cys Ala Arg Gly Val Ser Gly Phe Asp Ser Trp
1               5                   10

<210> SEQ ID NO 166
<211> LENGTH: 13
<212> TYPE: PRT
<213> ORGANISM: Artificial Sequence
```

-continued

```
<220> FEATURE:
<223> OTHER INFORMATION: SK14 Light Chain CDR1

<400> SEQUENCE: 166

Cys Arg Ala Ser Gln Ser Ile Ser Ser His Leu Ala Trp
1               5                   10

<210> SEQ ID NO 167
<211> LENGTH: 10
<212> TYPE: PRT
<213> ORGANISM: Artificial Sequence
<220> FEATURE:
<223> OTHER INFORMATION: SK14 Light Chain CDR2

<400> SEQUENCE: 167

Asp Thr Ser Asn Arg Ala Thr Gly Ile Pro
1               5                   10

<210> SEQ ID NO 168
<211> LENGTH: 12
<212> TYPE: PRT
<213> ORGANISM: Artificial Sequence
<220> FEATURE:
<223> OTHER INFORMATION: SK14 Light Chain CDR3

<400> SEQUENCE: 168

Tyr Cys Gln Gln Ser Tyr Ser Thr Pro Phe Thr Phe
1               5                   10

<210> SEQ ID NO 169
<211> LENGTH: 34
<212> TYPE: DNA
<213> ORGANISM: Artificial Sequence
<220> FEATURE:
<223> OTHER INFORMATION: SK15 Heavy Chain CDR1

<400> SEQUENCE: 169
ccttcagcag ctatgccatg cattgggttc gcca                                   34

<210> SEQ ID NO 170
<211> LENGTH: 49
<212> TYPE: DNA
<213> ORGANISM: Artificial Sequence
<220> FEATURE:
<223> OTHER INFORMATION: SK15 Heavy Chain CDR2

<400> SEQUENCE: 170
tgagcgccat caacggcagc ggcggcagca cctattatgc cgatagcgt                    49

<210> SEQ ID NO 171
<211> LENGTH: 43
<212> TYPE: DNA
<213> ORGANISM: Artificial Sequence
<220> FEATURE:
<223> OTHER INFORMATION: SK15 Heavy Chain CDR3

<400> SEQUENCE: 171
actactgtgc ccgcggcctg cagggctttg attattgggg aca                         43

<210> SEQ ID NO 172
<211> LENGTH: 43
<212> TYPE: DNA
<213> ORGANISM: Artificial Sequence
<220> FEATURE:
<223> OTHER INFORMATION: SK15 Light Chain CDR1

<400> SEQUENCE: 172
```

```
catgccaggc cagccaggat atcaccaact atctgaactg gta                          43
```

<210> SEQ ID NO 173
<211> LENGTH: 40
<212> TYPE: DNA
<213> ORGANISM: Artificial Sequence
<220> FEATURE:
<223> OTHER INFORMATION: SK15 Light Chain CDR2

<400> SEQUENCE: 173

```
tgctgatcta tgatgccagc agcctggaaa ccggcatccc                              40
```

<210> SEQ ID NO 174
<211> LENGTH: 49
<212> TYPE: DNA
<213> ORGANISM: Artificial Sequence
<220> FEATURE:
<223> OTHER INFORMATION: SK15 Light Chain CDR3

<400> SEQUENCE: 174

```
tgtattattg tcagcagagc tatagcaccc ctatcacctt cggtcaggg                     49
```

<210> SEQ ID NO 175
<211> LENGTH: 12
<212> TYPE: PRT
<213> ORGANISM: Artificial Sequence
<220> FEATURE:
<223> OTHER INFORMATION: SK15 Heavy Chain CDR1

<400> SEQUENCE: 175

```
Phe Thr Phe Ser Ser Tyr Ala Met His Trp Val Arg
1               5                   10
```

<210> SEQ ID NO 176
<211> LENGTH: 13
<212> TYPE: PRT
<213> ORGANISM: Artificial Sequence
<220> FEATURE:
<223> OTHER INFORMATION: SK15 Heavy Chain CDR2

<400> SEQUENCE: 176

```
Ala Ile Asn Gly Ser Gly Gly Ser Thr Tyr Tyr Ala Asp
1               5                   10
```

<210> SEQ ID NO 177
<211> LENGTH: 12
<212> TYPE: PRT
<213> ORGANISM: Artificial Sequence
<220> FEATURE:
<223> OTHER INFORMATION: SK15 Heavy Chain CDR3

<400> SEQUENCE: 177

```
Tyr Cys Ala Arg Gly Leu Gln Gly Phe Asp Tyr Trp
1               5                   10
```

<210> SEQ ID NO 178
<211> LENGTH: 13
<212> TYPE: PRT
<213> ORGANISM: Artificial Sequence
<220> FEATURE:
<223> OTHER INFORMATION: SK15 Light Chain CDR1

<400> SEQUENCE: 178

```
Cys Gln Ala Ser Gln Asp Ile Thr Asn Tyr Leu Asn Trp
1               5                   10
```

<210> SEQ ID NO 179
<211> LENGTH: 10
<212> TYPE: PRT
<213> ORGANISM: Artificial Sequence
<220> FEATURE:
<223> OTHER INFORMATION: SK15 Light Chain CDR2

<400> SEQUENCE: 179

Asp Ala Ser Ser Leu Glu Thr Gly Ile Pro
1               5               10

<210> SEQ ID NO 180
<211> LENGTH: 12
<212> TYPE: PRT
<213> ORGANISM: Artificial Sequence
<220> FEATURE:
<223> OTHER INFORMATION: SK15 Light Chain CDR3

<400> SEQUENCE: 180

Tyr Cys Gln Gln Ser Tyr Ser Thr Pro Ile Thr Phe
1               5               10

<210> SEQ ID NO 181
<211> LENGTH: 34
<212> TYPE: DNA
<213> ORGANISM: Artificial Sequence
<220> FEATURE:
<223> OTHER INFORMATION: SK16 Heavy Chain CDR1

<400> SEQUENCE: 181
ccttcagcag ctatgccatg agctgggttc gcca                                    34

<210> SEQ ID NO 182
<211> LENGTH: 49
<212> TYPE: DNA
<213> ORGANISM: Artificial Sequence
<220> FEATURE:
<223> OTHER INFORMATION: SK16 Heavy Chain CDR2

<400> SEQUENCE: 182
tgagcgccat caacggcagc ggcggcagca ccctgtatgc cgatagcgt                    49

<210> SEQ ID NO 183
<211> LENGTH: 40
<212> TYPE: DNA
<213> ORGANISM: Artificial Sequence
<220> FEATURE:
<223> OTHER INFORMATION: SK16 Heavy Chain CDR3

<400> SEQUENCE: 183
actactgtgc ccgcggcgtg agcggctttg atagctgggg                              40

<210> SEQ ID NO 184
<211> LENGTH: 43
<212> TYPE: DNA
<213> ORGANISM: Artificial Sequence
<220> FEATURE:
<223> OTHER INFORMATION: SK16 Light Chain CDR1

<400> SEQUENCE: 184
catgccgcat cagccagagc atcagcagct atctgaactg gta                          43

<210> SEQ ID NO 185
<211> LENGTH: 40
<212> TYPE: DNA
<213> ORGANISM: Artificial Sequence -continued

```
<220> FEATURE:
<223> OTHER INFORMATION: SK16 Light Chain CDR2

<400> SEQUENCE: 185
tgctgatcta tgatgccagc ctgcgcgcca ccggcatccc                            40

<210> SEQ ID NO 186
<211> LENGTH: 49
<212> TYPE: DNA
<213> ORGANISM: Artificial Sequence
<220> FEATURE:
<223> OTHER INFORMATION: SK16 Light Chain CDR3

<400> SEQUENCE: 186
tgtattattg tcagcagagc tataaaaccc ctatcacctt cggtcaggg                   49

<210> SEQ ID NO 187
<211> LENGTH: 12
<212> TYPE: PRT
<213> ORGANISM: Artificial Sequence
<220> FEATURE:
<223> OTHER INFORMATION: SK16 Heavy Chain CDR1

<400> SEQUENCE: 187

Phe Thr Phe Ser Ser Tyr Ala Met Ser Trp Val Arg
1               5                   10

<210> SEQ ID NO 188
<211> LENGTH: 13
<212> TYPE: PRT
<213> ORGANISM: Artificial Sequence
<220> FEATURE:
<223> OTHER INFORMATION: SK16 Heavy Chain CDR2

<400> SEQUENCE: 188

Ala Ile Asn Gly Ser Gly Gly Ser Thr Leu Tyr Ala Asp
1               5                   10

<210> SEQ ID NO 189
<211> LENGTH: 12
<212> TYPE: PRT
<213> ORGANISM: Artificial Sequence
<220> FEATURE:
<223> OTHER INFORMATION: SK16 Heavy Chain CDR3

<400> SEQUENCE: 189

Tyr Cys Ala Arg Gly Val Ser Gly Phe Asp Ser Trp
1               5                   10

<210> SEQ ID NO 190
<211> LENGTH: 13
<212> TYPE: PRT
<213> ORGANISM: Artificial Sequence
<220> FEATURE:
<223> OTHER INFORMATION: SK16 Light Chain CDR1

<400> SEQUENCE: 190

Cys Arg Ile Ser Gln Ser Ile Ser Ser Tyr Leu Asn Trp
1               5                   10

<210> SEQ ID NO 191
<211> LENGTH: 10
<212> TYPE: PRT
<213> ORGANISM: Artificial Sequence
<220> FEATURE:
<223> OTHER INFORMATION: SK16 Light Chain CDR2
```

-continued

<400> SEQUENCE: 191

Asp Ala Ser Leu Arg Ala Thr Gly Ile Pro
1               5                   10

<210> SEQ ID NO 192
<211> LENGTH: 13
<212> TYPE: PRT
<213> ORGANISM: Artificial Sequence
<220> FEATURE:
<223> OTHER INFORMATION: SK16 Light Chain CDR3

<400> SEQUENCE: 192

Tyr Tyr Cys Gln Gln Ser Tyr Lys Thr Pro Ile Thr Phe
1               5                   10

<210> SEQ ID NO 193
<211> LENGTH: 34
<212> TYPE: DNA
<213> ORGANISM: Artificial Sequence
<220> FEATURE:
<223> OTHER INFORMATION: SK17 Heavy Chain CDR1

<400> SEQUENCE: 193
ccttcagcag ctattattgg agctgggttc gcca                                    34

<210> SEQ ID NO 194
<211> LENGTH: 49
<212> TYPE: DNA
<213> ORGANISM: Artificial Sequence
<220> FEATURE:
<223> OTHER INFORMATION: SK17 Heavy Chain CDR2

<400> SEQUENCE: 194
tgagcaccat caccggcagc ggcggcagca ccgattatgc caacagcgt                    49

<210> SEQ ID NO 195
<211> LENGTH: 40
<212> TYPE: DNA
<213> ORGANISM: Artificial Sequence
<220> FEATURE:
<223> OTHER INFORMATION: SK17 Heavy Chain CDR3

<400> SEQUENCE: 195
actactgtgc caccggcggc ggcatctttg actattgggg                              40

<210> SEQ ID NO 196
<211> LENGTH: 43
<212> TYPE: DNA
<213> ORGANISM: Artificial Sequence
<220> FEATURE:
<223> OTHER INFORMATION: SK17 Light Chain CDR1

<400> SEQUENCE: 196
catgccaggc cagccagacc atcagcaact atctgaactg gta                          43

<210> SEQ ID NO 197
<211> LENGTH: 40
<212> TYPE: DNA
<213> ORGANISM: Artificial Sequence
<220> FEATURE:
<223> OTHER INFORMATION: SK17 Light Chain CDR2

<400> SEQUENCE: 197
tgctgatcta tgatgccagc aaccgcgcca ccggcatccc                              40

-continued

```
<210> SEQ ID NO 198
<211> LENGTH: 49
<212> TYPE: DNA
<213> ORGANISM: Artificial Sequence
<220> FEATURE:
<223> OTHER INFORMATION: SK17 Light Chain CDR3

<400> SEQUENCE: 198
tgtattattg tcagcagtac aacagctatc ctcctagctt cggtcaggg                49

<210> SEQ ID NO 199
<211> LENGTH: 12
<212> TYPE: PRT
<213> ORGANISM: Artificial Sequence
<220> FEATURE:
<223> OTHER INFORMATION: SK17 Heavy Chain CDR1

<400> SEQUENCE: 199

Phe Thr Phe Ser Ser Tyr Tyr Trp Ser Trp Val Arg
1               5                   10

<210> SEQ ID NO 200
<211> LENGTH: 13
<212> TYPE: PRT
<213> ORGANISM: Artificial Sequence
<220> FEATURE:
<223> OTHER INFORMATION: SK17 Heavy Chain CDR2

<400> SEQUENCE: 200

Thr Ile Thr Gly Ser Gly Gly Ser Thr Asp Tyr Ala Asn
1               5                   10

<210> SEQ ID NO 201
<211> LENGTH: 12
<212> TYPE: PRT
<213> ORGANISM: Artificial Sequence
<220> FEATURE:
<223> OTHER INFORMATION: SK17 Heavy Chain CDR3

<400> SEQUENCE: 201

Tyr Cys Ala Thr Gly Gly Gly Ile Phe Asp Tyr Trp
1               5                   10

<210> SEQ ID NO 202
<211> LENGTH: 13
<212> TYPE: PRT
<213> ORGANISM: Artificial Sequence
<220> FEATURE:
<223> OTHER INFORMATION: SK17 Light Chain CDR1

<400> SEQUENCE: 202

Cys Gln Ala Ser Gln Thr Ile Ser Asn Tyr Leu Asn Trp
1               5                   10

<210> SEQ ID NO 203
<211> LENGTH: 10
<212> TYPE: PRT
<213> ORGANISM: Artificial Sequence
<220> FEATURE:
<223> OTHER INFORMATION: SK17 Light Chain CDR2

<400> SEQUENCE: 203

Asp Ala Ser Asn Arg Ala Thr Gly Ile Pro
1               5                   10

<210> SEQ ID NO 204
<211> LENGTH: 12
```

-continued

```
<212> TYPE: PRT
<213> ORGANISM: Artificial Sequence
<220> FEATURE:
<223> OTHER INFORMATION: SK17 Light Chain CDR3

<400> SEQUENCE: 204

Tyr Cys Gln Gln Tyr Asn Ser Tyr Pro Pro Ser Phe
1               5                   10

<210> SEQ ID NO 205
<211> LENGTH: 34
<212> TYPE: DNA
<213> ORGANISM: Artificial Sequence
<220> FEATURE:
<223> OTHER INFORMATION: SL18 Heavy Chain CDR1

<400> SEQUENCE: 205
tcaccttcag cgattatcat atgcattggg ttcg                         34

<210> SEQ ID NO 206
<211> LENGTH: 34
<212> TYPE: DNA
<213> ORGANISM: Artificial Sequence
<220> FEATURE:
<223> OTHER INFORMATION: SL18 Heavy Chain CDR2

<400> SEQUENCE: 206
tcagcagcag cggcggctat acctattatg ccga                         34

<210> SEQ ID NO 207
<211> LENGTH: 34
<212> TYPE: DNA
<213> ORGANISM: Artificial Sequence
<220> FEATURE:
<223> OTHER INFORMATION: SL18 Heavy Chain CDR3

<400> SEQUENCE: 207
cccgatcgat acgcctgcct ctggattatt gggg                         34

<210> SEQ ID NO 208
<211> LENGTH: 37
<212> TYPE: DNA
<213> ORGANISM: Artificial Sequence
<220> FEATURE:
<223> OTHER INFORMATION: SL18 Light Chain CDR1

<400> SEQUENCE: 208
gcggcaacaa catcggcagc aaaggcgtgc attggta                      37

<210> SEQ ID NO 209
<211> LENGTH: 34
<212> TYPE: DNA
<213> ORGANISM: Artificial Sequence
<220> FEATURE:
<223> OTHER INFORMATION: SL18 Light Chain CDR2

<400> SEQUENCE: 209
atgaagatag caaacgccct agcggcgtgc gtga                         34

<210> SEQ ID NO 210
<211> LENGTH: 34
<212> TYPE: DNA
<213> ORGANISM: Artificial Sequence
<220> FEATURE:
<223> OTHER INFORMATION: SL18 Light Chain CDR3

<400> SEQUENCE: 210
```

-continued

```
gctatgatag caccaaaggc gtggtgtttg gtgg                                    34

<210> SEQ ID NO 211
<211> LENGTH: 12
<212> TYPE: PRT
<213> ORGANISM: Artificial Sequence
<220> FEATURE:
<223> OTHER INFORMATION: SL18 Heavy Chain CDR1

<400> SEQUENCE: 211

Phe Thr Phe Ser Asp Tyr His Met His Trp Val Arg
1               5                   10

<210> SEQ ID NO 212
<211> LENGTH: 13
<212> TYPE: PRT
<213> ORGANISM: Artificial Sequence
<220> FEATURE:
<223> OTHER INFORMATION: SL18 Heavy Chain CDR2

<400> SEQUENCE: 212

Thr Ile Ser Ser Ser Gly Gly Tyr Thr Tyr Tyr Ala Glu
1               5                   10

<210> SEQ ID NO 213
<211> LENGTH: 13
<212> TYPE: PRT
<213> ORGANISM: Artificial Sequence
<220> FEATURE:
<223> OTHER INFORMATION: SL18 Heavy Chain CDR3

<400> SEQUENCE: 213

Tyr Cys Ala Arg Ser Ile Arg Leu Pro Leu Asp Tyr Trp
1               5                   10

<210> SEQ ID NO 214
<211> LENGTH: 13
<212> TYPE: PRT
<213> ORGANISM: Artificial Sequence
<220> FEATURE:
<223> OTHER INFORMATION: SL18 Light Chain CDR1

<400> SEQUENCE: 214

Cys Ser Gly Asn Asn Ile Gly Ser Lys Gly Val His Trp
1               5                   10

<210> SEQ ID NO 215
<211> LENGTH: 10
<212> TYPE: PRT
<213> ORGANISM: Artificial Sequence
<220> FEATURE:
<223> OTHER INFORMATION: SL18 Light Chain CDR2

<400> SEQUENCE: 215

Glu Asp Ser Lys Arg Pro Ser Gly Val Arg
1               5                   10

<210> SEQ ID NO 216
<211> LENGTH: 13
<212> TYPE: PRT
<213> ORGANISM: Artificial Sequence
<220> FEATURE:
<223> OTHER INFORMATION: SL18 Light Chain CDR3

<400> SEQUENCE: 216

Tyr Cys Gln Ser Tyr Asp Ser Thr Lys Gly Val Val Phe
```

-continued

```
1               5                    10
```

<210> SEQ ID NO 217
<211> LENGTH: 34
<212> TYPE: DNA
<213> ORGANISM: Artificial Sequence
<220> FEATURE:
<223> OTHER INFORMATION: CB301_H3L1_A10 Heavy Chain CDR1

<400> SEQUENCE: 217
tcagcagcta cggtatgcat tgggtcagac aggc                               34

<210> SEQ ID NO 218
<211> LENGTH: 43
<212> TYPE: DNA
<213> ORGANISM: Artificial Sequence
<220> FEATURE:
<223> OTHER INFORMATION: CB301_H3L1_A10 Heavy Chain CDR2

<400> SEQUENCE: 218
ctgcaattag cggtagcggt ggtagcactt actacgcaga cag                     43

<210> SEQ ID NO 219
<211> LENGTH: 40
<212> TYPE: DNA
<213> ORGANISM: Artificial Sequence
<220> FEATURE:
<223> OTHER INFORMATION: CB301_H3L1_A10 Heavy Chain CDR3

<400> SEQUENCE: 219
actgcgtgcg tggttacggt gcaatggacg tgtggggaca                         40

<210> SEQ ID NO 220
<211> LENGTH: 43
<212> TYPE: DNA
<213> ORGANISM: Artificial Sequence
<220> FEATURE:
<223> OTHER INFORMATION: CB301_H3L1_A10 Light Chain CDR1

<400> SEQUENCE: 220
gctgcactcg tagcagcggt agcatcgcaa gcaactacgt gca                     43

<210> SEQ ID NO 221
<211> LENGTH: 31
<212> TYPE: DNA
<213> ORGANISM: Artificial Sequence
<220> FEATURE:
<223> OTHER INFORMATION: CB301_H3L1_A10 Light Chain CDR2

<400> SEQUENCE: 221
accgcaacaa ccagcgccct agtggtgtgc c                                  31

<210> SEQ ID NO 222
<211> LENGTH: 40
<212> TYPE: DNA
<213> ORGANISM: Artificial Sequence
<220> FEATURE:
<223> OTHER INFORMATION: CB301_H3L1_A10 Light Chain CDR3

<400> SEQUENCE: 222
actgcagcag ctacactact agcagcactc tggtgttcgg                         40

<210> SEQ ID NO 223
<211> LENGTH: 12
<212> TYPE: PRT
<213> ORGANISM: Artificial Sequence
<220> FEATURE:
<223> OTHER INFORMATION: CB301_H3L1_A10 Heavy Chain CDR1

<400> SEQUENCE: 223

Phe Thr Phe Ser Ser Tyr Gly Met His Trp Val Arg
1               5                   10

<210> SEQ ID NO 224
<211> LENGTH: 13
<212> TYPE: PRT
<213> ORGANISM: Artificial Sequence
<220> FEATURE:
<223> OTHER INFORMATION: CB301_H3L1_A10 Heavy Chain CDR2

<400> SEQUENCE: 224

Ala Ile Ser Gly Ser Gly Gly Ser Thr Tyr Tyr Ala Asp
1               5                   10

<210> SEQ ID NO 225
<211> LENGTH: 12
<212> TYPE: PRT
<213> ORGANISM: Artificial Sequence
<220> FEATURE:
<223> OTHER INFORMATION: CB301_H3L1_A10 Heavy Chain CDR3

<400> SEQUENCE: 225

Tyr Cys Val Arg Gly Tyr Gly Ala Met Asp Val Trp
1               5                   10

<210> SEQ ID NO 226
<211> LENGTH: 15
<212> TYPE: PRT
<213> ORGANISM: Artificial Sequence
<220> FEATURE:
<223> OTHER INFORMATION: CB301_H3L1_A10 Light Chain CDR1

<400> SEQUENCE: 226

Cys Thr Arg Ser Ser Gly Ser Ile Ala Ser Asn Tyr Val Gln Trp
1               5                   10                  15

<210> SEQ ID NO 227
<211> LENGTH: 10
<212> TYPE: PRT
<213> ORGANISM: Artificial Sequence
<220> FEATURE:
<223> OTHER INFORMATION: CB301_H3L1_A10 Light Chain CDR2

<400> SEQUENCE: 227

Arg Asn Asn Gln Arg Pro Ser Gly Val Pro
1               5                   10

<210> SEQ ID NO 228
<211> LENGTH: 13
<212> TYPE: PRT
<213> ORGANISM: Artificial Sequence
<220> FEATURE:
<223> OTHER INFORMATION: CB301_H3L1_A10 Light Chain CDR3

<400> SEQUENCE: 228

Tyr Cys Ser Ser Tyr Thr Thr Ser Ser Thr Leu Val Phe
1               5                   10

<210> SEQ ID NO 229
<211> LENGTH: 34
<212> TYPE: DNA
<213> ORGANISM: Artificial Sequence
<220> FEATURE:

<223> OTHER INFORMATION: CB301_H3L1_A12 Heavy Chain CDR1

<400> SEQUENCE: 229
tcagcagcta cgcaatgcat tgggtcagac aggc                                    34

<210> SEQ ID NO 230
<211> LENGTH: 43
<212> TYPE: DNA
<213> ORGANISM: Artificial Sequence
<220> FEATURE:
<223> OTHER INFORMATION: CB301_H3L1_A12 Heavy Chain CDR2

<400> SEQUENCE: 230
ctgcaattag cggtagcggt ggtagcactt actacgcaga cag                          43

<210> SEQ ID NO 231
<211> LENGTH: 40
<212> TYPE: DNA
<213> ORGANISM: Artificial Sequence
<220> FEATURE:
<223> OTHER INFORMATION: CB301_H3L1_A12 Heavy Chain CDR3

<400> SEQUENCE: 231
actgcgcaag cggctacggt ctgatggacg tatggggaca                              40

<210> SEQ ID NO 232
<211> LENGTH: 46
<212> TYPE: DNA
<213> ORGANISM: Artificial Sequence
<220> FEATURE:
<223> OTHER INFORMATION: CB301_H3L1_A12 Light Chain CDR1

<400> SEQUENCE: 232
gctgcactgg tactagcagc gacgtgggta actacaacct ggtgag                       46

<210> SEQ ID NO 233
<211> LENGTH: 31
<212> TYPE: DNA
<213> ORGANISM: Artificial Sequence
<220> FEATURE:
<223> OTHER INFORMATION: CB301_H3L1_A12 Light Chain CDR2

<400> SEQUENCE: 233
acagcaacaa ccagcgccct agtggtgtgc c                                       31

<210> SEQ ID NO 234
<211> LENGTH: 40
<212> TYPE: DNA
<213> ORGANISM: Artificial Sequence
<220> FEATURE:
<223> OTHER INFORMATION: CB301_H3L1_A12 Light Chain CDR3

<400> SEQUENCE: 234
actgcagcag ctacactggt agcaacgctc tgttgttcgg                              40

<210> SEQ ID NO 235
<211> LENGTH: 12
<212> TYPE: PRT
<213> ORGANISM: Artificial Sequence
<220> FEATURE:
<223> OTHER INFORMATION: CB301_H3L1_A12 Heavy Chain CDR1

<400> SEQUENCE: 235

Phe Thr Phe Ser Ser Tyr Ala Met His Trp Val Arg
1               5                   10

<210> SEQ ID NO 236
<211> LENGTH: 13
<212> TYPE: PRT
<213> ORGANISM: Artificial Sequence
<220> FEATURE:
<223> OTHER INFORMATION: CB301_H3L1_A12 Heavy Chain CDR2

<400> SEQUENCE: 236

Ala Ile Ser Gly Ser Gly Gly Ser Thr Tyr Tyr Ala Asp
1               5                   10

<210> SEQ ID NO 237
<211> LENGTH: 12
<212> TYPE: PRT
<213> ORGANISM: Artificial Sequence
<220> FEATURE:
<223> OTHER INFORMATION: CB301_H3L1_A12 Heavy Chain CDR3

<400> SEQUENCE: 237

Tyr Cys Ala Ser Gly Tyr Gly Leu Met Asp Val Trp
1               5                   10

<210> SEQ ID NO 238
<211> LENGTH: 16
<212> TYPE: PRT
<213> ORGANISM: Artificial Sequence
<220> FEATURE:
<223> OTHER INFORMATION: CB301_H3L1_A12 Light Chain CDR1

<400> SEQUENCE: 238

Cys Thr Gly Thr Ser Ser Asp Val Gly Asn Tyr Asn Leu Val Ser Trp
1               5                   10                  15

<210> SEQ ID NO 239
<211> LENGTH: 10
<212> TYPE: PRT
<213> ORGANISM: Artificial Sequence
<220> FEATURE:
<223> OTHER INFORMATION: CB301_H3L1_A12 Light Chain CDR2

<400> SEQUENCE: 239

Ser Asn Asn Gln Arg Pro Ser Gly Val Pro
1               5                   10

<210> SEQ ID NO 240
<211> LENGTH: 13
<212> TYPE: PRT
<213> ORGANISM: Artificial Sequence
<220> FEATURE:
<223> OTHER INFORMATION: CB301_H3L1_A12 Light Chain CDR3

<400> SEQUENCE: 240

Tyr Cys Ser Ser Tyr Thr Gly Ser Asn Ala Leu Leu Phe
1               5                   10

<210> SEQ ID NO 241
<211> LENGTH: 31
<212> TYPE: DNA
<213> ORGANISM: Artificial Sequence
<220> FEATURE:
<223> OTHER INFORMATION: CB301_H3L1_E6 Heavy Chain CDR1

<400> SEQUENCE: 241
tcagcagcta cgcaatgagc tgggtcagac a                                                                              31

<210> SEQ ID NO 242

```
<211> LENGTH: 43
<212> TYPE: DNA
<213> ORGANISM: Artificial Sequence
<220> FEATURE:
<223> OTHER INFORMATION: CB301_H3L1_E6 Heavy Chain CDR2

<400> SEQUENCE: 242
ctgcaattag cggtagcggt ggtagcactt actacgcaga cag                43

<210> SEQ ID NO 243
<211> LENGTH: 40
<212> TYPE: DNA
<213> ORGANISM: Artificial Sequence
<220> FEATURE:
<223> OTHER INFORMATION: CB301_H3L1_E6 Heavy Chain CDR3

<400> SEQUENCE: 243
actgcgcacg ctggcattac agcttcgact actggggaca                    40

<210> SEQ ID NO 244
<211> LENGTH: 37
<212> TYPE: DNA
<213> ORGANISM: Artificial Sequence
<220> FEATURE:
<223> OTHER INFORMATION: CB301_H3L1_E6 Light Chain CDR1

<400> SEQUENCE: 244
gctgccgtgg taacaacatc ggtagcaagc gtgtgca                       37

<210> SEQ ID NO 245
<211> LENGTH: 31
<212> TYPE: DNA
<213> ORGANISM: Artificial Sequence
<220> FEATURE:
<223> OTHER INFORMATION: CB301_H3L1_E6 Light Chain CDR2

<400> SEQUENCE: 245
acagctacaa ccaccgtcct agcggtgtgc c                             31

<210> SEQ ID NO 246
<211> LENGTH: 43
<212> TYPE: DNA
<213> ORGANISM: Artificial Sequence
<220> FEATURE:
<223> OTHER INFORMATION: CB301_H3L1_E6 Light Chain CDR3

<400> SEQUENCE: 246
actgcaacac ttgggacgac agcctggagg gtcctgtgtt cgg                43

<210> SEQ ID NO 247
<211> LENGTH: 12
<212> TYPE: PRT
<213> ORGANISM: Artificial Sequence
<220> FEATURE:
<223> OTHER INFORMATION: CB301_H3L1_E6 Heavy Chain CDR1

<400> SEQUENCE: 247

Phe Thr Phe Ser Ser Tyr Ala Met Ser Trp Val Arg
1               5                   10

<210> SEQ ID NO 248
<211> LENGTH: 13
<212> TYPE: PRT
<213> ORGANISM: Artificial Sequence
<220> FEATURE:
<223> OTHER INFORMATION: CB301_H3L1_E6 Heavy Chain CDR2
```

<400> SEQUENCE: 248

Ala Ile Ser Gly Ser Gly Gly Ser Thr Tyr Tyr Ala Asp
1               5                   10

<210> SEQ ID NO 249
<211> LENGTH: 12
<212> TYPE: PRT
<213> ORGANISM: Artificial Sequence
<220> FEATURE:
<223> OTHER INFORMATION: CB301_H3L1_E6 Heavy Chain CDR3

<400> SEQUENCE: 249

Tyr Cys Ala Arg Trp His Tyr Ser Phe Asp Tyr Trp
1               5                   10

<210> SEQ ID NO 250
<211> LENGTH: 13
<212> TYPE: PRT
<213> ORGANISM: Artificial Sequence
<220> FEATURE:
<223> OTHER INFORMATION: CB301_H3L1_E6 Light Chain CDR1

<400> SEQUENCE: 250

Cys Arg Gly Asn Asn Ile Gly Ser Lys Arg Val His Trp
1               5                   10

<210> SEQ ID NO 251
<211> LENGTH: 10
<212> TYPE: PRT
<213> ORGANISM: Artificial Sequence
<220> FEATURE:
<223> OTHER INFORMATION: CB301_H3L1_E6 Light Chain CDR2

<400> SEQUENCE: 251

Ser Tyr Asn His Arg Pro Ser Gly Val Pro
1               5                   10

<210> SEQ ID NO 252
<211> LENGTH: 14
<212> TYPE: PRT
<213> ORGANISM: Artificial Sequence
<220> FEATURE:
<223> OTHER INFORMATION: CB301_H3L1_E6 Light Chain CDR3

<400> SEQUENCE: 252

Tyr Cys Asn Thr Trp Asp Asp Ser Leu Glu Gly Pro Val Phe
1               5                   10

<210> SEQ ID NO 253
<211> LENGTH: 31
<212> TYPE: DNA
<213> ORGANISM: Artificial Sequence
<220> FEATURE:
<223> OTHER INFORMATION: CB301_H3L1_F4 Heavy Chain CDR1

<400> SEQUENCE: 253
tcagcggcta cgcaatgagc tgggtcagac a                                         31

<210> SEQ ID NO 254
<211> LENGTH: 43
<212> TYPE: DNA
<213> ORGANISM: Artificial Sequence
<220> FEATURE:
<223> OTHER INFORMATION: CB301_H3L1_F4 Heavy Chain CDR2

<400> SEQUENCE: 254

-continued

```
ctgcaattag cggtagcggt ggtagcactt actacgcaga cag                          43

<210> SEQ ID NO 255
<211> LENGTH: 43
<212> TYPE: DNA
<213> ORGANISM: Artificial Sequence
<220> FEATURE:
<223> OTHER INFORMATION: CB301_H3L1_F4 Heavy Chain CDR3

<400> SEQUENCE: 255
actgcgcacg tagtcctagc ggtctgttcg actactgggg aca                          43

<210> SEQ ID NO 256
<211> LENGTH: 37
<212> TYPE: DNA
<213> ORGANISM: Artificial Sequence
<220> FEATURE:
<223> OTHER INFORMATION: CB301_H3L1_F4 Light Chain CDR1

<400> SEQUENCE: 256
gctgcggtgg taacaacatc ggtagcaagc gtgtgca                                 37

<210> SEQ ID NO 257
<211> LENGTH: 31
<212> TYPE: DNA
<213> ORGANISM: Artificial Sequence
<220> FEATURE:
<223> OTHER INFORMATION: CB301_H3L1_F4 Light Chain CDR2

<400> SEQUENCE: 257
acaacactag caacaagcat agcggtgtgc c                                       31

<210> SEQ ID NO 258
<211> LENGTH: 37
<212> TYPE: DNA
<213> ORGANISM: Artificial Sequence
<220> FEATURE:
<223> OTHER INFORMATION: CB301_H3L1_F4 Light Chain CDR3

<400> SEQUENCE: 258
actgcagcag ctacctacag cagcactctc tgttcgg                                 37

<210> SEQ ID NO 259
<211> LENGTH: 12
<212> TYPE: PRT
<213> ORGANISM: Artificial Sequence
<220> FEATURE:
<223> OTHER INFORMATION: CB301_H3L1_F4 Heavy Chain CDR1

<400> SEQUENCE: 259

Phe Thr Phe Ser Gly Tyr Ala Met Ser Trp Val Arg
1               5                   10

<210> SEQ ID NO 260
<211> LENGTH: 13
<212> TYPE: PRT
<213> ORGANISM: Artificial Sequence
<220> FEATURE:
<223> OTHER INFORMATION: CB301_H3L1_F4 Heavy Chain CDR2

<400> SEQUENCE: 260

Ala Ile Ser Gly Ser Gly Gly Ser Thr Tyr Tyr Ala Asp
1               5                   10

<210> SEQ ID NO 261
<211> LENGTH: 13
```

<212> TYPE: PRT
<213> ORGANISM: Artificial Sequence
<220> FEATURE:
<223> OTHER INFORMATION: CB301_H3L1_F4 Heavy Chain CDR3

<400> SEQUENCE: 261

Tyr Cys Ala Arg Ser Pro Ser Gly Leu Phe Asp Tyr Trp
1               5                   10

<210> SEQ ID NO 262
<211> LENGTH: 13
<212> TYPE: PRT
<213> ORGANISM: Artificial Sequence
<220> FEATURE:
<223> OTHER INFORMATION: CB301_H3L1_F4 Light Chain CDR1

<400> SEQUENCE: 262

Cys Gly Gly Asn Asn Ile Gly Ser Lys Arg Val His Trp
1               5                   10

<210> SEQ ID NO 263
<211> LENGTH: 10
<212> TYPE: PRT
<213> ORGANISM: Artificial Sequence
<220> FEATURE:
<223> OTHER INFORMATION: CB301_H3L1_F4 Light Chain CDR2

<400> SEQUENCE: 263

Asn Thr Ser Asn Lys His Ser Gly Val Pro
1               5                   10

<210> SEQ ID NO 264
<211> LENGTH: 12
<212> TYPE: PRT
<213> ORGANISM: Artificial Sequence
<220> FEATURE:
<223> OTHER INFORMATION: CB301_H3L1_F4 Light Chain CDR3

<400> SEQUENCE: 264

Tyr Cys Ser Ser Tyr Leu Gln Gln His Ser Leu Phe
1               5                   10

<210> SEQ ID NO 265
<211> LENGTH: 29
<212> TYPE: DNA
<213> ORGANISM: Artificial Sequence
<220> FEATURE:
<223> OTHER INFORMATION: CB301_H3L1_G11 Heavy Chain CDR1

<400> SEQUENCE: 265
agcagctacg caatgagctg ggtcagaca                                          29

<210> SEQ ID NO 266
<211> LENGTH: 43
<212> TYPE: DNA
<213> ORGANISM: Artificial Sequence
<220> FEATURE:
<223> OTHER INFORMATION: CB301_H3L1_G11 Heavy Chain CDR2

<400> SEQUENCE: 266
ctgcaattag cggtagcggt ggtagcactt actacgcaga cag                          43

<210> SEQ ID NO 267
<211> LENGTH: 49
<212> TYPE: DNA
<213> ORGANISM: Artificial Sequence
<220> FEATURE:

-continued

<223> OTHER INFORMATION: CB301_H3L1_G11 Heavy Chain CDR3

<400> SEQUENCE: 267
actgcacacg tttcgtgggt gcaatcggtg cattcgacta ctggggaca                   49

<210> SEQ ID NO 268
<211> LENGTH: 37
<212> TYPE: DNA
<213> ORGANISM: Artificial Sequence
<220> FEATURE:
<223> OTHER INFORMATION: CB301_H3L1_G11 Light Chain CDR1

<400> SEQUENCE: 268
gctgcagtgg taacaacatc ggtagccgta gcgtgca                   37

<210> SEQ ID NO 269
<211> LENGTH: 31
<212> TYPE: DNA
<213> ORGANISM: Artificial Sequence
<220> FEATURE:
<223> OTHER INFORMATION: CB301_H3L1_G11 Light Chain CDR2

<400> SEQUENCE: 269
accgcaacaa ccagcgccct agtggtgtgc c                   31

<210> SEQ ID NO 270
<211> LENGTH: 43
<212> TYPE: DNA
<213> ORGANISM: Artificial Sequence
<220> FEATURE:
<223> OTHER INFORMATION: CB301_H3L1_G11 Light Chain CDR3

<400> SEQUENCE: 270
actgcgcagc atgggacgac agcctgagcg gtcctgtgtt cgg                   43

<210> SEQ ID NO 271
<211> LENGTH: 12
<212> TYPE: PRT
<213> ORGANISM: Artificial Sequence
<220> FEATURE:
<223> OTHER INFORMATION: CB301_H3L1_G11 Heavy Chain CDR1

<400> SEQUENCE: 271

Phe Thr Phe Ser Ser Tyr Ala Met Ser Trp Val Arg
1               5                   10

<210> SEQ ID NO 272
<211> LENGTH: 13
<212> TYPE: PRT
<213> ORGANISM: Artificial Sequence
<220> FEATURE:
<223> OTHER INFORMATION: CB301_H3L1_G11 Heavy Chain CDR2

<400> SEQUENCE: 272

Ala Ile Ser Gly Ser Gly Gly Ser Thr Tyr Tyr Ala Asp
1               5                   10

<210> SEQ ID NO 273
<211> LENGTH: 15
<212> TYPE: PRT
<213> ORGANISM: Artificial Sequence
<220> FEATURE:
<223> OTHER INFORMATION: CB301_H3L1_G11 Heavy Chain CDR3

<400> SEQUENCE: 273

Tyr Cys Thr Arg Phe Val Gly Ala Ile Gly Ala Phe Asp Tyr Trp

-continued

```
1              5              10             15
```

<210> SEQ ID NO 274
<211> LENGTH: 13
<212> TYPE: PRT
<213> ORGANISM: Artificial Sequence
<220> FEATURE:
<223> OTHER INFORMATION: CB301_H3L1_G11 Light Chain CDR1

<400> SEQUENCE: 274

Cys Ser Gly Asn Asn Ile Gly Ser Arg Ser Val His Trp
1              5              10

<210> SEQ ID NO 275
<211> LENGTH: 10
<212> TYPE: PRT
<213> ORGANISM: Artificial Sequence
<220> FEATURE:
<223> OTHER INFORMATION: CB301_H3L1_G11 Light Chain CDR2

<400> SEQUENCE: 275

Arg Asn Asn Gln Arg Pro Ser Gly Val Pro
1              5              10

<210> SEQ ID NO 276
<211> LENGTH: 14
<212> TYPE: PRT
<213> ORGANISM: Artificial Sequence
<220> FEATURE:
<223> OTHER INFORMATION: CB301_H3L1_G11 Light Chain CDR3

<400> SEQUENCE: 276

Tyr Cys Ala Ala Trp Asp Asp Ser Leu Ser Gly Pro Val Phe
1              5              10

<210> SEQ ID NO 277
<211> LENGTH: 31
<212> TYPE: DNA
<213> ORGANISM: Artificial Sequence
<220> FEATURE:
<223> OTHER INFORMATION: CB301_OPALTL_B5 Heavy Chain CDR1

<400> SEQUENCE: 277
tcagccatta cgcaatgagc tgggtcagac a                          31

<210> SEQ ID NO 278
<211> LENGTH: 43
<212> TYPE: DNA
<213> ORGANISM: Artificial Sequence
<220> FEATURE:
<223> OTHER INFORMATION: CB301_OPALTL_B5 Heavy Chain CDR2

<400> SEQUENCE: 278
ctgcaattag cggtagcggt ggtagcactt actacgcaga cag             43

<210> SEQ ID NO 279
<211> LENGTH: 55
<212> TYPE: DNA
<213> ORGANISM: Artificial Sequence
<220> FEATURE:
<223> OTHER INFORMATION: CB301_OPALTL_B5 Heavy Chain CDR3

<400> SEQUENCE: 279
actgcgcacg tggttgggac agccctactc tgacatactt cgacagctgg ggaca    55

<210> SEQ ID NO 280

-continued

```
<211> LENGTH: 43
<212> TYPE: DNA
<213> ORGANISM: Artificial Sequence
<220> FEATURE:
<223> OTHER INFORMATION: CB301_OPALTL_B5 Light Chain CDR1

<400> SEQUENCE: 280
gctgcagcgg tactagcagc aacatcggta acaacgacgt gag                           43

<210> SEQ ID NO 281
<211> LENGTH: 31
<212> TYPE: DNA
<213> ORGANISM: Artificial Sequence
<220> FEATURE:
<223> OTHER INFORMATION: CB301_OPALTL_B5 Light Chain CDR2

<400> SEQUENCE: 281
accaggacac taagcgtcct agcggtgtgc c                                        31

<210> SEQ ID NO 282
<211> LENGTH: 43
<212> TYPE: DNA
<213> ORGANISM: Artificial Sequence
<220> FEATURE:
<223> OTHER INFORMATION: CB301_OPALTL_B5 Light Chain CDR3

<400> SEQUENCE: 282
actgcgcagc atgggacgac agcctgagcg gtcctgtgtt cgg                           43

<210> SEQ ID NO 283
<211> LENGTH: 12
<212> TYPE: PRT
<213> ORGANISM: Artificial Sequence
<220> FEATURE:
<223> OTHER INFORMATION: CB301_OPALTL_B5 Heavy Chain CDR1

<400> SEQUENCE: 283

Phe Thr Phe Ser His Tyr Ala Met Ser Trp Val Arg
1               5                   10

<210> SEQ ID NO 284
<211> LENGTH: 13
<212> TYPE: PRT
<213> ORGANISM: Artificial Sequence
<220> FEATURE:
<223> OTHER INFORMATION: CB301_OPALTL_B5 Heavy Chain CDR2

<400> SEQUENCE: 284

Ala Ile Ser Gly Ser Gly Gly Ser Thr Tyr Tyr Ala Asp
1               5                   10

<210> SEQ ID NO 285
<211> LENGTH: 17
<212> TYPE: PRT
<213> ORGANISM: Artificial Sequence
<220> FEATURE:
<223> OTHER INFORMATION: CB301_OPALTL_B5 Heavy Chain CDR3

<400> SEQUENCE: 285

Tyr Cys Ala Arg Gly Trp Asp Ser Pro Thr Leu Thr Tyr Phe Asp Ser
1               5                   10                  15

Trp

<210> SEQ ID NO 286
<211> LENGTH: 15
<212> TYPE: PRT
```

-continued

<213> ORGANISM: Artificial Sequence
<220> FEATURE:
<223> OTHER INFORMATION: CB301_OPALTL_B5 Light Chain CDR1

<400> SEQUENCE: 286

Cys Ser Gly Thr Ser Ser Asn Ile Gly Asn Asn Asp Val Ser Trp
1               5                   10                  15

<210> SEQ ID NO 287
<211> LENGTH: 10
<212> TYPE: PRT
<213> ORGANISM: Artificial Sequence
<220> FEATURE:
<223> OTHER INFORMATION: CB301_OPALTL_B5 Light Chain CDR2

<400> SEQUENCE: 287

Gln Asp Thr Lys Arg Pro Ser Gly Val Pro
1               5                   10

<210> SEQ ID NO 288
<211> LENGTH: 14
<212> TYPE: PRT
<213> ORGANISM: Artificial Sequence
<220> FEATURE:
<223> OTHER INFORMATION: CB301_OPALTL_B5 Light Chain CDR3

<400> SEQUENCE: 288

Tyr Cys Ala Ala Trp Asp Asp Ser Leu Ser Gly Pro Val Phe
1               5                   10

<210> SEQ ID NO 289
<211> LENGTH: 27
<212> TYPE: DNA
<213> ORGANISM: Artificial Sequence
<220> FEATURE:
<223> OTHER INFORMATION: CB301_OPALTL_E6 Heavy Chain CDR1

<400> SEQUENCE: 289
agcagctacg gtatgcattg ggtcaga                                27

<210> SEQ ID NO 290
<211> LENGTH: 39
<212> TYPE: DNA
<213> ORGANISM: Artificial Sequence
<220> FEATURE:
<223> OTHER INFORMATION: CB301_OPALTL_E6 Heavy Chain CDR2

<400> SEQUENCE: 290
gcaatcagcg gtagcggtgg ttacacttac tacgcagac                  39

<210> SEQ ID NO 291
<211> LENGTH: 36
<212> TYPE: DNA
<213> ORGANISM: Artificial Sequence
<220> FEATURE:
<223> OTHER INFORMATION: CB301_OPALTL_E6 Heavy Chain CDR3

<400> SEQUENCE: 291
tgcgcacgct ggcattacag cttcgactac tgggga                     36

<210> SEQ ID NO 292
<211> LENGTH: 39
<212> TYPE: DNA
<213> ORGANISM: Artificial Sequence
<220> FEATURE:
<223> OTHER INFORMATION: CB301_OPALTL_E6 Light Chain CDR1

-continued

<400> SEQUENCE: 292
tgcagcggta gcagcagcaa catcggtaac aactacgtg                                          39

<210> SEQ ID NO 293
<211> LENGTH: 27
<212> TYPE: DNA
<213> ORGANISM: Artificial Sequence
<220> FEATURE:
<223> OTHER INFORMATION: CB301_OPALTL_E6 Light Chain CDR2

<400> SEQUENCE: 293
cgcaacaacc agcgccctag tggtgtg                                                       27

<210> SEQ ID NO 294
<211> LENGTH: 33
<212> TYPE: DNA
<213> ORGANISM: Artificial Sequence
<220> FEATURE:
<223> OTHER INFORMATION: CB301_OPALTL_E6 Light Chain CDR3

<400> SEQUENCE: 294
tgccagagct acgacaacag caacgtgctg ttc                                                33

<210> SEQ ID NO 295
<211> LENGTH: 12
<212> TYPE: PRT
<213> ORGANISM: Artificial Sequence
<220> FEATURE:
<223> OTHER INFORMATION: CB301_OPALTL_E6 Heavy Chain CDR1

<400> SEQUENCE: 295

Phe Thr Phe Ser Ser Tyr Gly Met His Trp Val Arg
1               5                   10

<210> SEQ ID NO 296
<211> LENGTH: 13
<212> TYPE: PRT
<213> ORGANISM: Artificial Sequence
<220> FEATURE:
<223> OTHER INFORMATION: CB301_OPALTL_E6 Heavy Chain CDR2

<400> SEQUENCE: 296

Ala Ile Ser Gly Ser Gly Gly Tyr Thr Tyr Tyr Ala Asp
1               5                   10

<210> SEQ ID NO 297
<211> LENGTH: 12
<212> TYPE: PRT
<213> ORGANISM: Artificial Sequence
<220> FEATURE:
<223> OTHER INFORMATION: CB301_OPALTL_E6 Heavy Chain CDR3

<400> SEQUENCE: 297

Tyr Cys Ala Arg Trp His Tyr Ser Phe Asp Tyr Trp
1               5                   10

<210> SEQ ID NO 298
<211> LENGTH: 15
<212> TYPE: PRT
<213> ORGANISM: Artificial Sequence
<220> FEATURE:
<223> OTHER INFORMATION: CB301_OPALTL_E6 Light Chain CDR1

<400> SEQUENCE: 298

Cys Ser Gly Ser Ser Ser Asn Ile Gly Asn Asn Tyr Val Ser Trp
1               5                   10                  15

<210> SEQ ID NO 299
<211> LENGTH: 10
<212> TYPE: PRT
<213> ORGANISM: Artificial Sequence
<220> FEATURE:
<223> OTHER INFORMATION: CB301_OPALTL_E6 Light Chain CDR2

<400> SEQUENCE: 299

Arg Asn Asn Gln Arg Pro Ser Gly Val Pro
1               5                   10

<210> SEQ ID NO 300
<211> LENGTH: 12
<212> TYPE: PRT
<213> ORGANISM: Artificial Sequence
<220> FEATURE:
<223> OTHER INFORMATION: CB301_OPALTL_E6 Light Chain CDR3

<400> SEQUENCE: 300

Tyr Cys Gln Ser Tyr Asp Asn Ser Asn Val Leu Phe
1               5                   10

<210> SEQ ID NO 301
<211> LENGTH: 348
<212> TYPE: DNA
<213> ORGANISM: Artificial Sequence
<220> FEATURE:
<223> OTHER INFORMATION: CK1 Heavy chain variable region

<400> SEQUENCE: 301
gaagtgcagc tgctggaaag tggaggtgga ctggtgcagc ctggcggcag cctgcgcctg      60
agctgtgccg ccagcggatt caccttcagc cgctatgcca tgacctgggt tcgccaagca     120
cctggcaaag gcctggaatg ggtgagcagc atgagcggca ccggcggcac cacctattat     180
gccgatagcg tgaaaggtcg ctttaccatc agccgcgata acagcaaaaa caccctgtat     240
ctgcagatga acagcctgcg cgccgaggac accgcagtct actactgtgc ccgcggcgcc     300
tatggctttg atcattgggg acaaggtact ctggtgaccg tgagcagc                   348

<210> SEQ ID NO 302
<211> LENGTH: 321
<212> TYPE: DNA
<213> ORGANISM: Artificial Sequence
<220> FEATURE:
<223> OTHER INFORMATION: CK1 Light Chain Variable Region

<400> SEQUENCE: 302
gaaatcgtgc tgacccagag ccctggcacc ctgagcctga gccctggcga acgcgcaaca      60
ctgtcatgcc gcgccagcca gagcatcggc aactatctga actggtatca gcagaaacca     120
ggtcaggctc acgtctgct gatctatgat gccagcaacc tggaaaccgg catccctgat      180
cgcttctcag atctggaag cggtaccgat tttaccctga ccatcagccg cctggaacct      240
gaggactttg ccgtgtatta ttgtcagcag agtagcgcca tcccttatac cttcggtcag     300
ggcactaaag tggaaatcaa a                                                321

<210> SEQ ID NO 303
<211> LENGTH: 116
<212> TYPE: PRT
<213> ORGANISM: Artificial Sequence
<220> FEATURE:
<223> OTHER INFORMATION: CK1 Heavy Chain Variable Region

<400> SEQUENCE: 303

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Ala Met Thr Trp Val Arg Gln Ala Pro Gly Lys Gly Leu Glu Trp Val
        35                  40                  45

Ser Ser Met Ser Gly Thr Gly Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Ala Tyr Gly Phe Asp His Trp Gly Gln Gly Thr Leu Val
            100                 105                 110

Thr Val Ser Ser
        115
```

<210> SEQ ID NO 304
<211> LENGTH: 107
<212> TYPE: PRT
<213> ORGANISM: Artificial Sequence
<220> FEATURE:
<223> OTHER INFORMATION: CK1 Light Chain Variable Region

<400> SEQUENCE: 304

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Gly Asn Tyr
            20                  25                  30

Leu Asn Trp Tyr Gln Gln Lys Pro Gly Gln Ala Pro Arg Leu Leu Ile
        35                  40                  45

Tyr Asp Ala Ser Asn Leu Glu Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Ser Ser Ala Ile Pro Tyr
                85                  90                  95

Thr Phe Gly Gln Gly Thr Lys Val Glu Ile Lys
            100                 105
```

<210> SEQ ID NO 305
<211> LENGTH: 348
<212> TYPE: DNA
<213> ORGANISM: Artificial Sequence
<220> FEATURE:
<223> OTHER INFORMATION: CK2 Heavy Chain Variable Region

<400> SEQUENCE: 305

```
gaagtgcagc tgctggaaag tggaggtgga ctggtgcagc ctggcggcag cctgcgcctg      60
agctgtgccg ccagcggatt caccttcagc agctatggca tgcattgggt tcgccaagca     120
cctggcaaag gcctggaatg ggtgagcgcc atcagcggca gcggcaccag catctattat     180
gccgatagcg tgaaaggccg ctttaccatc agccgcgata acagcaaaaa caccctgtat     240
ctgcagatga acagcctgcg cgccgaggac accgcagtct actactgtgc ccgcggcggc     300
accgcctttg attattgggg acaaggtact ctggtgaccg tgagcagc                  348
```

<210> SEQ ID NO 306
<211> LENGTH: 321
<212> TYPE: DNA
<213> ORGANISM: Artificial Sequence
<220> FEATURE:
<223> OTHER INFORMATION: CK2 Light Chain Variable Region

<400> SEQUENCE: 306
gaaatcgtgc tgacccagag ccctggcacc ctgagcctga gccctggcga acgcgcaaca      60
ctgtcatgcc gcgccagcca gagatcagac aactatctgg cctggtatca gcagaaacca     120
ggtcaggctc cacgtctgct gatctatgat gccagcaacc gcgccaccgg catccctgat     180
cgcttctcag gatctggaag cggtaccgat tttaccctga ccatcagccg cctggaacct     240
gaggactttg ccgtgtatta ttgtcagcag agctatagca cccctttttac cttcggtcag     300 ggcactaaag tggaaaccaa a                                                321

<210> SEQ ID NO 307
<211> LENGTH: 116
<212> TYPE: PRT
<213> ORGANISM: Artificial Sequence
<220> FEATURE:
<223> OTHER INFORMATION: CK2 Heavy Chain Variable Region

<400> SEQUENCE: 307

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ser Ala Ile Ser Gly Ser Gly Thr Ser Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Thr Ala Phe Asp Tyr Trp Gly Gln Gly Thr Leu Val
            100                 105                 110

Thr Val Ser Ser
        115

<210> SEQ ID NO 308
<211> LENGTH: 107
<212> TYPE: PRT
<213> ORGANISM: Artificial Sequence
<220> FEATURE:
<223> OTHER INFORMATION: CK2 Light Chain Variable Region

<400> SEQUENCE: 308

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Arg Ser Asp Asn Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro

-continued

```
65             70             75             80
Glu Asp Phe Ala Val Tyr Tyr Cys Gln Gln Ser Tyr Ser Thr Pro Phe
                85                 90                 95

Thr Phe Gly Gln Gly Thr Lys Val Glu Thr Lys
            100                 105
```

<210> SEQ ID NO 309
<211> LENGTH: 357
<212> TYPE: DNA
<213> ORGANISM: Artificial Sequence
<220> FEATURE:
<223> OTHER INFORMATION: CK3 Heavy Chain Variable Region

<400> SEQUENCE: 309

```
cgagtgcagc tgctggaaag tggaggtgga ctggtgcagc ctggcggcag cctgcgcctg    60
agctgtgccg ccagcggatt caccttcagc agctatgcca tcagctgggt tcgccaagca   120
cctggcaaag gcctggaatg ggtgagcgcc accagcggca gcggccgcgc cacctattat   180
gccgatagcg tgaaaggccg ctttaccatc agccgcgata acagcaaaaa caccctgtat   240
ctgcagatga cagcctgcg cgccgaggac accgcagtct actactgtgc gcgcgatacc   300
tggtgggaag ctatttttga tctgtgggga caaggtactc tggtgaccgt gagcagc       357
```

<210> SEQ ID NO 310
<211> LENGTH: 318
<212> TYPE: DNA
<213> ORGANISM: Artificial Sequence
<220> FEATURE:
<223> OTHER INFORMATION: CK3 Light Chain Variable Region

<400> SEQUENCE: 310

```
gaaatcgtgc tgacccagag ccctggcacc ctgagcctga ccctggcga acgcgcaaca    60 ctgtcatgcc aggccagcca tatcagcacc catctgaact ggtatcagca gaaaccaggt   120
caggctccac gtctgctgat ctatggcgcc agcagccgcg ccaccggcat ccctgatcgc   180
ttctcaggat ctggaagcgg taccgatttt accctgacca tcagccgcct ggaacctgag   240
gactttgccg tgtattattg tcagcagtat aacacctatc tcctaccttt cggtcagggc   300
actaaagtgg aaatcaaa                                                   318
```

<210> SEQ ID NO 311
<211> LENGTH: 119
<212> TYPE: PRT
<213> ORGANISM: Artificial Sequence
<220> FEATURE:
<223> OTHER INFORMATION: CK3 Heavy Chain Variable Region

<400> SEQUENCE: 311

```
Arg Val Gln Leu Leu Glu Ser Gly Gly Gly Leu Val Gln Pro Gly Gly
1               5                  10                 15

Ser Leu Arg Leu Ser Cys Ala Ala Ser Gly Phe Thr Phe Ser Ser Tyr
            20                 25                 30

Ala Ile Ser Trp Val Arg Gln Ala Pro Gly Lys Gly Leu Glu Trp Val
        35                 40                 45

Ser Ala Thr Ser Gly Ser Gly Arg Ala Thr Tyr Tyr Ala Asp Ser Val
    50                 55                 60

Lys Gly Arg Phe Thr Ile Ser Arg Asp Asn Ser Lys Asn Thr Leu Tyr
65                 70                 75                 80

Leu Gln Met Asn Ser Leu Arg Ala Glu Asp Thr Ala Val Tyr Tyr Cys
            85                 90                 95
```

```
Ala Arg Asp Thr Trp Trp Glu Gly Tyr Phe Asp Leu Trp Gly Gln Gly
            100                 105                 110

Thr Leu Val Thr Val Ser Ser
        115
```

<210> SEQ ID NO 312
<211> LENGTH: 106
<212> TYPE: PRT
<213> ORGANISM: Artificial Sequence
<220> FEATURE:
<223> OTHER INFORMATION: CK3 Light Chain Variable Region

<400> SEQUENCE: 312

```
Glu Ile Val Leu Thr Gln Ser Pro Gly Thr Leu Ser Leu Ser Pro Gly
1               5                   10                  15

Glu Arg Ala Thr Leu Ser Cys Gln Ala Ser His Ile Ser Thr His Leu
            20                  25                  30

Asn Trp Tyr Gln Gln Lys Pro Gly Gln Ala Pro Arg Leu Leu Ile Tyr
        35                  40                  45

Gly Ala Ser Ser Arg Ala Thr Gly Ile Pro Asp Arg Phe Ser Gly Ser
    50                  55                  60

Gly Ser Gly Thr Asp Phe Thr Leu Thr Ile Ser Arg Leu Glu Pro Glu
65                  70                  75                  80

Asp Phe Ala Val Tyr Tyr Cys Gln Gln Tyr Asn Thr Tyr Pro Pro Thr
                85                  90                  95

Phe Gly Gln Gly Thr Lys Val Glu Ile Lys
            100                 105
```

<210> SEQ ID NO 313
<211> LENGTH: 348
<212> TYPE: DNA
<213> ORGANISM: Artificial Sequence
<220> FEATURE:
<223> OTHER INFORMATION: CL4 Heavy Chain Variable Region

<400> SEQUENCE: 313

```
cgagtgcagc tgctggaaag tggaggtgga ctggtgcagc ctggcggcag cctgcgcctg      60
agctgtgccg ccagcggatt caccttcggc agcaactata tgagctgggt tcgccaagca     120
cctggcaaag gcctggaatg ggtgagcacc atcagcggca gcggcaccag cacctattat     180
gccgatagct tgaaaggccg ctttaccatc agccgcgata acagcaaaaa caccctgtat     240
ctgcagatga acagcctgcg cgccgaggac accgcagtct actactgtgc cgcgggcatg     300
tggggcatgg atgtgtgggg acaaggtact ctggtgaccg tgagcagc                  348
```

<210> SEQ ID NO 314
<211> LENGTH: 312
<212> TYPE: DNA
<213> ORGANISM: Artificial Sequence
<220> FEATURE:
<223> OTHER INFORMATION: CL4 Light Chain Variable Region

<400> SEQUENCE: 314

```
cagagcgtgc tgacccagcc tcctagcgcc tccggtacac caggacagcg cgtgactatt      60
agctgtaccg gcaaacatcg gcacaccgtg aactggtacc agctactgcc tggaactgca     120
cctaagctgc tgatctatct ggatagcgaa cgccctagcg gcgtacctga tcgctttagc     180
ggtagcaaat caggcaccag cgccagcctg gccatcagcg gccttcgctc cgaagatgaa     240
gccgattatt attgtcagag ctatgatagc agcagcgtgg tgtttggtgg cggtaccaag     300
```

-continued

```
ctgaccgtgc tg                                                    312

<210> SEQ ID NO 315
<211> LENGTH: 116
<212> TYPE: PRT
<213> ORGANISM: Artificial Sequence
<220> FEATURE:
<223> OTHER INFORMATION: CL4 Heavy Chain Variable Region

<400> SEQUENCE: 315

Arg Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Ser Asn
            20                  25                  30

Tyr Met Ser Trp Val Arg Gln Ala Pro Gly Lys Gly Leu Glu Trp Val
        35                  40                  45

Ser Thr Ile Ser Gly Ser Gly Thr Ser Thr Tyr Tyr Ala Asp Ser Leu
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Met Trp Gly Met Asp Val Trp Gly Gln Gly Thr Leu Val
            100                 105                 110

Thr Val Ser Ser
        115

<210> SEQ ID NO 316
<211> LENGTH: 104
<212> TYPE: PRT
<213> ORGANISM: Artificial Sequence
<220> FEATURE:
<223> OTHER INFORMATION: CL4 Light Chain Variable Region

<400> SEQUENCE: 316

Gln Ser Val Leu Thr Gln Pro Pro Ser Ala Ser Gly Thr Pro Gly Gln
1               5                   10                  15

Arg Val Thr Ile Ser Cys Thr Gly Lys His Arg His Thr Val Asn Trp
            20                  25                  30

Tyr Gln Leu Leu Pro Gly Thr Ala Pro Lys Leu Leu Ile Tyr Leu Asp
        35                  40                  45

Ser Glu Arg Pro Ser Gly Val Pro Asp Arg Phe Ser Gly Ser Lys Ser
    50                  55                  60

Gly Thr Ser Ala Ser Leu Ala Ile Ser Gly Leu Arg Ser Glu Asp Glu
65                  70                  75                  80

Ala Asp Tyr Tyr Cys Gln Ser Tyr Asp Ser Ser Val Val Phe Gly
                85                  90                  95

Gly Gly Thr Lys Leu Thr Val Leu
            100

<210> SEQ ID NO 317
<211> LENGTH: 351
<212> TYPE: DNA
<213> ORGANISM: Artificial Sequence
<220> FEATURE:
<223> OTHER INFORMATION: CL5 Heavy Chain Variable Region

<400> SEQUENCE: 317
cgagtgcagc tgctggaaag tggaggtgga ctggtgcagc ctggcggcag cctgcgcctg     60
```

```
agctgtgccg ccagcggatt caccttcagc agctatgcca tgcattgggt tcgccaagca    120
cctggcaaag gcctggaatg ggtgagcagc atcagcggcg gcggctatgg cacctattat    180
gccgatagcg tgaaaggccg ctttaccatc agccgcgata acagcaaaaa caccctgtat    240
ctgcagatga acagcctgcg cgccgaggac accgcagtct actactgtgc ccgcagcacc    300
gtgtgggcct ttgatatctg gggacaaggt actctggtga ccgtgagcag c             351
```

```
<210> SEQ ID NO 318
<211> LENGTH: 321
<212> TYPE: DNA
<213> ORGANISM: Artificial Sequence
<220> FEATURE:
<223> OTHER INFORMATION: CL5 Light Chain Variable Region

<400> SEQUENCE: 318
```

```
cagagcgtgc tgacccagcc tcctagcgcc tccggtacac caggacagcg cgtgactatt     60
agctgtagcg gcaacaacat cggcagcaaa agcgtgcatt ggtaccagca actgcctgga    120
actgcaccta agctgctgat ctatgatgtg agcaaacgcc tagcgagcg tcctgatcgc    180 tttagcggta gcaaatcagg caccagcgcc agtctggcca tcagcgacct tcgctccgaa    240
gatgaagccg attattattg tcagagcttt gatagcagcg gcacctggat ctttggtggc    300
ggtaccaagc tgaccgtgct g                                              321
```

```
<210> SEQ ID NO 319
<211> LENGTH: 117
<212> TYPE: PRT
<213> ORGANISM: Artificial Sequence
<220> FEATURE:
<223> OTHER INFORMATION: CL5 Heavy Chain Variable Region

<400> SEQUENCE: 319
```

```
Arg Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ser Ser Ile Ser Gly Gly Gly Tyr Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Thr Val Trp Ala Phe Asp Ile Trp Gly Gln Gly Thr Leu
            100                 105                 110

Val Thr Val Ser Ser
        115
```

```
<210> SEQ ID NO 320
<211> LENGTH: 107
<212> TYPE: PRT
<213> ORGANISM: Artificial Sequence
<220> FEATURE:
<223> OTHER INFORMATION: CL5 Light Chain Variable Region

<400> SEQUENCE: 320
```

```
Gln Ser Val Leu Thr Gln Pro Pro Ser Ala Ser Gly Thr Pro Gly Gln
1               5                   10                  15
```

```
Arg Val Thr Ile Ser Cys Ser Gly Asn Asn Ile Gly Ser Lys Ser Val
            20                  25                  30

His Trp Tyr Gln Gln Leu Pro Gly Thr Ala Pro Lys Leu Leu Ile Tyr
        35                  40                  45

Asp Val Ser Lys Arg Pro Ser Glu Arg Pro Asp Arg Phe Ser Gly Ser
    50                  55                  60

Lys Ser Gly Thr Ser Ala Ser Leu Ala Ile Ser Asp Leu Arg Ser Glu
65                  70                  75                  80

Asp Glu Ala Asp Tyr Tyr Cys Gln Ser Phe Asp Ser Ser Gly Thr Trp
                85                  90                  95

Ile Phe Gly Gly Gly Thr Lys Leu Thr Val Leu
            100                 105
```

```
<210> SEQ ID NO 321
<211> LENGTH: 357
<212> TYPE: DNA
<213> ORGANISM: Artificial Sequence
<220> FEATURE:
<223> OTHER INFORMATION: CL6 Heavy Chain Variable Region

<400> SEQUENCE: 321
gaggtgcagc tgttggagtc tggtggaggc ttggtacagc ctggaggttc tcttcgcctc        60
tcctgtgcag cctccggatt cactttcagc agctacggta tgcattgggt cagacaggca       120
ccaggtaagg gactggagtg ggtctctgca attagcggta gcggtggtag cacttactac       180
gcagacagcg tgaagggtcg cttcaccatc tcacgcgaca actccaagaa caccctgtac       240
ctgcagatga acagccttcg cgcagaggac actgccgtgt attactgcgc agtcagtggt       300
gcaggtcgtg gtttcttcga ctactgggga caaggtactc tggtcactgt ctcctca         357
```

```
<210> SEQ ID NO 322
<211> LENGTH: 327
<212> TYPE: DNA
<213> ORGANISM: Artificial Sequence
<220> FEATURE:
<223> OTHER INFORMATION: CL6 Light Chain Variable Region

<400> SEQUENCE: 322
cagtctgtgc tgactcagcc accttcagca tctggtactc caggtcagcg cgtcaccatc        60
agctgcagcg gtagcagcag caacattggt agcaactacg tgtactggta tcagcaactc       120
ccaggcaccg ctcctaagct cctgatttac gaggacaaca gcgtcctag tggtgtgcct        180 gatcgctttt ctgggtccaa gtctggcacc tcagcctctc tggctatcag tggacttcgc       240
tccgaggacg aggctgacta ttactgcagc agctacacta gcagcagcac tgtgatcttc       300
ggcggtggga ccaaactgac cgtccta                                           327
```

```
<210> SEQ ID NO 323
<211> LENGTH: 119
<212> TYPE: PRT
<213> ORGANISM: Artificial Sequence
<220> FEATURE:
<223> OTHER INFORMATION: CL6 Heavy Chain Variable Region

<400> SEQUENCE: 323

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30
```

```
Gly Met His Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Val Ser Gly Ala Gly Arg Gly Phe Phe Asp Tyr Trp Gly Gln Gly
                100                 105                 110

Thr Leu Val Thr Val Ser Ser
        115
```

<210> SEQ ID NO 324
<211> LENGTH: 109
<212> TYPE: PRT
<213> ORGANISM: Artificial Sequence
<220> FEATURE:
<223> OTHER INFORMATION: CL6 Light Chain Variable Region

<400> SEQUENCE: 324

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
                20                  25                  30

Tyr Val Tyr Trp Tyr Gln Gln Leu Pro Gly Thr Ala Pro Lys Leu Leu
        35                  40                  45

Ile Tyr Glu Asp Asn Lys Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ser Ser Tyr Thr Ser Ser Ser
                85                  90                  95

Thr Val Ile Phe Gly Gly Gly Thr Lys Leu Thr Val Leu
                100                 105
```

<210> SEQ ID NO 325
<211> LENGTH: 351
<212> TYPE: DNA
<213> ORGANISM: Artificial Sequence
<220> FEATURE:
<223> OTHER INFORMATION: CL7 Heavy Chain Variable Region

<400> SEQUENCE: 325

```
gaggtgcagc tgttggagtc tggtggaggc ttggtacagc ctggaggttc tcttcgcctc    60
tcctgtgcag cctccggatt cactttcagc cgctacgcaa tgagctgggt cagacaggca   120
ccaggtaagg gactggagtg ggtctctgca attagcggta gcggtggtag cacttactac   180
gcagacagcg tgaagggtcg cttcaccatc tcacgcgaca actccaagaa caccctgtac   240
ctgcagatga acagccttcg cgcagaggac actgccgtgt attactgcgc acgtagcagc   300
cagggtatct tcgacatctg gggacaaggt actctggtca ctgtctcctc a            351
```

<210> SEQ ID NO 326
<211> LENGTH: 324
<212> TYPE: DNA
<213> ORGANISM: Artificial Sequence
<220> FEATURE:
<223> OTHER INFORMATION: CL7 Light Chain Variable Region -continued

<400> SEQUENCE: 326
cagtctgtgc tgactcagcc accttcagca tctggtactc caggtcagcg cgtcaccatc      60
agctgcagtg gtaacaatat cggtactaga cgcgtgcatt ggtatcagca actcccagac     120
accgctccta agctcctgat ttacagtaag aacaaccgtc ctagtggtgt gcctgatcgc     180
ttttctgggt ccaagtctgg cacctcagcc tctctggcta tcagtggact tcgctccgag     240
gacgaggctg actattactg cgcagcatgg gacgacagcc tgagcggtcc tgtgttcggc     300
ggtgggacca aactgaccgt ccta                                           324

<210> SEQ ID NO 327
<211> LENGTH: 117
<212> TYPE: PRT
<213> ORGANISM: Artificial Sequence
<220> FEATURE:
<223> OTHER INFORMATION: CL7 Heavy Chain Variable Region

<400> SEQUENCE: 327

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Ser Gln Gly Ile Phe Asp Ile Trp Gly Gln Gly Thr Leu
            100                 105                 110

Val Thr Val Ser Ser
        115

<210> SEQ ID NO 328
<211> LENGTH: 108
<212> TYPE: PRT
<213> ORGANISM: Artificial Sequence
<220> FEATURE:
<223> OTHER INFORMATION: CL7 Light Chain Variable Region

<400> SEQUENCE: 328

Gln Ser Val Leu Thr Gln Pro Pro Ser Ala Ser Gly Thr Pro Gly Gln
1               5                   10                  15

Arg Val Thr Ile Ser Cys Ser Gly Asn Asn Ile Gly Thr Arg Arg Val
            20                  25                  30

His Trp Tyr Gln Gln Leu Pro Asp Thr Ala Pro Lys Leu Leu Ile Tyr
        35                  40                  45

Ser Lys Asn Asn Arg Pro Ser Gly Val Pro Asp Arg Phe Ser Gly Ser
    50                  55                  60

Lys Ser Gly Thr Ser Ala Ser Leu Ala Ile Ser Gly Leu Arg Ser Glu
65                  70                  75                  80

Asp Glu Ala Asp Tyr Tyr Cys Ala Ala Trp Asp Asp Ser Leu Ser Gly
                85                  90                  95

Pro Val Phe Gly Gly Gly Thr Lys Leu Thr Val Leu
            100                 105

-continued

<210> SEQ ID NO 329
<211> LENGTH: 354
<212> TYPE: DNA
<213> ORGANISM: Artificial Sequence
<220> FEATURE:
<223> OTHER INFORMATION: CL8 Heavy Chain Variable Region

<400> SEQUENCE: 329
gaggtgcagc tgttggagtc tggtggaggc ttggtacagc ctggaggttc tcttcgcctc      60
tcctgtgcag cctccggatt cactttcagc agctacgcaa tgagctgggt cagacaggca     120
ccaggtaagg gactggagtg ggtctctgca attagcggta gcggtggtag cacttactac     180
gcagacagcg tgaagggtcg cttcaccatc tcacgcaaca actccaagaa caccctgtac     240
ctgcagatga acagccttcg cgcagaggac actgccgtgt attactgcgc acgtagcggt     300
cgttacgcag acttgacatc tggggggacaa ggtactctgg tcactgtctc ctca          354

<210> SEQ ID NO 330
<211> LENGTH: 327
<212> TYPE: DNA
<213> ORGANISM: Artificial Sequence
<220> FEATURE:
<223> OTHER INFORMATION: CL8 Light Chain Variable Region

<400> SEQUENCE: 330
cagtctgtgc tgactcagcc accttcagca tctggtactc caggtcagcg cgtcaccatc      60
agctgcagcg gtagcaacag caacatcggt aacaactacg tgagctggta tcagcaactc     120
ccagacaccc ctcctaagct cctgatttac gacaacaaca gcgtcctag tggtgtgcct     180 gatcgctttt ctgggtccaa gtctggcacc tcagcctctc tggctatcag tggacttcgc     240
tccgaggacg aggctgacta ttactgcagc agctacacta gcagcagcac tgtgatgttc     300
ggcggtggga ccaaactgac cgtccta                                         327

<210> SEQ ID NO 331
<211> LENGTH: 118
<212> TYPE: PRT
<213> ORGANISM: Artificial Sequence
<220> FEATURE:
<223> OTHER INFORMATION: CL8 Heavy Chain Variable Region

<400> SEQUENCE: 331

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asn Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Gly Arg Tyr Ala Asp Leu Thr Ser Gly Gly Gln Gly Thr
            100                 105                 110

Leu Val Thr Val Ser Ser
        115

-continued

```
<210> SEQ ID NO 332
<211> LENGTH: 109
<212> TYPE: PRT
<213> ORGANISM: Artificial Sequence
<220> FEATURE:
<223> OTHER INFORMATION: CL8 Light Chain Variable Region

<400> SEQUENCE: 332

Gln Ser Val Leu Thr Gln Pro Pro Ser Ala Ser Gly Thr Pro Gly Gln
1               5                   10                  15

Arg Val Thr Ile Ser Cys Ser Gly Ser Asn Ser Asn Ile Gly Asn Asn
            20                  25                  30

Tyr Val Ser Trp Tyr Gln Gln Leu Pro Asp Thr Pro Pro Lys Leu Leu
        35                  40                  45

Ile Tyr Asp Asn Asn Lys Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ser Ser Tyr Thr Ser Ser Ser
                85                  90                  95

Thr Val Met Phe Gly Gly Gly Thr Lys Leu Thr Val Leu
            100                 105
```

```
<210> SEQ ID NO 333
<211> LENGTH: 351
<212> TYPE: DNA
<213> ORGANISM: Artificial Sequence
<220> FEATURE:
<223> OTHER INFORMATION: CL9 Heavy Chain Variable Region

<400> SEQUENCE: 333
gaggtgcagc tgttggagtc tggtggaggc ttggtacagc ctggaggttc tcttcgcctc    60
tcctgtgcag cctccggatt cactttcagc agctactact ggagctgggt cagacaggca   120
ccaggtaagg gactggagtg ggtctctgca attagcggta cggtggtag cacttactac     180 gcagacagcg tgaagggtcg cttcaccatc tcacgcgaca actccaagaa caccctgtac   240
ctgcagatga acagccttcg cgcagaggac actgccgtgt attactgcgc acgtatcgac   300
gtgtacggtt cgacatctg gggacaaggt actctggtca ctgtctcctc a             351
```

```
<210> SEQ ID NO 334
<211> LENGTH: 327
<212> TYPE: DNA
<213> ORGANISM: Artificial Sequence
<220> FEATURE:
<223> OTHER INFORMATION: CL9 Light Chain Variable Region

<400> SEQUENCE: 334
cagtctgtgc tgactcagcc accttcagca tctggtactc caggtcagcg cgtcaccatc    60
agctgcagcg gtagcactag caacatcggt actaactacg tgtactggta tcagcaactc   120
ccaggcaccg ctcctaagct cctgatttac gacaacaaca accgtcctag tggtgtgcct   180
gatcgctttt ctgggtccaa gtctggcacc tcagcctctc tggctatcag tggacttcgc   240
tccgaggacg aggctgacta ttactgccag acttgggaca gcagcactga cgtagtgttc   300
ggcggtggga ccaaactgac cgtccta                                       327
```

```
<210> SEQ ID NO 335
<211> LENGTH: 117
<212> TYPE: PRT
<213> ORGANISM: Artificial Sequence
```

<220> FEATURE:
<223> OTHER INFORMATION: CL9 Heavy Chain Variable Region

<400> SEQUENCE: 335

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Tyr Trp Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Asp Val Tyr Gly Phe Asp Ile Trp Gly Gln Gly Thr Leu
            100                 105                 110

Val Thr Val Ser Ser
        115

<210> SEQ ID NO 336
<211> LENGTH: 109
<212> TYPE: PRT
<213> ORGANISM: Artificial Sequence
<220> FEATURE:
<223> OTHER INFORMATION: CL9 Light Chain Variable Region

<400> SEQUENCE: 336

Gln Ser Val Leu Thr Gln Pro Pro Ser Ala Ser Gly Thr Pro Gly Gln
1               5                   10                  15

Arg Val Thr Ile Ser Cys Ser Gly Ser Thr Ser Asn Ile Gly Thr Asn
            20                  25                  30

Tyr Val Tyr Trp Tyr Gln Gln Leu Pro Gly Thr Ala Pro Lys Leu Leu
        35                  40                  45

Ile Tyr Asp Asn Asn Asn Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gln Thr Trp Asp Ser Ser Thr
                85                  90                  95

Asp Val Val Phe Gly Gly Gly Thr Lys Leu Thr Val Leu
            100                 105

<210> SEQ ID NO 337
<211> LENGTH: 348
<212> TYPE: DNA
<213> ORGANISM: Artificial Sequence
<220> FEATURE:
<223> OTHER INFORMATION: CL10 Heavy Chain Variable Region

<400> SEQUENCE: 337
gaggtgcagc tgttggagtc tggtggaggc ttggtacagc ctggaggttc tcttcgcctc      60
tcctgtgcag cctccggatt cactttcagc agctacggta tgcattgggt cagacaggca     120
ccaggtaagg gactggagtg ggtctctgca attagcggta gcggtggtag cacttactac     180
gcagacagcg tgaagggtcg cttcaccatc tcacgcgaca actccaagaa cacccctgtac    240 ctgcagatga acagccttcg cgcagaggac actgccgtgt attactgcgc aagcggttac     300

-continued

```
ggtctgatgg acgtgtgggg acaaggtact ctggtcactg tctcctca              348
```

<210> SEQ ID NO 338
<211> LENGTH: 324
<212> TYPE: DNA
<213> ORGANISM: Artificial Sequence
<220> FEATURE:
<223> OTHER INFORMATION: CL10 Light Chain Variable Region

<400> SEQUENCE: 338

```
tctgtgctga ctcagccacc ttcagcatct ggtactccag gtcagcgcgt caccatcagc    60
tgcactcgta gcagcggtat catcgcaagc aactacgtgc agtggtatca gcaactccca   120
ggcaccgctc ctaagctcct gatttaccgc aacaaccagc gccctagtgg tgtgcctgat   180
cgcttttctg gtccaagtc tggcacctca gcctctctgg ctatcagtgg acttcgctcc   240
gaggacgagg ctgactatta ctgcagcagc tacgcaggta caacaacct ggtgttcggc   300 ggtgggacca aactgaccgt ccta                                         324
```

<210> SEQ ID NO 339
<211> LENGTH: 116
<212> TYPE: PRT
<213> ORGANISM: Artificial Sequence
<220> FEATURE:
<223> OTHER INFORMATION: CL10 Heavy Chain Variable Region

<400> SEQUENCE: 339

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Gly Tyr Gly Leu Met Asp Val Trp Gly Gln Gly Thr Leu Val
            100                 105                 110

Thr Val Ser Ser
        115
```

<210> SEQ ID NO 340
<211> LENGTH: 109
<212> TYPE: PRT
<213> ORGANISM: Artificial Sequence
<220> FEATURE:
<223> OTHER INFORMATION: CL10 Light Chain Variable Region

<400> SEQUENCE: 340

```
Gln Ser Val Leu Thr Gln Pro Pro Ser Ala Ser Gly Thr Pro Gly Gln
1               5                   10                  15

Arg Val Thr Ile Ser Cys Thr Arg Ser Ser Gly Ile Ile Ala Ser Asn
            20                  25                  30

Tyr Val Gln Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ser
```

-continued

```
          50               55               60
Gly Ser Lys Ser Gly Thr Ser Ala Ser Leu Ala Ile Ser Gly Leu Arg
65                   70               75               80

Ser Glu Asp Glu Ala Asp Tyr Tyr Cys Ser Ser Tyr Ala Gly Asn Asn
                    85               90               95

Asn Leu Val Phe Gly Gly Gly Thr Lys Leu Thr Val Leu
            100             105

<210> SEQ ID NO 341
<211> LENGTH: 348
<212> TYPE: DNA
<213> ORGANISM: Artificial Sequence
<220> FEATURE:
<223> OTHER INFORMATION: SK11 Heavy Chain Variable Region

<400> SEQUENCE: 341
cgagtgcagc tgctggaaag tggaggtgga ctggtgcagc ctggcggcag cctgcgcctg      60
agctgtgccg ccagcggatt caccttcagc acctatggca tgcattgggt tcgccaagca     120
cctggcaaag gcctggaatg ggtgagcgcc atcagcggca gcggcggcag cacctattat     180
gccgatagcg tgaaaggccg ctttaccatc agccgcgata acagcaaaaa caccctgtat     240
ctgcagatga acagcctgcg cgccgaggac accgcagtct actactgtgc cgcggcctg      300 agcggccttg attattgggg acaaggtact ctggtgaccg tgagcagc                  348

<210> SEQ ID NO 342
<211> LENGTH: 321
<212> TYPE: DNA
<213> ORGANISM: Artificial Sequence
<220> FEATURE:
<223> OTHER INFORMATION: SK11 Light Chain Variable Region

<400> SEQUENCE: 342
gaaatcgtgc tgacccagag ccctggcacc ctgagcctga ccctggcga acgcgcaaca      60 ctgtcatgcc gctccagcca gggcatcacc aactatctgg cctggtatca gcagaaacca     120
ggtcaggctc cacgtctgct gatctatgat gccagcaacc gcgccaccgg catccctgat     180
cgcttctcag gatctggaag cggtaccgat tttaccctga ccatcagccg cctggaacct     240
gaggactttg ccgtgtatta ttgtcagcag agctatagca cccctctgac cttcggtcag     300
ggcactaaag tggaaatcaa a                                               321

<210> SEQ ID NO 343
<211> LENGTH: 116
<212> TYPE: PRT
<213> ORGANISM: Artificial Sequence
<220> FEATURE:
<223> OTHER INFORMATION: SK11 Heavy Chain Variable Region

<400> SEQUENCE: 343

Arg Val Gln Leu Leu Glu Ser Gly Gly Gly Leu Val Gln Pro Gly Gly
1               5               10              15

Ser Leu Arg Leu Ser Cys Ala Ala Ser Gly Phe Thr Phe Ser Thr Tyr
            20              25              30

Gly Met His Trp Val Arg Gln Ala Pro Gly Lys Gly Leu Glu Trp Val
        35              40              45

Ser Ala Ile Ser Gly Ser Gly Gly Ser Thr Tyr Tyr Ala Asp Ser Val
    50              55              60

Lys Gly Arg Phe Thr Ile Ser Arg Asp Asn Ser Lys Asn Thr Leu Tyr
65              70              75              80
```

```
Leu Gln Met Asn Ser Leu Arg Ala Glu Asp Thr Ala Val Tyr Tyr Cys
                85                  90                  95

Ala Arg Gly Leu Ser Gly Leu Asp Tyr Trp Gly Gln Gly Thr Leu Val
            100                 105                 110

Thr Val Ser Ser
        115
```

<210> SEQ ID NO 344
<211> LENGTH: 107
<212> TYPE: PRT
<213> ORGANISM: Artificial Sequence
<220> FEATURE:
<223> OTHER INFORMATION: SK11 Light Chain Variable Region

<400> SEQUENCE: 344

```
Glu Ile Val Leu Thr Gln Ser Pro Gly Thr Leu Ser Leu Ser Pro Gly
1               5                   10                  15

Glu Arg Ala Thr Leu Ser Cys Arg Ser Ser Gln Gly Ile Thr Asn Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Ser Tyr Ser Thr Pro Leu
            85                  90                  95

Thr Phe Gly Gln Gly Thr Lys Val Glu Ile Lys
            100                 105
```

<210> SEQ ID NO 345
<211> LENGTH: 348
<212> TYPE: DNA
<213> ORGANISM: Artificial Sequence
<220> FEATURE:
<223> OTHER INFORMATION: SK12 Heavy Chain Variable Region

<400> SEQUENCE: 345

```
cgagtgcagc tgctggaaag tggaggtgga ctggtgcagc ctggcggcag cctgcgcctg      60
agctgtgccg ccagcggatt caccttcagc agctatgcca tgcattgggt tcgccaagca     120
cctggcaaag gcctggaatg ggtgagcgcc atcagcggca gcggcggcga tacctatcat     180
gccgatagcg tgaaaggccg ctttaccatc agccgcgata acagcaaaaa caccctgtat     240
ctgcagatga acagcctgcg cgccgaggac accgcagtct actactgtac ccgcggcctg     300
agcggctttg attattgggg acaaggtact ctggtgaccg tgagcagc                  348
```

<210> SEQ ID NO 346
<211> LENGTH: 321
<212> TYPE: DNA
<213> ORGANISM: Artificial Sequence
<220> FEATURE:
<223> OTHER INFORMATION: SK12 Light Chain Variable Region

<400> SEQUENCE: 346

```
gaaatcgtgc tgacccagag ccctggcacc ctgagcctga gccctggcga acgcgcaaca      60
ctgtcatgcc gcgccagcca gagcatcagc agctatctga actggtatca gcagaaacca     120
ggtcaggctc acgtctgct gatctatgat gccagcaacc gcgccctgg catccctgat      180
```
cgcttctcag gatctggaag cggtaccgat tttaccctga ccatcagccg cctggaacct          240
gaggactttg ccgtgtatta ttgtcagcag agctatagca tccctatcac cttcggtcag          300
ggcactaaag tggaaatcaa a          321

<210> SEQ ID NO 347
<211> LENGTH: 116
<212> TYPE: PRT
<213> ORGANISM: Artificial Sequence
<220> FEATURE:
<223> OTHER INFORMATION: SK12 Heavy Chain Variable Region

<400> SEQUENCE: 347

Arg Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ser Ala Ile Ser Gly Ser Gly Gly Asp Thr Tyr His Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Gly Leu Ser Gly Phe Asp Tyr Trp Gly Gln Gly Thr Leu Val
            100                 105                 110

Thr Val Ser Ser
        115

<210> SEQ ID NO 348
<211> LENGTH: 110
<212> TYPE: PRT
<213> ORGANISM: Artificial Sequence
<220> FEATURE:
<223> OTHER INFORMATION: SK12 Light Chain Variable Region

<400> SEQUENCE: 348

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Ser Ser Tyr
            20                  25                  30

Leu Asn Trp Tyr Gln Gln Lys Pro Gly Gln Ala Pro Arg Leu Leu Ile
        35                  40                  45

Tyr Asp Ala Ser Asn Arg Ala Pro Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Ser Tyr Ser Ile Pro Ile
                85                  90                  95

Thr Phe Gly Gln Gly Thr Lys Val Glu Ile Lys Phe Ser Asp
            100                 105                 110

<210> SEQ ID NO 349
<211> LENGTH: 348
<212> TYPE: DNA
<213> ORGANISM: Artificial Sequence
<220> FEATURE:
<223> OTHER INFORMATION: SK13 Heavy Chain Variable Region -continued

<400> SEQUENCE: 349
cgagtgcagc tgctggaaag tggaggtgga ctggtgcagc ctggcggcag cctgcgcctg     60
agctgtgccg ccagcggatt caccttcagc gattatgcca tgagctgggt tcgccaagca    120
cctggcaaag gcctggaatg ggtgagcagc atcagcagca gcagcagcta tatctactat    180
accgatagcg tgaaaggccg ctttaccatc agccgcgata acagcaaaaa caccctgtat    240
ctgcagatga acagcctgcg cgccgaggac accgcagtct actactgtgc cgcggcggc     300 tatggctttg attattgggg acaaggtacc ctggtgaccg tgagcagc                 348

<210> SEQ ID NO 350
<211> LENGTH: 321
<212> TYPE: DNA
<213> ORGANISM: Artificial Sequence
<220> FEATURE:
<223> OTHER INFORMATION: SK13 Light Chain Variable Region

<400> SEQUENCE: 350
gaaatcgtgc tgacccagag ccctggcacc ctgagcctga ccctggcga acgcgcaaca     60 ctgtcatgcc gcgccagcca gagcatcagc agctatctga actggtatca gcagaaacca    120
ggtcaggctc cacgtctgct gatctatagc gccagcagcc gccacacggg catcccccgat   180 cgcttctcag gatctggaag cggtaccgat tttaccctga ccatcagccg cctggaacct    240
gaggactttg ccgtgtatta ttgtcagcag tatgatgatc tgccttttac cttcggtcag    300
ggcactaaag tggaaatcaa a                                                321

<210> SEQ ID NO 351
<211> LENGTH: 116
<212> TYPE: PRT
<213> ORGANISM: Artificial Sequence
<220> FEATURE:
<223> OTHER INFORMATION: SK13 Heavy Chain Variable Region

<400> SEQUENCE: 351

Arg Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Val Arg Gln Ala Pro Gly Lys Gly Leu Glu Trp Val
        35                  40                  45

Ser Ser Ile Ser Ser Ser Ser Ser Tyr Ile Tyr Tyr Thr Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Tyr Gly Phe Asp Tyr Trp Gly Gln Gly Thr Leu Val
            100                 105                 110

Thr Val Ser Ser
        115

<210> SEQ ID NO 352
<211> LENGTH: 107
<212> TYPE: PRT
<213> ORGANISM: Artificial Sequence
<220> FEATURE:
<223> OTHER INFORMATION: SK13 Light Chain Variable Region

<400> SEQUENCE: 352

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Ser Ser Tyr
            20                  25                  30

Leu Asn Trp Tyr Gln Gln Lys Pro Gly Gln Ala Pro Arg Leu Leu Ile
        35                  40                  45

Tyr Ser Ala Ser Ser Arg Pro Gln Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Asp Asp Leu Pro Phe
                85                  90                  95

Thr Phe Gly Gln Gly Thr Lys Val Glu Ile Lys
            100                 105
```

<210> SEQ ID NO 353
<211> LENGTH: 346
<212> TYPE: DNA
<213> ORGANISM: Artificial Sequence
<220> FEATURE:
<223> OTHER INFORMATION: SK14 Heavy Chain Variable Region

<400> SEQUENCE: 353

```
gaagtgcagc tgctggaaag tggaggtgga ctggtgcagc ctggcggcag cctgcgcctg      60
agctgtgccg ccagcggatt caccttcagc aactttgcga tcgcctgggt tcgccaagca     120
cctggcaaag gcctggaatg ggtgagcgcc atcagcggcc gcggcaccag cacctattat     180
gccgatagcg tgaaaggccg ctttaccatc agccgcgata acagcaaaaa caccctgtat     240
ctgcagatga acagcctgcg cgccgaggac accgcagtct actactgtgc cgcggcgtg      300 agcggctttg atagctgggg acaaggtact ctggtgaccg tgagca                    346
```

<210> SEQ ID NO 354
<211> LENGTH: 321
<212> TYPE: DNA
<213> ORGANISM: Artificial Sequence
<220> FEATURE:
<223> OTHER INFORMATION: SK14 Light Chain Variable Region

<400> SEQUENCE: 354

```
gaaatcgtgc tgacccagag ccctggcacc ctgagcctga gccctggcga acgcgcaaca      60
ctgtcatgcc gcgccagcca gagcatcagc agccatctgg cctggtatca gcagaaacca     120
ggtcaggctc cacgtctgct gatctatgat accagcaacc gcgccaccgg catccctgat     180
cgcttctcag gatctgggag cggtaccgat tttaccctga ccatcagccg cctggaacct     240
gaggactttg ccgtgtacta ttgtcagcag agctatagca ccccttttac cttcggtcag     300
ggcactaaag tggaaatcaa a                                               321
```

<210> SEQ ID NO 355
<211> LENGTH: 116
<212> TYPE: PRT
<213> ORGANISM: Artificial Sequence
<220> FEATURE:
<223> OTHER INFORMATION: SK14 Heavy Chain Variable Region

<400> SEQUENCE: 355

```
Glu Val Gln Leu Leu Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Asn Phe
        20                  25                  30

Ala Ile Ala Trp Val Arg Gln Ala Pro Gly Lys Gly Leu Glu Trp Val
        35                  40                  45

Ser Ala Ile Ser Gly Arg Gly Thr Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Val Ser Gly Phe Asp Ser Trp Gly Gln Gly Thr Leu Val
            100                 105                 110

Thr Val Ser Ser
        115

<210> SEQ ID NO 356
<211> LENGTH: 107
<212> TYPE: PRT
<213> ORGANISM: Artificial Sequence
<220> FEATURE:
<223> OTHER INFORMATION: SK14 Light Chain Variable Region

<400> SEQUENCE: 356

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Ser Ser His
        20                  25                  30

Leu Ala Trp Tyr Gln Gln Lys Pro Gly Gln Ala Pro Arg Leu Leu Ile
        35                  40                  45

Tyr Asp Thr Ser Asn Arg Ala Thr Gly Ile Pro Asp Arg Phe Ser Gly
        50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Ser Tyr Ser Thr Pro Phe
                85                  90                  95

Thr Phe Gly Gln Gly Thr Lys Val Glu Ile Lys
            100                 105

<210> SEQ ID NO 357
<211> LENGTH: 349
<212> TYPE: DNA
<213> ORGANISM: Artificial Sequence
<220> FEATURE:
<223> OTHER INFORMATION: SK15 Heavy Chain Variable Region

<400> SEQUENCE: 357
cgagtgcagc tgctggaaag tggaggtgga ctggtgcagc ctggcggcag cctgcgcctg      60
agctgtgccg ccagcggatt caccttcagc agctatgcca tgcattgggt tcgccaagca     120
cctggcaaag gcctggaatg ggtgagcgcc atcaacggca cgggcggcag cacctattat     180
gccgatagcg tgaaaggccg ctttaccatc agccgcgata cagcaaaaa caccctgtat      240 ctgcagacga cagcctgcg cgccgaggac accgcagtct actactgtgc ccgcggcctg      300
cagggctttg attattgggg acaaggtact ctggtgaccg tgagcagca                 349

<210> SEQ ID NO 358
<211> LENGTH: 321
<212> TYPE: DNA
<213> ORGANISM: Artificial Sequence
```

```
<220> FEATURE:
<223> OTHER INFORMATION: SK15 Light Chain Variable Region

<400> SEQUENCE: 358
gaaatcgtgc tgacccagag ccctggcacc ctgagcctga gccctggcga acgcgcaaca     60
ctgtcatgcc aggccagcca ggatatcacc aactatctga actggtatca gcagaaacca    120
ggtcaggctc cacgtctgct gatctatgat gccagcagcc tggaaaccgg catccctgat    180
cgtttctcag gatctggaag cggtaccgat tttaccctga ccatcagccg cctggaacct    240
gaggactttg ccgtgtatta ttgtcagcag agctatagca ccctatcac cttcggtcag     300 ggcactaaag tggaaatcaa a                                             321

<210> SEQ ID NO 359
<211> LENGTH: 116
<212> TYPE: PRT
<213> ORGANISM: Artificial Sequence
<220> FEATURE:
<223> OTHER INFORMATION: SK15 Heavy Chain Variable Region

<400> SEQUENCE: 359

Arg Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ser Ala Ile Asn Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Thr Asn Ser Leu Arg Ala Glu Asp Thr Ala Val Tyr Tyr Cys
                85                  90                  95

Ala Arg Gly Leu Gln Gly Phe Asp Tyr Trp Gly Gln Gly Thr Leu Val
            100                 105                 110

Thr Val Ser Ser
        115

<210> SEQ ID NO 360
<211> LENGTH: 107
<212> TYPE: PRT
<213> ORGANISM: Artificial Sequence
<220> FEATURE:
<223> OTHER INFORMATION: SK15 Light Chain Variable Region

<400> SEQUENCE: 360

Glu Ile Val Leu Thr Gln Ser Pro Gly Thr Leu Ser Leu Ser Pro Gly
1               5                   10                  15

Glu Arg Ala Thr Leu Ser Cys Gln Ala Ser Gln Asp Ile Thr Asn Tyr
            20                  25                  30

Leu Asn Trp Tyr Gln Gln Lys Pro Gly Gln Ala Pro Arg Leu Leu Ile
        35                  40                  45

Tyr Asp Ala Ser Ser Leu Glu Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Ser Tyr Ser Thr Pro Ile
                85                  90                  95
```

Thr Phe Gly Gln Gly Thr Lys Val Glu Ile Lys
            100                 105

<210> SEQ ID NO 361
<211> LENGTH: 349
<212> TYPE: DNA
<213> ORGANISM: Artificial Sequence
<220> FEATURE:
<223> OTHER INFORMATION: SK16 Heavy Chain Variable Region

<400> SEQUENCE: 361
cgagtgcagc tgctggaaag tggaggtgga ctggtgcagc ctggcggcag cctgcgcctg      60
agctgtgccg ccagcggatt caccttcagc agctatgcca tgagctgggt tcgccaagca     120
cctggcaaag gcctggaatg ggtgagcgcc atcaacggca gcggcggcag caccctgtat     180
gccgatagcg tgaaaggccg ctttaccatc agccgcgata acagcaaaaa caccctgtat     240
ctgcagatga acagcctgcg cgccgaggac accgcagtct actactgtgc ccgcggcgtg     300
agcggctttg atagctgggg acaaggtact ctggtgaccg tgagcagcg               349

<210> SEQ ID NO 362
<211> LENGTH: 321
<212> TYPE: DNA
<213> ORGANISM: Artificial Sequence
<220> FEATURE:
<223> OTHER INFORMATION: SK16 Light Chain Variable Region

<400> SEQUENCE: 362
gaaatcgtgc tgacccagag ccctggcacc ctgagcctga gccctggcga acgcgcaaca      60
ctgtcatgcc gcatcagcca gagcatcagc agctatctga ctggtatca gcagaaacca     120 ggtcaggctc cacgtctgct gatctatgat gccagcctgc gcgccaccgg catccctgat     180
cgcttctcag gatctggaag cggtaccgat tttaccctga ccatcagccg cctggaacct     240
gaggactttg ccgtgtatta ttgtcagcag agctataaaa ccctatcac cttcggtcag     300 ggcactaaag tggaaatcaa a                                              321

<210> SEQ ID NO 363
<211> LENGTH: 116
<212> TYPE: PRT
<213> ORGANISM: Artificial Sequence
<220> FEATURE:
<223> OTHER INFORMATION: SK16 Heavy Chain Variable Region

<400> SEQUENCE: 363

Arg Val Gln Leu Leu Glu Ser Gly Gly Gly Leu Val Gln Pro Gly Gly
1                   5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Asn Gly Ser Gly Gly Ser Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Val Ser Gly Phe Asp Ser Trp Gly Gln Gly Thr Leu Val
            100                 105                 110

Thr Val Ser Ser

115

<210> SEQ ID NO 364
<211> LENGTH: 107
<212> TYPE: PRT
<213> ORGANISM: Artificial Sequence
<220> FEATURE:
<223> OTHER INFORMATION: SK16 Light Chain Variable Region

<400> SEQUENCE: 364

Glu Ile Val Leu Thr Gln Ser Pro Gly Thr Leu Ser Leu Ser Pro Gly
1               5                   10                  15

Glu Arg Ala Thr Leu Ser Cys Arg Ile Ser Gln Ser Ile Ser Ser Tyr
            20                  25                  30

Leu Asn Trp Tyr Gln Gln Lys Pro Gly Gln Ala Pro Arg Leu Leu Ile
        35                  40                  45

Tyr Asp Ala Ser Leu Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Ser Tyr Lys Thr Pro Ile
                85                  90                  95

Thr Phe Gly Gln Gly Thr Lys Val Glu Ile Lys
            100                 105

<210> SEQ ID NO 365
<211> LENGTH: 349
<212> TYPE: DNA
<213> ORGANISM: Artificial Sequence
<220> FEATURE:
<223> OTHER INFORMATION: SK17 Heavy Chain Variable Region

<400> SEQUENCE: 365
gaagtgcagc tgctggaaag tggaggtgga ctggtgcagc ctggcggcag cctgcgcctg      60
agctgtgccg ccagcggatt caccttcagc agctattatt ggagctgggt tcgccaagca     120
cctggcaaag gcctggaatg ggtgagcacc atcaccggca gcggcggcag caccgattat     180
gccaacagcg tgaaaggccg ctttaccatc agccgcgata acagcaaaaa caccctgtat     240
ctgcagatga acagcctgcg cgccgaggac accgcagtct actactgtgc caccggcggc     300
ggcatctttg actattgggg acaaggtact ctggtgaccg tgagcagcg               349

<210> SEQ ID NO 366
<211> LENGTH: 321
<212> TYPE: DNA
<213> ORGANISM: Artificial Sequence
<220> FEATURE:
<223> OTHER INFORMATION: SK17 Light Chain Variable Region

<400> SEQUENCE: 366
gaaatcgtgc tgacccagag ccctggcacc ctgagcctga ccctggcga acgcgcaaca      60 ctgtcatgcc aggccagcca gaccatcagc aactatctga ctggtatca gcagaaacca     120 ggtcaggctc cacgtctgct gatctatgat gccagcaacc gcgccaccgg catccctgat     180
cgcttctcag atctggaag cggtaccgat tttaccctga ccatcagccg cctggaacct     240
gaggactttg ccgtgtatta ttgtcagcag tacaacagct atcctcctag cttcggtcag     300
ggcactaaag tggaaatcaa a                                              321

<210> SEQ ID NO 367

-continued

```
<211> LENGTH: 116
<212> TYPE: PRT
<213> ORGANISM: Artificial Sequence
<220> FEATURE:
<223> OTHER INFORMATION: SK17 Heavy Chain Variable Region

<400> SEQUENCE: 367

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Tyr Trp Ser Trp Val Arg Gln Ala Pro Gly Lys Gly Leu Glu Trp Val
        35                  40                  45

Ser Thr Ile Thr Gly Ser Gly Gly Ser Thr Asp Tyr Ala Asn Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Gly Gly Gly Ile Phe Asp Tyr Trp Gly Gln Gly Thr Leu Val
            100                 105                 110

Thr Val Ser Ser
        115

<210> SEQ ID NO 368
<211> LENGTH: 107
<212> TYPE: PRT
<213> ORGANISM: Artificial Sequence
<220> FEATURE:
<223> OTHER INFORMATION: SK17 Light Chain Variable Region

<400> SEQUENCE: 368

Glu Ile Val Leu Thr Gln Ser Pro Gly Thr Leu Ser Leu Ser Pro Gly
1               5                   10                  15

Glu Arg Ala Thr Leu Ser Cys Gln Ala Ser Gln Thr Ile Ser Asn Tyr
            20                  25                  30

Leu Asn Trp Tyr Gln Gln Lys Pro Gly Gln Ala Pro Arg Leu Leu Ile
        35                  40                  45

Tyr Asp Ala Ser Asn Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Asn Ser Tyr Pro Pro
                85                  90                  95

Ser Phe Gly Gln Gly Thr Lys Val Glu Ile Lys
            100                 105

<210> SEQ ID NO 369
<211> LENGTH: 352
<212> TYPE: DNA
<213> ORGANISM: Artificial Sequence
<220> FEATURE:
<223> OTHER INFORMATION: SL18 Heavy Chain Variable Region

<400> SEQUENCE: 369
cgagtgcagc tgctggaaag tggaggtgga ctggtgcagc ctggcggcag cctgcgcctg      60
agctgtgccg ccagcggatt caccttcagc gattatcata tgcattgggt tcgccaagca     120
cctggcaaag gcctggaatg ggtgagcacc atcagcagca gcggcggcta tacctattat     180
```

```
gccgaaagcg tgaaaagccg ctttaccatc agccgcgata acagcaaaaa caccctgtat      240
ctgcagatga acagcctgcg cgccgaggac accgcagtct actactgtgc ccgatcgata      300
cgcctgcctc tggattattg gggacaaggt actctggtga ccgtgagcag ca             352
```

```
<210> SEQ ID NO 370
<211> LENGTH: 321
<212> TYPE: DNA
<213> ORGANISM: Artificial Sequence
<220> FEATURE:
<223> OTHER INFORMATION: SL18 Light Chain Variable Region

<400> SEQUENCE: 370
cagagcgtgc tgacccagcc tcctagcgcc tccggtacac caggacagcg cgtgactatt       60
agctgtagcg caacaacat cggcagcaaa ggcgtgcatt ggtatcagca actgcctgga      120
actgcaccta agctgctgat ctatgaagat agcaaacgcc ctagcggcgt gcgtgatcgc      180
tttagcggta gcaaatcagg caccagcgcc agcctggcca tcagcggcct tcgctccgaa      240
gatgaagccg attattattg tcagagctat gatagcacca aaggcgtggt gtttggtggc      300
ggtaccaagc tgaccgtgct g                                              321
```

```
<210> SEQ ID NO 371
<211> LENGTH: 117
<212> TYPE: PRT
<213> ORGANISM: Artificial Sequence
<220> FEATURE:
<223> OTHER INFORMATION: SL18 Heavy Chain Variable Region

<400> SEQUENCE: 371

Arg Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

His Met His Trp Val Arg Gln Ala Pro Gly Lys Gly Leu Glu Trp Val
        35                  40                  45

Ser Thr Ile Ser Ser Ser Gly Gly Tyr Thr Tyr Tyr Ala Glu Ser Val
    50                  55                  60

Lys Ser Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Ile Arg Leu Pro Leu Asp Tyr Trp Gly Gln Gly Thr Leu
            100                 105                 110

Val Thr Val Ser Ser
        115
```

```
<210> SEQ ID NO 372
<211> LENGTH: 107
<212> TYPE: PRT
<213> ORGANISM: Artificial Sequence
<220> FEATURE:
<223> OTHER INFORMATION: SL18 Light Chain Variable Region

<400> SEQUENCE: 372

Gln Ser Val Leu Thr Gln Pro Pro Ser Ala Ser Gly Thr Pro Gly Gln
1               5                   10                  15

Arg Val Thr Ile Ser Cys Ser Gly Asn Asn Ile Gly Ser Lys Gly Val
            20                  25                  30

His Trp Tyr Gln Gln Leu Pro Gly Thr Ala Pro Lys Leu Leu Ile Tyr
```

-continued

```
            35                  40                  45

Glu Asp Ser Lys Arg Pro Ser Gly Val Arg Asp Arg Phe Ser Gly Ser
    50                  55                  60

Lys Ser Gly Thr Ser Ala Ser Leu Ala Ile Ser Gly Leu Arg Ser Glu
65                  70                  75                  80

Asp Glu Ala Asp Tyr Tyr Cys Gln Ser Tyr Asp Ser Thr Lys Gly Val
                85                  90                  95

Val Phe Gly Gly Gly Thr Lys Leu Thr Val Leu
            100                 105
```

<210> SEQ ID NO 373
<211> LENGTH: 348
<212> TYPE: DNA
<213> ORGANISM: Artificial Sequence
<220> FEATURE:
<223> OTHER INFORMATION: CB301_H3L1_A10 Heavy Chain Variable Region

<400> SEQUENCE: 373

```
gaggtgcagc tgttggagtc tggtggaggc ttggtacagt ctggaggttc tcttcgcctc      60
tcctgtgcag cctccggatt cactttcagc agctacggta tgcattgggt cagacaggca     120
ccaggtaagg gactggagtg ggtctctgca attagcggta gcggtggtag cacttactac     180
gcagacagcg tgaagggtcg cttcaccatc tcacgcgaca actccaagaa caccctgtac     240
ctgcagatga acagccttcg cgcagaggac actgccgtgt attactgcgt gcgtggttac     300
ggtgcaatgg acgtgtgggg acaaggtact ctggtcactg tctcctca                  348
```

<210> SEQ ID NO 374
<211> LENGTH: 327
<212> TYPE: DNA
<213> ORGANISM: Artificial Sequence
<220> FEATURE:
<223> OTHER INFORMATION: CB301_H3L1_A10 Light Chain Variable Region

<400> SEQUENCE: 374

```
cagtctgtgc tgactcagcc accttcagca tctggtactc caggtcagcg cgtcaccatc      60
agctgcactc gtagcagcgg tagcatcgca agcaactacg tgcagtggta tcagcaactc     120
ccaggcaccg ctcctaagct cctgatttac cgcaacaacc agcgccctag tggtgtgcct     180
gatcgctttt ctgggtccaa gtctggcacc tcagcctctc tggctatcag tggacttcgc     240
tccgaggacg aggctgacta ttactgcagc agctacacta ctagcagcac tctggtgttc     300
ggcggtggga ccaaactgac cgtccta                                         327
```

<210> SEQ ID NO 375
<211> LENGTH: 116
<212> TYPE: PRT
<213> ORGANISM: Artificial Sequence
<220> FEATURE:
<223> OTHER INFORMATION: CB301_H3L1_A10 Heavy Chain Variable Region

<400> SEQUENCE: 375

```
Glu Val Gln Leu Leu Glu Ser Gly Gly Gly Leu Val Gln Ser Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60
```

-continued

```
Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Arg Gly Tyr Gly Ala Met Asp Val Trp Gly Gln Gly Thr Leu Val
            100                 105                 110

Thr Val Ser Ser
        115
```

```
<210> SEQ ID NO 376
<211> LENGTH: 109
<212> TYPE: PRT
<213> ORGANISM: Artificial Sequence
<220> FEATURE:
<223> OTHER INFORMATION: CB301_H3L1_A10 Light Chain Variable Region

<400> SEQUENCE: 376
```

```
Gln Ser Val Leu Thr Gln Pro Pro Ser Ala Ser Gly Thr Pro Gly Gln
1               5                   10                  15

Arg Val Thr Ile Ser Cys Thr Arg Ser Ser Gly Ser Ile Ala Ser Asn
                20                  25                  30

Tyr Val Gln Trp Tyr Gln Gln Leu Pro Gly Thr Ala Pro Lys Leu Leu
            35                  40                  45

Ile Tyr Arg Asn Asn Gln Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ser Ser Tyr Thr Thr Ser Ser
                85                  90                  95

Thr Leu Val Phe Gly Gly Gly Thr Lys Leu Thr Val Leu
            100                 105
```

```
<210> SEQ ID NO 377
<211> LENGTH: 348
<212> TYPE: DNA
<213> ORGANISM: Artificial Sequence
<220> FEATURE:
<223> OTHER INFORMATION: CB301_H3L1_A12 Heavy Chain Variable Region

<400> SEQUENCE: 377
```

```
gaggtgcagc tgttggagtc tggtggaggc ttggtacagc ctggaggttc tcttcgcctc      60
tcctgtgcag cctccggatt cactttcagc agctacgcaa tgcattgggt cagacaggca     120
ccaggtaagg gactggagtg ggtctctgca attagcggta gcggtggtag cacttactac     180
gcagacagcg tgaagggtcg cttcaccatc tcacgcgaca actccaagaa caccctgtac     240
ctgcagatga acagccttcg cgcaaaggac actgccgtgt attactgcgc aagcggctac     300
ggtctgatgg acgtatgggg acaaggtact ctggtcactg tctcctca                  348
```

```
<210> SEQ ID NO 378
<211> LENGTH: 330
<212> TYPE: DNA
<213> ORGANISM: Artificial Sequence
<220> FEATURE:
<223> OTHER INFORMATION: CB301_H3L1_A12 Light Chain Variable Region

<400> SEQUENCE: 378
```

```
cagtctgtgc tgactcagcc accttcagca tctggtactc caggtcagcg cgtcaccatc      60
agctgcactg gtactagcag cgacgtgggt aactacaacc tggtgagctg gtatcagcaa     120
```

-continued

```
ctcccaggca ccgctcctaa gctcctgatt tacagcaaca accagcgccc tagtggtgtg      180
cctgatcgct tttctgggtc caagtctggc acctcagcct ctctggctat cagtggactt      240
cgctccgagg acgaggctga ctattactgc agcagctaca ctggtagcaa cgctctgttg      300
ttcggcggtg ggaccaaact gaccgtccta                                       330
```

<210> SEQ ID NO 379
<211> LENGTH: 116
<212> TYPE: PRT
<213> ORGANISM: Artificial Sequence
<220> FEATURE:
<223> OTHER INFORMATION: CB301_H3L1_A12 Heavy Chain Variable Region

<400> SEQUENCE: 379

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Lys Asp Thr Ala Val Tyr Tyr Cys
                85                  90                  95

Ala Ser Gly Tyr Gly Leu Met Asp Val Trp Gly Gln Gly Thr Leu Val
            100                 105                 110

Thr Val Ser Ser
        115

<210> SEQ ID NO 380
<211> LENGTH: 110
<212> TYPE: PRT
<213> ORGANISM: Artificial Sequence
<220> FEATURE:
<223> OTHER INFORMATION: CB301_H3L1_A12 Light Chain Variable Region

<400> SEQUENCE: 380

Gln Ser Val Leu Thr Gln Pro Pro Ser Ala Ser Gly Thr Pro Gly Gln
1               5                   10                  15

Arg Val Thr Ile Ser Cys Thr Gly Thr Ser Ser Asp Val Gly Asn Tyr
            20                  25                  30

Asn Leu Val Ser Trp Tyr Gln Gln Leu Pro Gly Thr Ala Pro Lys Leu
        35                  40                  45

Leu Ile Tyr Ser Asn Asn Gln Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ser Ser Tyr Thr Gly Ser
                85                  90                  95

Asn Ala Leu Leu Phe Gly Gly Gly Thr Lys Leu Thr Val Leu
            100                 105                 110

<210> SEQ ID NO 381
<211> LENGTH: 348
<212> TYPE: DNA
<213> ORGANISM: Artificial Sequence -continued

```
<220> FEATURE:
<223> OTHER INFORMATION: CB301_H3L1_E6 Heavy Chain Variable Region

<400> SEQUENCE: 381
gaggtgcagc tgttggagtc tggtggaggc ttggtacagc ctggaggttc tcttcgcctc        60
tcctgtgcag cctccggatt cactttcagc agctacgcaa tgagctgggt cagacaggca       120
ccaggtaagg gactggagtg ggtctctgca attagcggta gcggtggtag cacttactac       180
gcagacagcg tgaagggtcg cttcaccatc tcacgcgaca actccaagaa caccctgtac       240
ctgcagatga acagccttcg cgcagaggac actgccgtgt attactgcgc acgctggcat       300
tacagcttcg actactgggg acaaggtact ctggtcactg tctcctca                    348

<210> SEQ ID NO 382
<211> LENGTH: 324
<212> TYPE: DNA
<213> ORGANISM: Artificial Sequence
<220> FEATURE:
<223> OTHER INFORMATION: CB301_H3L1_E6 Light Chain Variable Region

<400> SEQUENCE: 382
cagtctgtgc tgactcagcc accttcagca tctggtactc caggtcagcg cgtcaccatc        60
agctgccgtg gtaacaacat cggtagcaag cgtgtgcatt ggtatcagca actcccaggc       120
accgctccta agctcctgat ttacagctac aaccaccgtc ctagcggtgt gcctgatcgc       180
ttttctgggt ccaagtctgg cacctcagcc tctctggcta tcactggact tcgctccgag       240
gacgaagctg actattactg caacacttgg gacgacagcc tggagggtcc tgtgttcggc       300
ggtgggacca aactgaccgt ccta                                               324

<210> SEQ ID NO 383
<211> LENGTH: 116
<212> TYPE: PRT
<213> ORGANISM: Artificial Sequence
<220> FEATURE:
<223> OTHER INFORMATION: CB301_H3L1_E6 Heavy Chain Variable Region

<400> SEQUENCE: 383

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp His Tyr Ser Phe Asp Tyr Trp Gly Gln Gly Thr Leu Val
            100                 105                 110

Thr Val Ser Ser
        115

<210> SEQ ID NO 384
<211> LENGTH: 108
<212> TYPE: PRT
<213> ORGANISM: Artificial Sequence
<220> FEATURE:
```

<223> OTHER INFORMATION: CB301_H3L1_E6 Light Chain Variable Region

<400> SEQUENCE: 384

Gln Ser Val Leu Thr Gln Pro Pro Ser Ala Ser Gly Thr Pro Gly Gln
1               5                   10                  15

Arg Val Thr Ile Ser Cys Arg Gly Asn Asn Ile Gly Ser Lys Arg Val
            20                  25                  30

His Trp Tyr Gln Gln Leu Pro Gly Thr Ala Pro Lys Leu Leu Ile Tyr
        35                  40                  45

Ser Tyr Asn His Arg Pro Ser Gly Val Pro Asp Arg Phe Ser Gly Ser
    50                  55                  60

Lys Ser Gly Thr Ser Ala Ser Leu Ala Ile Thr Gly Leu Arg Ser Glu
65                  70                  75                  80

Asp Glu Ala Asp Tyr Tyr Cys Asn Thr Trp Asp Asp Ser Leu Glu Gly
                85                  90                  95

Pro Val Phe Gly Gly Gly Thr Lys Leu Thr Val Leu
            100                 105

<210> SEQ ID NO 385
<211> LENGTH: 352
<212> TYPE: DNA
<213> ORGANISM: Artificial Sequence
<220> FEATURE:
<223> OTHER INFORMATION: CB301_H3L1_F4 Heavy Chain Variable Region

<400> SEQUENCE: 385
gaggtgcagc tgttggagtc tggtggaggc ttggtacagc ctggaggttc tcttcgcctc      60
tcctgtgcag cctccggatt cactttcagc ggctacgcaa tgagctgggt cagacaggca     120
ccaggtaagg gactggagtg ggtctctgca attagcggta gcggtggtag cacttactac     180
gcagacagcg tgaagggtcg cttcaccatc tcacgcgaca actccaagaa caccctgtac     240
ctgcagatga acagccttcg cgcagaggac actgccgtgt attactgcgc acgtagtcct     300
agcggtctgt tcgactactg gggacaaggt actctggtca ctgtctcctc ag            352

<210> SEQ ID NO 386
<211> LENGTH: 318
<212> TYPE: DNA
<213> ORGANISM: Artificial Sequence
<220> FEATURE:
<223> OTHER INFORMATION: CB301_H3L1_F4 Light Chain Variable Region

<400> SEQUENCE: 386
cagtctgtgc tgactcagcc accttcagca tctggtactc caggtcagcg cgtcaccatc      60
agctgcggtg gtaacaacat cggtagcaag cgtgtgcatt ggtatcagca actcccaggc     120
accgctccta agctcctgat ttacaacact agcaacaagc atagcggtgt gcctgatcgc     180
ttttctgggt ccaagtctgg cacctcagcc tctctggcta tcagtggact tcgctccgag     240
gacgaggctg actattactg cagcagctac ctacagcagc actctctgtt cggcggtggg     300
accaaactaa ccgtccta                                                    318

<210> SEQ ID NO 387
<211> LENGTH: 117
<212> TYPE: PRT
<213> ORGANISM: Artificial Sequence
<220> FEATURE:
<223> OTHER INFORMATION: CB301_H3L1_F4 Heavy Chain Variable Region

<400> SEQUENCE: 387

Glu Val Gln Leu Leu Glu Ser Gly Gly Gly Leu Val Gln Pro Gly Gly
1               5               10              15

Ser Leu Arg Leu Ser Cys Ala Ala Ser Gly Phe Thr Phe Ser Gly Tyr
            20              25              30

Ala Met Ser Trp Val Arg Gln Ala Pro Gly Lys Gly Leu Glu Trp Val
        35              40              45

Ser Ala Ile Ser Gly Ser Gly Gly Ser Thr Tyr Tyr Ala Asp Ser Val
    50              55              60

Lys Gly Arg Phe Thr Ile Ser Arg Asp Asn Ser Lys Asn Thr Leu Tyr
65              70              75              80

Leu Gln Met Asn Ser Leu Arg Ala Glu Asp Thr Ala Val Tyr Tyr Cys
            85              90              95

Ala Arg Ser Pro Ser Gly Leu Phe Asp Tyr Trp Gly Gln Gly Thr Leu
            100             105             110

Val Thr Val Ser Ser
        115

<210> SEQ ID NO 388
<211> LENGTH: 106
<212> TYPE: PRT
<213> ORGANISM: Artificial Sequence
<220> FEATURE:
<223> OTHER INFORMATION: CB301_H3L1_F4 Light Chain Variable Region

<400> SEQUENCE: 388

Gln Ser Val Leu Thr Gln Pro Pro Ser Ala Ser Gly Thr Pro Gly Gln
1               5               10              15

Arg Val Thr Ile Ser Cys Gly Gly Asn Asn Ile Gly Ser Lys Arg Val
            20              25              30

His Trp Tyr Gln Gln Leu Pro Gly Thr Ala Pro Lys Leu Leu Ile Tyr
        35              40              45

Asn Thr Ser Asn Lys His Ser Gly Val Pro Asp Arg Phe Ser Gly Ser
    50              55              60

Lys Ser Gly Thr Ser Ala Ser Leu Ala Ile Ser Gly Leu Arg Ser Glu
65              70              75              80

Asp Glu Ala Asp Tyr Tyr Cys Ser Ser Tyr Leu Gln Gln His Ser Leu
            85              90              95

Phe Gly Gly Gly Thr Lys Leu Thr Val Leu
            100             105

<210> SEQ ID NO 389
<211> LENGTH: 360
<212> TYPE: DNA
<213> ORGANISM: Artificial Sequence
<220> FEATURE:
<223> OTHER INFORMATION: CB301_H3L1_G11 Heavy Chain Variable Region

<400> SEQUENCE: 389
gaggtgcagc tgttggagtc tggtggaggc ttggtacagc ctggaggttc ctcttccgcc      60
tcctcctgtg cagcctccgg attcactttc agcagctacg caatgagctg ggtcagacag     120
gcaccaggta agggactgga gtgggtctct gcaattagcg gtagcggtgg tagcacttac     180
tacgcagaca gcgtgaaggg tcgcttcacc atctcacgcg acaactccaa gaacaccctg     240
tacctgcaga tgaacagcct tcgcgcagag gacactgccg tgtattactg cacacgtttc     300
gtgggtgcaa tcggtgcatt cgactactgg ggacaaggta ctctggtcac tgtctcctca     360

<210> SEQ ID NO 390

-continued

```
<211> LENGTH: 324
<212> TYPE: DNA
<213> ORGANISM: Artificial Sequence
<220> FEATURE:
<223> OTHER INFORMATION: CB301_H3L1_G11 Light Chain Variable Region

<400> SEQUENCE: 390
cagtctgtgc tgactcagcc accttcagca tctggtactc caggtcagcg cgtcaccatc      60
agctgcagtg gtaacaacat cggtagccgt agcgtgcatt ggtatcagca actcccaggc     120
accgctccta agctcctgat ttaccgcaac aaccagcgcc ctagtggtgt gcctgatcgc     180
ttttctgggt ccaagtctgg cacctcagcc tctctggcta tcagtggact tcgctccgag     240
gacgaggctg actattactg cgcagcatgg gacgacagcc tgagcggtcc tgtgttcggc     300
ggtgggacca aactgaccgt ccta                                            324

<210> SEQ ID NO 391
<211> LENGTH: 120
<212> TYPE: PRT
<213> ORGANISM: Artificial Sequence
<220> FEATURE:
<223> OTHER INFORMATION: CB301_H3L1_G11 Heavy Chain Variable Region

<400> SEQUENCE: 391

Glu Val Gln Leu Leu Glu Ser Gly Gly Gly Leu Val Gln Pro Gly Gly
1               5                   10                  15

Ser Ser Ser Ala Ser Ser Cys Ala Ala Ser Gly Phe Thr Phe Ser Ser
            20                  25                  30

Tyr Ala Met Ser Trp Val Arg Gln Ala Pro Gly Lys Gly Leu Glu Trp
        35                  40                  45

Val Ser Ala Ile Ser Gly Ser Gly Gly Ser Thr Tyr Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Thr Arg Phe Val Gly Ala Ile Gly Ala Phe Asp Tyr Trp Gly Gln
            100                 105                 110

Gly Thr Leu Val Thr Val Ser Ser
        115                 120

<210> SEQ ID NO 392
<211> LENGTH: 108
<212> TYPE: PRT
<213> ORGANISM: Artificial Sequence
<220> FEATURE:
<223> OTHER INFORMATION: CB301_H3L1_G11 Light Chain Variable Region

<400> SEQUENCE: 392

Gln Ser Val Leu Thr Gln Pro Pro Ser Ala Ser Gly Thr Pro Gly Gln
1               5                   10                  15

Arg Val Thr Ile Ser Cys Ser Gly Asn Asn Ile Gly Ser Arg Ser Val
            20                  25                  30

His Trp Tyr Gln Gln Leu Pro Gly Thr Ala Pro Lys Leu Leu Ile Tyr
        35                  40                  45

Arg Asn Asn Gln Arg Pro Ser Gly Val Pro Asp Arg Phe Ser Gly Ser
    50                  55                  60

Lys Ser Gly Thr Ser Ala Ser Leu Ala Ile Ser Gly Leu Arg Ser Glu
65                  70                  75                  80
```

-continued

```
Asp Glu Ala Asp Tyr Tyr Cys Ala Ala Trp Asp Asp Ser Leu Ser Gly
                85                  90                  95

Pro Val Phe Gly Gly Gly Thr Lys Leu Thr Val Leu
            100                 105
```

<210> SEQ ID NO 393
<211> LENGTH: 363
<212> TYPE: DNA
<213> ORGANISM: Artificial Sequence
<220> FEATURE:
<223> OTHER INFORMATION: CB301_OPALTL_B5 Heavy Chain Variable Region

<400> SEQUENCE: 393

```
gaggtgcagc tgttggagtc tggtggaggc ttggtacagc ctggaggttc tcttcgcctc      60
tcctgtgcag cctccggatt cactttcagc cattacgcaa tgagctgggt cagacaggca     120
ccaggtaagg gactggagtg ggtctctgca attagcggta gcggtggtag cacttactac     180
gcagacagcg tgaagggtcg cttcaccatc tcacgcgaca actccaagaa caccctgtac     240
ctgcagatga acagccttcg cgcagaggac actgccgtgt attactgcgc acgtggttgg     300
gacagcccta ctctgacata cttcgacagc tggggacaag gtactctggt cactgtctcc     360
tca                                                                    363
```

<210> SEQ ID NO 394
<211> LENGTH: 330
<212> TYPE: DNA
<213> ORGANISM: Artificial Sequence
<220> FEATURE:
<223> OTHER INFORMATION: CB301_OPALTL_B5 Light Chain Variable Region

<400> SEQUENCE: 394

```
cagtctgtgc tgactcagcc accttcagca tctggtactc caggtcagcg cgtcaccatc      60
agctgcagcg gtactagcag caacatcggt aacaacgacg tgagctggta tcagcaactc     120
ccaggcaccg ctcctaagct cctgatttac caggacacta gcgtcctag cggtgtgcct      180 gatcgctttt ctgggtccaa gtctggcacc tcagcctctc tggctatcag tggacttcgc     240
tccgaggacg aggctgacta ttactgcgca gcatgggacg acagcctgag cggtcctgtg     300
ttcggcggtg ggaccaaact gaccgtccta                                      330
```

<210> SEQ ID NO 395
<211> LENGTH: 121
<212> TYPE: PRT
<213> ORGANISM: Artificial Sequence
<220> FEATURE:
<223> OTHER INFORMATION: CB301_OPALTL_B5 Heavy Chain Variable Region

<400> SEQUENCE: 395

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
            20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

```
Ala Arg Gly Trp Asp Ser Pro Thr Leu Thr Tyr Phe Asp Ser Trp Gly
            100                 105                 110

Gln Gly Thr Leu Val Thr Val Ser Ser
        115                 120

<210> SEQ ID NO 396
<211> LENGTH: 110
<212> TYPE: PRT
<213> ORGANISM: Artificial Sequence
<220> FEATURE:
<223> OTHER INFORMATION: CB301_OPALTL_B5 Light Chain Variable Region

<400> SEQUENCE: 396

Gln Ser Val Leu Thr Gln Pro Pro Ser Ala Ser Gly Thr Pro Gly Gln
1               5                   10                  15

Arg Val Thr Ile Ser Cys Ser Gly Thr Ser Ser Asn Ile Gly Asn Asn
            20                  25                  30

Asp Val Ser Trp Tyr Gln Gln Leu Pro Gly Thr Ala Pro Lys Leu Leu
        35                  40                  45

Ile Tyr Gln Asp Thr Lys Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Pro Val Phe Gly Gly Gly Thr Lys Leu Thr Val Leu
            100                 105                 110

<210> SEQ ID NO 397
<211> LENGTH: 348
<212> TYPE: DNA
<213> ORGANISM: Artificial Sequence
<220> FEATURE:
<223> OTHER INFORMATION: CB301_OPALTL_E6 Heavy Chain Variable Region

<400> SEQUENCE: 397
gaggtgcagc tgttggagtc tggtggaggc ttggtacagc ctggaggttc tcttcgcctc      60
tcctgtgcag cctccggatt cactttcagc agctacggta tgcattgggt cagacaggca     120
ccaggtaagg gactggagtg ggtctctgca atcagcggta gcggtggtta cacttactac     180
gcagacagcg tgaagggtcg cttcaccatc tcacgcgaca actccaagaa caccctgtac     240
ctgcagatga acagccttcg cgcagaggac actgccgtgt attactgcgc acgctggcat     300
tacagcttcg actactgggg acaaggtact ctggtcactg tctcctca                  348

<210> SEQ ID NO 398
<211> LENGTH: 324
<212> TYPE: DNA
<213> ORGANISM: Artificial Sequence
<220> FEATURE:
<223> OTHER INFORMATION: CB301_OPALTL_E6 Light Chain Variable Region

<400> SEQUENCE: 398
cagtctgtgc tgactcagcc accttcagca tctggtactc caggtcagcg cgtcaccatc      60
agctgcagcg gtagcagcag caacatcggt aacaactacg tgagctggta tcagcaactc     120
ccaggcaccg ctcctaagct cctgatttac cgcaacaacc agcgccctag tggtgtgcct     180
gatcgctttt ctgggtccaa gtctggcacc tcagcctctc tggctatcag tggacttcgc     240
tccgaggacg aggctgacta ttactgccag agctacgaca cagcaacgt gctgttcggc      300
```

-continued ggtgggacca aactgaccgt ccta                                                    324

<210> SEQ ID NO 399
<211> LENGTH: 116
<212> TYPE: PRT
<213> ORGANISM: Artificial Sequence
<220> FEATURE:
<223> OTHER INFORMATION: CB301_OPALTL_E6 Heavy Chain Variable Region

<400> SEQUENCE: 399

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ser Ala Ile Ser Gly Ser Gly Gly Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp His Tyr Ser Phe Asp Tyr Trp Gly Gln Gly Thr Leu Val
            100                 105                 110

Thr Val Ser Ser
        115

<210> SEQ ID NO 400
<211> LENGTH: 108
<212> TYPE: PRT
<213> ORGANISM: Artificial Sequence
<220> FEATURE:
<223> OTHER INFORMATION: CB301_OPALTL_E6 Light Chain Variable Region

<400> SEQUENCE: 400

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gln Ser Tyr Asp Asn Ser Asn
                85                  90                  95

Val Leu Phe Gly Gly Gly Thr Lys Leu Thr Val Leu
            100                 105

<210> SEQ ID NO 401
<211> LENGTH: 489
<212> TYPE: DNA
<213> ORGANISM: Artificial Sequence
<220> FEATURE:
<223> OTHER INFORMATION: CD300c ECD

<400> SEQUENCE: 401
ggctattttc tctctgagcca ccccatgacc gtggcgggcc ccgtgggggg atccctgagt      60

-continued

```
gtgcagtgtc gctatgagaa ggaacacagg accctcaaca aattctggtg cagaccacca      120
cagattctcc gatgtgacaa gattgtggag accaaagggt cagcagggaa aaggaatggc      180
cgagtgtcca tcagggacag tcctgcaaac ctcagcttca cagtgaccct ggagaatctc      240
acagaggagg acgcaggcac ctactggtgt ggggtggata caccgtggct ccgagacttt      300
catgatccca ttgtcgaggt tgaggtgtcc gtgttcccgg ccgggacgac cacagcctcc      360 agccccccaga gctccatggg cacctcaggt cctcccacga agctgcccgt gcacacctgg      420
cccagcgtga ccagaaagga cagcccccgaa cccagcccac accctggctc cctgttcagc      480
aatgtccgc                                                              489
```

<210> SEQ ID NO 402
<211> LENGTH: 163
<212> TYPE: PRT
<213> ORGANISM: Artificial Sequence
<220> FEATURE:
<223> OTHER INFORMATION: CD300c ECD

<400> SEQUENCE: 402

```
Gly Tyr Phe Pro Leu Ser His Pro Met Thr Val Ala Gly Pro Val Gly
1               5                   10                  15

Gly Ser Leu Ser Val Gln Cys Arg Tyr Glu Lys Glu His Arg Thr Leu
                20                  25                  30

Asn Lys Phe Trp Cys Arg Pro Pro Gln Ile Leu Arg Cys Asp Lys Ile
            35                  40                  45

Val Glu Thr Lys Gly Ser Ala Gly Lys Arg Asn Gly Arg Val Ser Ile
        50                  55                  60

Arg Asp Ser Pro Ala Asn Leu Ser Phe Thr Val Thr Leu Glu Asn Leu
65                  70                  75                  80

Thr Glu Glu Asp Ala Gly Thr Tyr Trp Cys Gly Val Asp Thr Pro Trp
                85                  90                  95

Leu Arg Asp Phe His Asp Pro Ile Val Glu Val Glu Val Ser Val Phe
            100                 105                 110

Pro Ala Gly Thr Thr Thr Ala Ser Ser Pro Gln Ser Ser Met Gly Thr
            115                 120                 125

Ser Gly Pro Pro Thr Lys Leu Pro Val His Thr Trp Pro Ser Val Thr
        130                 135                 140

Arg Lys Asp Ser Pro Glu Pro Ser Pro His Pro Gly Ser Leu Phe Ser
145                 150                 155                 160

Asn Val Arg
```

<210> SEQ ID NO 403
<211> LENGTH: 12
<212> TYPE: PRT
<213> ORGANISM: Artificial Sequence
<220> FEATURE:
<223> OTHER INFORMATION: Heavy chain CDR1 of anti-CD300c monoclonal
      antibody or antigen binding fragment thereof
<220> FEATURE:
<221> NAME/KEY: MISC_FEATURE
<222> LOCATION: (5)..(5)
<223> OTHER INFORMATION: Xaa = R, S, or D
<220> FEATURE:
<221> NAME/KEY: MISC_FEATURE
<222> LOCATION: (7)..(7)
<223> OTHER INFORMATION: Xaa = A, G, or H
<220> FEATURE:
<221> NAME/KEY: MISC_FEATURE
<222> LOCATION: (9)..(9)
<223> OTHER INFORMATION: Xaa = T, H, or S -continued

<400> SEQUENCE: 403

Phe Thr Phe Ser Xaa Tyr Xaa Met Xaa Trp Val Arg
1               5                   10

<210> SEQ ID NO 404
<211> LENGTH: 13
<212> TYPE: PRT
<213> ORGANISM: Artificial Sequence
<220> FEATURE:
<223> OTHER INFORMATION: Heavy chain CDR2 of anti-CD300c monoclonal
      antibody or antigen binding fragment thereof
<220> FEATURE:
<221> NAME/KEY: MISC_FEATURE
<222> LOCATION: (1)..(1)
<223> OTHER INFORMATION: Xaa = S, A, or T
<220> FEATURE:
<221> NAME/KEY: MISC_FEATURE
<222> LOCATION: (2)..(2)
<223> OTHER INFORMATION: Xaa = M or I
<220> FEATURE:
<221> NAME/KEY: MISC_FEATURE
<222> LOCATION: (4)..(4)
<223> OTHER INFORMATION: Xaa = G or S
<220> FEATURE:
<221> NAME/KEY: MISC_FEATURE
<222> LOCATION: (5)..(5)
<223> OTHER INFORMATION: Xaa = T or S
<220> FEATURE:
<221> NAME/KEY: MISC_FEATURE
<222> LOCATION: (8)..(8)
<223> OTHER INFORMATION: Xaa = T, S, or Y
<220> FEATURE:
<221> NAME/KEY: MISC_FEATURE
<222> LOCATION: (13)..(13)
<223> OTHER INFORMATION: Xaa = D or E

<400> SEQUENCE: 404

Xaa Xaa Ser Xaa Xaa Gly Gly Xaa Thr Tyr Tyr Ala Xaa
1               5                   10

<210> SEQ ID NO 405
<211> LENGTH: 15
<212> TYPE: PRT
<213> ORGANISM: Artificial Sequence
<220> FEATURE:
<223> OTHER INFORMATION: Heavy chain CDR3 of anti-CD300c monoclonal
      antibody or antigen binding fragment thereof
<220> FEATURE:
<221> NAME/KEY: MISC_FEATURE
<222> LOCATION: (4)..(4)
<223> OTHER INFORMATION: Xaa = R, V, or S
<220> FEATURE:
<221> NAME/KEY: MISC_FEATURE
<222> LOCATION: (5)..(5)
<223> OTHER INFORMATION: Xaa = G or S
<220> FEATURE:
<221> NAME/KEY: MISC_FEATURE
<222> LOCATION: (6)..(6)
<223> OTHER INFORMATION: Xaa = A, G, S, Y, or I
<220> FEATURE:
<221> NAME/KEY: MISC_FEATURE
<222> LOCATION: (7)..(7)
<223> OTHER INFORMATION: Xaa = Y, A, Q, G, or R
<220> FEATURE:
<221> NAME/KEY: MISC_FEATURE
<222> LOCATION: (8)..(8)
<223> OTHER INFORMATION: Xaa = G or L
<220> FEATURE:
<221> NAME/KEY: MISC_FEATURE
<222> LOCATION: (9)..(9)
<223> OTHER INFORMATION: Xaa = F, R, I, M, or P
<220> FEATURE:
<221> NAME/KEY: MISC_FEATURE
<222> LOCATION: (10)..(10)

```
<223> OTHER INFORMATION: Xaa = D, G, F, or L
<220> FEATURE:
<221> NAME/KEY: MISC_FEATURE
<222> LOCATION: (11)..(11)
<223> OTHER INFORMATION: Xaa = H, F, D, or V
<220> FEATURE:
<221> NAME/KEY: MISC_FEATURE
<222> LOCATION: (12)..(12)
<223> OTHER INFORMATION: Xaa = F, I, Y, or not present
<220> FEATURE:
<221> NAME/KEY: MISC_FEATURE
<222> LOCATION: (13)..(13)
<223> OTHER INFORMATION: Xaa = D or not present
<220> FEATURE:
<221> NAME/KEY: MISC_FEATURE
<222> LOCATION: (14)..(14)
<223> OTHER INFORMATION: Xaa = Y or not present

<400> SEQUENCE: 405

Tyr Cys Ala Xaa Xaa Xaa Xaa Xaa Xaa Xaa Xaa Xaa Xaa Xaa Trp
1               5                   10                  15

<210> SEQ ID NO 406
<211> LENGTH: 15
<212> TYPE: PRT
<213> ORGANISM: Artificial Sequence
<220> FEATURE:
<223> OTHER INFORMATION: Light chain CDR1 of anti-CD300c monoclonal
      antibody or antigen binding fragment thereof
<220> FEATURE:
<221> NAME/KEY: MISC_FEATURE
<222> LOCATION: (2)..(2)
<223> OTHER INFORMATION: Xaa = R, S, or T
<220> FEATURE:
<221> NAME/KEY: MISC_FEATURE
<222> LOCATION: (3)..(3)
<223> OTHER INFORMATION: Xaa = A, G, or R
<220> FEATURE:
<221> NAME/KEY: MISC_FEATURE
<222> LOCATION: (4)..(4)
<223> OTHER INFORMATION: Xaa = S or N
<220> FEATURE:
<221> NAME/KEY: MISC_FEATURE
<222> LOCATION: (5)..(5)
<223> OTHER INFORMATION: Xaa = Q, S, or N
<220> FEATURE:
<221> NAME/KEY: MISC_FEATURE
<222> LOCATION: (6)..(6)
<223> OTHER INFORMATION: Xaa = S, I, or G
<220> FEATURE:
<221> NAME/KEY: MISC_FEATURE
<222> LOCATION: (7)..(7)
<223> OTHER INFORMATION: Xaa = I, N, or G
<220> FEATURE:
<221> NAME/KEY: MISC_FEATURE
<222> LOCATION: (8)..(8)
<223> OTHER INFORMATION: Xaa = G, I, T, or S
<220> FEATURE:
<221> NAME/KEY: MISC_FEATURE
<222> LOCATION: (9)..(9)
<223> OTHER INFORMATION: Xaa = N, G, R, A, or K
<220> FEATURE:
<221> NAME/KEY: MISC_FEATURE
<222> LOCATION: (10)..(10)
<223> OTHER INFORMATION: Xaa = Y, S, R, or G
<220> FEATURE:
<221> NAME/KEY: MISC_FEATURE
<222> LOCATION: (11)..(11)
<223> OTHER INFORMATION: Xaa = N or not present
<220> FEATURE:
<221> NAME/KEY: MISC_FEATURE
<222> LOCATION: (12)..(12)
<223> OTHER INFORMATION: Xaa = Y or not present
<220> FEATURE:
<221> NAME/KEY: MISC_FEATURE
<222> LOCATION: (13)..(13)
<223> OTHER INFORMATION: Xaa = L or V
```

```
<220> FEATURE:
<221> NAME/KEY: MISC_FEATURE
<222> LOCATION: (14)..(14)
<223> OTHER INFORMATION: Xaa = N, Y, H, or Q

<400> SEQUENCE: 406

Cys Xaa Xaa Xaa Xaa Xaa Xaa Xaa Xaa Xaa Xaa Xaa Xaa Xaa Trp
1               5                   10                  15

<210> SEQ ID NO 407
<211> LENGTH: 10
<212> TYPE: PRT
<213> ORGANISM: Artificial Sequence
<220> FEATURE:
<223> OTHER INFORMATION: Light chain CDR2 of anti-CD300c monoclonal
      antibody or antigen binding fragment thereof
<220> FEATURE:
<221> NAME/KEY: MISC_FEATURE
<222> LOCATION: (1)..(1)
<223> OTHER INFORMATION: Xaa = D, E, S, or R
<220> FEATURE:
<221> NAME/KEY: MISC_FEATURE
<222> LOCATION: (2)..(2)
<223> OTHER INFORMATION: Xaa = A, D, K, or N
<220> FEATURE:
<221> NAME/KEY: MISC_FEATURE
<222> LOCATION: (3)..(3)
<223> OTHER INFORMATION: Xaa = S or N
<220> FEATURE:
<221> NAME/KEY: MISC_FEATURE
<222> LOCATION: (4)..(4)
<223> OTHER INFORMATION: Xaa = N, K, or Q
<220> FEATURE:
<221> NAME/KEY: MISC_FEATURE
<222> LOCATION: (5)..(5)
<223> OTHER INFORMATION: Xaa = L or R
<220> FEATURE:
<221> NAME/KEY: MISC_FEATURE
<222> LOCATION: (6)..(6)
<223> OTHER INFORMATION: Xaa = E or P
<220> FEATURE:
<221> NAME/KEY: MISC_FEATURE
<222> LOCATION: (7)..(7)
<223> OTHER INFORMATION: Xaa = T or S
<220> FEATURE:
<221> NAME/KEY: MISC_FEATURE
<222> LOCATION: (9)..(9)
<223> OTHER INFORMATION: Xaa = I or V
<220> FEATURE:
<221> NAME/KEY: MISC_FEATURE
<222> LOCATION: (10)..(10)
<223> OTHER INFORMATION: Xaa = P or R

<400> SEQUENCE: 407

Xaa Xaa Xaa Xaa Xaa Xaa Xaa Gly Xaa Xaa
1               5                   10

<210> SEQ ID NO 408
<211> LENGTH: 14
<212> TYPE: PRT
<213> ORGANISM: Artificial Sequence
<220> FEATURE:
<223> OTHER INFORMATION: Light chain CDR3 of anti-CD300c monoclonal
      antibody or antigen binding fragment thereof
<220> FEATURE:
<221> NAME/KEY: MISC_FEATURE
<222> LOCATION: (3)..(3)
<223> OTHER INFORMATION: Xaa = Q, S, or A
<220> FEATURE:
<221> NAME/KEY: MISC_FEATURE
<222> LOCATION: (4)..(4)
<223> OTHER INFORMATION: Xaa = Q, S, or A
<220> FEATURE:
<221> NAME/KEY: MISC_FEATURE
<222> LOCATION: (5)..(5)
```

-continued

```
<223> OTHER INFORMATION: Xaa = S, Y, or W
<220> FEATURE:
<221> NAME/KEY: MISC_FEATURE
<222> LOCATION: (6)..(6)
<223> OTHER INFORMATION: Xaa = S, T, D, or A
<220> FEATURE:
<221> NAME/KEY: MISC_FEATURE
<222> LOCATION: (7)..(7)
<223> OTHER INFORMATION: Xaa = A, S, D, or G
<220> FEATURE:
<221> NAME/KEY: MISC_FEATURE
<222> LOCATION: (8)..(8)
<223> OTHER INFORMATION: Xaa = I, S, N, or T
<220> FEATURE:
<221> NAME/KEY: MISC_FEATURE
<222> LOCATION: (9)..(9)
<223> OTHER INFORMATION: Xaa = P, S, L, N, or K
<220> FEATURE:
<221> NAME/KEY: MISC_FEATURE
<222> LOCATION: (10)..(10)
<223> OTHER INFORMATION: Xaa = Y, T, S, N, or G
<220> FEATURE:
<221> NAME/KEY: MISC_FEATURE
<222> LOCATION: (11)..(11)
<223> OTHER INFORMATION: Xaa = V, G, L, or not present
<220> FEATURE:
<221> NAME/KEY: MISC_FEATURE
<222> LOCATION: (12)..(12)
<223> OTHER INFORMATION: Xaa  = P or not present
<220> FEATURE:
<221> NAME/KEY: MISC_FEATURE
<222> LOCATION: (13)..(13)
<223> OTHER INFORMATION: Xaa = T, I, or V

<400> SEQUENCE: 408

Tyr Cys Xaa Xaa Xaa Xaa Xaa Xaa Xaa Xaa Xaa Xaa Xaa Phe
1               5                   10

<210> SEQ ID NO 409
<211> LENGTH: 63
<212> TYPE: DNA
<213> ORGANISM: Artificial Sequence
<220> FEATURE:
<223> OTHER INFORMATION: CD8alpha signal peptide

<400> SEQUENCE: 409
atggccttac cagtgaccgc cttgctcctg ccgctggcct tgctgctcca cgccgccagg        60
ccg                                                                      63

<210> SEQ ID NO 410
<211> LENGTH: 21
<212> TYPE: PRT
<213> ORGANISM: Artificial Sequence
<220> FEATURE:
<223> OTHER INFORMATION: CD8alpha signal peptide

<400> SEQUENCE: 410

Met Ala Leu Pro Val Thr Ala Leu Leu Leu Pro Leu Ala Leu Leu Leu
1               5                   10                  15

His Ala Ala Arg Pro
            20

<210> SEQ ID NO 411
<211> LENGTH: 714
<212> TYPE: DNA
<213> ORGANISM: Artificial Sequence
<220> FEATURE:
<223> OTHER INFORMATION: CK1 scFv

<400> SEQUENCE: 411
```

```
gaagtgcagc tgctggaaag tggaggtgga ctggtgcagc ctggcggcag cctgcgcctg      60
agctgtgccg ccagcggatt caccttcagc cgctatgcca tgacctgggt tcgccaagca     120
cctggcaaag gcctggaatg ggtgagcagc atgagcggca ccggcggcac cacctattat     180
gccgatagcg tgaaaggtcg ctttaccatc agccgcgata acagcaaaaa caccctgtat     240
ctgcagatga acagcctgcg cgccgaggac accgcagtct actactgtgc ccgcggcgcc     300
tatggctttg atcattgggg acaaggtact ctggtgaccg tgagcagcag tggaggaggt     360
agcggaggtg gtggatctgg aggtggaggt agtgaaatcg tgctgaccca gagccctggc     420
accctgagcc tgagccctgg cgaacgcgca cacactgtcat gccgcgccag ccagagcatc     480
ggcaactatc tgaactggta tcagcagaaa ccaggtcagg ctccacgtct gctgatctat     540
gatgccagca acctggaaac cggcatccct gatcgcttct caggatctgg aagcggtacc     600
gattttaccc tgaccatcag ccgcctggaa cctgaggact ttgccgtgta ttattgtcag     660
cagagtagcg ccatcccta taccttcggt cagggcacta aagtggaaat caaa           714
```

```
<210> SEQ ID NO 412
<211> LENGTH: 238
<212> TYPE: PRT
<213> ORGANISM: Artificial Sequence
<220> FEATURE:
<223> OTHER INFORMATION: CK1 scFv

<400> SEQUENCE: 412

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Ala Met Thr Trp Val Arg Gln Ala Pro Gly Lys Gly Leu Glu Trp Val
        35                  40                  45

Ser Ser Met Ser Gly Thr Gly Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Ala Tyr Gly Phe Asp His Trp Gly Gln Gly Thr Leu Val
            100                 105                 110

Thr Val Ser Ser Ser Gly Gly Gly Ser Gly Gly Gly Gly Ser Gly Gly
        115                 120                 125

Gly Gly Ser Glu Ile Val Leu Thr Gln Ser Pro Gly Thr Leu Ser Leu
    130                 135                 140

Ser Pro Gly Glu Arg Ala Thr Leu Ser Cys Arg Ala Ser Gln Ser Ile
145                 150                 155                 160

Gly Asn Tyr Leu Asn Trp Tyr Gln Gln Lys Pro Gly Gln Ala Pro Arg
                165                 170                 175

Leu Leu Ile Tyr Asp Ala Ser Asn Leu Glu Thr Gly Ile Pro Asp Arg
            180                 185                 190

Phe Ser Gly Ser Gly Ser Gly Thr Asp Phe Thr Leu Thr Ile Ser Arg
        195                 200                 205

Leu Glu Pro Glu Asp Phe Ala Val Tyr Tyr Cys Gln Gln Ser Ser Ala
    210                 215                 220

Ile Pro Tyr Thr Phe Gly Gln Gly Thr Lys Val Glu Ile Lys
225                 230                 235
```

-continued

```
<210> SEQ ID NO 413
<211> LENGTH: 729
<212> TYPE: DNA
<213> ORGANISM: Artificial Sequence
<220> FEATURE:
<223> OTHER INFORMATION: CL6 scFv

<400> SEQUENCE: 413
gaggtgcagc tgttggagtc tggtggaggc ttggtacagc ctggaggttc tcttcgcctc      60
tcctgtgcag cctccggatt cactttcagc agctacggta tgcattgggt cagacaggca     120
ccaggtaagg gactggagtg ggtctctgca attagcggta gcggtggtag cacttactac     180
gcagacagcg tgaagggtcg cttcaccatc tcacgcgaca actccaagaa caccctgtac     240
ctgcagatga acagccttcg cgcagaggac actgccgtgt attactgcgc agtcagtggt     300
gcaggtcgtg gtttcttcga ctactgggga caaggtactc tggtcactgt ctcctcaggt     360
ggaggcggtt caggcggagg tggatctggc ggtggcggat cccagtctgt gctgactcag     420
ccaccttcag catctggtac tccaggtcag cgcgtcacca tcagctgcag cggtagcagc     480
agcaacattg gtagcaacta cgtgtactgg tatcagcaac tcccaggcac cgctcctaag     540
ctcctgattt acgaggacaa caagcgtcct agtggtgtgc ctgatcgctt ttctgggtcc     600
aagtctggca cctcagcctc tctggctatc agtggacttc gctccgagga cgaggctgac     660
tattactgca gcagctacac tagcagcagc actgtgatct cggcggtgg gaccaaactg     720 accgtccta                                                            729

<210> SEQ ID NO 414
<211> LENGTH: 243
<212> TYPE: PRT
<213> ORGANISM: Artificial Sequence
<220> FEATURE:
<223> OTHER INFORMATION: CL6 scFv

<400> SEQUENCE: 414

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Val Ser Gly Ala Gly Arg Gly Phe Phe Asp Tyr Trp Gly Gln Gly
            100                 105                 110

Thr Leu Val Thr Val Ser Ser Gly Gly Gly Ser Gly Gly Gly Gly
        115                 120                 125

Ser Gly Gly Gly Gly Ser Gln Ser Val Leu Thr Gln Pro Pro Ser Ala
    130                 135                 140

Ser Gly Thr Pro Gly Gln Arg Val Thr Ile Ser Cys Ser Gly Ser Ser
145                 150                 155                 160

Ser Asn Ile Gly Ser Asn Tyr Val Tyr Trp Tyr Gln Gln Leu Pro Gly
                165                 170                 175
```

-continued

```
Thr Ala Pro Lys Leu Leu Ile Tyr Glu Asp Asn Lys Arg Pro Ser Gly
            180             185             190

Val Pro Asp Arg Phe Ser Gly Ser Lys Ser Gly Thr Ser Ala Ser Leu
        195             200             205

Ala Ile Ser Gly Leu Arg Ser Glu Asp Glu Ala Asp Tyr Tyr Cys Ser
        210             215             220

Ser Tyr Thr Ser Ser Ser Thr Val Ile Phe Gly Gly Gly Thr Lys Leu
225             230             235             240

Thr Val Leu

<210> SEQ ID NO 415
<211> LENGTH: 720
<212> TYPE: DNA
<213> ORGANISM: Artificial Sequence
<220> FEATURE:
<223> OTHER INFORMATION: CL7 scFv

<400> SEQUENCE: 415
gaggtgcagc tgttggagtc tggtggaggc ttggtacagc ctggaggttc tcttcgcctc      60
tcctgtgcag cctccggatt cactttcagc cgctacgcaa tgagctgggt cagacaggca     120
ccaggtaagg gactggagtg ggtctctgca attagcggta gcggtggtag cacttactac     180
gcagacagcg tgaagggtcg cttcaccatc tcacgcgaca actccaagaa caccctgtac     240
ctgcagatga acagccttcg cgcagaggac actgccgtgt attactgcgc acgtagcagc     300
cagggtatct tcgacatctg gggacaaggt actctggtca ctgtctcctc aggtggaggc     360
ggttcaggcg gaggtggatc tggcggtggc ggatcccagt ctgtgctgac tcagccacct     420
tcagcatctg gtactccagg tcagcgcgtc accatcagct gcagtggtaa caatatcggt     480
actagacgcg tgcattggta tcagcaactc ccagacaccg tcctaagct cctgatttac     540 agtaagaaca accgtcctag tggtgtgcct gatcgctttt ctgggtccaa gtctggcacc     600
tcagcctctc tggctatcag tggacttcgc tccgaggacg aggctgacta ttactgcgca     660
gcatgggacg acagcctgag cggtcctgtg ttcggcggtg ggaccaaact gaccgtccta     720

<210> SEQ ID NO 416
<211> LENGTH: 240
<212> TYPE: PRT
<213> ORGANISM: Artificial Sequence
<220> FEATURE:
<223> OTHER INFORMATION: CL7 scFv

<400> SEQUENCE: 416

Glu Val Gln Leu Leu Glu Ser Gly Gly Gly Leu Val Gln Pro Gly Gly
1               5               10              15

Ser Leu Arg Leu Ser Cys Ala Ala Ser Gly Phe Thr Phe Ser Arg Tyr
            20              25              30

Ala Met Ser Trp Val Arg Gln Ala Pro Gly Lys Gly Leu Glu Trp Val
        35              40              45

Ser Ala Ile Ser Gly Ser Gly Gly Ser Thr Tyr Tyr Ala Asp Ser Val
        50              55              60

Lys Gly Arg Phe Thr Ile Ser Arg Asp Asn Ser Lys Asn Thr Leu Tyr
65              70              75              80

Leu Gln Met Asn Ser Leu Arg Ala Glu Asp Thr Ala Val Tyr Tyr Cys
            85              90              95

Ala Arg Ser Ser Gln Gly Ile Phe Asp Ile Trp Gly Gln Gly Thr Leu
            100             105             110
```

-continued

```
Val Thr Val Ser Ser Gly Gly Gly Ser Gly Gly Gly Gly Ser Gly
        115                 120                 125

Gly Gly Gly Ser Gln Ser Val Leu Thr Gln Pro Pro Ser Ala Ser Gly
    130                 135                 140

Thr Pro Gly Gln Arg Val Thr Ile Ser Cys Ser Gly Asn Asn Ile Gly
145                 150                 155                 160

Thr Arg Arg Val His Trp Tyr Gln Gln Leu Pro Asp Thr Ala Pro Lys
                165                 170                 175

Leu Leu Ile Tyr Ser Lys Asn Asn Arg Pro Ser Gly Val Pro Asp Arg
                180                 185                 190

Phe Ser Gly Ser Lys Ser Gly Thr Ser Ala Ser Leu Ala Ile Ser Gly
                195                 200                 205

Leu Arg Ser Glu Asp Glu Ala Asp Tyr Tyr Cys Ala Ala Trp Asp Asp
        210                 215                 220

Ser Leu Ser Gly Pro Val Phe Gly Gly Gly Thr Lys Leu Thr Val Leu
225                 230                 235                 240
```

<210> SEQ ID NO 417
<211> LENGTH: 720
<212> TYPE: DNA
<213> ORGANISM: Artificial Sequence
<220> FEATURE:
<223> OTHER INFORMATION: CL10 scFv

<400> SEQUENCE: 417

```
gaggtgcagc tgttggagtc tggtggaggc ttggtacagc ctggaggttc tcttcgcctc     60
tcctgtgcag cctccggatt cactttcagc agctacggta tgcattgggt cagacaggca    120
ccaggtaagg gactggagtg ggtctctgca attagcggta gcggtggtag cacttactac    180
gcagacagcg tgaagggtcg cttcaccatc tcacgcgaca actccaagaa caccctgtac    240
ctgcagatga acagccttcg cgcagaggac actgccgtgt attactgcgc aagcggttac    300
ggtctgatgg acgtgtgggg acaaggtact ctggtcactg tctcctcagg tggaggcggt    360
tcaggcggag gtggatctgg cggtggcgga tcccagtctg tgctgactca gccaccttca    420
gcatctggta ctccaggtca gcgcgtcacc atcagctgca ctcgtagcag cggtatcatc    480
gcaagcaact acgtgcagtg gtatcagcaa ctcccaggca ccgctcctaa gctcctgatt    540
taccgcaaca accagcgccc tagtggtgtg cctgatcgct tttctgggtc caagtctggc    600
acctcagcct ctctggctat cagtggactt cgctccgagg acgaggctga ctattactgc    660
agcagctacg caggtaacaa caacctggtg ttcggcggtg ggaccaaact gaccgtccta    720
```

<210> SEQ ID NO 418
<211> LENGTH: 240
<212> TYPE: PRT
<213> ORGANISM: Artificial Sequence
<220> FEATURE:
<223> OTHER INFORMATION: CL10 scFv

<400> SEQUENCE: 418

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60
```

-continued

---

```
Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Gly Tyr Gly Leu Met Asp Val Trp Gly Gln Gly Thr Leu Val
            100                 105                 110

Thr Val Ser Ser Gly Gly Gly Gly Ser Gly Gly Gly Gly Ser Gly Gly
            115                 120                 125

Gly Gly Ser Gln Ser Val Leu Thr Gln Pro Pro Ser Ala Ser Gly Thr
    130                 135                 140

Pro Gly Gln Arg Val Thr Ile Ser Cys Thr Arg Ser Ser Gly Ile Ile
145                 150                 155                 160

Ala Ser Asn Tyr Val Gln Trp Tyr Gln Gln Leu Pro Gly Thr Ala Pro
                165                 170                 175

Lys Leu Leu Ile Tyr Arg Asn Asn Gln Arg Pro Ser Gly Val Pro Asp
            180                 185                 190

Arg Phe Ser Gly Ser Lys Ser Gly Thr Ser Ala Ser Leu Ala Ile Ser
            195                 200                 205

Gly Leu Arg Ser Glu Asp Glu Ala Asp Tyr Tyr Cys Ser Ser Tyr Ala
    210                 215                 220

Gly Asn Asn Asn Leu Val Phe Gly Gly Gly Thr Lys Leu Thr Val Leu
225                 230                 235                 240
```

<210> SEQ ID NO 419
<211> LENGTH: 717
<212> TYPE: DNA
<213> ORGANISM: Artificial Sequence
<220> FEATURE:
<223> OTHER INFORMATION: SL18 scFv

<400> SEQUENCE: 419

```
cgagtgcagc tgctggaaag tggaggtgga ctggtgcagc ctggcggcag cctgcgcctg       60
agctgtgccg ccagcggatt caccttcagc gattatcata tgcattgggt tcgccaagca      120
cctggcaaag gcctggaatg ggtgagcacc atcagcagca gcggcggcta tacctattat      180
gccgaaagcg tgaaaagccg ctttaccatc agccgcgata acagcaaaaa caccctgtat      240
ctgcagatga acagcctgcg cgccgaggac accgcagtct actactgtgc cgatcgata       300 cgcctgcctc tggattattg gggacaaggt actctggtga ccgtgagcag cagtggagga      360
ggtagcggag gtggtggatc tggaggtgga ggtagtcaga gcgtgctgac ccagcctcct      420
agcgcctccg gtaccaggg acagcgcgtg actattagct gtagcggcaa caacatcggc      480
agcaaaggcg tgcattggta tcagcaactg cctggaactg cacctaagct gctgatctat      540
gaagatagca aacgccctag cggcgtgcgt gatcgcttta gcggtagcaa atcaggcacc      600
agcgccagcc tggccatcag cggccttcgc tccgaagatg aagccgatta ttattgtcag      660
agctatgata gcaccaaagg cgtggtgttt ggtggcggta ccaagctgac cgtgctg        717
```

<210> SEQ ID NO 420
<211> LENGTH: 239
<212> TYPE: PRT
<213> ORGANISM: Artificial Sequence
<220> FEATURE:
<223> OTHER INFORMATION: SL18 scFv

<400> SEQUENCE: 420

```
Arg Val Gln Leu Leu Glu Ser Gly Gly Gly Leu Val Gln Pro Gly Gly
```

```
1                   5                   10                  15

Ser Leu Arg Leu Ser Cys Ala Ala Ser Gly Phe Thr Phe Ser Asp Tyr
            20                  25                  30

His Met His Trp Val Arg Gln Ala Pro Gly Lys Gly Leu Glu Trp Val
        35                  40                  45

Ser Thr Ile Ser Ser Ser Gly Gly Tyr Thr Tyr Tyr Ala Glu Ser Val
    50                  55                  60

Lys Ser Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Ile Arg Leu Pro Leu Asp Tyr Trp Gly Gln Gly Thr Leu
            100                 105                 110

Val Thr Val Ser Ser Ser Gly Gly Gly Ser Gly Gly Gly Gly Ser Gly
            115                 120                 125

Gly Gly Ser Gln Ser Val Leu Thr Gln Pro Pro Ser Ala Ser Gly
    130                 135                 140

Thr Pro Gly Gln Arg Val Thr Ile Ser Cys Ser Gly Asn Asn Ile Gly
145                 150                 155                 160

Ser Lys Gly Val His Trp Tyr Gln Gln Leu Pro Gly Thr Ala Pro Lys
                165                 170                 175

Leu Leu Ile Tyr Glu Asp Ser Lys Arg Pro Ser Gly Val Arg Asp Arg
            180                 185                 190

Phe Ser Gly Ser Lys Ser Gly Thr Ser Ala Ser Leu Ala Ile Ser Gly
            195                 200                 205

Leu Arg Ser Glu Asp Glu Ala Asp Tyr Tyr Cys Gln Ser Tyr Asp Ser
    210                 215                 220

Thr Lys Gly Val Val Phe Gly Gly Gly Thr Lys Leu Thr Val Leu
225                 230                 235
```

```
<210> SEQ ID NO 421
<211> LENGTH: 30
<212> TYPE: DNA
<213> ORGANISM: Artificial Sequence
<220> FEATURE:
<223> OTHER INFORMATION: GS linker

<400> SEQUENCE: 421
ggtggcggag gttctggagg tggaggttcc                                    30

<210> SEQ ID NO 422
<211> LENGTH: 10
<212> TYPE: PRT
<213> ORGANISM: Artificial Sequence
<220> FEATURE:
<223> OTHER INFORMATION: GS linker

<400> SEQUENCE: 422

Gly Gly Gly Gly Ser Gly Gly Gly Gly Ser
1               5                   10

<210> SEQ ID NO 423
<211> LENGTH: 135
<212> TYPE: DNA
<213> ORGANISM: Artificial Sequence
<220> FEATURE:
<223> OTHER INFORMATION: CD8 hinge

<400> SEQUENCE: 423
```

-continued

```
accacgacgc cagcgccgcg accaccaaca ccggcgccca ccatcgcgtc gcagcccctg        60
tccctgcgcc cagaggcgtg ccggccagcg gcggggggcg cagtgcacac gaggggggctg      120 gacttcgcct gtgat                                                        135
```

<210> SEQ ID NO 424
<211> LENGTH: 45
<212> TYPE: PRT
<213> ORGANISM: Artificial Sequence
<220> FEATURE:
<223> OTHER INFORMATION: CD8 hinge

<400> SEQUENCE: 424

```
Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45
```

<210> SEQ ID NO 425
<211> LENGTH: 81
<212> TYPE: DNA
<213> ORGANISM: Artificial Sequence
<220> FEATURE:
<223> OTHER INFORMATION: CD28 transmembrane domain

<400> SEQUENCE: 425

```
ttttgggtgc tggtggtggt tgtggagtc ctggcttgct atagcttgct agtaacagtg        60
gcctttatta ttttctgggt g                                                  81
```

<210> SEQ ID NO 426
<211> LENGTH: 27
<212> TYPE: PRT
<213> ORGANISM: Artificial Sequence
<220> FEATURE:
<223> OTHER INFORMATION: CD28 transmembrane domain

<400> SEQUENCE: 426

```
Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25
```

<210> SEQ ID NO 427
<211> LENGTH: 123
<212> TYPE: DNA
<213> ORGANISM: Artificial Sequence
<220> FEATURE:
<223> OTHER INFORMATION: CD28 intracellular domain

<400> SEQUENCE: 427

```
aggagtaaga ggagcaggct cctgcacagt gactacatga acatgactcc ccgccgcccc       60
gggcccaccc gcaagcatta ccagccctat gccccaccac gcgacttcgc agcctatcgc      120
tcc                                                                     123
```

<210> SEQ ID NO 428
<211> LENGTH: 41
<212> TYPE: PRT
<213> ORGANISM: Artificial Sequence
<220> FEATURE:
<223> OTHER INFORMATION: CD28 intracellular domain -continued

```
<400> SEQUENCE: 428

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 429
<211> LENGTH: 339
<212> TYPE: DNA
<213> ORGANISM: Artificial Sequence
<220> FEATURE:
<223> OTHER INFORMATION: CD3zeta intracellular domain

<400> SEQUENCE: 429
agagtgaagt tcagcaggag cgcagacgcc cccgcgtacc agcagggcca gaaccagctc      60
tataacgagc tcaatctagg acgaagagag gagtacgatg ttttggacaa gagacgtggc     120
cgggaccctg agatggggggg aaagccgaga aggaagaacc ctcaggaagg cctgtacaat     180
gaactgcaga aagataagat ggcggaggcc tacagtgaga ttgggatgaa aggcgagcgc     240 cggagggggca aggggcacga tggcctttac cagggtctca gtacagccac caaggacacc     300
tacgacgccc ttcacatgca ggccctgccc cctcgctaa                             339

<210> SEQ ID NO 430
<211> LENGTH: 112
<212> TYPE: PRT
<213> ORGANISM: Artificial Sequence
<220> FEATURE:
<223> OTHER INFORMATION: CD3zeta intracellular domain

<400> SEQUENCE: 430

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 431
<211> LENGTH: 1485
<212> TYPE: DNA
<213> ORGANISM: Artificial Sequence
<220> FEATURE:
<223> OTHER INFORMATION: CK1 CAR

<400> SEQUENCE: 431
atggccttac cagtgaccgc cttgctcctg ccgctggcct tgctgctcca cgccgccagg      60
ccggaagtgc agctgctgga aagtggaggt ggactggtgc agcctggcgg cagcctcgcc     120
ctgagctgtg ccgccagcgg attcaccttc agccgctatg ccatgacctg ggttcgccaa     180
```

-continued

```
gcacctggca aaggcctgga atgggtgagc agcatgagcg gcaccggcgg caccacctat      240
tatgccgata gcgtgaaagg tcgctttacc atcagccgcg ataacagcaa aaacaccctg      300
tatctgcaga tgaacagcct gcgcgccgag gacaccgcag tctactactg tgcccgcggc      360
gcctatggct ttgatcattg gggacaaggt actctggtga ccgtgagcag cagtggagga      420
ggtagcggag gtggtggatc tggaggtgga ggtagtgaaa tcgtgctgac ccagagccct      480
ggcaccctga gcctgagccc tggcgaacgc gcaacactgt catgccgcgc cagccagagc      540
atcggcaact atctgaactg gtatcagcag aaaccaggtc aggctccacg tctgctgatc      600
tatgatgcca gcaacctgga aaccggcatc cctgatcgct tctcaggatc tggaagcggt      660
accgatttta ccctgaccat cagccgcctg gaacctgagg actttgccgt gtattattgt      720
cagcagagta gcgccatccc ttataccttc ggtcagggca ctaaagtgga aatcaaaggt      780
ggcggaggtt ctggaggtgg aggttccacc acgacgccag cgccgcgacc accaacaccg      840
gcgcccacca tcgcgtcgca gcccctgtcc ctgcgcccag aggcgtgccg gccagcggcg      900
gggggcgcag tgcacacgag ggggctggac ttcgcctgtg atttttgggt gctggtggtg      960
gttggtggag tcctggcttg ctatagcttg ctagtaacag tggcctttat tattttctgg     1020
gtgaggagta agaggagcag gctcctgcac agtgactaca tgaacatgac tccccgccgc     1080
cccgggccca cccgcaagca ttaccagccc tatgccccac cacgcgactt cgcagcctat     1140
cgctccagag tgaagttcag caggagcgca gacgcccccg cgtaccagca gggccagaac     1200
cagctctata cgagctcaa tctaggacga agagaggagt acgatgtttt ggacaagaga     1260
cgtggccggg accctgagat ggggggaaag ccgagaagga agaaccctca ggaaggcctg     1320
tacaatgaac tgcagaaaga taagatggcg gaggcctaca gtgagattgg gatgaaaggc     1380
gagcgccgga ggggcaaggg cacgatggc ctttaccagg tctcagtac agccaccaag     1440 gacacctacg acgcccttca catgcaggcc ctgcccccctc gctaa                    1485
```

<210> SEQ ID NO 432
<211> LENGTH: 494
<212> TYPE: PRT
<213> ORGANISM: Artificial Sequence
<220> FEATURE:
<223> OTHER INFORMATION: CK1 CAR

<400> SEQUENCE: 432

```
Met Ala Leu Pro Val Thr Ala Leu Leu Leu Pro Leu Ala Leu Leu Leu
1               5                   10                  15

His Ala Ala Arg Pro Glu Val Gln Leu Leu Glu Ser Gly Gly Gly Leu
                20                  25                  30

Val Gln Pro Gly Gly Ser Leu Arg Leu Ser Cys Ala Ala Ser Gly Phe
            35                  40                  45

Thr Phe Ser Arg Tyr Ala Met Thr Trp Val Arg Gln Ala Pro Gly Lys
        50                  55                  60

Gly Leu Glu Trp Val Ser Ser Met Ser Gly Thr Gly Gly Thr Thr Tyr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Arg Gly Ala Tyr Gly Phe Asp His Trp Gly
            115                 120                 125
```

```
Gln Gly Thr Leu Val Thr Val Ser Ser Ser Gly Gly Ser Gly Gly
    130                 135                 140

Gly Gly Ser Gly Gly Gly Gly Ser Glu Ile Val Leu Thr Gln Ser Pro
145                 150                 155                 160

Gly Thr Leu Ser Leu Ser Pro Gly Glu Arg Ala Thr Leu Ser Cys Arg
                165                 170                 175

Ala Ser Gln Ser Ile Gly Asn Tyr Leu Asn Trp Tyr Gln Gln Lys Pro
            180                 185                 190

Gly Gln Ala Pro Arg Leu Leu Ile Tyr Asp Ala Ser Asn Leu Glu Thr
            195                 200                 205

Gly Ile Pro Asp Arg Phe Ser Gly Ser Gly Ser Gly Thr Asp Phe Thr
    210                 215                 220

Leu Thr Ile Ser Arg Leu Glu Pro Glu Asp Phe Ala Val Tyr Tyr Cys
225                 230                 235                 240

Gln Gln Ser Ser Ala Ile Pro Tyr Thr Phe Gly Gln Gly Thr Lys Val
                245                 250                 255

Glu Ile Lys Gly Gly Gly Gly Ser Gly Gly Gly Gly Ser Thr Thr Thr
            260                 265                 270

Pro Ala Pro Arg Pro Pro Thr Pro Ala Pro Thr Ile Ala Ser Gln Pro
            275                 280                 285

Leu Ser Leu Arg Pro Glu Ala Cys Arg Pro Ala Ala Gly Gly Ala Val
    290                 295                 300

His Thr Arg Gly Leu Asp Phe Ala Cys Asp Phe Trp Val Leu Val Val
305                 310                 315                 320

Val Gly Gly Val Leu Ala Cys Tyr Ser Leu Leu Val Thr Val Ala Phe
                325                 330                 335

Ile Ile Phe Trp Val Arg Ser Lys Arg Ser Arg Leu Leu His Ser Asp
                340                 345                 350

Tyr Met Asn Met Thr Pro Arg Arg Pro Gly Pro Thr Arg Lys His Tyr
            355                 360                 365

Gln Pro Tyr Ala Pro Pro Arg Asp Phe Ala Ala Tyr Arg Ser Arg Val
    370                 375                 380

Lys Phe Ser Arg Ser Ala Asp Ala Pro Ala Tyr Gln Gln Gly Gln Asn
385                 390                 395                 400

Gln Leu Tyr Asn Glu Leu Asn Leu Gly Arg Arg Glu Glu Tyr Asp Val
            405                 410                 415

Leu Asp Lys Arg Arg Gly Arg Asp Pro Glu Met Gly Gly Lys Pro Arg
            420                 425                 430

Arg Lys Asn Pro Gln Glu Gly Leu Tyr Asn Glu Leu Gln Lys Asp Lys
            435                 440                 445

Met Ala Glu Ala Tyr Ser Glu Ile Gly Met Lys Gly Glu Arg Arg Arg
    450                 455                 460

Gly Lys Gly His Asp Gly Leu Tyr Gln Gly Leu Ser Thr Ala Thr Lys
465                 470                 475                 480

Asp Thr Tyr Asp Ala Leu His Met Gln Ala Leu Pro Pro Arg
                485                 490
```

```
<210> SEQ ID NO 433
<211> LENGTH: 1500
<212> TYPE: DNA
<213> ORGANISM: Artificial Sequence
<220> FEATURE:
<223> OTHER INFORMATION: CL6 CAR

<400> SEQUENCE: 433
```

-continued

```
atggccttac cagtgaccgc cttgctcctg ccgctggcct tgctgctcca cgccgccagg       60
ccggaggtgc agctgttgga gtctggtgga ggcttggtac agcctggagg ttctcttcgc      120
ctctcctgtg cagcctccgg attcactttc agcagctacg gtatgcattg ggtcagacag      180
gcaccaggta agggactgga gtgggtctct gcaattagcg gtagcggtgg tagcacttac      240
tacgcagaca gcgtgaaggg tcgcttcacc atctcacgcg acaactccaa gaacaccctg      300
tacctgcaga tgaacagcct tcgcgcagag gacactgccg tgtattactg cgcagtcagt      360
ggtgcaggtc gtggtttctt cgactactgg ggacaaggta ctctggtcac tgtctcctca      420 ggtgaggcg gttcaggcgg aggtggatct ggcggtggcg gatcccagtc tgtgctgact      480
cagccacctt cagcatctgg tactccaggt cagcgcgtca ccatcagctg cagcggtagc      540
agcagcaaca ttggtagcaa ctacgtgtac tggtatcagc aactcccagg caccgctcct      600
aagctcctga tttacgagga caacaagcgt cctagtggtg tgcctgatcg cttttctggg      660
tccaagtctg gcacctcagc ctctctggct atcagtggac ttcgctccga ggacgaggct      720
gactattact gcagcagcta cactagcagc agcactgtga tcttcggcgg tgggaccaaa      780
ctgaccgtcc taggtggcgg aggttctgga ggtggaggtt ccaccacgac gccagcgccg      840
cgaccaccaa caccggcgcc caccatcgcg tcgcagcccc tgtccctgcg cccagaggcg      900
tgccggccag cggcgggggg cgcagtgcac acgagggggc tggacttcgc ctgtgatttt      960
tgggtgctgg tggtggttgg tggagtcctg gcttgctata gcttgctagt aacagtggcc     1020
tttattattt tctgggtgag gagtaagagg agcaggctcc tgcacagtga ctacatgaac     1080
atgactcccc gccgccccgg gcccacccgc aagcattacc agccctatgc cccaccacgc     1140
gacttcgcag cctatcgctc cagagtgaag ttcagcagga gcgcagacgc ccccgcgtac     1200
cagcagggcc agaaccagct ctataacgag ctcaatctag gacgaagaga ggagtacgat     1260
gttttggaca gagacgtggc cgggaccct gagatggggg gaaagccgag aaggaagaac      1320
cctcaggaag gcctgtacaa tgaactgcag aaagataaga tggcggaggc ctacagtgag     1380
attgggatga aaggcgagcg ccggaggggc aagggggacg atggcctta ccagggtctc      1440 agtacagcca ccaaggacac ctacgacgcc cttcacatgc aggccctgcc ccctcgctaa     1500
```

<210> SEQ ID NO 434
<211> LENGTH: 499
<212> TYPE: PRT
<213> ORGANISM: Artificial Sequence
<220> FEATURE:
<223> OTHER INFORMATION: CL6 CAR

<400> SEQUENCE: 434

```
Met Ala Leu Pro Val Thr Ala Leu Leu Leu Pro Leu Ala Leu Leu Leu
1               5                   10                  15

His Ala Ala Arg Pro Glu Val Gln Leu Leu Glu Ser Gly Gly Gly Leu
            20                  25                  30

Val Gln Pro Gly Gly Ser Leu Arg Leu Ser Cys Ala Ala Ser Gly Phe
        35                  40                  45

Thr Phe Ser Ser Tyr Gly Met His Trp Val Arg Gln Ala Pro Gly Lys
    50                  55                  60

Gly Leu Glu Trp Val Ser Ala Ile Ser Gly Ser Gly Gly Ser Thr Tyr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
```

```
              100               105               110
Ala Val Tyr Tyr Cys Ala Val Ser Gly Ala Gly Arg Gly Phe Phe Asp
              115               120               125

Tyr Trp Gly Gln Gly Thr Leu Val Thr Val Ser Ser Gly Gly Gly Gly
    130               135               140

Ser Gly Gly Gly Gly Ser Gly Gly Gly Gly Ser Gln Ser Val Leu Thr
145               150               155               160

Gln Pro Pro Ser Ala Ser Gly Thr Pro Gly Gln Arg Val Thr Ile Ser
              165               170               175

Cys Ser Gly Ser Ser Ser Asn Ile Gly Ser Asn Tyr Val Tyr Trp Tyr
              180               185               190

Gln Gln Leu Pro Gly Thr Ala Pro Lys Leu Leu Ile Tyr Glu Asp Asn
              195               200               205

Lys Arg Pro Ser Gly Val Pro Asp Arg Phe Ser Gly Ser Lys Ser Gly
    210               215               220

Thr Ser Ala Ser Leu Ala Ile Ser Gly Leu Arg Ser Glu Asp Glu Ala
225               230               235               240

Asp Tyr Tyr Cys Ser Ser Tyr Thr Ser Ser Ser Thr Val Ile Phe Gly
              245               250               255

Gly Gly Thr Lys Leu Thr Val Leu Gly Gly Gly Gly Ser Gly Gly Gly
              260               265               270

Gly Ser Thr Thr Thr Pro Ala Pro Arg Pro Pro Thr Pro Ala Pro Thr
    275               280               285

Ile Ala Ser Gln Pro Leu Ser Leu Arg Pro Glu Ala Cys Arg Pro Ala
    290               295               300

Ala Gly Gly Ala Val His Thr Arg Gly Leu Asp Phe Ala Cys Asp Phe
305               310               315               320

Trp Val Leu Val Val Val Gly Gly Val Leu Ala Cys Tyr Ser Leu Leu
              325               330               335

Val Thr Val Ala Phe Ile Ile Phe Trp Val Arg Ser Lys Arg Ser Arg
              340               345               350

Leu Leu His Ser Asp Tyr Met Asn Met Thr Pro Arg Arg Pro Gly Pro
              355               360               365

Thr Arg Lys His Tyr Gln Pro Tyr Ala Pro Pro Arg Asp Phe Ala Ala
    370               375               380

Tyr Arg Ser Arg Val Lys Phe Ser Arg Ser Ala Asp Ala Pro Ala Tyr
385               390               395               400

Gln Gln Gly Gln Asn Gln Leu Tyr Asn Glu Leu Asn Leu Gly Arg Arg
              405               410               415

Glu Glu Tyr Asp Val Leu Asp Lys Arg Arg Gly Arg Asp Pro Glu Met
              420               425               430

Gly Gly Lys Pro Arg Arg Lys Asn Pro Gln Glu Gly Leu Tyr Asn Glu
              435               440               445

Leu Gln Lys Asp Lys Met Ala Glu Ala Tyr Ser Glu Ile Gly Met Lys
    450               455               460

Gly Glu Arg Arg Arg Gly Lys Gly His Asp Gly Leu Tyr Gln Gly Leu
465               470               475               480

Ser Thr Ala Thr Lys Asp Thr Tyr Asp Ala Leu His Met Gln Ala Leu
              485               490               495

Pro Pro Arg
```

<210> SEQ ID NO 435
<211> LENGTH: 1491

-continued

```
<212> TYPE: DNA
<213> ORGANISM: Artificial Sequence
<220> FEATURE:
<223> OTHER INFORMATION: CL7 CAR

<400> SEQUENCE: 435
atggccttac cagtgaccgc cttgctcctg ccgctggcct tgctgctcca cgccgccagg      60
ccggaggtgc agctgttgga gtctggtgga ggcttggtac agcctggagg ttctcttcgc     120
ctctcctgtg cagcctccgg attcactttc agccgctacg caatgagctg ggtcagacag     180
gcaccaggta aagggactgga gtgggtctct gcaattagcg gtagcggtgg tagcacttac     240
tacgcagaca gcgtgaaggg tcgcttcacc atctcacgcg acaactccaa gaacaccctg     300
tacctgcaga tgaacagcct tcgcgcagag gacactgccg tgtattactg cgcacgtagc     360
agccagggta tcttcgacat ctggggacaa ggtactctgg tcactgtctc ctcaggtgga     420
ggcggttcag gcggaggtgg atctggcggt ggcggatccc agtctgtgct gactcagcca     480
ccttcagcat ctggtactcc aggtcagcgc gtcaccatca gctgcagtgg taacaatatc     540
ggtactagac gcgtgcattg gtatcagcaa ctcccagaca ccgctcctaa gctcctgatt     600
tacagtaaga caaccgtcc tagtggtgtg cctgatcgct tttctgggtc caagtctggc     660
acctcagcct ctctggctat cagtggactt cgctccgagg acgaggctga ctattactgc     720
gcagcatggg acgacagcct gagcggtcct gtgttcggcg gtgggaccaa actgaccgtc     780
ctaggtggcg gaggttctgg aggtggaggt tccaccacga cgccagcgcc gcgaccacca     840
acaccggcgc ccaccatcgc gtcgcagccc ctgtccctgc gcccagaggc gtgccggcca     900
gcggcggggg gcgcagtgca cacgaggggg ctggacttcg cctgtgattt ttgggtgctg     960
gtggtggttg gtggagtcct ggcttgctat agcttgctag taacagtggc ctttattatt    1020
ttctgggtga ggagtaagag gagcaggctc ctgcacagtg actacatgaa catgactccc    1080
cgccgccccg ggcccacccg caagcattac agccctatg ccccaccacg cgacttcgca     1140
gcctatcgct ccagagtgaa gttcagcagg agcgcagacg cccccgcgta ccagcagggc    1200
cagaaccagc tctataacga gctcaatcta ggacgaagag aggagtacga tgttttggac    1260
aagagacgtg gccgggaccc tgagatgggg ggaaagccga gaaggaagaa ccctcaggaa    1320
ggcctgtaca atgaactgca gaaagataag atggcggagg cctacagtga gattgggatg    1380
aaaggcgagc gccggagggg caagggggcac gatggccttt accagggtct cagtacagcc    1440
accaaggaca cctacgacgc ccttcacatg caggccctgc cccctcgcta a             1491
```

```
<210> SEQ ID NO 436
<211> LENGTH: 496
<212> TYPE: PRT
<213> ORGANISM: Artificial Sequence
<220> FEATURE:
<223> OTHER INFORMATION: CL7 CAR

<400> SEQUENCE: 436

Met Ala Leu Pro Val Thr Ala Leu Leu Leu Pro Leu Ala Leu Leu Leu
1               5                   10                  15

His Ala Ala Arg Pro Glu Val Gln Leu Leu Glu Ser Gly Gly Gly Leu
            20                  25                  30

Val Gln Pro Gly Gly Ser Leu Arg Leu Ser Cys Ala Ala Ser Gly Phe
        35                  40                  45

Thr Phe Ser Arg Tyr Ala Met Ser Trp Val Arg Gln Ala Pro Gly Lys
    50                  55                  60
```

-continued

```
Gly Leu Glu Trp Val Ser Ala Ile Ser Gly Ser Gly Gly Ser Thr Tyr
65              70              75              80

Tyr Ala Asp Ser Val Lys Gly Arg Phe Thr Ile Ser Arg Asp Asn Ser
            85              90              95

Lys Asn Thr Leu Tyr Leu Gln Met Asn Ser Leu Arg Ala Glu Asp Thr
        100             105             110

Ala Val Tyr Tyr Cys Ala Arg Ser Ser Gln Gly Ile Phe Asp Ile Trp
        115             120             125

Gly Gln Gly Thr Leu Val Thr Val Ser Ser Gly Gly Gly Ser Gly
    130             135             140

Gly Gly Gly Ser Gly Gly Gly Ser Gln Ser Val Leu Thr Gln Pro
145             150             155             160

Pro Ser Ala Ser Gly Thr Pro Gly Gln Arg Val Thr Ile Ser Cys Ser
            165             170             175

Gly Asn Asn Ile Gly Thr Arg Arg Val His Trp Tyr Gln Gln Leu Pro
            180             185             190

Asp Thr Ala Pro Lys Leu Leu Ile Tyr Ser Lys Asn Asn Arg Pro Ser
        195             200             205

Gly Val Pro Asp Arg Phe Ser Gly Ser Lys Ser Gly Thr Ser Ala Ser
    210             215             220

Leu Ala Ile Ser Gly Leu Arg Ser Glu Asp Glu Ala Asp Tyr Tyr Cys
225             230             235             240

Ala Ala Trp Asp Asp Ser Leu Ser Gly Pro Val Phe Gly Gly Gly Thr
            245             250             255

Lys Leu Thr Val Leu Gly Gly Gly Gly Ser Gly Gly Gly Ser Thr
            260             265             270

Thr Thr Pro Ala Pro Arg Pro Pro Thr Pro Ala Pro Thr Ile Ala Ser
        275             280             285

Gln Pro Leu Ser Leu Arg Pro Glu Ala Cys Arg Pro Ala Ala Gly Gly
    290             295             300

Ala Val His Thr Arg Gly Leu Asp Phe Ala Cys Asp Phe Trp Val Leu
305             310             315             320

Val Val Val Gly Gly Val Leu Ala Cys Tyr Ser Leu Leu Val Thr Val
            325             330             335

Ala Phe Ile Ile Phe Trp Val Arg Ser Lys Arg Ser Arg Leu Leu His
            340             345             350

Ser Asp Tyr Met Asn Met Thr Pro Arg Arg Pro Gly Pro Thr Arg Lys
        355             360             365

His Tyr Gln Pro Tyr Ala Pro Pro Arg Asp Phe Ala Ala Tyr Arg Ser
    370             375             380

Arg Val Lys Phe Ser Arg Ser Ala Asp Ala Pro Ala Tyr Gln Gln Gly
385             390             395             400

Gln Asn Gln Leu Tyr Asn Glu Leu Asn Leu Gly Arg Arg Glu Glu Tyr
            405             410             415

Asp Val Leu Asp Lys Arg Arg Gly Arg Asp Pro Glu Met Gly Gly Lys
            420             425             430

Pro Arg Arg Lys Asn Pro Gln Glu Gly Leu Tyr Asn Glu Leu Gln Lys
        435             440             445

Asp Lys Met Ala Glu Ala Tyr Ser Glu Ile Gly Met Lys Gly Glu Arg
    450             455             460

Arg Arg Gly Lys Gly His Asp Gly Leu Tyr Gln Gly Leu Ser Thr Ala
465             470             475             480

Thr Lys Asp Thr Tyr Asp Ala Leu His Met Gln Ala Leu Pro Pro Arg
```

-continued

<210> SEQ ID NO 437
<211> LENGTH: 1491
<212> TYPE: DNA
<213> ORGANISM: Artificial Sequence
<220> FEATURE:
<223> OTHER INFORMATION: CL10 CAR

<400> SEQUENCE: 437
atggccttac cagtgaccgc cttgctcctg ccgctggcct tgctgctcca cgccgccagg       60
ccggaggtgc agctgttgga gtctggtgga ggcttggtac agcctggagg ttctcttcgc      120
ctctcctgtg cagcctccgg attcactttc agcagctacg gtatgcattg ggtcagacag      180
gcaccaggta agggactgga gtgggtctct gcaattagcg gtagcggtgg tagcacttac      240
tacgcagaca gcgtgaaggg tcgcttcacc atctcacgcg acaactccaa gaacaccctg      300
tacctgcaga tgaacagcct tcgcgcagag gacactgccg tgtattactg cgcaagcggt      360
tacggtctga tggacgtgtg gggacaaggt actctggtca ctgtctcctc aggtggaggc      420
ggttcaggcg gaggtggatc tggcggtggc ggatcccagt ctgtgctgac tcagccacct      480
tcagcatctg gtactccagg tcagcgcgtc accatcagct gcactcgtag cagcggtatc      540
atcgcaagca actacgtgca gtggtatcag caactcccag gcaccgctcc taagctcctg      600
atttaccgca acaaccagcg ccctagtggt gtgcctgatc gcttttctgg gtccaagtct      660
ggcacctcag cctctctggc tatcagtgga cttcgctccg aggacgaggc tgactattac      720
tgcagcagct acgcaggtaa caacaacctg gtgttcggcg gtgggaccaa actgaccgtc      780
ctaggtggcg gaggttctgg aggtggaggt tccaccacga cgccagcgcc gcgaccacca      840
acaccggcgc ccaccatcgc gtcgcagccc ctgtccctgc gcccagaggc gtgccggcca      900
gcggcggggg cgcagtgca cacgagggggg ctggacttcg cctgtgattt ttgggtgctg      960
gtggtggttg gtggagtcct ggcttgctat agcttgctag taacagtggc ctttattatt     1020
ttctgggtga ggagtaagag gagcaggctc ctgcacagtg actacatgaa catgactccc     1080
cgccgccccg ggcccacccg caagcattac agcccctatg ccccaccacg cgacttcgca     1140
gcctatcgct ccagagtgaa gttcagcagg agcgcagacg cccccgcgta ccagcagggc     1200
cagaaccagc tctataacga gctcaatcta ggacgaagag aggagtacga tgttttggac     1260
aagagacgtg gccgggaccc tgagatgggg ggaaagccga gaaggaagaa ccctcaggaa     1320
ggcctgtaca atgaactgca gaaagataag atggcggagg cctacagtga gattgggatg     1380
aaaggcgagc gccggagggg caaggggcac gatggccttt accagggtct cagtacagcc     1440
accaaggaca cctacgacgc ccttcacatg caggccctgc ccctcgcta a               1491

<210> SEQ ID NO 438
<211> LENGTH: 496
<212> TYPE: PRT
<213> ORGANISM: Artificial Sequence
<220> FEATURE:
<223> OTHER INFORMATION: CL10 CAR

<400> SEQUENCE: 438

Met Ala Leu Pro Val Thr Ala Leu Leu Leu Pro Leu Ala Leu Leu Leu
1               5                   10                  15

His Ala Ala Arg Pro Glu Val Gln Leu Leu Glu Ser Gly Gly Gly Leu
            20                  25                  30

Val Gln Pro Gly Gly Ser Leu Arg Leu Ser Cys Ala Ala Ser Gly Phe

```
                35                  40                  45

Thr Phe Ser Ser Tyr Gly Met His Trp Val Arg Gln Ala Pro Gly Lys
    50                  55                  60

Gly Leu Glu Trp Val Ser Ala Ile Ser Gly Ser Gly Gly Ser Thr Tyr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Ser Gly Tyr Gly Leu Met Asp Val Trp Gly
            115                 120                 125

Gln Gly Thr Leu Val Thr Val Ser Ser Gly Gly Gly Ser Gly Gly
    130                 135                 140

Gly Gly Ser Gly Gly Gly Gly Ser Gln Ser Val Leu Thr Gln Pro Pro
145                 150                 155                 160

Ser Ala Ser Gly Thr Pro Gly Gln Arg Val Thr Ile Ser Cys Thr Arg
                165                 170                 175

Ser Ser Gly Ile Ile Ala Ser Asn Tyr Val Gln Trp Tyr Gln Gln Leu
            180                 185                 190

Pro Gly Thr Ala Pro Lys Leu Leu Ile Tyr Arg Asn Asn Gln Arg Pro
            195                 200                 205

Ser Gly Val Pro Asp Arg Phe Ser Gly Ser Lys Ser Gly Thr Ser Ala
    210                 215                 220

Ser Leu Ala Ile Ser Gly Leu Arg Ser Glu Asp Glu Ala Asp Tyr Tyr
225                 230                 235                 240

Cys Ser Ser Tyr Ala Gly Asn Asn Asn Leu Val Phe Gly Gly Gly Thr
                245                 250                 255

Lys Leu Thr Val Leu Gly Gly Gly Gly Ser Gly Gly Gly Gly Ser Thr
            260                 265                 270

Thr Thr Pro Ala Pro Arg Pro Pro Thr Pro Ala Pro Thr Ile Ala Ser
    275                 280                 285

Gln Pro Leu Ser Leu Arg Pro Glu Ala Cys Arg Pro Ala Ala Gly Gly
    290                 295                 300

Ala Val His Thr Arg Gly Leu Asp Phe Ala Cys Asp Phe Trp Val Leu
305                 310                 315                 320

Val Val Val Gly Gly Val Leu Ala Cys Tyr Ser Leu Leu Val Thr Val
            325                 330                 335

Ala Phe Ile Ile Phe Trp Val Arg Ser Lys Arg Ser Arg Leu Leu His
            340                 345                 350

Ser Asp Tyr Met Asn Met Thr Pro Arg Arg Pro Gly Pro Thr Arg Lys
            355                 360                 365

His Tyr Gln Pro Tyr Ala Pro Pro Arg Asp Phe Ala Ala Tyr Arg Ser
    370                 375                 380

Arg Val Lys Phe Ser Arg Ser Ala Asp Ala Pro Ala Tyr Gln Gln Gly
385                 390                 395                 400

Gln Asn Gln Leu Tyr Asn Glu Leu Asn Leu Gly Arg Arg Glu Glu Tyr
                405                 410                 415

Asp Val Leu Asp Lys Arg Arg Gly Arg Asp Pro Glu Met Gly Gly Lys
            420                 425                 430

Pro Arg Arg Lys Asn Pro Gln Glu Gly Leu Tyr Asn Glu Leu Gln Lys
            435                 440                 445

Asp Lys Met Ala Glu Ala Tyr Ser Glu Ile Gly Met Lys Gly Glu Arg
    450                 455                 460
```

-continued

Arg Arg Gly Lys Gly His Asp Gly Leu Tyr Gln Gly Leu Ser Thr Ala
465             470             475             480

Thr Lys Asp Thr Tyr Asp Ala Leu His Met Gln Ala Leu Pro Pro Arg
            485             490             495

<210> SEQ ID NO 439
<211> LENGTH: 1488
<212> TYPE: DNA
<213> ORGANISM: Artificial Sequence
<220> FEATURE:
<223> OTHER INFORMATION: SL18 CAR

<400> SEQUENCE: 439
atggccttac cagtgaccgc cttgctcctg ccgctggcct tgctgctcca cgccgccagg      60
ccgcgagtgc agctgctgga aagtggaggt ggactggtgc agcctggcgg cagcctgcgc     120
ctgagctgtg ccgccagcgg attcaccttc agcgattatc atatgcattg ggttcgccaa     180
gcacctggca aaggcctgga atgggtgagc accatcagca gcagcggcgg ctatacctat     240
tatgccgaaa gcgtgaaaag ccgctttacc atcagccgcg ataacagcaa aaacaccctg     300
tatctgcaga tgaacagcct gcgcgccgag gacaccgcag tctactactg tgcccgatcg     360
atacgcctgc ctctggatta ttggggacaa ggtactctgg tgaccgtgag cagcagtgga     420
ggaggtagcg gaggtggtgg atctggaggt ggaggtagtc agagcgtgct gacccagcct     480
cctagcgcct ccggtacacc aggacagcgc gtgactatta gctgtagcgg caacaacatc     540
ggcagcaaag cgtgcattg gtatcagcaa ctgcctggaa ctgcacctaa gctgctgatc     600
tatgaagata gcaaacgccc tagcggcgtg cgtgatcgct ttagcggtag caaatcaggc     660
accagcgcca gcctggccat cagcggcctt cgctccgaag atgaagccga ttattattgt     720
cagagctatg atagcaccaa aggcgtggtg tttggtggcg gtaccaagct gaccgtgctg     780
ggtggcggag gttctggagg tggaggttcc accacgacgc cagcgccgcg accaccaaca     840
ccggcgccca ccatcgcgtc gcagcccctg tccctgcgcc cagaggcgtg ccggccagcg     900 gcgggggggcg cagtgcacac gagggggctg gacttcgcct gtgatttttg ggtgctggtg     960
gtggttggtg gagtcctggc ttgctatagc ttgctagtaa cagtggcctt tattattttc    1020
tgggtgagga gtaagaggag caggctcctg cacagtgact acatgaacat gactccccgc    1080
cgcccggggc ccacccgcaa gcattaccag ccctatgccc caccacgcga cttcgcagcc    1140
tatcgctcca gagtgaagtt cagcaggagc gcagacgccc ccgcgtacca gcagggccag    1200
aaccagctct ataacgagct caatctagga cgaagagagg agtacgatgt tttggacaag    1260
agacgtggcc gggaccctga gatggggggga aagccgagaa ggaagaaccc tcaggaaggc    1320
ctgtacaatg aactgcagaa agataagatg gcggaggcct acagtgagat tgggatgaaa    1380
ggcgagcgcc ggagggggcaa ggggcacgat ggcctttacc agggtctcag tacagccacc    1440
aaggacacct acgacgccct tcacatgcag gccctgcccc ctcgctaa                 1488

<210> SEQ ID NO 440
<211> LENGTH: 495
<212> TYPE: PRT
<213> ORGANISM: Artificial Sequence
<220> FEATURE:
<223> OTHER INFORMATION: SL18 CAR

<400> SEQUENCE: 440

Met Ala Leu Pro Val Thr Ala Leu Leu Leu Pro Leu Ala Leu Leu Leu
1               5                   10                  15

-continued

```
His Ala Ala Arg Pro Arg Val Gln Leu Leu Glu Ser Gly Gly Gly Leu
                20                  25                  30

Val Gln Pro Gly Gly Ser Leu Arg Leu Ser Cys Ala Ala Ser Gly Phe
            35                  40                  45

Thr Phe Ser Asp Tyr His Met His Trp Val Arg Gln Ala Pro Gly Lys
        50                  55                  60

Gly Leu Glu Trp Val Ser Thr Ile Ser Ser Ser Gly Gly Tyr Thr Tyr
65                  70                  75                  80

Tyr Ala Glu Ser Val Lys Ser Arg Phe Thr Ile Ser Arg Asp Asn Ser
                85                  90                  95

Lys Asn Thr Leu Tyr Leu Gln Met Asn Ser Leu Arg Ala Glu Asp Thr
                100                 105                 110

Ala Val Tyr Tyr Cys Ala Arg Ser Ile Arg Leu Pro Leu Asp Tyr Trp
            115                 120                 125

Gly Gln Gly Thr Leu Val Thr Val Ser Ser Ser Gly Gly Gly Ser Gly
        130                 135                 140

Gly Gly Gly Ser Gly Gly Gly Gly Ser Gln Ser Val Leu Thr Gln Pro
145                 150                 155                 160

Pro Ser Ala Ser Gly Thr Pro Gly Gln Arg Val Thr Ile Ser Cys Ser
                165                 170                 175

Gly Asn Asn Ile Gly Ser Lys Gly Val His Trp Tyr Gln Gln Leu Pro
                180                 185                 190

Gly Thr Ala Pro Lys Leu Leu Ile Tyr Glu Asp Ser Lys Arg Pro Ser
            195                 200                 205

Gly Val Arg Asp Arg Phe Ser Gly Ser Lys Ser Gly Thr Ser Ala Ser
        210                 215                 220

Leu Ala Ile Ser Gly Leu Arg Ser Glu Asp Glu Ala Asp Tyr Tyr Cys
225                 230                 235                 240

Gln Ser Tyr Asp Ser Thr Lys Gly Val Val Phe Gly Gly Gly Thr Lys
                245                 250                 255

Leu Thr Val Leu Gly Gly Gly Gly Ser Gly Gly Gly Gly Ser Thr Thr
                260                 265                 270

Thr Pro Ala Pro Arg Pro Pro Thr Pro Ala Pro Thr Ile Ala Ser Gln
            275                 280                 285

Pro Leu Ser Leu Arg Pro Glu Ala Cys Arg Pro Ala Ala Gly Gly Ala
        290                 295                 300

Val His Thr Arg Gly Leu Asp Phe Ala Cys Asp Phe Trp Val Leu Val
305                 310                 315                 320

Val Val Gly Gly Val Leu Ala Cys Tyr Ser Leu Leu Val Thr Val Ala
                325                 330                 335

Phe Ile Ile Phe Trp Val Arg Ser Lys Arg Ser Arg Leu Leu His Ser
                340                 345                 350

Asp Tyr Met Asn Met Thr Pro Arg Arg Pro Gly Pro Thr Arg Lys His
            355                 360                 365

Tyr Gln Pro Tyr Ala Pro Pro Arg Asp Phe Ala Ala Tyr Arg Ser Arg
        370                 375                 380

Val Lys Phe Ser Arg Ser Ala Asp Ala Pro Ala Tyr Gln Gln Gly Gln
385                 390                 395                 400

Asn Gln Leu Tyr Asn Glu Leu Asn Leu Gly Arg Arg Glu Glu Tyr Asp
                405                 410                 415

Val Leu Asp Lys Arg Arg Gly Arg Asp Pro Glu Met Gly Gly Lys Pro
                420                 425                 430
```

-continued

```
Arg Arg Lys Asn Pro Gln Glu Gly Leu Tyr Asn Glu Leu Gln Lys Asp
        435                 440                 445

Lys Met Ala Glu Ala Tyr Ser Glu Ile Gly Met Lys Gly Glu Arg Arg
        450                 455                 460

Arg Gly Lys Gly His Asp Gly Leu Tyr Gln Gly Leu Ser Thr Ala Thr
465                 470                 475                 480

Lys Asp Thr Tyr Asp Ala Leu His Met Gln Ala Leu Pro Pro Arg
                485                 490                 495

<210> SEQ ID NO 441
<211> LENGTH: 1260
<212> TYPE: DNA
<213> ORGANISM: Artificial Sequence
<220> FEATURE:
<223> OTHER INFORMATION: CD300c ECD CAR

<400> SEQUENCE: 441
atggccttac cagtgaccgc cttgctcctg ccgctggcct tgctgctcca cgccgccagg     60
ccgggctatt ttcctctgag ccaccccatg accgtggcgg ccccgtggg gggatccctg    120 agtgtgcagt gtcgctatga gaaggaacac aggaccctca acaaattctg gtgcagacca    180
ccacagattc tccgatgtga caagattgtg agaccaaag ggtcagcagg gaaaaggaat    240
ggccgagtgt ccatcaggga cagtcctgca aacctcagct tcacagtgac cctggagaat    300
ctcacagagg aggacgcagg cacctactgg tgtggggtgg atacaccgtg gctccgagac    360
tttcatgatc ccattgtcga ggttgaggtg tccgtgttcc cggccgggac gaccacagcc    420
tccagccccc agagctccat gggcacctca ggtcctccca cgaagctgcc cgtgcacacc    480
tggcccagcg tgaccagaaa ggacagcccc gaacccagcc cacaccctgg ctccctgttc    540
agcaatgtcc gcggtggcgg aggttctgga ggtggaggtt ccaccacgac gccagcgccg    600
cgaccaccaa caccggcgcc caccatcgcg tcgcagcccc tgtccctgcg cccagaggcg    660
tgccggccag cggcggggg cgcagtgcac acgaggggc tggacttcgc ctgtgatttt    720
tgggtgctgg tggtggttgg tggagtcctg gcttgctata gcttgctagt aacagtggcc    780
tttattattt tctgggtgag gagtaagagg agcaggctcc tgcacagtga ctacatgaac    840
atgactcccc gccgccccgg gcccacccgc aagcattacc agccctatgc cccaccacgc    900
gacttcgcag cctatcgctc cagagtgaag ttcagcagga gcgcagacgc ccccgcgtac    960
cagcagggcc agaaccagct ctataacgag ctcaatctag gacgaagaga ggagtacgat   1020
gttttggaca gagacgtgg ccgggacccct gagatggggg gaaagccgag aaggaagaac   1080
cctcaggaag gcctgtacaa tgaactgcag aaagataaga tggcggaggc ctacagtgag   1140
attgggatga aggcgagcg ccggaggggc aaggggcacg atggccttta ccagggtctc   1200
agtacagcca ccaaggacac ctacgacgcc cttcacatgc aggccctgcc ccctcgctaa   1260

<210> SEQ ID NO 442
<211> LENGTH: 419
<212> TYPE: PRT
<213> ORGANISM: Artificial Sequence
<220> FEATURE:
<223> OTHER INFORMATION: CD300c ECD CAR

<400> SEQUENCE: 442

Met Ala Leu Pro Val Thr Ala Leu Leu Leu Pro Leu Ala Leu Leu Leu
1               5                   10                  15

His Ala Ala Arg Pro Gly Tyr Phe Pro Leu Ser His Pro Met Thr Val
            20                  25                  30
```

```
Ala Gly Pro Val Gly Gly Ser Leu Ser Val Gln Cys Arg Tyr Glu Lys
        35              40              45

Glu His Arg Thr Leu Asn Lys Phe Trp Cys Arg Pro Pro Gln Ile Leu
    50              55              60

Arg Cys Asp Lys Ile Val Glu Thr Lys Gly Ser Ala Gly Lys Arg Asn
65              70              75              80

Gly Arg Val Ser Ile Arg Asp Ser Pro Ala Asn Leu Ser Phe Thr Val
            85              90              95

Thr Leu Glu Asn Leu Thr Glu Glu Asp Ala Gly Thr Tyr Trp Cys Gly
            100             105             110

Val Asp Thr Pro Trp Leu Arg Asp Phe His Asp Pro Ile Val Glu Val
            115             120             125

Glu Val Ser Val Phe Pro Ala Gly Thr Thr Thr Ala Ser Ser Pro Gln
    130             135             140

Ser Ser Met Gly Thr Ser Gly Pro Pro Thr Lys Leu Pro Val His Thr
145             150             155             160

Trp Pro Ser Val Thr Arg Lys Asp Ser Pro Glu Pro Ser Pro His Pro
            165             170             175

Gly Ser Leu Phe Ser Asn Val Arg Gly Gly Gly Ser Gly Gly Gly
            180             185             190

Gly Ser Thr Thr Thr Pro Ala Pro Arg Pro Pro Thr Pro Ala Pro Thr
            195             200             205

Ile Ala Ser Gln Pro Leu Ser Leu Arg Pro Glu Ala Cys Arg Pro Ala
    210             215             220

Ala Gly Gly Ala Val His Thr Arg Gly Leu Asp Phe Ala Cys Asp Phe
225             230             235             240

Trp Val Leu Val Val Val Gly Gly Val Leu Ala Cys Tyr Ser Leu Leu
            245             250             255

Val Thr Val Ala Phe Ile Ile Phe Trp Val Arg Ser Lys Arg Ser Arg
            260             265             270

Leu Leu His Ser Asp Tyr Met Asn Met Thr Pro Arg Arg Pro Gly Pro
            275             280             285

Thr Arg Lys His Tyr Gln Pro Tyr Ala Pro Pro Arg Asp Phe Ala Ala
    290             295             300

Tyr Arg Ser Arg Val Lys Phe Ser Arg Ser Ala Asp Ala Pro Ala Tyr
305             310             315             320

Gln Gln Gly Gln Asn Gln Leu Tyr Asn Glu Leu Asn Leu Gly Arg Arg
            325             330             335

Glu Glu Tyr Asp Val Leu Asp Lys Arg Arg Gly Arg Asp Pro Glu Met
            340             345             350

Gly Gly Lys Pro Arg Arg Lys Asn Pro Gln Glu Gly Leu Tyr Asn Glu
            355             360             365

Leu Gln Lys Asp Lys Met Ala Glu Ala Tyr Ser Glu Ile Gly Met Lys
    370             375             380

Gly Glu Arg Arg Arg Gly Lys Gly His Asp Gly Leu Tyr Gln Gly Leu
385             390             395             400

Ser Thr Ala Thr Lys Asp Thr Tyr Asp Ala Leu His Met Gln Ala Leu
            405             410             415

Pro Pro Arg
```

```
<210> SEQ ID NO 443
<211> LENGTH: 12
<212> TYPE: PRT
```

```
<213> ORGANISM: Artificial Sequence
<220> FEATURE:
<223> OTHER INFORMATION: Formula (1)
<220> FEATURE:
<221> NAME/KEY: VARIANT
<222> LOCATION: (5)..(5)
<223> OTHER INFORMATION: X= R, S, or D
<220> FEATURE:
<221> NAME/KEY: VARIANT
<222> LOCATION: (7)..(7)
<223> OTHER INFORMATION: X= A, G, or H
<220> FEATURE:
<221> NAME/KEY: VARIANT
<222> LOCATION: (9)..(9)
<223> OTHER INFORMATION: X= T, H, or S

<400> SEQUENCE: 443

Phe Thr Phe Ser Xaa Tyr Xaa Met Xaa Trp Val Arg
1               5                   10

<210> SEQ ID NO 444
<211> LENGTH: 13
<212> TYPE: PRT
<213> ORGANISM: Artificial Sequence
<220> FEATURE:
<223> OTHER INFORMATION: Formula (2)
<220> FEATURE:
<221> NAME/KEY: VARIANT
<222> LOCATION: (1)..(1)
<223> OTHER INFORMATION: X= S, A, or T
<220> FEATURE:
<221> NAME/KEY: VARIANT
<222> LOCATION: (2)..(2)
<223> OTHER INFORMATION: X= M or I
<220> FEATURE:
<221> NAME/KEY: VARIANT
<222> LOCATION: (4)..(4)
<223> OTHER INFORMATION: X= G or S
<220> FEATURE:
<221> NAME/KEY: VARIANT
<222> LOCATION: (5)..(5)
<223> OTHER INFORMATION: X= T or S
<220> FEATURE:
<221> NAME/KEY: VARIANT
<222> LOCATION: (8)..(8)
<223> OTHER INFORMATION: X= T, S, or Y
<220> FEATURE:
<221> NAME/KEY: VARIANT
<222> LOCATION: (13)..(13)
<223> OTHER INFORMATION: X= D or E

<400> SEQUENCE: 444

Xaa Xaa Ser Xaa Xaa Gly Gly Xaa Thr Tyr Tyr Ala Xaa
1               5                   10

<210> SEQ ID NO 445
<211> LENGTH: 15
<212> TYPE: PRT
<213> ORGANISM: Artificial Sequence
<220> FEATURE:
<223> OTHER INFORMATION: Formula (3)
<220> FEATURE:
<221> NAME/KEY: VARIANT
<222> LOCATION: (4)..(4)
<223> OTHER INFORMATION: X= R, V, or S
<220> FEATURE:
<221> NAME/KEY: VARIANT
<222> LOCATION: (5)..(5)
<223> OTHER INFORMATION: X= G or S
<220> FEATURE:
<221> NAME/KEY: VARIANT
<222> LOCATION: (6)..(6)
<223> OTHER INFORMATION: X= A, G, S, Y, or I
<220> FEATURE:
<221> NAME/KEY: VARIANT
```

```
<222> LOCATION: (7)..(7)
<223> OTHER INFORMATION: X= Y, A, Q, G, or R
<220> FEATURE:
<221> NAME/KEY: VARIANT
<222> LOCATION: (8)..(8)
<223> OTHER INFORMATION: X= G or L
<220> FEATURE:
<221> NAME/KEY: VARIANT
<222> LOCATION: (9)..(9)
<223> OTHER INFORMATION: X= F, R, I, M, or P
<220> FEATURE:
<221> NAME/KEY: VARIANT
<222> LOCATION: (10)..(10)
<223> OTHER INFORMATION: X= D, G, F, or L
<220> FEATURE:
<221> NAME/KEY: VARIANT
<222> LOCATION: (11)..(11)
<223> OTHER INFORMATION: X= H, F, D, or V
<220> FEATURE:
<221> NAME/KEY: VARIANT
<222> LOCATION: (12)..(12)
<223> OTHER INFORMATION: X= F, I, Y or not present
<220> FEATURE:
<221> NAME/KEY: VARIANT
<222> LOCATION: (13)..(13)
<223> OTHER INFORMATION: X= D or not present
<220> FEATURE:
<221> NAME/KEY: VARIANT
<222> LOCATION: (14)..(14)
<223> OTHER INFORMATION: X= Y or not present

<400> SEQUENCE: 445

Tyr Cys Ala Xaa Xaa Xaa Xaa Xaa Xaa Xaa Xaa Xaa Xaa Xaa Trp
1               5                   10                  15

<210> SEQ ID NO 446
<211> LENGTH: 15
<212> TYPE: PRT
<213> ORGANISM: Artificial Sequence
<220> FEATURE:
<223> OTHER INFORMATION: Formula (4)
<220> FEATURE:
<221> NAME/KEY: VARIANT
<222> LOCATION: (2)..(2)
<223> OTHER INFORMATION: X= R, S, or T
<220> FEATURE:
<221> NAME/KEY: VARIANT
<222> LOCATION: (3)..(3)
<223> OTHER INFORMATION: X= A, G, or R
<220> FEATURE:
<221> NAME/KEY: VARIANT
<222> LOCATION: (4)..(4)
<223> OTHER INFORMATION: X= S or N
<220> FEATURE:
<221> NAME/KEY: VARIANT
<222> LOCATION: (5)..(5)
<223> OTHER INFORMATION: X= Q, S, or N
<220> FEATURE:
<221> NAME/KEY: VARIANT
<222> LOCATION: (6)..(6)
<223> OTHER INFORMATION: X= S, I, or G
<220> FEATURE:
<221> NAME/KEY: VARIANT
<222> LOCATION: (7)..(7)
<223> OTHER INFORMATION: X= I, N, or G
<220> FEATURE:
<221> NAME/KEY: VARIANT
<222> LOCATION: (8)..(8)
<223> OTHER INFORMATION: X= G, I, T, or S
<220> FEATURE:
<221> NAME/KEY: VARIANT
<222> LOCATION: (9)..(9)
<223> OTHER INFORMATION: X= N, G, R, A, or K
<220> FEATURE:
<221> NAME/KEY: VARIANT
<222> LOCATION: (10)..(10)
<223> OTHER INFORMATION: X= Y, S, R, or G
```

-continued

```
<220> FEATURE:
<221> NAME/KEY: VARIANT
<222> LOCATION: (11)..(11)
<223> OTHER INFORMATION: X= N or not present
<220> FEATURE:
<221> NAME/KEY: VARIANT
<222> LOCATION: (12)..(12)
<223> OTHER INFORMATION: X= Y or not present
<220> FEATURE:
<221> NAME/KEY: VARIANT
<222> LOCATION: (13)..(13)
<223> OTHER INFORMATION: X= L or V
<220> FEATURE:
<221> NAME/KEY: VARIANT
<222> LOCATION: (14)..(14)
<223> OTHER INFORMATION: X= N, Y, H, or Q

<400> SEQUENCE: 446

Cys Xaa Xaa Xaa Xaa Xaa Xaa Xaa Xaa Xaa Xaa Xaa Xaa Xaa Trp
1               5                   10                  15

<210> SEQ ID NO 447
<211> LENGTH: 10
<212> TYPE: PRT
<213> ORGANISM: Artificial Sequence
<220> FEATURE:
<223> OTHER INFORMATION: Formula (5)
<220> FEATURE:
<221> NAME/KEY: VARIANT
<222> LOCATION: (1)..(1)
<223> OTHER INFORMATION: X= D, E, S, or R
<220> FEATURE:
<221> NAME/KEY: VARIANT
<222> LOCATION: (2)..(2)
<223> OTHER INFORMATION: X= A, D, K, or N
<220> FEATURE:
<221> NAME/KEY: VARIANT
<222> LOCATION: (3)..(3)
<223> OTHER INFORMATION: X= S or N
<220> FEATURE:
<221> NAME/KEY: VARIANT
<222> LOCATION: (4)..(4)
<223> OTHER INFORMATION: X= N, K, or Q
<220> FEATURE:
<221> NAME/KEY: VARIANT
<222> LOCATION: (5)..(5)
<223> OTHER INFORMATION: X= L or R
<220> FEATURE:
<221> NAME/KEY: VARIANT
<222> LOCATION: (6)..(6)
<223> OTHER INFORMATION: X= E or P
<220> FEATURE:
<221> NAME/KEY: VARIANT
<222> LOCATION: (7)..(7)
<223> OTHER INFORMATION: X= T or S
<220> FEATURE:
<221> NAME/KEY: VARIANT
<222> LOCATION: (9)..(9)
<223> OTHER INFORMATION: X= I or V
<220> FEATURE:
<221> NAME/KEY: VARIANT
<222> LOCATION: (10)..(10)
<223> OTHER INFORMATION: X= P or R

<400> SEQUENCE: 447

Xaa Xaa Xaa Xaa Xaa Xaa Xaa Gly Xaa Xaa
1               5                   10

<210> SEQ ID NO 448
<211> LENGTH: 14
<212> TYPE: PRT
<213> ORGANISM: Artificial Sequence
<220> FEATURE:
<223> OTHER INFORMATION: Formula (6)
<220> FEATURE:
```

```
<221> NAME/KEY: VARIANT
<222> LOCATION: (3)..(3)
<223> OTHER INFORMATION: X= Q, S, or A
<220> FEATURE:
<221> NAME/KEY: VARIANT
<222> LOCATION: (4)..(4)
<223> OTHER INFORMATION: X= Q, S, or A
<220> FEATURE:
<221> NAME/KEY: VARIANT
<222> LOCATION: (5)..(5)
<223> OTHER INFORMATION: X= S, Y, or W
<220> FEATURE:
<221> NAME/KEY: VARIANT
<222> LOCATION: (6)..(6)
<223> OTHER INFORMATION: X= S, T, D, or A
<220> FEATURE:
<221> NAME/KEY: VARIANT
<222> LOCATION: (7)..(7)
<223> OTHER INFORMATION: X= A, S, D, or G
<220> FEATURE:
<221> NAME/KEY: VARIANT
<222> LOCATION: (8)..(8)
<223> OTHER INFORMATION: X= I, S, N, or T
<220> FEATURE:
<221> NAME/KEY: VARIANT
<222> LOCATION: (9)..(9)
<223> OTHER INFORMATION: X= P, S, L, N, or K
<220> FEATURE:
<221> NAME/KEY: VARIANT
<222> LOCATION: (10)..(10)
<223> OTHER INFORMATION: X= Y, T, S, N, or G
<220> FEATURE:
<221> NAME/KEY: VARIANT
<222> LOCATION: (11)..(11)
<223> OTHER INFORMATION: X= V, G, L or not present
<220> FEATURE:
<221> NAME/KEY: VARIANT
<222> LOCATION: (12)..(12)
<223> OTHER INFORMATION: X = P or not present
<220> FEATURE:
<221> NAME/KEY: VARIANT
<222> LOCATION: (13)..(13)
<223> OTHER INFORMATION: X= T, I, or V

<400> SEQUENCE: 448

Tyr Cys Xaa Xaa Xaa Xaa Xaa Xaa Xaa Xaa Xaa Xaa Xaa Phe
1               5                   10
```

CHIMERIC ANTIGEN RECEPTOR SPECIFICALLY BINDING TO CD 300C ANTIGEN OR RECEPTOR THEREOF

CROSS REFERENCE

This application is a bypass continuation-in-part application and claims benefits of PCT/KR2020/017230 filed Nov. 30, 2020, which claims priority based on Korean Patent Application Nos. 10-2019-0155027 filed Nov. 28, 2019 and 10-2020-0162200 filed on Nov. 27, 2020, and this application is a bypass continuation of PCT/KR2022/007384 filed May 24, 2022, which claims priority based on Korean Patent Application No. 10-2021-0066547 filed May 24, 2021, of which the contents are incorporated by reference in their entireties.

SEQUENCE LISTING

The content of the electronically submitted sequence listing, file name: Q276211_ST25; size: 220,190 bytes; and date of creation: May 16, 2022, filed herewith, is incorporated herein by reference in its entirety.

TECHNICAL FIELD

The present disclosure relates to a chimeric antigen receptor that specifically binds to a CD300c antigen or a receptor thereof, immune cells expressing the same, uses thereof, and the like.

BACKGROUND ART

Cancer is one of the diseases that account for the largest share of the causes of death in modern people. This disease is caused by changes in normal cells due to genetic mutations that result from various causes and refers to a malignant tumor that does not follow differentiation, proliferation, growth pattern, or the like of normal cells. Cancer is characterized by "uncontrolled cell growth." This abnormal cell growth causes formation of a mass of cells called a tumor, which infiltrates the surrounding tissues and, in severe cases, may metastasize to other organs of the body. Cancer is an intractable chronic disease that is not fundamentally cured in many cases even if it is treated with surgery, radiotherapy, chemotherapy, and the like, causes pain to patients, and ultimately leads to death. In particular, in recent years, the global cancer incidence rate is increasing by 5% or higher every year due to increased elderly population, environmental deterioration, or the like. According to the WHO report, it is estimated that within the next 25 years the number of cancer patients will increase to 30 million, of which 20 million will die from cancer.

Cancer drug treatments, that is, cancer chemotherapies are generally cytotoxic compounds, and treat cancer by attacking and killing cancer cells. However, these chemotherapies exhibit high adverse effects since they damage not only cancer cells but also normal cells. Thus, targeted cancer chemotherapies have been developed to decrease adverse effects. These targeted cancer chemotherapies were able to exhibit decreased adverse effects, but had a limitation in that resistance occurs with a high probability. Therefore, in recent years, interest in cancer immunotherapies, which use the body's immune system to decrease problems due to toxicity and resistance, is rapidly increasing. As an example of such cancer immunotherapies, immune checkpoint inhibitors have been developed which specifically bind to PD-L1 on the surface of cancer cells and inhibit its binding to PD-1 on T cells so that T cells are activated and attack cancer cells. However, even these immune checkpoint inhibitors are not effective in various types of cancer. Therefore, there is a need to develop novel cancer immune therapeutics that exhibit an equivalent therapeutic effect in various cancers.

Meanwhile, chimeric antigen receptors (CARs) are artificial receptors designed to deliver antigen specificity to T cells, and comprise an antigen-specific domain that activates T cells and provides specific immunity, a transmembrane domain, an intracellular domain, and the like. Recently, studies are actively conducted on cancer immunotherapy using cells into which a gene encoding such a chimeric antigen receptor has been introduced, that is, a method for treating cancer through a therapy in which T cells are collected from a patient, a gene encoding a chimeric antigen receptor is introduced into these T cells and amplified, and transferred back into the patient.

RELEVANT ART LITERATURE

Patent Literature (Patent Literature 1) Korean Patent Laid-Open Publication No. 10-2016-0016725 A.

DISCLOSURE

Technical Problem

An object of the present disclosure is to solve all of the above-mentioned problems.

One object of the present disclosure is to provide a chimeric antigen receptor for preventing or treating cancer, comprising a binding domain that specifically binds to a CD300c antigen or a receptor thereof.

Another object of the present disclosure is to provide an immune cell expressing the chimeric antigen receptor.

Yet another object of the present disclosure is to provide an isolated nucleic acid molecule encoding the chimeric antigen receptor.

Still yet another object of the present disclosure is to provide a vector comprising the nucleic acid molecule that encodes the chimeric antigen receptor.

Still yet another object of the present disclosure is to provide an anticancer therapy using the chimeric antigen receptor or the immune cells comprising the same.

Still yet another object of the present disclosure is to provide a method for preventing or treating cancer which uses the chimeric antigen receptor or the immune cells comprising the same.

Still yet another object of the present disclosure is to provide a use of the chimeric antigen receptor or the immune cells comprising the same for the prevention or treatment of cancer.

Still yet another object of the present disclosure is to provide a use of the chimeric antigen receptor or the immune cells comprising the same for the manufacture of a medicament for preventing or treating cancer.

The object of the present disclosure is not limited to the objects as mentioned above. The object of the present disclosure will become clearer from the following description, and will be realized by the means as described in the claims and combinations thereof.

Solution to Problem

Representative configurations of the present disclosure for achieving the above-mentioned objects are as follows.

According to an aspect of the present disclosure, there is provided a chimeric antigen receptor comprising a binding domain that specifically binds to a CD300c antigen or a receptor thereof.

According to another aspect of the present disclosure, there is provided an immune cell comprising the chimeric antigen receptor.

According to yet another aspect of the present disclosure, there is provided a nucleic acid encoding the chimeric antigen receptor.

According to still yet another aspect of the present disclosure, there is provided a vector expressing the chimeric antigen receptor.

According to still yet another aspect of the present disclosure, there is provided a pharmaceutical composition comprising the chimeric antigen receptor or the immune cells comprising the same.

According to still yet another aspect of the present disclosure, there is provided a method for preventing or treating cancer, comprising administering to a subject the chimeric antigen receptor or the immune cells comprising the same.

According to still yet another aspect of the present disclosure, there is provided an anticancer therapy using the chimeric antigen receptor or the immune cells comprising the same.

According to still yet another aspect of the present disclosure, there is provided a use of the chimeric antigen receptor or the immune cells comprising the same for the prevention or treatment of cancer According to still yet another aspect of the present disclosure, there is provided a use of the chimeric antigen receptor or the immune cells comprising the same for the manufacture of a medicament for preventing or treating cancer.

Advantageous Effects of Invention

The chimeric antigen receptor that specifically binds to a CD300c antigen or a receptor thereof, according to the present disclosure, is able to specifically recognize cancer cells expressing the CD300c antigen or the CD300c receptor so that growth, metastasis, development, and the like of cancer can be suppressed in a direct and effective manner. Thus, the chimeric antigen receptor can be effectively used for the treatment of various cancers expressing the CD300c antigen or the CD300c receptor on the surface.

BRIEF DESCRIPTION OF DRAWINGS

FIGS. 1a to 1y respectively illustrate heavy chain and light chain variable region sequences (nucleotide and amino acid sequences) of 25 anti-CD300c monoclonal antibodies according to the present disclosure. In each drawing, the CDR regions (CDR1, CDR2, and CDR3) are sequentially indicated. The sequence identifiers of the sequences 1aa through 1yd are shown in Table 2 and Table 3.

FIG. 2 illustrates a schematic diagram, briefly showing the mechanism by which the anti-CD300c monoclonal antibody and/or CD300c siRNA of the present disclosure exhibits an anticancer effect.

FIG. 3 illustrates a schematic diagram, briefly showing the mechanism by which the anti-CD300c monoclonal antibody of the present disclosure acts on monocytes, T cells, and cancer cells, respectively.

FIG. 4 illustrates results obtained by performing SDS-PAGE on the anti-CD300c monoclonal antibodies under a non-reducing condition, according to an embodiment of the present disclosure.

FIG. 5 illustrates results obtained by performing SDS-PAGE on the anti-CD300c monoclonal antibodies under a reducing condition, according to an embodiment of the present disclosure.

FIG. 6 illustrates results obtained by comparing the expression of CD300c in normal cells, immune cells, and a cancer cell line, according to an embodiment of the present disclosure.

FIG. 7 illustrates results obtained by identifying the binding affinity, to a CD300c antigen, of the anti-CD300c monoclonal antibody, according to an embodiment of the present disclosure.

FIG. 8 illustrates results obtained by identifying an anti-cancer effect of the anti-CD300c monoclonal antibody through T cell activation, according to an embodiment of the present disclosure.

FIGS. 9 and 10 illustrate results obtained by identifying the effect of the anti-CD300c monoclonal antibody on differentiation into M1 macrophages, according to an embodiment of the present disclosure.

FIGS. 11 and 12 illustrate results obtained by identifying the concentration-dependent effect of the anti-CD300c monoclonal antibody on differentiation into M1 macrophages, according to an embodiment of the present disclosure.

FIG. 13 illustrates results obtained by identifying the effect of the anti-CD300c monoclonal antibody on differentiation into M1 macrophages, according to an embodiment of the present disclosure.

FIG. 14 illustrates results obtained by identifying again whether the anti-CD300c monoclonal antibody promotes differentiation of human monocytes into M1 macrophages, according to an embodiment of the present disclosure.

FIGS. 15 to 18 illustrate results obtained by comparing capacity for causing differentiation into M1 macrophages between the anti-CD300c monoclonal antibody and conventional immunotherapies, using ELISA, according to an embodiment of the present disclosure.

FIG. 19 illustrates results obtained by comparing capacity for causing differentiation from M0 macrophages into M1 macrophages between the anti-CD300c monoclonal antibody and a conventional immunotherapy, using ELISA, according to an embodiment of the present disclosure.

FIG. 20 illustrates results obtained by comparing capacity for causing differentiation into M1 macrophages between the anti-CD300c monoclonal antibody and a conventional immunotherapy using ELISA, according to an embodiment of the present disclosure.

FIGS. 21 to 23 illustrate results obtained by identifying whether the anti-CD300c monoclonal antibody is able to induce redifferentiation from M2 macrophages into M1 macrophages, using ELISA, according to an embodiment of the present disclosure.

FIG. 24 illustrates results obtained by identifying capacity of the anti-CD300c monoclonal antibody for causing differentiation and redifferentiation into M1 macrophages, according to an embodiment of the present disclosure.

FIGS. 25 to 27 illustrate results obtained by identifying signal transduction of MAPK (FIG. 25), NF-κB (FIG. 26), and IkB (FIG. 27), which are signals of M1 macrophage differentiation, caused by co-treatment with the anti-CD300c monoclonal antibody and a cancer immunotherapy, according to an embodiment of the present disclosure.

FIG. 28 illustrates results obtained by identifying cancer cell growth inhibitory effects of the anti-CD300c monoclonal antibody at a 0% FBS condition, according to an embodiment of the present disclosure.

FIG. 29 illustrates results obtained by identifying cancer cell growth inhibitory effects of the anti-CD300c monoclonal antibody at a 0.1% FBS condition, according to an embodiment of the present disclosure.

FIG. 30 illustrates results obtained by comparing cancer cell (lung cancer) growth inhibitory effects between the anti-CD300c monoclonal antibodies and a conventional immunotherapy, according to an embodiment of the present disclosure.

FIG. 31 illustrates results obtained by comparing cancer cell (breast cancer) growth inhibitory effects between the anti-CD300c monoclonal antibodies and a conventional immunotherapy, according to an embodiment of the present disclosure.

FIG. 32 illustrates results obtained by identifying cancer cell growth inhibitory effects of the anti-CD300c monoclonal antibody depending on its concentrations, according to an embodiment of the present disclosure.

FIG. 33 illustrates results obtained by identifying changes in apoptosis signal caused by co-treatment with the anti-CD300c monoclonal antibody and a cancer immunotherapy, according to an embodiment of the present disclosure.

FIGS. 34 and 35 illustrate results obtained by identifying cancer cell growth inhibitory effects caused by co-treatment with the anti-CD300c monoclonal antibody and a cancer immunotherapy, according to an embodiment of the present disclosure.

FIG. 36 illustrates results of the binding ELISA, according to an embodiment of the present disclosure.

FIG. 37 illustrates results obtained by identifying results obtained by identifying whether the anti-CD300c monoclonal antibody is able to promote differentiation from mouse macrophages into M1 macrophages, according to an embodiment of the present disclosure.

FIG. 38 illustrates results obtained by identifying whether the anti-CD300c monoclonal antibody exhibits an anticancer effect in a mouse cancer cell line, according to an embodiment of the present disclosure.

FIG. 39 schematically illustrates the experimental method used in an embodiment of the present disclosure.

FIG. 40 illustrates cancer growth inhibitory effects in vivo observed in a case where mice transplanted with a colorectal cancer cell line were administered with the anti-CD300c monoclonal antibody and an anti-PD-1 antibody alone or in combination, according to an embodiment of the present disclosure.

Figure 41:
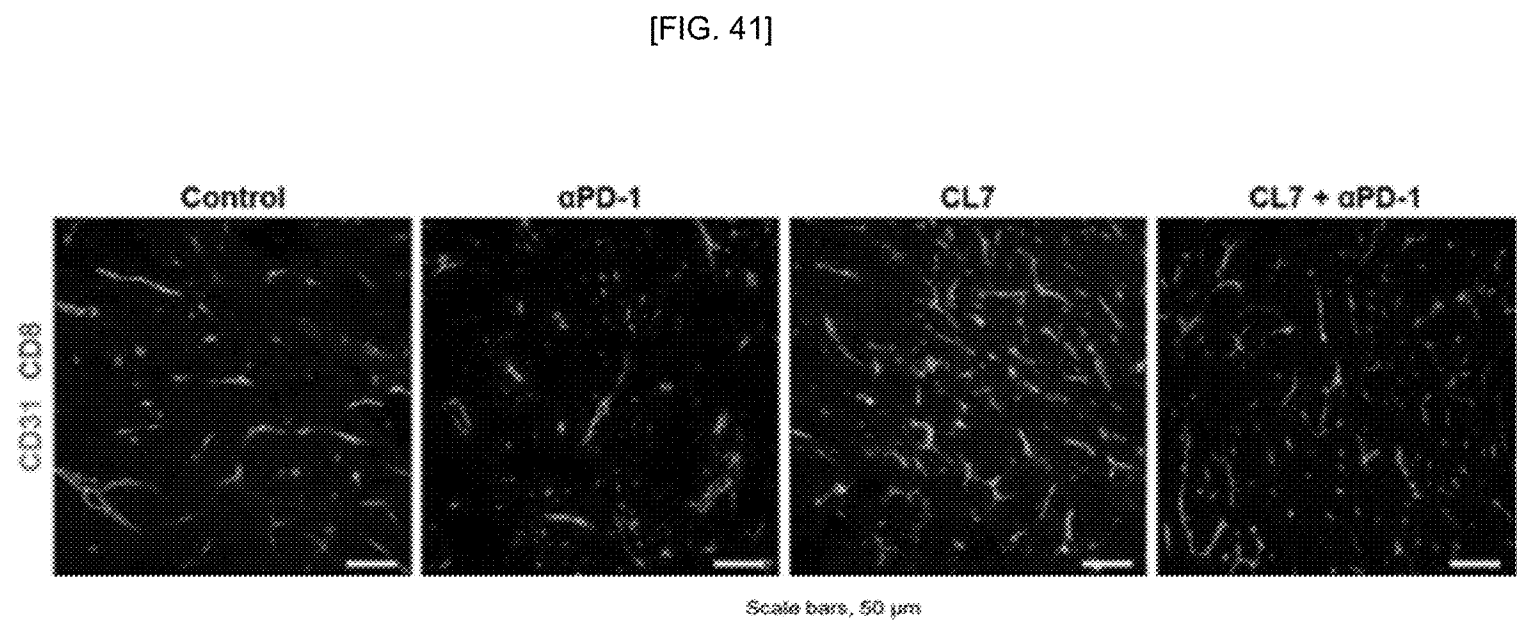

FIG. 41 illustrates results obtained by identifying whether the anti-CD300c monoclonal antibody promotes CD8+ T cell immunity in a mouse tumor model, according to an embodiment of the present disclosure.

FIG. 42 illustrates results obtained by identifying whether the anti-CD300c monoclonal antibody increases M1 macrophages in cancer tissues of a mouse model, according to an embodiment of the present disclosure.

FIG. 43 schematically illustrates gene arrangement for constructing a chimeric antigen receptor that specifically binds to a CD300c antigen or a receptor thereof, according to an embodiment of the present disclosure.

FIG. 44 illustrates a vector map for constructing a chimeric antigen receptor that specifically binds to a CD300c antigen or a receptor thereof, according to an embodiment of the present disclosure.

FIG. 45 illustrates results obtained by identifying, through Western blotting, the Jurkat cell line expressing a chimeric antigen receptor that specifically binds to a CD300c antigen or a receptor thereof, according to an embodiment of the present disclosure.

FIG. 46 illustrates results obtained by identifying anti-cancer effects of the Jurkat cell line expressing the chimeric antigen receptor that specifically binds to the CD300c antigen or a receptor thereof, according to an embodiment of the present disclosure.

BEST MODE

The following detailed description of the present disclosure will be described, with reference to specific drawings, for specific embodiments in which the present disclosure may be practiced. However, the present disclosure is not limited thereto, and the scope of the present disclosure is defined only by the appended claims, appropriately interpreted, along with the full range of equivalents to which the claims are entitled. It is to be understood that the various embodiments of the present disclosure, although different from each other, are not necessarily mutually exclusive. For example, a particular feature, structure, or characteristic described herein may vary from one embodiment to another or be implemented as a combination of embodiments without departing from the spirit and scope of the present disclosure. Technical and scientific terms used herein have the same meanings as commonly used in the art to which the present disclosure belongs, unless otherwise defined. . . . For the purpose of interpreting this specification, the following definitions will apply, and the singular forms "a," "an," and "the" include plural referents and vice versa unless the context clearly dictates otherwise.

Definition

As used herein, the term "about" means within an acceptable error range for the particular value which is known to one of ordinary skill in the art.

The term "(antigen-) binding domain" refers to a portion of a protein which binds to an antigen. The antigen-binding domain may be a synthetic polypeptide, an enzymatically obtainable polypeptide, or a genetically engineered polypeptide, and may be an immunoglobulin (for example, an antibody) or a portion thereof (for example, an antigen-binding fragment) which binds to an antigen.

The term "antibody" is used broadly and includes monoclonal antibodies (including full length antibodies) of any isotype such as IgG, IgM, IgA, IgD, and IgE, polyclonal antibodies, multispecific antibodies (for example, bispecific antibodies), antibody fusions (for example, a fusion of an antibody with a (poly) peptide or a fusion of an antibody with a compound), and antibody fragments (including antigen-binding fragments). As used herein, the prefix "anti-", when in conjunction with an antigen, indicates that the given antibody is reactive with the given antigen. An antibody reactive with a specific antigen can be generated, without limitation, by synthetic and/or recombinant methods such as selection of libraries of recombinant antibodies in phage or similar vectors, or by immunizing an animal with the antigen or an antigen-encoding nucleic acid. A typical IgG antibody is comprised of two identical heavy chains and two identical light chains that are joined by disulfide bonds. Each heavy and light chain contains a constant region and a variable region. Heavy chain variable regions (HVRs) and light chain variable regions (LVRs) contain three segments, referred to as "complementarity determining regions" ("CDRs") or "hypervariable regions", respectively, which are primarily responsible for binding an epitope of an antigen. They are usually referred to as CDR1, CDR2, and CDR3, numbered sequentially from the N-terminus. The more highly conserved portions of the variable regions outside of the CDRs are called the "framework regions" ("FRs"). An antibody herein may be, for example, an animal antibody, a chimeric antibody, a humanized antibody, or a human antibody.

The term "single domain antibody" is an antibody specific for the CD300c antigen, in which a CDR is a portion of a single domain polypeptide, and may be generally produced using only two heavy chains and an antigen-binding site. However, the single domain antibody may include all of antibodies naturally devoid of light chains, single-domain antibodies derived from conventional 4-chain antibodies, engineered antibodies, and single domain scaffolds other than those derived from antibodies.

The term "single-chain variable fragment (scFv)" refers to a protein in which light chain and heavy chain variable regions of an antibody are linked to each other via a linker consisting of a peptide sequence having about 15 amino acid residues. The scFv may be in an order of light chain variable domain-linker-heavy chain variable region, or an order of heavy chain variable region-linker-light chain variable region, and has the same or similar antigen specificity as its original antibody. The linking site is a hydrophilic flexible peptide chain mainly composed of glycine and serine. The 15-amino acid sequence of "(Gly-Gly-Gly-Gly-Ser)₃" or a sequence similar thereto is mainly used. The antibody refers to an immunoglobulin molecule that is immunologically reactive with a specific antigen, and includes all of polyclonal antibodies, monoclonal antibodies, and functional fragments thereof. In addition, the term may include forms produced by genetic engineering, such as chimeric antibodies (for example, humanized murine antibodies) and heterologous antibodies (for example, bispecific antibodies). Among these, the monoclonal antibodies are antibodies that exhibit single binding specificity and affinity against a single antigenic site (epitope). Unlike polyclonal antibodies including antibodies that exhibit specificity against different epitopes, the monoclonal antibodies exhibit binding specificity and affinity against a single epitope on an antigen, which allows for easy quality control as a therapeutic agent. In particular, the anti-CD300c monoclonal antibody of the present disclosure not only exhibits anticancer activity by itself by specifically binding to CD300c-expressing cancer cells, but also stimulates immune cells, thereby exhibiting maximized cancer cell-dependent anticancer activity. The antibody includes variable region(s) of a heavy chain and/or a light chain in terms of the constitution, wherein the variable region includes, as a primary structure thereof, a portion that forms an antigen-binding site of the antibody molecule. The antibody of the present disclosure may be composed of a partial fragment containing the variable region.

The term "humanization (also called reshaping or CDR-grafting) includes a well-established technique for reducing the immunogenicity of monoclonal antibodies from xenogeneic sources (commonly rodent) and for improving their affinity or effector function (ADCC, complement activation, C1q binding).

The term "monoclonal antibody" as used herein refers to an antibody obtained from a population of substantially homogeneous antibodies, that is, the individual antibodies comprising the population are identical except for possible naturally occurring mutations and/or post-translation modifications (for example, isomerizations, amidations) that may be present in minor amounts. Monoclonal antibodies are highly specific, being directed against a single antigenic site. The monoclonal antibody is obtained from a substantially homogeneous population of antibodies, displays the nature of an antibody, and is not to be construed as requiring production of the antibody by any particular method. For example, monoclonal antibodies to be used in accordance with the present disclosure may be made by a variety of techniques, including but not limited to the hybridoma method, recombinant DNA methods, phage-display methods, and methods utilizing transgenic animals containing all or part of the human immunoglobulin loci.

The term "antigen-binding fragment" refers to a portion of an antibody having specific binding ability to an antigen or a polypeptide comprising the same. The terms "antibody" and "antigen-binding fragment" may be used interchangeably except for a case where it is understood in the context that the "antibody" specifically excludes the "antigen-binding fragment," and the "antibody" may be interpreted as including the "antigen-binding fragment." Examples of the antigen-binding fragment include, but are not limited to, Fv, Fab, Fab', Fab'-SH, F(ab')2, diabodies, triabodies, tetrabodies, cross-Fab fragments, linear antibodies, single chain antibody molecules (for example, scFv), and multispecific antibodies formed of antibody fragments and single domain antibodies.

The term "chimeric antigen receptor" or "CAR" is defined as a cell surface receptor that comprises an extracellular target-binding domain, a transmembrane domain, and an intracellular signaling domain. The chimeric antigen receptor of the present disclosure is intended primarily for use with lymphocytes such as T cells and natural killer (NK) cells.

The term "cancer therapy" collectively refers to known agents used in conventional cancer treatment which act on various metabolic pathways of cells and exhibit cytotoxic or cytostatic effects on cancer cells. The cancer therapy includes chemotherapies, targeted chemotherapies, and immunotherapies.

The term "immunotherapy" (also referred to as "cancer immunotherapy") refers to a cancer therapy or an anticancer agent which activates immune cells to kill cancer cells.

The term "subject" is used interchangeably with "patient" and may be a mammal who is in need of prevention or treatment of cancer, such as primates (for example, humans), companion animals (for example, dogs and cats), livestock (for example, cows, pigs, horses, sheep, and goats), and laboratory animals (for example, rats, mice, and guinea pigs). In an embodiment of the present disclosure, the subject is a human.

The term "treatment" generally means obtaining a desired pharmacological and/or physiological effect. The effect may be therapeutic in terms of partially or completely curing a disease and/or adverse effect attributed to the disease. Desirable therapeutic effects include, but are not limited to, prevention of onset or recurrence of disease, alleviation of symptoms, diminishment of any direct or indirect pathological consequences of the disease, prevention of metastasis, decreasing the rate of disease progression, amelioration or slowing of the disease state, and remission or improved prognosis. Preferably, the "treatment" may refer to medical intervention of a disease or disorder that has already developed.

The term "prevention" relates to a prophylactic treatment, that is, to a measure or procedure, the purpose of which is to prevent, rather than to cure a disease. "Prevention" means that a desired pharmacological and/or physiological effect is obtained which is prophylactic in terms of completely or partially preventing a disease or symptom thereof.

The term "administration" means providing a substance (for example, an anti-CD300c antibody or an antigen-binding fragment thereof and another cancer therapy) to a subject to achieve a prophylactic or therapeutic purpose (for example, prevention or treatment of cancer).

The term "biological sample" encompasses a variety of sample types obtained from a subject and may be used in diagnostic or monitoring assays. The biological sample includes, but is not limited to, blood and other liquid samples of biological origin, and solid tissue samples such as a biopsy specimen or tissue cultures or cells derived therefrom and the progeny thereof. Thus, the biological sample encompasses a clinical sample, and also includes cells in culture, cell supernatants, cell lysates, serum, plasma, biological fluid, and tissue samples, in particular, tumor samples. The term "biological data" refers to any analytical data obtained using the biological sample.

Chimeric Antigen Receptor

According to an aspect of the present disclosure, there is provided a chimeric antigen receptor comprising a binding domain that specifically binds to a CD300c antigen or a receptor thereof. The chimeric antigen receptor (CAR) is an artificially constructed hybrid protein or polypeptide which contains an antigen-binding domain of an antibody (for example, scFv) linked to a T-cell signaling domain. The chimeric antigen receptor is able to induce T-cell specificity and reactivity towards a selected target in a non-MHC-restricted manner by exploiting the antigen-binding ability of a monoclonal antibody. The chimeric antigen receptor may comprise an (extracellular) antigen-binding domain, a transmembrane domain, and an intracellular signaling domain. In addition, the chimeric antigen receptor may further comprise a GS linker. In addition, the chimeric antigen receptor may further comprise a signal peptide. In an embodiment, the chimeric antigen receptor may comprise an (extracellular) antigen-binding domain, a GS linker, a transmembrane domain, and an intracellular signaling domain. In another embodiment, the chimeric antigen receptor may comprise an (extracellular) antigen-binding domain, a signal peptide, a GS linker, a transmembrane domain, and an intracellular signaling domain. In addition to the components listed above, the chimeric antigen receptor of the present disclosure may comprise any component of chimeric antigen receptors commonly known in the art.

In an embodiment, the binding domain may comprise any one or more selected from the group consisting of an antibody, a single domain antibody, and a single chain variable fragment, each of which specifically binds to the CD300c antigen or a receptor thereof, and an antigen.

Specifically, the binding domain may be a CD300c antigen. The CD300c antigen may comprise the entire CD300c antigen sequence or only an extracellular domain (ECD) of the CD300c antigen sequence, for binding to a receptor thereof. The extracellular domain sequence of the CD300c antigen may comprise or consist of the amino acid sequence represented by SEQ ID NO: 402. In addition, the extracellular domain sequence may comprise an amino acid sequence that has 70% or more, 80% or more, 85% or more, 90% or more, 95% or more, or 98% or more sequence identity to SEQ ID NO: 402.

In addition, the binding domain may be an anti-CD300c antibody (preferably an anti-CD300c monoclonal antibody) or an antigen-binding fragment thereof. However, the binding domain may include any substance as long as it is able to specifically bind to the CD300c antigen or a receptor thereof. In this regard, in a case where the binding domain is an antibody or an antigen binding fragment thereof, such binding domain may be prepared by any antibody production technique known in the art.

In an embodiment, the binding domain may comprise:

(i) a heavy chain variable region that comprises CDR1 comprising or consisting of an amino acid sequence selected from the group consisting of SEQ ID NO: 7, SEQ ID NO: 19, SEQ ID NO: 31, SEQ ID NO: 43, SEQ ID NO: 55, SEQ ID NO: 67, SEQ ID NO: 79, SEQ ID NO: 91, SEQ ID NO: 103, SEQ ID NO: 115, SEQ ID NO: 127, SEQ ID NO: 139, SEQ ID NO: 151, SEQ ID NO: 163, SEQ ID NO: 175, SEQ ID NO: 187, SEQ ID NO: 199, SEQ ID NO: 211, SEQ ID NO: 223, SEQ ID NO: 235, SEQ ID NO: 247, SEQ ID NO: 259, SEQ ID NO: 271, SEQ ID NO: 283, and SEQ ID NO: 295;

CDR2 comprising or consisting of an amino acid sequence selected from the group consisting of SEQ ID NO: 8, SEQ ID NO: 20, SEQ ID NO: 32, SEQ ID NO: 44, SEQ ID NO: 56, SEQ ID NO: 68, SEQ ID NO: 80, SEQ ID NO: 92, SEQ ID NO: 104, SEQ ID NO: 116, SEQ ID NO: 128, SEQ ID NO: 140, SEQ ID NO: 152, SEQ ID NO: 164, SEQ ID NO: 176, SEQ ID NO: 188, SEQ ID NO: 200, SEQ ID NO: 212, SEQ ID NO: 224, SEQ ID NO: 236, SEQ ID NO: 248, SEQ ID NO: 260, SEQ ID NO: 272, SEQ ID NO: 284, and SEQ ID NO: 296; and CDR3 comprising or consisting of an amino acid sequence selected from the group consisting of SEQ ID NO: 9, SEQ ID NO: 21, SEQ ID NO: 33, SEQ ID NO: 45, SEQ ID NO: 57, SEQ ID NO: 69, SEQ ID NO: 81, SEQ ID NO: 93, SEQ ID NO: 105, SEQ ID NO: 117, SEQ ID NO: 129, SEQ ID NO: 141, SEQ ID NO: 153, SEQ ID NO: 165, SEQ ID NO: 177, SEQ ID NO: 189, SEQ ID NO: 201, SEQ ID NO: 213, SEQ ID NO: 225, SEQ ID NO: 237, SEQ ID NO: 249, SEQ ID NO: 261, SEQ ID NO: 273, SEQ ID NO: 285, and SEQ ID NO: 297; and (ii) a light chain variable region that comprises CDR1 comprising or consisting of an amino acid sequence selected from the group consisting of SEQ ID NO: 10, SEQ ID NO: 22, SEQ ID NO: 34, SEQ ID NO: 46, SEQ ID NO: 58, SEQ ID NO: 70, SEQ ID NO: 82, SEQ ID NO: 94, SEQ ID NO: 106, SEQ ID NO: 118, SEQ ID NO: 130, SEQ ID NO: 142, SEQ ID NO: 154, SEQ ID NO: 166, SEQ ID NO: 178, SEQ ID NO: 190, SEQ ID NO: 202, SEQ ID NO: 214, SEQ ID NO: 226, SEQ ID NO: 238, SEQ ID NO: 250, SEQ ID NO: 262, SEQ ID NO: 274, SEQ ID NO: 286, and SEQ ID NO: 298;

CDR2 comprising or consisting of an amino acid sequence selected from the group consisting of SEQ ID NO: 11, SEQ ID NO: 23, SEQ ID NO: 35, SEQ ID NO: 47, SEQ ID NO: 59, SEQ ID NO: 71, SEQ ID NO: 83, SEQ ID NO: 95, SEQ ID NO: 107, SEQ ID NO: 119, SEQ ID NO: 131, SEQ ID NO: 143, SEQ ID NO: 155, SEQ ID NO: 167, SEQ ID NO: 179, SEQ ID NO: 191, SEQ ID NO: 203, SEQ ID NO: 215, SEQ ID NO: 227, SEQ ID NO: 239, SEQ ID NO: 251, SEQ ID NO: 263, SEQ ID NO: 275, SEQ ID NO: 287, and SEQ ID NO: 299; and CDR3 comprising or consisting of an amino acid sequence selected from the group consisting of SEQ ID NO: 12, SEQ ID NO: 24, SEQ ID NO: 36, SEQ ID NO: 48, SEQ ID NO: 60, SEQ ID NO: 72, SEQ ID NO: 84, SEQ ID NO: 96, SEQ ID NO: 108, SEQ ID NO: 120, SEQ ID NO: 132, SEQ ID NO: 144, SEQ ID NO: 156, SEQ ID NO: 168, SEQ ID NO: 180, SEQ ID NO: 192, SEQ ID NO: 204, SEQ ID NO: 216, SEQ ID NO: 228, SEQ ID NO: 240, SEQ ID NO: 252, SEQ ID NO: 264, SEQ ID NO: 276, SEQ ID NO: 288, and SEQ ID NO: 300.

In another embodiment, (i) the heavy chain variable region may comprise

CDR1 comprising or consisting of the amino acid sequence represented by SEQ ID NO: 7, SEQ ID NO: 67, SEQ ID NO: 79, SEQ ID NO: 115, or SEQ ID NO: 211;

CDR2 comprising or consisting of the amino acid sequence represented by SEQ ID NO: 8, SEQ ID NO: 68, SEQ ID NO: 80, SEQ ID NO: 116, or SEQ ID NO: 212; and CDR3 comprising or consisting of the amino acid sequence represented by SEQ ID NO: 9, SEQ ID NO: 69, SEQ ID NO: 81, SEQ ID NO: 117, or SEQ ID NO: 213; and (ii) the light chain variable region may comprise CDR1 comprising or consisting of the amino acid sequence represented by SEQ ID NO: 10, SEQ ID NO: 70, SEQ ID NO: 82, SEQ ID NO: 118, or SEQ ID NO: 214;

CDR2 comprising or consisting of the amino acid sequence represented by SEQ ID NO: 11, SEQ ID NO: 71, SEQ ID NO: 83, SEQ ID NO: 119, or SEQ ID NO: 215; and CDR3 comprising or consisting of the amino acid sequence represented by SEQ ID NO: 12, SEQ ID NO: 72, SEQ ID NO: 84, SEQ ID NO: 120, or SEQ ID NO: 216.

In yet another embodiment, the heavy chain variable region may comprise the amino acid sequence represented by SEQ ID NO: 303, SEQ ID NO: 323, SEQ ID NO: 327, SEQ ID NO: 339 or SEQ ID NO: 371, and the light chain variable region may comprise the amino acid sequence represented by SEQ ID NO: 304, SEQ ID NO: 324, SEQ ID NO: 328, SEQ ID NO: 340, or SEQ ID NO: 372. Preferably, the heavy chain variable region may comprise the amino acid sequence represented by SEQ ID NO: 303 and the light chain variable region may comprise the amino acid sequence represented by SEQ ID NO: 304; the heavy chain variable region may comprise the amino acid sequence represented by SEQ ID NO: 323 and the light chain variable region may comprise the amino acid sequence represented by SEQ ID NO: 324; the heavy chain variable region may comprise the amino acid sequence represented by SEQ ID NO: 327 and the light chain variable region may comprise the amino acid sequence represented by SEQ ID NO: 328; the heavy chain variable region may comprise the amino acid sequence represented by SEQ ID NO: 339 and the light chain variable region may comprise the amino acid sequence represented by SEQ ID NO: 340; the heavy chain variable region may comprise the amino acid sequence represented by SEQ ID NO: 371 and the heavy chain variable region may comprise the amino acid sequence represented by SEQ ID NO: 372.

In still yet another embodiment, the binding domain of the chimeric antigen receptor may comprise a heavy chain variable region that comprises CDR1 to CDR3 comprising or consisting of amino acid sequences, respectively, represented by Formulas (1) to (3), and a light chain variable region that comprises CDR1 to CDR3 comprising or consisting of amino acid sequences, respectively, represented by Formulas (4) to (6) (each amino acid sequence is shown in N→C direction):

(1)

(SEQ ID NO: 403)

FTFSX1YX2MX3WVR

In the above formula,

X1=R, S, or D

X2=A, G, or H

X3=T, H, or S (2)

(SEQ ID NO: 404)

X1X2SX3X4GGX5TYYAX6

In the above formula,

X1=S, A, or T

X2=M or I

X3=G or S

X4=T or S

X5=T, S, or Y

X6=D or E (3)

(SEQ ID NO: 405)

YCAX1X2X3X4X5X6X7X8X9X10X11W

In the above formula,

X1=R, V, or S

X2=G or S

X3=A, G, S, Y, or I

X4=Y, A, Q, G, or R

X5=G or L

X6=F, R, I, M, or P.

X7=D, G, F, or L

X8=H, F, D, or V

X9=F, L, Y, or not present

X10=D or not present

X11=Y or not present (4)

(SEQ ID NO: 406)

CX1X2X3X4X5X6X7X8X9X10X11X12X13W

In the above formula,

X1=R, S, or T

X2=A, G, or R.

X3=S or N

X4=Q. S or N

X5=S, I or G

X6=I, N or G

X7=G, L, T, or S.

X8=N, G, R, A, or K

X9=Y, S, R, or G

X10=N or not present

X11=Y or not present

X12=L or V

X13=N, Y, H, or Q (5)

(SEQ ID NO: 407)

X1X2X3X4X5X6X7GX8X9

In the above formula,

X1=D, E, S, or R

X2=A, D, K, or N

X3=S or N
X4=N, K, or Q
X5=L or R
X6=E or P
X7=T or S
X8=I or V
X9=P or R (6)

(SEQ ID NO: 408)

YCX1X2X3X4X5X6X7X8X9X10X11F

In the above formula,

X1=Q, S, or A
X2=Q, S, or A
X3=S, Y, or W
X4=S, T, D, or A
X5=A, S, D, or G
X6=I, S, N, or T
X7=P, S, L, N, or K
X8=Y, T, S, N, or G
X9=V, G, L, or not present
X10=P or not present
X11=T, I, or V.

In certain embodiments, the binding domain may be a single chain variable segment (scFv) and may comprise or consist of an amino acid sequence selected from the group consisting of SEQ ID NOs: 412, 414, 416, 418, 420, 422, 424, 426, 428, 430, 432, 434, 436, 438, and 440. Preferably, the binding domain may comprise or consist of SEQ ID NO: 412, 414, 416, 418, or 440.

The binding domain may comprise a sequence having 80% or more, preferably 90% or more, more preferably 95% or more, and most preferably 98% or more sequence identity to any of the above-described amino acid sequences.

In certain embodiments, amino acid sequence variants of the antibodies of the present disclosure are contemplated. For example, it may be desirable to improve the binding affinity and/or other biological properties of the antibody. Amino acid sequence variants of the antibody may be prepared by introducing appropriate modifications into the nucleotide sequence encoding the molecules, or by peptide synthesis. Such modifications include, for example, deletions from, and/or insertions into and/or substitutions of residues within the amino acid sequence of the antibody. Any combination of deletion, insertion, and substitution can be made to arrive at the final construct, provided that the final construct possesses the desired characteristics, for example, antigen-binding. Sites of interest for substitutional mutagenesis include heavy chain variable regions (HVRs) and framework regions (FRs). Conservative substitutions are provided in Table 1 under the heading "Preferred Substitutions" and further described below in reference to amino acid side chain classes (1) to (6). Amino acid substitutions may be introduced into the molecule of interest and the products screened for a desired activity, for example, retained/improved antigen binding, decreased immunogenicity, or improved ADCC or CDC.

TABLE 1

| Original residue | Exemplary substitutions | Preferred substitutions |
| --- | --- | --- |
| Ala (A) | Val; Leu; Ile | Val |
| Arg (R) | Lys; Gln; Asn | Lys |
| Asn (N) | Gln; His; Asp; Lys; Arg | Gln |

TABLE 1-continued

| Original residue | Exemplary substitutions | Preferred substitutions |
| --- | --- | --- |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Ile |
| Phe (F) | Trp; Leu; Val; Ile; Ala; Tyr | Tyr |
| Pro (P) | Ala | Ala |
| Ser (S) | Thr | Thr |
| Thr (T) | Va;; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; norleucine | Leu |

Amino acids may be grouped according to common side-chain properties:

(1) hydrophobic: norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

As used herein, the term "amino acid sequence variant" includes substantial variants wherein there are amino acid substitutions in one or more hypervariable region residues of a parent antigen binding molecule (for example, a humanized or human antibody). In general, the resulting variant(s) selected for further study will have modifications (for example, improvements) in certain biological properties (for example, increased affinity, reduced immunogenicity) relative to the parent antigen binding molecule and/or will have substantially retained certain biological properties of the parent antigen binding molecule. An exemplary substitutional variant is an affinity matured antibody, which may be conveniently generated, for example, using phage display-based affinity maturation techniques known in the art. Briefly, one or more HVR residues are mutated and the variant antigen binding molecules displayed on phage and screened for a particular biological activity (for example, binding affinity). In certain embodiments, substitutions, insertions, or deletions may occur within one or more HVRs so long as such alterations do not substantially reduce the ability of the antigen binding molecule to bind antigen. For example, conservative alterations (for example, conservative substitutions as provided herein) that do not substantially reduce binding affinity may be made in HVRs.

In addition, there are provided variants of the antibody or an antigen-binding fragment thereof of the present disclosure which have improved affinity for the CD300c antigen or a receptor thereof. Such variants can be obtained by a number of affinity maturation protocols including mutating the CDRs (Yang et al., J. Mol. Biol., 254, 392-403, 1995), chain shuffling (Marks et al., Bio/Technology, 10, 779-783, 1992), use of mutator strains of E. coli (Low et al., J. Mol. Biol., 250, 359-368, 1996), DNA shuffling (Patten et al., Curr. Opin. Biotechnol., 8, 724-733, 1997), phage display (Thompson et al., J. Mol. Biol., 256, 77-88, 1996), and sexual PCR (Crameri et al., Nature, 391, 288-291, 1998).

Vaughan et al. (Science, 239, 1534-1536, 1988) discuss these methods of affinity maturation.

The anti-CD300c monoclonal antibody or an antigen-binding fragment thereof may have inter-species cross-reactivity. Specifically, the anti-CD300c monoclonal antibody or an antigen-binding fragment thereof may exhibit cross-reactivity between human and mouse CD300c antigens. Such cross-reactivity is identified in Experimental Examples 6.3 and 6.4.

In certain embodiments, the signal peptide may be or comprise a CD8a signal peptide.

In certain embodiments, the GS linker may be a 5- to 15-peptide consisting of glycine and serine. Specifically, the GS linker may comprise or consist of the amino acid sequence represented by SEQ ID NO: 422.

In certain embodiments, the transmembrane domain may be or comprise a CD8 hinge (hinge of cluster of differentiation 8) and/or a CD28 transmembrane domain. The CD8 hinge may comprise or consist of the amino acid sequence represented by SEQ ID NO: 424. The CD28 transmembrane domain may comprise or consist of the amino acid sequence represented by SEQ ID NO: 426.

In certain embodiments, the intracellular signaling domain may be or comprise a CD28 intracellular domain and/or a CD3ζ intracellular domain. The CD28 intracellular domain may comprise or consist of the amino acid sequence represented by SEQ ID NO: 428. The CD3ζ intracellular domain may comprise or consist of the amino acid sequence represented by SEQ ID NO: 430.

Polynucleotide, Vector, and Immune Cell

According to another aspect of the present disclosure, there are provided a polynucleotide comprising a nucleic acid sequence encoding the chimeric antigen receptor, a vector (for example, expression vector) comprising the polynucleotide, and an immune cell expressing the chimeric antigen receptor.

The polynucleotide of the present disclosure may comprise any nucleic acid sequence encoding an amino acid sequence that constitutes or is included in the chimeric antigen receptor, and may also comprise a nucleic acid sequence having 80% or more, preferably 90% or more, more preferably 95% or more, and most preferably 98% or more identity thereto.

The "vector" refers to a nucleic acid molecule capable of transporting another nucleic acid to which it has been linked. One type of vector is a "plasmid," which refers to a circular double stranded DNA loop into which additional DNA segments can be inserted. Another type of vector is a viral vector, wherein virally-derived DNA or RNA sequences are present in the vector for packaging into a virus. Certain vectors are capable of autonomous replication in a host cell into which they are introduced (for example, bacterial vectors having a bacterial origin of replication and episomal mammalian vectors). Other vectors (for example, non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids. In the present specification, "plasmid" and "vector" may be used interchangeably as the plasmid is the most commonly used form of vector. However, the present disclosure is intended to include such other forms of expression vectors, such as viral vectors (for example, lentiviruses, replication defective retroviruses, adenoviruses, and adeno-associated viruses), which serve equivalent functions.

The immune cells expressing the chimeric antigen receptor of the present disclosure may be produced by transforming immune cells with the vector. For example, the immune cells may be produced by introducing into immune cells a lentiviral vector comprising a nucleic acid sequence that encodes a desired chimeric antigen receptor.

In an embodiment, the immune cells may be any one or more selected from the group consisting of monocytes, macrophages, T cells, natural killer cells (NK cells), and dendritic cells. In addition, any immune cells may be included therein as long as they can be used for the prevention or treatment of cancer. Preferably, the immune cells of the present disclosure may be T cells. For purposes of the present disclosure, the T cell may be any T cell, such as a cultured T cell, for example, a primary T cell, or a T cell from a cultured T cell line, for example, Jurkat, SupT1, or the like, or a T cell obtained from a mammal. In a case of being obtained from a mammal, the T cell can be obtained from a number of sources including, but not limited to, bone marrow, blood, lymph nodes, thymus, or other tissues or body fluids. The T cell may also be enriched or purified. The T cell may be a human T cell. The T cell may be a T cell isolated from a human. The T cell can be any type of T cell and can be of any developmental stage, including but not limited to, CD4+/CD8+ double positive T cells, CD8+ T cells (for example, cytotoxic T cells), CD4+ helper T cells, for example, Th1 and Th2 cells, peripheral blood mononuclear cells (PBMCs), peripheral blood leukocytes (PBLs), tumor infiltrating lymphocytes (TILs), memory T cells, naive T cells, and the like. The T cell may be a CD8+ T cell or a CD4+ T cell.

Method for Prevention or Treatment of Cancer

According to yet another aspect of the present disclosure, there is provided a method for preventing or treating cancer, improving or decreasing severity of at least one symptom or sign of cancer, inhibiting metastasis, or inhibiting growth of cancer, the method comprising using the immune cells of the present disclosure. As used herein, "preventing or treating cancer" may include inhibiting proliferation, survival, metastasis, recurrence, or therapy resistance of cancer. Such a method may comprise a step of administering the immune cells of the present disclosure to a subject in need of prevention or treatment of cancer. Accordingly, there is provided a use of a composition that comprises the immune cells as an active ingredient, for preventing or treating cancer As used herein, the term "cancer" refers to a physiological condition that is typically characterized by unregulated cell growth in mammals. The cancer to be prevented or treated in the present disclosure may include, depending on the site of occurrence, colorectal cancer, small intestine cancer, rectal cancer, colon cancer, thyroid cancer, endocrine adenocarcinoma, oral cancer, tongue cancer, pharyngeal cancer, laryngeal cancer, esophageal cancer, cervical cancer, uterine cancer, fallopian tube cancer, ovarian cancer, brain cancer, head and neck cancer, lung cancer, lymph gland cancer, gallbladder cancer, bladder cancer, kidney cancer, liver cancer, pancreatic cancer, prostate cancer, skin cancer (or melanoma), breast cancer, stomach cancer, bone cancer, blood cancer, and the like. However, any cancer can be included therein as long as it expresses a CD300c protein on the surface of cancer cells. In an embodiment, the cancer may include at least any one selected from the group consisting of colorectal cancer, rectal cancer, colon cancer, thyroid cancer, oral cancer, pharyngeal cancer, laryngeal cancer, cervical cancer, brain cancer, lung cancer, ovarian cancer, bladder cancer, kidney cancer, liver cancer, pancreatic cancer, prostate cancer, skin cancer, tongue cancer, breast cancer, uterine cancer, stomach cancer, bone cancer, and blood cancer. In another embodiment, the cancer may be a solid cancer.

In an embodiment, the method may further comprise a step of administering one or more cancer therapies (for example, immunotherapies). In a case where (i) the immune cells of the present disclosure are used in combination with (ii) one or more immunotherapies, (i) and (ii) may be administered simultaneously or sequentially.

"Administered sequentially" means that one ingredient is first administered and the other ingredient is administered immediately or at a predetermined interval after the first administration, wherein the ingredients may be administered in any order. That is, the immune cells may be first administered and one or more immunotherapies may be administered immediately or at a predetermined interval after the first administration, or vice versa. In addition, any of the one or more immunotherapies may be first administered first, followed by the immune cells, and then the other of the one or more immunotherapies.

Cancer immunotherapies have a novel mechanism by which immune cells in the body are activated to kill cancer cells, and thus are advantageous in that they can be widely used for most cancers without specific genetic mutations. In addition, the immunotherapies have fewer adverse effects in that they treat cancer by strengthening the patient's own immune system, and have effects of improving the patient's quality of life and significantly extending the survival. These immunotherapies include immune checkpoint inhibitors, and may be manufactured by known methods or commercially available products. Examples of the immunotherapy include, but are not limited to, anti-PD-1, anti-PD-L1, anti-CTLA-4, anti-CD47, anti-KIR, anti-LAG3, anti-CD137, anti-OX40, anti-CD276, anti-CD27, anti-GITR, anti-TIM3, anti-41BB, anti-CD226, anti-CD40, anti-CD70, anti-ICOS, anti-CD40L, anti-BTLA, anti-TCR, and anti-TIGIT antibodies. In addition, examples of the immunotherapy include, but are not limited to, durvalumab (IMFINZI®), atezolizumab (TECENTRIQ®), avelumab (BAVENCIO®), pembrolizumab (KEYTRUDA®), nivolumab (OPDIVO®), αCD47, cemiplimab (LIBTAYO®), magrolimab (Hu5F9-G4), and ipilimumab (YERVOY®).

In an embodiment, the immunotherapy may include at least any one selected from the group consisting of anti-PD-1, anti-PD-L1, anti-CTLA-4, anti-CD47, anti-KIR, anti-LAG3, anti-CD137, anti-OX40, anti-CD276, anti-CD27, anti-GITR, anti-TIM3, anti-41BB, anti-CD226, anti-CD40, anti-CD70, anti-ICOS, anti-CD40L, anti-BTLA, anti-TCR, and anti-TIGIT antibodies. In one example, the immunotherapy may include at least any one selected from the group consisting of anti-PD-1, anti-PD-L1, anti-CTLA-4, and anti-CD47 antibodies.

In another embodiment, the immunotherapy may include at least any one selected from the group consisting of durvalumab (IMFINZI®), atezolizumab (TECENTRIQ®), pembrolizumab (KEYTRUDA®), nivolumab (OPDIVO®), αCD47, and ipilimumab (YERVOY®).

Each of the immune cells according to the present disclosure and optionally one or more additional cancer therapies may be administered in several ways depending on whether local or systemic treatment is desired and the area to be treated. Methods of administering these ingredients to a subject may vary depending on the purpose of administration, the site of the disease, the subject's condition, and the like. The route of administration may be oral, parenteral, inhalation, local or topical (for example, intralesional administration). For example, parenteral administration may include, but is not limited to, intravenous, subcutaneous, intraperitoneal, intrapulmonary, intraarterial, intramuscular, rectal, vaginal, intraarticular, intraprostatic, intranasal, intraocular, intravesical, intrathecal, or intraventricular administration (for example, intracerebroventricular administration). In addition, in a case of being used in combination, the immune cells and the additional cancer therapy may be administered by the same route or may be administered by different routes.

In the method, the number of the immune cells according to the present disclosure may vary depending on the age, sex, and body weight of an individual (patient). The immune cells may be included at about 1 to about 10 times the number of tumor cells in the individual. In addition, an effective amount of one or more additional cancer therapies may vary depending on the age, sex, and body weight of an individual (patient). In general, administration may be performed in an amount of about 0.01 mg to 100 mg, or 5 mg to about 50 mg, per kg of body. The amount may be administrated once a day or several times a day in divided doses. However, the effective amount may be increased or decreased depending on route and period of administration, severity of disease, sex, body weight, age, and the like. Thus, the scope of the present disclosure is not limited thereto.

Pharmaceutical Composition

According to still yet another aspect of the present disclosure, there is provided a pharmaceutical composition for preventing or treating cancer, comprising the immune cells according to the present disclosure as an active ingredient. In addition, there is provided a use of the immune cells according to the present disclosure for the manufacture of a medicament for preventing or treating cancer.

The immune cells may be included in the composition in a prophylactically or therapeutically effective amount. The pharmaceutical composition may be administered to a subject to inhibit proliferation, survival, metastasis, recurrence, or therapy resistance of cancer.

In an embodiment, the pharmaceutical composition may further comprise at least one additional cancer therapy (for example, immunotherapy). Specifically, the immune cells and optionally the additional immunotherapy may be included in the same composition or may be included in separate compositions. In a case of being included in separate compositions, the immune cells and the additional immunotherapy may be formulated respectively, and may be administered simultaneously or sequentially.

To prepare the pharmaceutical composition of the present disclosure, the immune cells and optionally the additional immunotherapy may be mixed with a pharmaceutically acceptable carrier and/or excipient. The pharmaceutical composition may be prepared in the form of a lyophilized preparation or an aqueous solution. For example, see Remington's Pharmaceutical Sciences and US Pharmacopeia: National Formulary, Mack Publishing Company, Easton, PA (1984).

Acceptable carriers and/or excipients (including stabilizers) are nontoxic to recipients at the dosages and concentrations employed, and include, but are not limited to, buffers (such as phosphate, citrate, and other organic acids); antioxidants (such as ascorbic acid and methionine); preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins (such as serum albumin, gelatin, or immunoglobulins); hydrophilic polymers (such as polyvinylpyrrolidone); amino acids (such as glycine, glutamine, asparagine, histidine, arginine, or lysine); monosaccharides, disaccharides, and other carbohydrates such as glucose, mannose, or dextrins; chelating agents (such as EDTA); sugars (such as sucrose, mannitol, trehalose or sorbitol); salt-forming counter-ions (such as sodium); metal complexes (such as Zn-protein complexes); and/or non-ionic surfactants (such as TWEEN™, PLURONICS™ or polyethylene glycol (PEG)).

The pharmaceutical composition of the present disclosure may be formulated in a suitable form known in the art depending on the route of administration.

As used herein, the term "prophylactically or therapeutically effective amount" or "effective amount" refers to an amount of an active ingredient in a composition which is effective for preventing or treating cancer in a subject. Also, this amount is sufficient for preventing or treating cancer at a reasonable benefit/risk ratio applicable to medical treatment and does not cause adverse effects. A level of the effective amount may be determined depending on the patient's health status, type of disease, severity of disease, activity of the drug, sensitivity to the drug, method of administration, frequency of administration, route of administration and rate of excretion, duration of treatment, drugs used in combination or coincidentally therewith, and other factors well known in the medical field. Here, it is important to administer a minimum amount that allows the maximum effect to be achieved with minimal or no adverse effects in consideration of all of the above factors, which can be easily determined by those skilled in the art.

For the effective amount of each of the active ingredients in the pharmaceutical composition of the present disclosure, refer to the description in the section on the method for preventing or treating cancer.

In another embodiment, the pharmaceutical composition is able to inhibit proliferation, survival, metastasis, recurrence, or therapy resistance of cancer.

Hereinafter, the present disclosure will be described in more detail by way of examples. However, the following examples are only for illustrating the present disclosure, and the scope of the present disclosure is not limited thereto.

EXAMPLES

I. Production of Anti-CD300c Monoclonal Antibody

Example 1. Production of Anti-CD300c Monoclonal Antibody

Example 1.1. Construction of Anti-CD300c Monoclonal Antibody Library

In order to select anti-CD300c monoclonal antibodies, biopanning was performed using a lambda phage library, a kappa phage library, a VH3VL1 phage library, and an OPALTL phage library. Specifically, a CD300c antigen was added at a concentration of 5 μg/mL to an immunotube, and reaction was allowed to proceed for 1 hour so that the antigen was adsorbed on the surface of the immunotube. 3% skim milk was added to suppress non-specific reactions. Then, 1012 PFU of the antibody phage library dispersed in 3% skim milk was added to each immunotube for antigen binding. Washing was performed 3 times using Tris buffered saline-Tween 20 (TBST) solution to remove non-specifically bound phages, and then single-chain variable fragment (scFv) phage antibodies, which are specifically bound to the CD300c antigen, were eluted using 100 mM triethylamine solution. The eluted phages were neutralized using 1.0 M Tris-HCl buffer (pH 7.8). Then, the resultant was subjected to E. coli ER2537 and infection was allowed to proceed at 37° C. for 1 hour. The infected E. coli was applied onto LB agar medium containing carbenicillin, and cultured at 37° C. for 16 hours. Then, the formed E. coli colonies were suspended using 3 mL of super broth (SB)-carbenicillin culture. Some of the suspension was stored at −80° C. until use with the addition of 15% glycerol, and the remaining portion was reinoculated into SB-carbenicillin-2% glucose solution and cultured at 37° C. Then, the obtained culture was centrifuged, and biopanning was repeated 3 times again using the supernatant containing phage particles to obtain and concentrate antigen-specific antibodies.

After repeating the biopanning 3 times, E. coli containing the antibody gene was applied onto LB agar medium containing carbenicillin and cultured at 37° C. for 16 hours. The formed E. coli colonies were inoculated again into SB-carbenicillin-2% glucose solution and cultured at 37° C. until the absorbance (at OD 600 nm) reached 0.5. Then, IPTG was added and further cultured at 30° C. for 16 hours. Thereafter, periplasmic extraction was performed. From the results, a library pool of antibodies, which specifically bind to the CD300c antigen, was primarily obtained.

Example 1.2. Selection of Anti-CD300c Monoclonal Antibody

In order to select anti-CD300c monoclonal antibodies that specifically bind, with high binding affinity, to a CD300c antigen, ELISA was performed using the library pool obtained in the same manner as in Example 1.1. More specifically, each of a CD300c antigen and a CD300a antigen in a coating buffer (0.1 M sodium carbonate, pH 9.0) was dispensed onto an ELISA plate at a concentration of 5 μg/mL per well, and then reaction was allowed to proceed at room temperature for 3 hours so that the antigen was bound to the plate. Washing was performed 3 times using phosphate buffered saline-Tween 20 (PBST) to remove unbound antigen, and then 350 μL of PBST supplemented with 2% bovine serum albumin (BSA) was added to each well. Reaction was allowed to proceed at room temperature for 1 hour, and washing was performed again using PBST. Then, 25 μg of periplasmic extract containing scFv obtained in the same manner as in Example 1.1 was added thereto, and reaction was allowed to proceed for 1 hour at room temperature for antigen binding. After 1 hour, washing was performed 3 times using PBST to remove unbound scFv, and then 4 μg/mL of an antibody for detection was added. Reaction was allowed to proceed again at room temperature for 1 hour. Subsequently, the unbound antibody for detection was removed using PBST. Then, anti-rabbit IgG to which HRP was bound was added and reaction was allowed to proceed at room temperature for 1 hour. The unbound antibody was removed again using PBST. Subsequently, 3,3',5,5'-tetramethylbenzidine (TMB) solution was added and reaction was allowed to proceed for 10 minutes for development. Then, 2 N sulfuric acid solution was added to terminate the development, and the absorbance was measured at 450 nm to identify the antibodies that specifically bind to the CD300c antigen.

Example 1.3. Identification of Anti-CD300c Monoclonal Antibody Sequences

The nucleotide sequences of the anti-CD300c monoclonal antibodies, which were selected using the same method as in Example 1.2, were identified. More specifically, for each of the selected antibody clones, plasmid DNA was extracted therefrom using a plasmid miniprep kit. Then, DNA sequencing was performed to analyze complementarity-determining region (CDR) sequences. As a result, 25 types of anti-CD300c monoclonal antibodies having different amino acid sequences were obtained.

The heavy chain and light chain variable regions of these 25 anti-CD300c monoclonal antibodies are shown in Tables 2 and 3.

TABLE 2

| Antibody name | Source (phage library) | Heavy chain variable region (nucleotide) | Light chain variable region (nucleotide) | Heavy chain variable region (amino acid) | Light chain variable region (amino acid) |
|---|---|---|---|---|---|
| CK1 | Kappa | FIG. 1aa (SEQ ID NO: 301) | FIG. 1ab (SEQ ID NO: 302) | FIG. 1ac (SEQ ID NO: 303) | FIG. 1ad (SEQ ID NO: 304) |
| CK2 | Kappa | FIG. 1ba (SEQ ID NO: 305) | FIG. 1bb (SEQ ID NO: 306) | FIG. 1bc (SEQ ID NO: 307) | FIG. 1bd (SEQ ID NO: 308) |
| CK3 | Kappa | FIG. 1ca (SEQ ID NO: 309) | FIG. 1cb (SEQ ID NO: 310) | FIG. 1cc (SEQ ID NO: 311) | FIG. 1cd (SEQ ID NO: 312) |
| CL4 | Lambda | FIG. 1da (SEQ ID NO: 313) | FIG. 1db (SEQ ID NO: 314) | FIG. 1dc (SEQ ID NO: 315) | FIG. 1dd (SEQ ID NO: 316) |
| CL5 | Lambda | FIG. 1ea (SEQ ID NO: 317) | FIG. 1eb (SEQ ID NO: 318) | FIG. 1ec (SEQ ID NO: 319) | FIG. 1ed (SEQ ID NO: 320) |
| CL6 | VH3VL1 | FIG. 1fa (SEQ ID NO: 321) | FIG. 1fb (SEQ ID NO: 322) | FIG. 1fc (SEQ ID NO: 323) | FIG. 1fd (SEQ ID NO: 324) |
| CL7 | VH3VL1 | FIG. 1ga (SEQ ID NO: 325) | FIG. 1gb (SEQ ID NO: 326) | FIG. 1gc (SEQ ID NO: 327) | FIG. 1gd (SEQ ID NO: 328) |
| CL8 | VH3VL1 | FIG. 1ha (SEQ ID NO: 329) | FIG. 1hb (SEQ ID NO: 330) | FIG. 1hc (SEQ ID NO: 331) | FIG. 1hd (SEQ ID NO: 332) |
| CL9 | VH3VL1 | FIG. 1ia (SEQ ID NO: 333) | FIG. 1ib (SEQ ID NO: 334) | FIG. 1ic (SEQ ID NO: 335) | FIG. 1id (SEQ ID NO: 336) |
| CL10 | VH3VL1 | FIG. 1ja (SEQ ID NO: 337) | FIG. 1jb (SEQ ID NO: 338) | FIG. 1jc (SEQ ID NO: 339) | FIG. 1jd (SEQ ID NO: 340) |
| SK11 | Kappa | FIG. 1ka (SEQ ID NO: 341) | FIG. 1kb (SEQ ID NO: 342) | FIG. 1kc (SEQ ID NO: 343) | FIG. 1kd (SEQ ID NO: 344) |
| SK12 | Kappa | FIG. 1la (SEQ ID NO: 345) | FIG. 1lb (SEQ ID NO: 346) | FIG. 1lc (SEQ ID NO: 347) | FIG. 1ld (SEQ ID NO: 348) |
| SK13 | Kappa | FIG. 1ma (SEQ ID NO: 349) | FIG. 1mb (SEQ ID NO: 350) | FIG. 1mc (SEQ ID NO: 351) | FIG. 1md (SEQ ID NO: 352) |
| SK14 | Kappa | FIG. 1na (SEQ ID NO: 353) | FIG. 1nb (SEQ ID NO: 354) | FIG. 1nc (SEQ ID NO: 355) | FIG. 1nd (SEQ ID NO: 356) |
| SK15 | Kappa | FIG. 1oa (SEQ ID NO: 357) | FIG. 1ob (SEQ ID NO: 358) | FIG. 1oc (SEQ ID NO: 359) | FIG. 1od (SEQ ID NO: 360) |
| SK16 | Kappa | FIG. 1pa (SEQ ID NO: 361) | FIG. 1pb (SEQ ID NO: 362) | FIG. 1pc (SEQ ID NO: 363) | FIG. 1pd (SEQ ID NO: 364) |
| SK17 | Kappa | FIG. 1qa (SEQ ID NO: 365) | FIG. 1qb (SEQ ID NO: 366) | FIG. 1qc (SEQ ID NO: 367) | FIG. 1qd (SEQ ID NO: 368) |

TABLE 3

| Antibody name | Source (phage library) | Heavy chain variable region (nucleotide) | Light chain variable region (nucleotide) | Heavy chain variable region (amino acid) | Light chain variable region (amino acid) |
|---|---|---|---|---|---|
| SL18 | Lambda | FIG. 1ra (SEQ ID NO: 369) | FIG. 1rb (SEQ ID NO: 370) | FIG. 1rc (SEQ ID NO: 371) | FIG. 1rd (SEQ ID NO: 372) |
| CB301_H3L1_A10 | VH3VL1 | FIG. 1sa (SEQ ID NO: 373) | FIG. 1sb (SEQ ID NO: 374) | FIG. 1sc (SEQ ID NO: 375) | FIG. 1sd (SEQ ID NO: 376) |
| CB301_H3L1_A12 | VH3VL1 | FIG. 1ta (SEQ ID NO: 377) | FIG. 1tb (SEQ ID NO: 378) | FIG. 1tc (SEQ ID NO: 379) | FIG. 1td (SEQ ID NO: 380) |
| CB301_H3L1_E6 | VH3VL1 | FIG. 1ua (SEQ ID NO: 381) | FIG. 1ub (SEQ ID NO: 382) | FIG. 1uc (SEQ ID NO: 383) | FIG. 1ud (SEQ ID NO: 384) |
| CB301_H3L1_F4 | VH3VL1 | FIG. 1va (SEQ ID NO: 385) | FIG. 1vb (SEQ ID NO: 386) | FIG. 1vc (SEQ ID NO: 387) | FIG. 1vd (SEQ ID NO: 388) |
| CB301_H3L1_G11 | VH3VL1 | FIG. 1wa (SEQ ID NO: 389) | FIG. 1wb (SEQ ID NO: 390) | FIG. 1wc (SEQ ID NO: 391) | FIG. 1wd (SEQ ID NO: 392) |
| CB301_OPALTL_B5 | OPALTL | FIG. 1xa (SEQ ID NO: 393) | FIG. 1xb (SEQ ID NO: 394) | FIG. 1xc (SEQ ID NO: 395) | FIG. 1xd (SEQ ID NO: 396) |
| CB301_OPALTL_E6 | OPALTL | FIG. 1ya (SEQ ID NO: 397) | FIG. 1yb (SEQ ID NO: 398) | FIG. 1yc (SEQ ID NO: 399) | FIG. 1yd (SEQ ID NO: 400) |

In each of the drawings mentioned in Tables 2 and 3, the CDR regions (CDR1, CDR2, and CDR3) are underlined and appear sequentially (that is, CDR1 appears, followed by CDR2, and then CDR3). In addition, the CDR regions included in each drawing are represented by SEQ ID NOs as shown in Table 4:

TABLE 4

| Related drawing | Antibody | Heavy chain/ Light chain | Aminoacid/ nucleotide | CDR1 | CDR2 | CDR3 |
|---|---|---|---|---|---|---|
| FIG. 1aa | CK1 | Heavy chain | Nucleotide | SEQ ID NO: 1 | SEQ ID NO: 2 | SEQ ID NO: 3 |
| FIG. 1ab | | Light chain | Nucleotide | SEQ ID NO: 4 | SEQ ID NO: 5 | SEQ ID NO: 6 |
| FIG. 1ac | | Heavy chain | Amino acid | SEQ ID NO: 7 | SEQ ID NO: 8 | SEQ ID NO: 9 |
| FIG. 1ad | | Light chain | Amino acid | SEQ ID NO: 10 | SEQ ID NO: 11 | SEQ ID NO: 12 |
| FIG. 1ba | CK2 | Heavy chain | Nucleotide | SEQ ID NO: 13 | SEQ ID NO: 14 | SEQ ID NO: 15 |
| FIG. 1bb | | Light chain | Nucleotide | SEQ ID NO: 16 | SEQ ID NO: 17 | SEQ ID NO: 18 |
| FIG. 1bc | | Heavy chain | Amino acid | SEQ ID NO: 19 | SEQ ID NO: 20 | SEQ ID NO: 21 |
| FIG. 1bd | | Light chain | Amino acid | SEQ ID NO: 22 | SEQ ID NO: 23 | SEQ ID NO: 24 |
| FIG. 1ca | CK3 | Heavy chain | Nucleotide | SEQ ID NO: 25 | SEQ ID NO: 26 | SEQ ID NO: 27 |
| FIG. 1cb | | Light chain | Nucleotide | SEQ ID NO: 28 | SEQ ID NO: 29 | SEQ ID NO: 30 |
| FIG. 1cc | | Heavy chain | Amino acid | SEQ ID NO: 31 | SEQ ID NO: 32 | SEQ ID NO: 33 |
| FIG. 1cd | | Light chain | Amino acid | SEQ ID NO: 34 | SEQ ID NO: 35 | SEQ ID NO: 36 |
| FIG. 1da | CL4 | Heavy chain | Nucleotide | SEQ ID NO: 37 | SEQ ID NO: 38 | SEQ ID NO: 39 |
| FIG. 1db | | Light chain | Nucleotide | SEQ ID NO: 40 | SEQ ID NO: 41 | SEQ ID NO: 42 |
| FIG. 1dc | | Heavy chain | Amino acid | SEQ ID NO: 43 | SEQ ID NO: 44 | SEQ ID NO: 45 |
| FIG. 1dd | | Light chain | Amino acid | SEQ ID NO: 46 | SEQ ID NO: 47 | SEQ ID NO: 48 |
| FIG. 1ea | CL5 | Heavy chain | Nucleotide | SEQ ID NO: 49 | SEQ ID NO: 50 | SEQ ID NO: 51 |
| FIG. 1eb | | Light chain | Nucleotide | SEQ ID NO: 52 | SEQ ID NO: 53 | SEQ ID NO: 54 |

TABLE 4-continued

| Related drawing | Antibody | Heavy chain/ Light chain | Aminoacid/ nucleotide | CDR1 | CDR2 | CDR3 |
|---|---|---|---|---|---|---|
| FIG. 1ec | | Heavy chain | Amino acid | SEQ ID NO: 55 | SEQ ID NO: 56 | SEQ ID NO: 57 |
| FIG. 1ed | | Light chain | Amino acid | SEQ ID NO: 58 | SEQ ID NO: 59 | SEQ ID NO: 60 |
| FIG. 1fa | CL6 | Heavy chain | Nucleotide | SEQ ID NO: 61 | SEQ ID NO: 62 | SEQ ID NO: 63 |
| FIG. 1fb | | Light chain | Nucleotide | SEQ ID NO: 64 | SEQ ID NO: 65 | SEQ ID NO: 66 |
| FIG. 1fc | | Heavy chain | Amino acid | SEQ ID NO: 67 | SEQ ID NO: 68 | SEQ ID NO: 69 |
| FIG. 1fd | | Light chain | Amino acid | SEQ ID NO: 70 | SEQ ID NO: 71 | SEQ ID NO: 72 |
| FIG. 1ga | CL7 | Heavy chain | Nucleotide | SEQ ID NO: 73 | SEQ ID NO: 74 | SEQ ID NO: 75 |
| FIG. 1gb | | Light chain | Nucleotide | SEQ ID NO: 76 | SEQ ID NO: 77 | SEQ ID NO: 78 |
| FIG. 1gc | | Heavy chain | Amino acid | SEQ ID NO: 79 | SEQ ID NO: 80 | SEQ ID NO: 81 |
| FIG. 1gd | | Light chain | Amino acid | SEQ ID NO: 82 | SEQ ID NO: 83 | SEQ ID NO: 84 |
| FIG. 1ha | CL8 | Heavy chain | Nucleotide | SEQ ID NO: 85 | SEQ ID NO: 86 | SEQ ID NO: 87 |
| FIG. 1hb | | Light chain | Nucleotide | SEQ ID NO: 88 | SEQ ID NO: 89 | SEQ ID NO: 90 |
| FIG. 1hc | | Heavy chain | Amino acid | SEQ ID NO: 91 | SEQ ID NO: 92 | SEQ ID NO: 93 |
| FIG. 1hd | | Light chain | Amino acid | SEQ ID NO: 94 | SEQ ID NO: 95 | SEQ ID NO: 96 |
| FIG. 1ia | CL9 | Heavy chain | Nucleotide | SEQ ID NO: 97 | SEQ ID NO: 98 | SEQ ID NO: 99 |
| FIG. 1ib | | Light chain | Nucleotide | SEQ ID NO: 100 | SEQ ID NO: 101 | SEQ ID NO: 102 |
| FIG. 1ic | | Heavy chain | Amino acid | SEQ ID NO: 103 | SEQ ID NO: 104 | SEQ ID NO: 105 |
| FIG. 1id | | Light chain | Amino acid | SEQ ID NO: 106 | SEQ ID NO: 107 | SEQ ID NO: 108 |
| FIG. 1ja | CL10 | Heavy chain | Nucleotide | SEQ ID NO: 109 | SEQ ID NO: 110 | SEQ ID NO: 111 |
| FIG. 1jb | | Light chain | Nucleotide | SEQ ID NO: 112 | SEQ ID NO: 113 | SEQ ID NO: 114 |
| FIG. 1jc | | Heavy chain | Amino acid | SEQ ID NO: 115 | SEQ ID NO: 116 | SEQ ID NO: 117 |
| FIG. 1jd | | Light chain | Amino acid | SEQ ID NO: 118 | SEQ ID NO: 119 | SEQ ID NO: 120 |
| FIG. 1ka | SK11 | Heavy chain | Nucleotide | SEQ ID NO: 121 | SEQ ID NO: 122 | SEQ ID NO: 123 |
| FIG. 1kb | | Light chain | Nucleotide | SEQ ID NO: 124 | SEQ ID NO: 125 | SEQ ID NO: 126 |
| FIG. 1kc | | Heavy chain | Amino acid | SEQ ID NO: 127 | SEQ ID NO: 128 | SEQ ID NO: 129 |
| FIG. 1kd | | Light chain | Amino acid | SEQ ID NO: 130 | SEQ ID NO: 131 | SEQ ID NO: 132 |
| FIG. 1la | SK12 | Heavy chain | Nucleotide | SEQ ID NO: 133 | SEQ ID NO: 134 | SEQ ID NO: 135 |
| FIG. 1lb | | Light chain | Nucleotide | SEQ ID NO: 136 | SEQ ID NO: 137 | SEQ ID NO: 138 |
| FIG. 1lc | | Heavy chain | Amino acid | SEQ ID NO: 139 | SEQ ID NO: 140 | SEQ ID NO: 141 |
| FIG. 1ld | | Light chain | Amino acid | SEQ ID NO: 142 | SEQ ID NO: 143 | SEQ ID NO: 144 |
| FIG. 1ma | SK13 | Heavy chain | Nucleotide | SEQ ID NO: 145 | SEQ ID NO: 146 | SEQ ID NO: 147 |
| FIG. 1mb | | Light chain | Nucleotide | SEQ ID NO: 148 | SEQ ID NO: 149 | SEQ ID NO: 150 |
| FIG. 1mc | | Heavy chain | Amino acid | SEQ ID NO: 151 | SEQ ID NO: 152 | SEQ ID NO: 153 |
| FIG. 1md | | Light chain | Amino acid | SEQ ID NO: 154 | SEQ ID NO: 155 | SEQ ID NO: 156 |
| FIG. 1na | SK14 | Heavy chain | Nucleotide | SEQ ID NO: 157 | SEQ ID NO: 158 | SEQ ID NO: 159 |
| FIG. 1nb | | Light chain | Nucleotide | SEQ ID NO: 160 | SEQ ID NO: 161 | SEQ ID NO: 162 |
| FIG. 1nc | | Heavy chain | Amino acid | SEQ ID NO: 163 | SEQ ID NO: 164 | SEQ ID NO: 165 |
| FIG. 1nd | | Light chain | Amino acid | SEQ ID NO: 166 | SEQ ID NO: 167 | SEQ ID NO: 168 |

TABLE 4-continued

| Related drawing | Antibody | Heavy chain/ Light chain | Aminoacid/ nucleotide | CDR1 | CDR2 | CDR3 |
|---|---|---|---|---|---|---|
| FIG. 1oa | SK15 | Heavy chain | Nucleotide | SEQ ID NO: 169 | SEQ ID NO: 170 | SEQ ID NO: 171 |
| FIG. 1ob | | Light chain | Nucleotide | SEQ ID NO: 172 | SEQ ID NO: 173 | SEQ ID NO: 174 |
| FIG. 1oc | | Heavy chain | Amino acid | SEQ ID NO: 175 | SEQ ID NO: 176 | SEQ ID NO: 177 |
| FIG. 1od | | Light chain | Amino acid | SEQ ID NO: 178 | SEQ ID NO: 179 | SEQ ID NO: 180 |
| FIG. 1pa | SK16 | Heavy chain | Nucleotide | SEQ ID NO: 181 | SEQ ID NO: 182 | SEQ ID NO: 183 |
| FIG. 1pb | | Light chain | Nucleotide | SEQ ID NO: 184 | SEQ ID NO: 185 | SEQ ID NO: 186 |
| FIG. 1pc | | Heavy chain | Amino acid | SEQ ID NO: 187 | SEQ ID NO: 188 | SEQ ID NO: 189 |
| FIG. 1pd | | Light chain | Amino acid | SEQ ID NO: 190 | SEQ ID NO: 191 | SEQ ID NO: 192 |
| FIG. 1qa | SK17 | Heavy chain | Nucleotide | SEQ ID NO: 193 | SEQ ID NO: 194 | SEQ ID NO: 195 |
| FIG. 1qb | | Light chain | Nucleotide | SEQ ID NO: 196 | SEQ ID NO: 197 | SEQ ID NO: 198 |
| FIG. 1qc | | Heavy chain | Amino acid | SEQ ID NO: 199 | SEQ ID NO: 200 | SEQ ID NO: 201 |
| FIG. 1qd | | Light chain | Amino acid | SEQ ID NO: 202 | SEQ ID NO: 203 | SEQ ID NO: 204 |
| FIG. 1ra | SL18 | Heavy chain | Nucleotide | SEQ ID NO: 205 | SEQ ID NO: 206 | SEQ ID NO: 207 |
| FIG. 1rb | | Light chain | Nucleotide | SEQ ID NO: 208 | SEQ ID NO: 209 | SEQ ID NO: 210 |
| FIG. 1rc | | Heavy chain | Amino acid | SEQ ID NO: 211 | SEQ ID NO: 212 | SEQ ID NO: 213 |
| FIG. 1rd | | Light chain | Amino acid | SEQ ID NO: 214 | SEQ ID NO: 215 | SEQ ID NO: 216 |
| FIG. 1sa | CB301_H3L1_A10 | Heavy chain | Nucleotide | SEQ ID NO: 217 | SEQ ID NO: 218 | SEQ ID NO: 219 |
| FIG. 1sb | | Light chain | Nucleotide | SEQ ID NO: 220 | SEQ ID NO: 221 | SEQ ID NO: 222 |
| FIG. 1sc | | Heavy chain | Amino acid | SEQ ID NO: 223 | SEQ ID NO: 224 | SEQ ID NO: 225 |
| FIG. 1sd | | Light chain | Amino acid | SEQ ID NO: 226 | SEQ ID NO: 227 | SEQ ID NO: 228 |
| FIG. 1ta | CB301_H3L1_A12 | Heavy chain | Nucleotide | SEQ ID NO: 229 | SEQ ID NO: 230 | SEQ ID NO: 231 |
| FIG. 1tb | | Light chain | Nucleotide | SEQ ID NO: 232 | SEQ ID NO: 233 | SEQ ID NO: 234 |
| FIG. 1tc | | Heavy chain | Amino acid | SEQ ID NO: 235 | SEQ ID NO: 236 | SEQ ID NO: 237 |
| FIG. 1td | | Light chain | Amino acid | SEQ ID NO: 238 | SEQ ID NO: 239 | SEQ ID NO: 240 |
| FIG. 1ua | CB301_H3L1_E6 | Heavy chain | Nucleotide | SEQ ID NO: 241 | SEQ ID NO: 242 | SEQ ID NO: 243 |
| FIG. 1ub | | Light chain | Nucleotide | SEQ ID NO: 244 | SEQ ID NO: 245 | SEQ ID NO: 246 |
| FIG. 1uc | | Heavy chain | Amino acid | SEQ ID NO: 247 | SEQ ID NO: 248 | SEQ ID NO: 249 |
| FIG. 1ud | | Light chain | Amino acid | SEQ ID NO: 250 | SEQ ID NO: 251 | SEQ ID NO: 252 |
| FIG. 1va | CB301_H3L1_F4 | Heavy chain | Nucleotide | SEQ ID NO: 253 | SEQ ID NO: 254 | SEQ ID NO: 255 |
| FIG. 1vb | | Light chain | Nucleotide | SEQ ID NO: 256 | SEQ ID NO: 257 | SEQ ID NO: 258 |
| FIG. 1vc | | Heavy chain | Amino acid | SEQ ID NO: 259 | SEQ ID NO: 260 | SEQ ID NO: 261 |
| FIG. 1vd | | Light chain | Amino acid | SEQ ID NO: 262 | SEQ ID NO: 263 | SEQ ID NO: 264 |
| FIG. 1wa | CB301_H3L1_G11 | Heavy chain | Nucleotide | SEQ ID NO: 265 | SEQ ID NO: 266 | SEQ ID NO: 267 |
| FIG. 1wb | | Light chain | Nucleotide | SEQ ID NO: 268 | SEQ ID NO: 269 | SEQ ID NO: 270 |
| FIG. 1wc | | Heavy chain | Amino acid | SEQ ID NO: 271 | SEQ ID NO: 272 | SEQ ID NO: 273 |
| FIG. 1wd | | Light chain | Amino acid | SEQ ID NO: 274 | SEQ ID NO: 275 | SEQ ID NO: 276 |
| FIG. 1xa | CB301_OPALTL_B5 | Heavy chain | Nucleotide | SEQ ID NO: 277 | SEQ ID NO: 278 | SEQ ID NO: 279 |
| FIG. 1xb | | Light chain | Nucleotide | SEQ ID NO: 280 | SEQ ID NO: 281 | SEQ ID NO: 282 |

TABLE 4-continued

| Related drawing | Antibody | Heavy chain/ Light chain | Aminoacid/ nucleotide | CDR1 | CDR2 | CDR3 |
|---|---|---|---|---|---|---|
| FIG. 1xc | | Heavy chain | Amino acid | SEQ ID NO: 283 | SEQ ID NO: 284 | SEQ ID NO: 285 |
| FIG. 1xd | | Light chain | Amino acid | SEQ ID NO: 286 | SEQ ID NO: 287 | SEQ ID NO: 288 |
| FIG. 1ya | CB301_OPALTL_E6 | Heavy chain | Nucleotide | SEQ ID NO: 289 | SEQ ID NO: 290 | SEQ ID NO: 291 |
| FIG. 1yb | | Light chain | Nucleotide | SEQ ID NO: 292 | SEQ ID NO: 293 | SEQ ID NO: 294 |
| FIG. 1yc | | Heavy chain | Amino acid | SEQ ID NO: 295 | SEQ ID NO: 296 | SEQ ID NO: 297 |
| FIG. 1yd | | Light chain | Amino acid | SEQ ID NO: 298 | SEQ ID NO: 299 | SEQ ID NO: 300 |

As described above, 25 types of anti-CD300c monoclonal antibodies were identified which specifically bind, with high binding affinity, to the CD300c antigen and can be used for the prevention or treatment of cancer.

Example 1.4. Production and Purification of Anti-CD300c Monoclonal Antibody

Using each of the nucleotide sequences of the anti-CD300c monoclonal antibodies identified in Example 1.3, expression vectors capable of expressing each antibody were prepared into which the heavy chain and the light chain are separately inserted. More specifically, the expression vectors were prepared by inserting genes into the pCIW3.3 vectors using the analyzed CDR sequences so that the vectors can express the heavy and light chains, respectively. The prepared expression vectors for heavy and light chains were mixed with polyethylenimine (PEI) in a mass ratio of 1:1 and transfected into 293T cells to induce antibody expression. Then, on day 8, the culture was centrifuged to remove the cells. The resulting culture was obtained. The obtained culture was filtered, and then resuspended using a mixed solution of 0.1 M $NaH_2PO_4$ and 0.1 M $Na_2HPO_4$ (pH 7.0). The resuspended solution was purified through affinity chromatography using protein A beads (GE Healthcare), and finally eluted using an elution buffer (Thermofisher).

In order to identify the produced antibody, each of reducing sample buffer and non-reducing sample buffer was added to 5 μg of purified antibody, and electrophoresis was performed using pre-made SDS-PAGE (Invitrogen). Then, the proteins were stained using Coomassie Blue. The respective results under a non-reducing condition are illustrated in FIG. 4, and the respective results under a reducing condition are illustrated in FIG. 5.

As illustrated in FIGS. 4 and 5, it was identified that the anti-CD300c monoclonal antibodies having a high purity were produced and purified.

II. Expression of CD300c in Cancer Cells and Binding of Anti-CD300c Monoclonal Antibody to CD300c Antigen

Experimental Example 1. Identification of Expression of CD300c in Cancer Cell Line To evaluate whether CD300c is expressed in various cancer cells, various cancer cell lines such as MKN45 (human gastric cancer cell line), IM95 (human gastric cancer cell line), HT-29 (human colorectal cancer cell line), A549 (human lung cancer cell line), HCT116 (human colorectal cancer cell line), MDA-MB-231 (human breast cancer cell line), and HepG2 (human liver cancer cell line) were cultured and expression of CD300c was evaluated at mRNA and protein levels. In addition, evaluation was also performed on THP-1 cells (human monocyte cell line) which are immune cells. Here, HEK293T (normal cell line) was used as a control.

Meanwhile, expression of the protein was identified by Western blot and flow cytometry (FACS) of fluorescently labeled cells. Specifically, each cultured cell line was fixed with 4% formaldehyde, and then blocked using 5% normal bovine serum albumin. Then, staining was performed with 0.5 μg of eFluor660-labeled anti-CD300c antibody (Invitrogen). Subsequently, the fluorescently labeled cells were identified using flow cytometry (FACS).

As a result, it was identified that the CD300c antigen was expressed at the mRNA and protein levels in various cancer cells such as colorectal cancer, lung cancer, and breast cancer. In addition, as illustrated in FIG. 6, according to analysis using flow cytometry (FACS), it was identified that significantly high expression of CD300c was observed in the human lung cancer cell line (A549) and the human monocyte cell line (THP-1) as compared with the normal cell line (HEK293T).

Experimental Example 2. Identification of Antigen-Binding Affinity of Anti-CD300c Monoclonal Antibody To identify the antigen-binding ability of the anti-CD300c monoclonal antibody produced in Example 1, binding ELISA was performed. Specifically, each of the CD300c antigen (11832-H08H, Sino Biological) or CD300a antigen (12449-H08H, Sino Biological) in a coating buffer (0.1 M sodium carbonate, pH 9.0) was dispensed onto an ELISA plate at a concentration of 8 μg/mL per well, and then reaction was allowed to proceed at room temperature for 3 hours so that the antigen was bound to the plate. Washing was performed 3 times using phosphate buffered saline-Tween 20 (PBST) to remove unbound antigen, and then 300 μL of PBST supplemented with 5% bovine serum albumin (BSA) was added to each well. Reaction was allowed to proceed at room temperature for 1 hour, and washing was performed again using PBST. Then, the anti-CD300c monoclonal antibody was diluted in quadruplicate and added thereto. Reaction was allowed to proceed for 1 hour at room temperature for antigen binding. After 1 hour, washing was performed 3 times using PBST to remove unbound anti-CD300c monoclonal antibody, and then 4 μg/mL of an antibody for detection (HRP conjugated anti-Fc IgG) was added. Reaction was allowed to proceed again at room temperature for 1 hour. Subsequently, the unbound antibody for detection was removed using PBST, and then TMB solution was added. Reaction was allowed to proceed for 10 minutes for development. Then, 2 N sulfuric acid solution was added to terminate the development, and the absorbance was measured at 450 nm to identify the antibodies that specifically bind to the CD300c antigen. The results are shown in Table 5 and FIG. 7.

TABLE 5

| CB301 antibody | EC50 (μg/mL) |
|---|---|
| CK1 | 0.056 |
| CK2 | 0.033 |
| CK3 | 0.793 |
| CL4 | 0.031 |
| CL5 | 0.032 |
| CL6 | 0.148 |
| CL7 | 0.047 |
| CL8 | 49.7 |
| CL9 | 0.094 |
| CL10 | 0.039 |
| SK11 | 0.052 |
| SK12 | 0.067 |
| SK13 | 0.044 |
| SK14 | 0.065 |
| SK15 | 14.74 |
| SK16 | 2.42 |
| SK17 | 0.054 |
| SL18 | 0.17 |

As shown in Table 5, as a result of measuring the EC50 (effective concentration of drug that causes 50% of the maximum response) values of the anti-CD300c monoclonal antibodies, it was identified that the remaining all 14 clones except for 4 clones (CK3, CL8, SK15, SK16) exhibited high binding affinity of 0.2 μg/mL or lower. In addition, as illustrated in FIG. 7, it was found that the anti-CD300c monoclonal antibodies of the present disclosure bound to the CD300c antigen with high binding affinity even in the sigmoid curves for the results of the binding ELISA.

Experimental Example 3. Identification of Binding Specificity of Anti-CD300c Monoclonal Antibody to CD300c Antigen To identify specificity of the anti-CD300c monoclonal antibody CL7 for the CD300c antigen, it was further checked whether CL7 exhibits cross-reactivity to the CD300a antigen that has been known to antagonize the CD300c antigen and has a similar protein sequence thereto. More specifically, treatment with the CD300a antigen (from Sino Biological) was performed at concentrations of 0.039, 0.63, and 10 μg/mL, and binding ELISA was performed in the same manner as in Experimental Example 2. The results are illustrated in FIG. 36.

As a result, as illustrated in FIG. 36, it was found that the anti-CD300c monoclonal antibody did not bind to antigens other than CD300c and showed high binding specificity only to the CD300c antigen.

III. Production of Cells Expressing Chimeric Antigen Receptor that Specifically Binds to CD300c Antigen or Receptor Thereof and Identification of Anticancer Effects Thereof Example 2. Construction of Expression Vector for Chimeric Antigen Receptor that Specifically Binds to CD300c Antigen or Receptor Thereof To produce a chimeric antigen receptor comprising a binding domain that specifically binds to a CD300c antigen or a receptor thereof, the following sequences were sequentially inserted into the pLVX-Puro vector (Addgene) to construct an expression vector for the chimeric antigen receptor (pLVX-Puro/αCD300c scFv or pLVX-Puro/CD300c ECD-CAR) that specifically binds to the CD300c antigen or a receptor thereof: a CD8a signal peptide (whose DNA sequence is represented by SEQ ID NO: 301) comprising the amino acid sequence represented by SEQ ID NO: 302 which allows the synthesized protein to pass through the cell membrane and move to the correct position; each of CK1, CL6, CL7, CL10, and SL18 comprising the amino acid sequences represented by SEQ ID NOs: 412, 414, 416, 418, and 420, respectively, which specifically bind to a CD300c antigen or a receptor thereof and are anti-CD300c single chain variable fragments (αCD300c scFvs; whose DNA sequences are represented by SEQ ID NO: 411, 413, 415, 417, and 419, respectively), or a CD300c extracellular domain (ECD) antigen comprising the amino acid sequence represented by SEQ ID NO: 402 (whose DNA sequence is represented by SEQ ID NO: 401); a GS linker comprising the amino acid sequence represented by SEQ ID NO: 422 (whose DNA sequence is represented by SEQ ID NO: 421); a CD8 hinge comprising the amino acid sequence represented by SEQ ID NO: 424 (whose DNA sequence is represented by SEQ ID NO: 423) and a CD28 transmembrane domain comprising the amino acid sequence represented by SEQ ID NO: 426 (whose DNA sequence is represented by SEQ ID NO: 425) as a transmembrane domain; a CD28 intracellular domain comprising the amino acid sequence represented by SEQ ID NO: 428 (whose DNA sequence is represented by SEQ ID NO: 427) as an intracytoplasmic domain involved in signal transduction for macrophage activation; and a CD3ζ intracellular domain comprising the amino acid sequence represented by SEQ ID NO: 430 (whose DNA sequence is represented by SEQ ID NO: 429). The gene and protein sequence combinations for the prepared respective vectors are shown in Table 6. A schematic diagram of the gene arrangement is illustrated in FIG. 43, and an example of the constructed vector map is illustrated in FIG. 44.

TABLE 6

| CAR name | DNA sequence combination | Protein sequence combination | SEQ ID NOs |
|---|---|---|---|
| CK1 CAR | Combination of SEQ ID NOs 409, 411, 421, 423, 425, 427, 429 | Combination of SEQ ID NOs 410, 412, 422, 424, 426, 428, 430 | 431 and 432 |
| CL6 CAR | Combination of SEQ ID NOs 409, 413, 421, 423, 425, 427, 429 | Combination of SEQ ID NOs 410, 414, 422, 424, 426, 428, 430 | 433 and 434 |
| CL7 CAR | Combination of SEQ ID NOs 409, 307, 421, 423, 425, 427, 429 | Combination of SEQ ID NOs 410, 416, 422, 424, 426, 428, 430 | 435 and 436 |
| CL10 CAR | Combination of SEQ ID NOs 409, 309, 421, 423, 425, 427, 429 | Combination of SEQ ID NOs 410, 418, 422, 424, 426, 428, 430 | 437 and 438 |

TABLE 6-continued

| CAR name | DNA sequence combination | Protein sequence combination | SEQ ID NOs |
|---|---|---|---|
| SL18 CAR | Combination of SEQ ID NOs 409, 311, 421, 423, 425, 427, 429 | Combination of SEQ ID NOs 410, 420, 422, 424, 426, 428, 430 | 439 and 440 |
| CD300c ECD CAR | Combination of SEQ ID NOs 409, 401, 421, 423, 425, 427, 429 | Combination of SEQ ID NOs 410, 402, 422, 424, 426, 428, 430 | 441 and 442 |

Example 3. Preparation of Recombinant Lentivirus for Expression of Chimeric Antigen Receptor that Specifically Binds to CD300c Antigen or Receptor Thereof HEK293T cell line (ATCC) required for preparation of a recombinant lentivirus for expression of the chimeric antigen receptor that specifically binds to a CD300c antigen or a receptor thereof was prepared as follows. A complete medium used for cell culture was prepared by adding heat-treated fetal bovine serum (FBS) to fresh DMEM (Gibco) to a concentration of 10%, adding 1× Penicillin-Streptomycin (Gibco) thereto, and performing uniform mixing by inverting the resultant up and down. The resulting complete medium was preheated to 37° C. and used. The HEK293T cell line was rapidly thawed for 2 to 3 minutes before use by quick transfer of its cryopreserved cell stock to a constant-temperature water bath at 37° C., inoculated into 30 mL of the complete medium, and cultured in a 5% $CO_2$ incubator at 37° C. When the cell confluency reached 80% or higher, the HEK293T cell line was maintained by subculture. For lentiviral transfection, the HEK293T cell line was inoculated into 10 mL of the complete medium at a concentration of 1 to $2 \times 10^6$ cells, cultured for 16 hours, and then subjected to lentiviral transfection.

LENTI-X™ Expression System (Takara) kit was used for lentiviral transfection for expression of the chimeric antigen receptor that specifically binds to a CD300c antigen or a receptor thereof. To 7 μg of the expression vector pLVX-Puro/αCD300C scFv or pLVX-Puro/CD300c ECD-CAR constructed in the same manner as in Example 2 was added sterile water (Invitrogen) to make 600 μL. Then, the resultant was placed in a tube of Lenti-X Packaging Single Shots in LENTI-X™ Expression System and mixing was performed to prepare a nanoparticle complex solution. The nanoparticle complex solution was allowed to react at room temperature for 10 minutes, added dropwise to the previously prepared HEK293T cells, and then mixing was performed by shaking the resultant left and right. Culture was performed for 4 hours in an incubator, 6 mL of the fresh complete medium was further added, and cultured for 48 hours. After the culture, the supernatant was collected, centrifuged to remove cell debris, filtered through a 0.45 μm filter, and stored at −80° C. until use.

20 μL of the obtained lentivirus supernatant was added to the sample well(S) of the GoStix cassette in LENTI-X™ Expression System, 3 drops of Chase solution were added to the sample well, and then reaction was allowed to occur at room temperature for 10 minutes. Subsequently, it was identified by presence or absence of a band whether a recombinant lentivirus at an effective dose of $5 \times 10^5$ IFU/mL or higher was obtained.

As a result, it was identified that a recombinant lentivirus expressing the chimeric antigen receptor that specifically binds to a CD300c antigen or a receptor thereof was prepared. It was found that the prepared lentiviruses expressed chimeric antigen receptors, each of which comprises the amino acid sequence of each of the single chain variable fragments CK1, CL6, CL7, CL10, and SL18.

Example 4. Production of Jurkat Cells Expressing Chimeric Antigen Receptor that Specifically Binds to CD300c Antigen or Receptor Thereof To produce Jurkat cells expressing the chimeric antigen receptor that specifically binds to a CD300c antigen or a receptor thereof, the recombinant lentivirus prepared in the same manner as in Example 2 was transfected into a Jurkat cell line. More specifically, the recombinant lentivirus at 0.1 to 10 MOI was inoculated in the complete medium supplemented with polybrene (Merk) of 8 μg/mL, and uniform mixing was performed by inverting the resultant up and down. 1 mL of the mixture was respectively added to the Jurkat cell line prepared in a 6-well plate, centrifuged at 1,800 rpm for 45 to 90 minutes, and cultured at a 5% $CO_2$ incubator at 37° C. for 24 hours. 24 hours later, subculture was performed at a concentration of $5 \times 10^5$ cells/mL.

To check whether the chimeric antigen receptor that specifically binds to a CD300c antigen or a receptor thereof is normally expressed in the transfected Jurkat cell line, total proteins of the cultured Jurkat cells were obtained using PRO-PREP® protein extraction solution (iNtRON). Concentrations of the obtained proteins were measured using a microBCA® protein assay kit (Thermo Fisher Scientific), and then Western blotting was performed using an equal amount of proteins. More specifically, the equal amount of proteins was subjected to electrophoresis by SDS-PAGE (Invitrogen), and the electrophoresed proteins were transferred to a nitrocellulose membrane (Invitrogen). The protein-bound nitrocellulose membrane was blocked using a 5% skim milk (BD) solution to block non-specific antibody reactions. An anti-CD3 antibody and an anti-GAPDH antibody (Cell Signaling Technologies, USA) as primary antibodies were respectively diluted to a concentration of 1:1,000 using 5% skim milk, and used to treat the nitrocellulose membrane. Reaction was allowed to occur, and then unbound antibodies were removed. A horseradish peroxidase (HRP)-conjugated secondary antibody (Cell Signaling Technologies) as a secondary antibody was diluted to a concentration of 1:2,000 and used to treat the nitrocellulose membrane. Then, treatment with ECL solution (Thermo Fisher Scientific) was performed to induce color development, and then the protein amount was quantified using an IBRIGHT™ 1500 luminescent image analyzer (Invitrogen). The results obtained by performing Western blotting are illustrated in FIG. 45.

As illustrated in FIG. 45, it was possible to identify the CD3ζ intracellular domain, to which the anti-CD3 antibody was bound. From these results, it was identified that a Jurkat cell line expressing the chimeric antigen receptor that specifically binds a CD300c antigen or a receptor thereof was produced.

Additionally, an expression level of the chimeric antigen receptor that specifically binds to a CD300c antigen or a receptor thereof was checked using a flow cytometer (FACS). More specifically, the Jurkat cell line was treated with a PE-fusion anti-IgG antibody (Jackson ImmunoResearch) and incubated at 4° C. for 30 minutes to allow reaction to occur. Then, identification was performed using a flow cytometer.

As a result of flow cytometry, it was identified that a Jurkat cell line expressing the chimeric antigen receptor that specifically binds a CD300c antigen or a receptor thereof was produced.

Experimental Example 4. Anticancer Effects of Jurkat Cells Expressing Chimeric Antigen Receptor that Specifically Binds to CD300c Antigen or Receptor Thereof To identify anticancer effects of Jurkat cells expressing the chimeric antigen receptor that specifically binds to a CD300c antigen or a receptor thereof, their cancer cell killing effects were checked using A549 cell line. More specifically, the A549 cell line was inoculated into a 96-well plate at a concentration of $1\times10^5$ cells/mL. Then, the Jurkat cells expressing the chimeric antigen receptor that specifically binds to a CD300c antigen or a receptor thereof, as produced in the same manner as in Example 4, were applied to the cancer cells to a concentration of 20:1 and co-culture was performed. Jurkat cells receiving no lentivirus transfection were used as a control. After co-culture for 24 hours, the co-cultured Jurkat cell line was removed from each well, and reaction was allowed to proceed for 1 hour using CCK-8 (DOJINDO™). Then, the absorbance was measured at $OD_{450\ nm}$ to identify the degree of cancer cell death. The results are illustrated in FIG. 46.

As illustrated in FIG. 46, it was identified that the Jurkat cell line expressing the chimeric antigen receptor that specifically binds to a CD300c antigen or a receptor thereof exhibited anticancer effects against the A549 cell line, and these anticancer effects were higher than those of the Jurkat cell line receiving no lentivirus transfection.

From these results, it was found that use of the immune cell line expressing the chimeric antigen receptor that specifically binds to a CD300c antigen or a receptor thereof results in increased cancer therapeutic effects so that cancer can be effectively treated. In addition, it was found that the immune cell line specifically responds only to cancer cells expressing the CD300c antigen on the surface, and thus is able to exhibit maximized therapeutic effects with decreased adverse effects.

IV. Anticancer Effect of Anti-CD300c Monoclonal Antibody

Experimental Example 5. Identification of Anticancer Effect Caused by Administration of Anti-CD300c Monoclonal Antibody

Experimental Example 5.1. Identification of T Cell Activation Effect

To identify whether the anti-CD300c monoclonal antibody produced in Example 1 can exhibit an anticancer effect by activating T cells, the production level of interleukin-2 (IL-2) was identified in a case where human T cells are subjected to treatment with the anti-CD300c monoclonal antibody. IL-2 is an immune factor that helps growth, proliferation, and differentiation of T cells. Increased production level of IL-2 means activation of T cells due to an increase in stimulation that induces increased differentiation, proliferation, and growth of T cells. Specifically, each of the anti-CD3 monoclonal antibody and the anti-CD28 monoclonal antibody was added to a 96-well plate at a concentration of 2 μg/well and fixed for 24 hours. Then, co-treatment with $1\times10^5$ cells/well of Jurkat T cells (human T lymphocyte cell line) and 10 μg/well of the anti-CD300c monoclonal antibody were performed. Subsequently, the production level of IL-2 was measured using an ELISA kit (IL-2 QUANTIKINE™ kit, R&D Systems), and then compared with the control group that had not been treated with the anti-CD300c monoclonal antibody. The results are illustrated in FIG. 8.

As illustrated in FIG. 8, it was identified that the production level of IL-2 increased in a case where Jurkat T cells activated by treatment with the anti-CD3 monoclonal antibody and the anti-CD28 monoclonal antibody were treated with the anti-CD300c monoclonal antibody. From these results, it was found that the anti-CD300c monoclonal antibody was able to activate T cells, indicating that the anti-CD300c monoclonal antibody is able to induce anticancer immune action to inhibit growth of cancer tissue.

Experimental Example 5.2. Identification of Promotion of Differentiation into M1 Macrophages (I): Measurement of Production Level of Differentiation Marker (TNF-α)

In order to identify that the anti-CD300c monoclonal antibody selected in Example 1 is able to promote differentiation of monocytes into M1 macrophages, THP-1 (human monocyte cell line) at $1.5\times10^4$ cells/well was dispensed onto a 96-well plate, and treatment with 10 μg/mL of the anti-CD300c monoclonal antibody and/or 100 ng/mL of LPS was performed. Reaction was allowed to proceed for 48 hours, and then the production level of tumor necrosis factor-α (TNF-α), which is a differentiation marker of M1 macrophages, was measured using an ELISA kit (Human TNF-α QUANTIKINE™ kit, R&D Systems). The results are illustrated in FIGS. 9 and 10.

As illustrated in FIG. 9, it was identified that the anti-CD300c monoclonal antibodies, CL4, CL7, CL10, and SL18, exhibited an increase in production level of TNF-α which is about 2 or more times higher than the control group (Con) treated with LPS alone.

In addition, as illustrated in FIG. 10, it was identified that all the experimental groups treated with the anti-CD300c monoclonal antibody alone without LPS treatment exhibited an increase in production level of TNF-α as compared with the control group (Con) treated with LPS alone.

Experimental Example 5.3. Identification of Increased Capacity for Causing Differentiation into M1 Macrophages Depending on Concentrations of Anti-CD300c Monoclonal Antibody In order to identify that induction of differentiation into M1 macrophages by the anti-CD300c monoclonal antibody increases with concentrations of the anti-CD300c monoclonal antibody, the production level of TNF-α was identified in the same manner as in Experimental Example 5.2. Treatment with the anti-CD300c monoclonal antibody was performed at concentrations of 10, 1, and 0.1 μg/mL. The results are illustrated in FIG. 11.

As illustrated in FIG. 11, it was identified that the production level of TNF-α increased as the treatment concentration of the anti-CD300c monoclonal antibody (CL7, CL10, or SL18) increased.

In order to identify results with further divided concentrations, treatment with the anti-CD300c monoclonal antibody CL7 was performed at concentrations of 10, 5, 2.5, 1.25, 0.625, 0.313, 0.157, and 0.079 µg/mL, and the production level of TNF-α was identified. The results are illustrated in FIG. 12.

As illustrated in FIG. 12, it was identified that the production level of TNF-α increased in a concentration-dependent manner with respect to the anti-CD300c monoclonal antibody.

Experimental Example 5.4. Identification of Promotion of Differentiation into M1 Macrophages (II): Observation of Cell Shape In order to identify, through cell shape, differentiation pattern into M1 macrophages in a case where monocytes are treated with the anti-CD300c monoclonal antibody, THP-1 was treated with 10 µg/mL of the anti-CD300c monoclonal antibody, cultured for 48 hours, and then the shape of the cells was observed under a microscope. The results are illustrated in FIG. 13.

As illustrated in FIG. 13, it was identified that for the experimental group (CL7) treated with the anti-CD300c monoclonal antibody, the shape of THP-1 cells was changed from suspension cells to circular adherent cells that are in the form of M1 macrophages. From these results, it was identified that differentiation of monocytes into M1 macrophages was promoted by treatment with the anti-CD300c monoclonal antibody.

Experimental Example 5.5. Reidentification of Promotion of Differentiation into M1 Macrophages In order to identify again whether the anti-CD300c monoclonal antibody CL7 promotes differentiation of human monocytes into M1 macrophages, the secretion levels of TNF-α, interleukin-1β (IL-1β), and interleukin-8 (IL-8) were measured using an ELISA kit. More specifically, THP-1 at $1.5 \times 10^4$ cells/well was dispensed onto a 96-well plate, and treatment with 10 µg/mL of the anti-CD300c monoclonal antibody was performed. Reaction was allowed to proceed for 48 hours, and then the production levels of TNF-α, IL-1β, and IL-8, which are markers for differentiation into M1 macrophages, were measured using an ELISA kit (Human TNF-α QUANTIKINE™ kit, R&D Systems). The results are illustrated in FIG. 14.

As illustrated in FIG. 14, it was identified that all three types of markers for differentiation into M1 macrophages increased in the experimental group (CL7) treated with the anti-CD300c monoclonal antibody, as compared with the control group (Con) not treated with the anti-CD300c monoclonal antibody.

Experimental Example 5.6. Identification of Capacity for Causing Redifferentiation of M2 Macrophages into M1 Macrophages In order to identify that the anti-CD300c monoclonal antibody is able to redifferentiate M2 macrophages into M1 macrophages, THP-1 at $1.5 \times 10^4$ cells/well was dispensed onto a 96-well plate, and pre-treated for 6 hours by treatment with 320 nM of PMA. Then, treatment with 20 ng/ml of interleukin-4 (IL-4) and interleukin-13 (IL-13), and with 10 µg/mL of the anti-CD300c monoclonal antibody was performed, and reaction was allowed to proceed for 18 hours.

The production levels of TNF-α, IL-1β, and IL-8 were identified using an ELISA kit. The results are illustrated in FIGS. 21 to 23.

As illustrated in FIGS. 21 to 23, it was identified that among the experimental groups not pre-treated with PMA, the experimental group co-treated with IL-4 & IL-13 and the anti-CD300c monoclonal antibody exhibited increased production levels of TNF-α, IL-1β, and IL-8; and among the experimental groups pre-treated with PMA, the experimental group co-treated with IL-4 & IL-13 and the anti-CD300c monoclonal antibody similarly exhibited increased production levels of TNF-α, IL-1β, and IL-8. From these results, it was found that the anti-CD300c monoclonal antibody was able to effectively redifferentiate M2 macrophages into M1 macrophages.

Experimental Example 5.7. Identification of Capacity for Causing Differentiation and Redifferentiation into M1 Macrophages In order to identify the anti-CD300c monoclonal antibody's capacity for causing differentiation and redifferentiation into M1 macrophages, THP-1 at $1.5 \times 10^4$ cells/well was dispensed onto a 96-well plate, pre-treated with 10 µg/mL of the anti-CD300c monoclonal antibody for 48 hours, and treated with 100 ng/ml of PMA, 100 ng/mL of LPS, and 20 ng/ml of IL-4 and IL-13. Reaction was allowed to proceed for 24 hours. The production level of TNF-α was identified using an ELISA kit. The results are illustrated in FIG. 24.

As illustrated in FIG. 24, it was identified that all experimental groups pre-treated with the anti-CD300c monoclonal antibody exhibited a significant increase in production level of TNF-α, as compared with the M0 macrophage control group treated with PMA alone, the M1 macrophage control group treated with LPS alone, and the M2 macrophage control group treated with IL-4 and IL-13 alone. From these results, it was found that the anti-CD300c monoclonal antibody had excellent capacity to differentiate M0 macrophages into M1 macrophages, to differentiate THP-1 into M1 macrophages, and to redifferentiate M2 macrophages into M1 macrophages.

Experimental Example 6. Identification of Inter-Species Cross-Reactivity of Anti-CD300c Monoclonal Antibody by Observation of Anticancer Effect

Experimental Example 6.1. Identification of Human Cancer Cell Growth Inhibitory Effect In order to identify an effect of the CD300c-targeting monoclonal antibody on growth of cancer cells, cell proliferation assay was performed using A549 (human lung cancer cell line). More specifically, the cells were dispensed onto a 96-well plate at $2 \times 10^4$ cells under a condition of 0% fetal bovine serum (FBS), and at $6 \times 10^3$ cells under a condition of 0.1% fetal bovine serum. Then, treatment with 10 µg/mL of anti-CD300c monoclonal antibody was performed and incubation was performed for 5 days. Treatment with CCK-8 (DOJINDO™) was performed and the absorbance was measured at OD450 nm to identify a cancer cell growth inhibitory effect of the anti-CD300c monoclonal antibody. The results are illustrated in FIGS. 28 and 29.

As illustrated in FIG. 28, it was identified that all anti-CD300c monoclonal antibodies except for SK11 and SK17 had an effect of inhibiting proliferation of cancer cells at a 0% FBS condition.

As illustrated in FIG. 29, it was identified that all anti-CD300c monoclonal antibodies used in the experiment had an effect of inhibiting proliferation of cancer cells at a 0.1% FBS condition.

Experimental Example 6.2. Identification of Cancer Cell Growth Inhibitory Effects of Anti-CD300c Monoclonal Antibody Depending on its Concentrations In order to identify cancer cell growth inhibitory effects of the anti-CD300c monoclonal antibody depending on its concentrations, A549 cells were dispensed onto a 96-well plate at $2 \times 10^4$ cells at a 0% fetal bovine serum (FBS) condition. Treatment with 10 µg/mL of the anti-CD300c monoclonal antibody was performed and incubation was performed for 5 days. Subsequently, treatment with CCK-8 (DOJINDO™) was performed and reaction was allowed to proceed for 3 hours. Then, the absorbance was measured at OD450 nm to identify cancer cell growth inhibitory effects of the anti-CD300c monoclonal antibody. The results are illustrated in FIG. 32.

As illustrated in FIG. 32, it was identified that growth of cancer cells was inhibited as the concentration of the anti-CD300c monoclonal antibody increased.

Experimental Example 6.3. Identification of Increased Capacity for Causing Differentiation into M1 Macrophages in Mice In order to identify whether the anti-CD300c monoclonal antibody is able to promote differentiation from mouse macrophages to M1 macrophages, mouse macrophages (Raw264.7) were dispensed onto a 96-well plate at a concentration of $1 \times 10^4$ cells/well, treatment with 10 µg/mL of the anti-CD300c monoclonal antibody was performed, and incubation was performed. The production level of TNF-α was checked with an ELISA kit. The results are illustrated in FIG. 37!

As illustrated in FIG. 37, it was identified that the production level of TNF-α increased in the experimental groups treated with the anti-CD300c monoclonal antibody. From these results, it can be seen that the anti-CD300c monoclonal antibody acts equally in humans as well as mice, indicating the cross-reactivity of the anti-CD300c monoclonal antibody which promotes differentiation into M1 macrophages.

Experimental Example 6.4. Identification of Cancer Cell Growth Inhibitory Effects in Mice In order to identify whether the anti-CD300c monoclonal antibodies CL7, CL10, and SL18 exhibit anticancer effects, CT26 (mouse colorectal cancer cell line) was dispensed onto a 96-well plate at a concentration of $1 \times 10^4$ cells/well, treatment with 10 µg/mL of each monoclonal antibody was performed, and incubation was performed for 5 days. Then, cell proliferation assay was performed by detection of CCK-8.

As illustrated in FIG. 38, the anti-CD300c monoclonal antibodies exerted cancer cell proliferation inhibitory effects which were 66% (CL7), 15% (CL10), and 38% (SL18), respectively, higher than the control group. From these results, it was identified that the anti-CD300c monoclonal antibodies exhibited cancer therapeutic effects in mice. Thus, it can be seen that the anti-CD300c monoclonal antibody acts equally in humans as well as mice, indicating the cross-reactivity of the anti-CD300c monoclonal antibody which results in an anticancer effect.

Experimental Example 7. Comparison of Anticancer Effects In Vitro Between Anti-CD300c Monoclonal Antibody and Conventional Cancer Immunotherapy The manufacturers of the respective immunotherapies used in the experimental examples below are as follows: IMFINZI® (AstraZeneca) and KEYTRUDA® (Merck Sharp & Dohme).

Experimental Example 7.1. Comparison of Capacity for Causing Differentiation into M1 Macrophages Between Anti-CD300c Monoclonal Antibody and Conventional Cancer Immunotherapy: Measurement of Production Levels of Three Differentiation Markers (TNF-α, IL-1β, and IL-8)

In order to compare capacity for causing differentiation into M1 macrophages between the anti-CD300c monoclonal antibodies and a conventional cancer immunotherapy, the production level of TNF-α was identified using an ELISA kit in the same manner as in Experimental Example 5.2. As the conventional cancer therapy, IMFINZI® was used at a concentration of 10 µg/mL. The results are illustrated in FIG. 15.

As illustrated in FIG. 15, it was identified that the anti-CD300c monoclonal antibody resulted in a remarkably increased production level of TNF-α as compared with the control group treated with IMFINZI® (Imf), which is known as a cancer immunotherapy, alone. From these results, it was found that the anti-CD300c monoclonal antibody resulted in remarkably increased capacity for causing differentiation into M1 macrophages as compared with the conventionally known cancer immunotherapy.

For comparison with other cancer immunotherapies, each of IMFINZI® which is an anti-PD-L1 immunotherapy, KEYTRUDA®, which is an anti-PD-1 immunotherapy, and an isotype control (immunoglobulin G) antibody was used at a concentration of 10 µg/mL, and the production levels of TNF-α, IL-1β, and IL-8 were identified using an ELISA kit. The results are illustrated in FIGS. 16 to 18.

As illustrated in FIGS. 16 to 18, it was identified that the anti-CD300c monoclonal antibody resulted in remarkably increased production levels of TNF-α, IL-1β, and IL-8 as compared with IMFINZI®, KEYTRUDA®, and the IgG antibody. From these results, it was found that the anti-CD300c monoclonal antibody was able to result in remarkably increased promotion of differentiation into M1 macrophages as compared with the conventional cancer immunotherapies.

Experimental Example 7.2. Comparison of Capacity for Causing Differentiation from M0 Macrophages into M1 Macrophages Between Anti-CD300c Monoclonal Antibody and Conventional Cancer Immunotherapy In order to compare capacity for causing differentiation from M0 macrophages into M1 macrophages between the anti-CD300c monoclonal antibodies and a cancer immunotherapy, THP-1 at $1.5 \times 10^4$ cells/well was dispensed onto a 96-well plate, and treatment with 10 µg/mL of the anti-CD300c monoclonal antibody, 10 µg/mL of IMFINZI®, and/or 200 nM of phorbol-12-myristate-13-acetate (PMA) was performed. Reaction was allowed to proceed for 48 hours, and then the production levels of TNF-α were measured using an ELISA kit. The results are illustrated in FIG. 19.

As illustrated in FIG. 19, it was identified that TNF-α was not produced in the comparative group treated with IMFINZI®, which is a cancer immunotherapy, alone, and the production level of TNF-α increased in the experimental group treated with the anti-CD300c monoclonal antibody alone. In addition, it was identified that even in a case where THP-1 cells differentiated into M0 macrophages by treatment with PMA, the experimental group treated with the anti-CD300c monoclonal antibody exhibited a remarkably increased production level of TNF-α as compared with the experimental group treated with IMFINZI®. From these results, it was found that the anti-CD300c monoclonal antibody promoted differentiation from M0 macrophages into M1 macrophages as compared with a conventional cancer immunotherapy.

Experimental Example 7.3. Comparison of Capacity for Causing Differentiation into M1 Macrophages Between Anti-CD300c Monoclonal Antibody and Conventional Cancer Immunotherapy In order to compare capacity for causing differentiation into M1 macrophages between the anti-CD300c monoclonal antibodies and cancer immunotherapies, the production level of TNF-α was identified in the same manner as in Experimental Example 5.2. The results are illustrated in FIG. 20.

As illustrated in FIG. 20, it was identified that in a case where monocytes differentiated into M1 macrophages by treatment with LPS, the experimental group co-treated with IMFINZI® and LPS did not exhibit a significant difference in production level of TNF-α, and the experimental group co-treated with the anti-CD300c monoclonal antibody and LPS exhibited a significant increase in production level of TNF-α as compared with the experimental group treated with the anti-CD300c monoclonal antibody alone.

Experimental Example 7.4. Comparison of Cancer Cell Growth Inhibitory Effects Between Anti-CD300c Monoclonal Antibody and Conventional Cancer Immunotherapy In order to compare cancer cell growth inhibitory effects of the anti-CD300c monoclonal antibody and a cancer immunotherapy, cell growth inhibitory effects were identified using A549 (human lung cancer cell line) and MDA-MB-231 (human breast cancer cell line). More specifically, the respective cells were dispensed onto a 96-well plate at $2\times10^4$ cells under a condition of 0% fetal bovine serum (FBS), and at $6\times10^3$ cells under a condition of 0.1% fetal bovine serum. Subsequently, treatment with 10 μg/mL of the anti-CD300c monoclonal antibody was performed and incubation was performed for 5 days. Then, observation was made under an optical microscope. The results are illustrated in FIGS. 30 and 31.

As illustrated in FIG. 30, it was identified that the anti-CD300c monoclonal antibody more effectively inhibited proliferation of cancer cells than IMFINZI®, which is an immunotherapy, in the A549 cell line.

As illustrated in FIG. 31, it was identified that the anti-CD300c monoclonal antibody more effectively inhibited proliferation of cancer cells than IMFINZI®, which is an immunotherapy, in the MDA-MB-231 cell line.

V. Combination of Anti-CD300c Monoclonal Antibody and Immunotherapy

Example 5. Co-Administration of Anti-CD300c Monoclonal Antibody (CL7) and Immunotherapy The anti-CD300c monoclonal antibody (CL7) produced in Example 1 was used in combination with other immunotherapies, for example, the anti-PD-L1 antibodies IMFINZI® and OPDIVO®, and the anti-PD-1 antibody KEYTRUDA®, an anti-CD47 antibody (αCD47), and an anti-CTLA-4 antibody. Then, the results were obtained.

The manufacturers of the respective immunotherapies are as follows: IMFINZI® (AstraZeneca); OPDIVO® and the anti-CTLA-4 antibody (Bristol Myers Squibb Company); KEYTRUDA® (Merck Sharp & Dohme); and the anti-CD47 antibody (Abcam).

Experimental Example 8. Identification of (Synergistically) Increased Macrophage Activity Caused by Combination

Experimental Example 8.1. Identification of Increased Capacity for Causing Differentiation into M1 Macrophages In order to identify whether differentiation of monocytes into M1 macrophages increases in a case where the monocytes are co-treated with the anti-CD300c monoclonal antibody CL7 and an immunotherapy such as an anti-PD-1 antibody, an anti-PD-L1 antibody, an anti-CTLA-4 antibody, and an anti-CD47 antibody, signal transduction of mitogen-activated protein kinase (MAPK), IκB, and NF-kB, which are representative signals of M1 macrophage differentiation, was checked. Specifically, THP-1 was dispensed onto a 6-well plate at $8.8\times10^5$ cells/well, and treated with 10 μg/mL of the anti-CD300c monoclonal antibody, 10 μg/mL of IMFINZI®, and/or 10 μg/mL of KEYTRUDA®. For a control group, treatment with the same amount of phosphate buffer solution (PBS) was performed. Incubation was performed for 48 hours. Then, Western blotting was conducted to identify phosphorylated SAPK/JNK, phosphorylated ERK, phosphorylated p38 for MAPK signal, phosphorylated NF-kB for NF-kB signal, and phosphorylated IkB for IkB signal. The results are illustrated in FIGS. 25 to 27.

FIGS. 25, 26, and 27 illustrate the results obtained by identifying signal transduction of MAPK, NF-Kb, and IkB, respectively. It was identified that the levels of phosphorylated MAPK, IkB, and NF-kB increased in a case where THP-1 was co-treated with the anti-CD300c monoclonal antibody and an immunotherapy such as an anti-PD-1 antibody, an anti-PD-L1 antibody, an anti-CTLA-4 antibody, and an anti-CD47 antibody as compared with a case where THP-1 was treated with the anti-CD300c monoclonal antibody alone. From these results, it was identified that cell signaling representing differentiation into M1 macrophages increased in a case where THP-1 was co-treated with the anti-CD300c monoclonal antibody and an immunotherapy such as an anti-PD-1 antibody, an anti-PD-L1 antibody, an anti-CTLA-4 antibody, and an anti-CD47 antibody as compared with a case where THP-1 was treated with the anti-CD300c monoclonal antibody alone.

Experimental Example 9. Identification of (Synergistically) Increased Cancer Cell Growth Inhibitory Effects Caused by Combination (In Vitro)

Experimental Example 9.1. Identification of Apoptosis Signals

It was identified whether apoptosis signals increase in a case where co-treatment with the anti-CD300c monoclonal antibody CL7 and an immunotherapy such as an anti-PD-1 antibody, an anti-PD-L1 antibody, an anti-CTLA-4 antibody, and an anti-CD47 antibody is performed. Specifically, A549 was dispensed onto a 6-well plate at $8 \times 10^5$ cells/well, and treated with 10 μg/mL of the anti-CD300c monoclonal antibody, and 10 μg/mL of IMFINZI®, KEYTRUDA®, OPDIVO®, and an anti-CD47 antibody alone or in combination. Incubation was performed for 48 hours, and then Western blotting was conducted to identify apoptosis signals or cell cycle signals. Cleaved caspase-9, caspase-3, caspase-2, and caspase-8 were identified as markers for the apoptosis signals, and cyclin D1, CDK2, p27kip1, CDK6, cyclin D3, P21 Waf1, Cip1, and the like were identified as markers for the cell cycle signals.

As illustrated in FIG. 33, the apoptosis signals increased in a case where co-treatment with the anti-CD300c monoclonal antibody and IMFINZI® that is an anti-PD-1 antibody was performed as compared with a case where treatment with the anti-CD300c monoclonal antibody alone was performed; and the levels of cleaved-caspase9 and p21 increased and the level of cyclin D1 decreased in a case where co-treatment with the anti-CD300c monoclonal antibody and an immunotherapy such as anti-PD-1 antibody, anti-PD-L1 antibody, anti-CTLA-4 antibody, and anti-CD47 antibody was performed. From these results, it was identified that apoptosis of cancer cells was better induced in a case where co-treatment with the anti-CD300c monoclonal antibody and an immunotherapy such as anti-PD-1 antibody, anti-PD-L1 antibody, anti-CTLA-4 antibody, and anti-CD47 antibody was performed than a case where treatment with the anti-CD300c monoclonal antibody alone was performed.

Experimental Example 9.2. Identification of Growth Inhibitory Effects on Cancer Cell Lines In order to identify cancer cell growth inhibitory effects caused by co-administration of the anti-CD300c monoclonal antibody CL7 and an immunotherapy, comparison of cancer cell growth inhibitory effects was performed using A549 (human lung cancer cell line) and MDA-MB-231 (human breast cancer cell line). Specifically, the cells were dispensed onto a 96-well plate at $2 \times 10^4$ cells (A549) or $3 \times 10^4$ cells (MDA-MB-231) under a condition of 0% fetal bovine serum (FBS), and at $6 \times 10^3$ cells (A549) or $1 \times 10^4$ cells (MDA-MB-231) under a condition of 0.1% fetal bovine serum. Subsequently, the cells were treated with the anti-CD300c monoclonal antibody and IMFINZI® at 10 μg/mL alone or in combination, and incubation was performed for 5 days. For a control group, treatment with the same amount of phosphate buffer solution (PBS) was performed. Then, treatment with CCK-8 (DOJINDO™) was performed, and the absorbance was measured at OD 450 nm. The results are illustrated in FIGS. 34 (A549) and 35 (MDA-MB-231).

As illustrated in FIG. 34, it was identified for the A549 cell line that under a condition of 0% FBS, as compared with the control, a 17% higher cell growth inhibitory effect was observed in a case where treatment with the anti-CD300c monoclonal antibody alone was performed, and a 34% higher cell growth inhibitory effect was observed in a case where co-treatment with the anti-CD300c monoclonal antibody and IMFINZI® was performed.

As illustrated in FIG. 35, it was identified for the MDA-MB-231 cell line that under a condition of 0% FBS, as compared with the control, a 19% higher cell growth inhibitory effect was observed in a case where treatment with the anti-CD300c monoclonal antibody alone was performed; a 45% higher cell growth inhibitory effect was observed in a case where co-treatment with the anti-CD300c monoclonal antibody and the anti-CD47 antibody was performed; and a 51% higher cell growth inhibitory effect was observed in a case where co-treatment with the anti-CD300c monoclonal antibody, the anti-CD47 antibody, and IMFINZI® was performed. Under a condition of 0.1% FBS, as compared with the control, a 19% higher cell growth inhibitory effect was observed in a case where treatment with the anti-CD300c monoclonal antibody alone was performed; a 22% higher cell growth inhibitory effect was observed in a case where co-treatment with the anti-CD300c monoclonal antibody and the anti-CD47 antibody was performed; and a 32% higher cell growth inhibitory effect was observed in a case where co-treatment with the anti-CD300c monoclonal antibody, the anti-CD47 antibody, and IMFINZI® was performed.

From these results, it was identified that growth of the cancer cells was further inhibited in a case where co-treatment with the anti-CD300c monoclonal antibody and an immunotherapy such as anti-PD-1 antibody, anti-PD-L1 antibody, anti-CTLA-4 antibody, and anti-CD47 antibody was performed as compared with a case where treatment with the anti-CD300c monoclonal antibody alone was performed.

Experimental Example 10. Identification of (Synergistically) Increased Anticancer Effects In Vivo Caused by Combination

Experimental Example 10.1. Identification of Cancer Growth Inhibitory Effects In Vivo In order to identify anticancer effects in vivo of the anti-CD300c monoclonal antibody CL7, a colorectal cancer cell line (CT26) at $2 \times 10^5$ cells was transplanted by subcutaneous injection into 8-week-old BALB/c mice to prepare a syngeneic mouse tumor model. Breeding and experiments for animals were all conducted in a SPF facility. On day 12 (D12) after transplantation of the colon cancer cell line, the mice with tumor size of 50 to 100 mm³ were administered with the anti-CD300c monoclonal antibody and an anti-PD-1 antibody purchased from BioXcell alone or in combination, and administered with an equal amount of phosphate buffered saline (PBS) as a control group. A schematic experimental method is illustrated in FIG. 39. Specifically, the mice were intraperitoneally injected with the respective antibodies (CL7: 10 mg/kg; and anti-PD-1 antibody: 10 mg/kg) alone or in combination, twice a week for two weeks (a total of 4 times on D12, D15, D19, and D22). The tumor volume was measured for 25 days. The results are illustrated in FIG. 40.

As can be seen from FIG. 40, it was identified that although cancer growth was inhibited relative to the control group even in the experimental group administered with the anti-CD300c monoclonal antibody alone, cancer growth was more effectively inhibited in a case where co-treatment with the anti-CD300c monoclonal antibody and an immunotherapy such as an anti-PD-1 antibody was performed than a case where treatment with the anti-CD300c monoclonal antibody alone was performed.

Experimental Example 10.2. Identification of Effect of Increasing M1 Macrophages In Vivo In order to identify whether the anti-CD300c monoclonal antibody increases M1 macrophages in cancer tissue of a mouse model, on day 25 of the experiment performed in the same manner as in Experimental Example 10.1, the mice were euthanized, injected intravascularly with 1% paraform-aldehyde (PFA), and then perfusion was performed to obtain cancer tissue. The obtained cancer tissue was fixed using 1% PFA, and sequentially dehydrated using 10%, 20%, and 30% sucrose solution. The dehydrated cancer tissue was frozen in OCT compound (optimal cutting temperature compound), and then the cancer tissue was sectioned to a thickness of 50 μm using a cryotome. The tissue was incubated for 1 hour at 37° C. in a mixed solution of collagenase D (20 mg/ml) and DNase I (2 mg/ml). Then, the resultant was filtered through a 70 μm cell strainer, subjected to lysis of red blood cells, and then filtered again through a nylon mesh to make them single cells. To suppress non-specific reactions in the single cell suspension, reaction with a CD16/32 antibody (Invitrogen) was allowed to proceed for 1 hour, and cell viability was checked. The resultant was stained with antibodies to the M1 macrophage marker iNOS and the M2 macrophage marker CD206, and checked by FACS.

As a result, as illustrated in FIG. 42, it was identified that as compared with the control group, M1 macrophages partially increased in the experimental group treated with the anti-PD-1 antibody, and M1 macrophages remarkably increased and M2 macrophages were hardly observed in the experimental group treated with the anti-CD300c monoclonal antibody. In addition, it was identified that M1 macrophages further increased in the experimental group co-administered with the anti-CD300c monoclonal antibody and the anti-PD-1 antibody. From these results, it was identified that differentiation into M1 macrophages could be effectively promoted in a case where co-treatment with the anti-CD300c monoclonal antibody and an immunotherapy, such as an anti-PD-1 antibody, an anti-PD-L1 antibody, an anti-CTLA-4 antibody, or an anti-CD47 antibody, was performed, than a case where treatment with the anti-CD300c monoclonal antibody alone was performed.

Experimental Example 10.3. Identification of Effect of Promoting CD8+ T Cell Immunity In Vivo In order to identify whether the anti-CD300c monoclonal antibody CL7 promotes CD8+ T cell immunity in a mouse tumor model, on day 25 of the experiment performed in the same manner as in Experimental Example 10.1, the mice were euthanized, injected intravascularly with 1% paraform-aldehyde (PFA), and then perfusion was performed to obtain cancer tissue. The obtained cancer tissue was fixed using 1% PFA, and sequentially dehydrated using 10%, 20%, and 30% sucrose solution. The dehydrated cancer tissue was frozen in OCT compound (optimal cutting temperature compound), and then the cancer tissue was sectioned to a thickness of 50 μm using a cryotome. Then, staining was performed on CD8+ and iNOS.

As illustrated in FIG. 41, it was identified that as compared with the control group, CD8+ T cells partially increased in the experimental group treated with the anti-PD-1 antibody, and CD8+ T cells remarkably increased in the experimental group treated with the anti-CD300c monoclonal antibody. In addition, it was identified that as compared with the group administered with the anti-PD-1 antibody alone, CD8+ T cells further increased in the experimental group co-administered with the anti-CD300c monoclonal antibody and the anti-PD-1 antibody. From these results, it was found that the anti-CD300c monoclonal antibody more effectively increased the number of CD8+ T cells in a case of being used in combination with a conventional cancer immunotherapy.

Through the above results, it was identified that the anti-CD300c monoclonal antibody of the present disclosure was able to bind with high specificity to the CD300c antigen and exhibited inter-species cross-reactivity such as for mice, indicating that it can be applied to various subjects. In addition, it was identified both in vitro and in vivo that the anti-CD300c monoclonal antibody was able to act as a cancer immunotherapy by activating T cells and promoting differentiation into M1 macrophages, thereby effectively inhibiting proliferation, metastasis, and the like of cancer cells, and it was identified that the anti-CD300c monoclonal antibody had a further increased therapeutic effect through co-administration with a conventional immunotherapy. Accordingly, it was found that the anti-CD300c monoclonal antibody could be effectively used for anticancer immuno-therapy against various cancers expressing the CD300c antigen.

The description of the present disclosure as described above is provided for illustration, and those of ordinary skill in the art to which the present disclosure pertains will be able to understand that the embodiments disclosed herein can be easily modified into other specific forms without changing the technical spirit or essential features of the present disclosure. Therefore, it should be understood that the embodiments as described above are illustrative and not restrictive in all respects.

The invention claimed is:

1. A chimeric antigen receptor comprising a binding domain specifically binding to a CD300c antigen or a receptor thereof,
  wherein the binding domain comprises:
  a heavy chain variable region comprising CDR1 to CDR3 comprising amino acid sequences represented by of Formulas (1) to (3), respectively, and
  a light chain variable region comprising CDR1 to CDR3 comprising amino acid sequences represented by Formulas (4) to (6), respectively:

(1)
                                        (SEQ ID NO: 443)
FTFSX1YX2MX3WVR, wherein X1=R, S, or D
X2=A, G, or H
X3=T, H, or S (2)
                                        (SEQ ID NO: 444)
X1X2SX3X4GGX5TYYAX6, wherein X1=S, A, or T
X2=M or I
X3=G or S
X4=T or S
X5=T, S, or Y
X6=D or E (3)
                                        (SEQ ID NO: 445)
YCAX1X2X3X4X5X6X7X8X9X10X11W, wherein X1=R, V, or S
X2=G or S
X3=A, G, S, Y, or I
X4=Y, A, Q, G, or R
X5=G or L X6=F, R, I, M, or P
X7=D, G, F, or L
X8=H, F, D, or V
X9=F, I, Y or not present
X10=D or not present
X11=Y or not present (4)

(SEQ ID NO: 446)
CX1X2X3X4X5X6X7X8X9X10X11X12X13W, wherein

X1=R, S, or T
X2=A, G, or R
X3=S or N
X4=Q, S, or N
X5=S, I, or G
X6=I, N, or G
X7=G, I, T, or S
X8=N, G, R, A, or K
X9=Y, S, R, or G
X10=N or not present
X11=Y or not present
X12=L or V
X13=N, Y, H, or Q (5)

(SEQ ID NO: 447)
X1X2X3X4X5X6X7GX8X9, wherein

X1=D, E, S, or R
X2=A, D, K, or N
X3=S or N
X4=N, K, or Q
X5=L or R
X6=E or P
X7=T or S
X8=I or V
X9=P or R; and (6)

(SEQ ID NO: 448)
YCX1X2X3X4X5X6X7X8X9X10X11F, wherein

X1=Q, S, or A
X2=Q, S, or A
X3=S, Y, or W
X4=S, T, D, or A
X5=A, S, D, or G
X6=I, S, N, or T
X7=P, S, L, N, or K
X8=Y, T, S, N, or G
X9=V, G, L or not present
X10=P or not present
X11=T, I, or V.

2. The chimeric antigen receptor of claim 1, further comprising a transmembrane domain and an intracellular signaling domain.

3. The chimeric antigen receptor of claim 1, wherein the binding domain comprises:

(i) a heavy chain variable region, comprising:

CDR1 comprising an amino acid sequence selected from the group consisting of SEQ ID NO: 7, SEQ ID NO: 19, SEQ ID NO: 31, SEQ ID NO: 43, SEQ ID NO: 55, SEQ ID NO: 67, SEQ ID NO: 79, SEQ ID NO: 91, SEQ ID NO: 103, SEQ ID NO: 115, SEQ ID NO: 127, SEQ ID NO: 139, SEQ ID NO: 151, SEQ ID NO: 163, SEQ ID NO: 175, SEQ ID NO: 187, SEQ ID NO: 199, SEQ ID NO: 211, SEQ ID NO: 223, SEQ ID NO: 235, SEQ ID NO: 247, SEQ ID NO: 259, SEQ ID NO: 271, SEQ ID NO: 283, and SEQ ID NO: 295;

CDR2 comprising an amino acid sequence selected from the group consisting of SEQ ID NO: 8, SEQ ID NO: 20, SEQ ID NO: 32, SEQ ID NO: 44, SEQ ID NO: 56, SEQ ID NO: 68, SEQ ID NO: 80, SEQ ID NO: 92, SEQ ID NO: 104, SEQ ID NO: 116, SEQ ID NO: 128, SEQ ID NO: 140, SEQ ID NO: 152, SEQ ID NO: 164, SEQ ID NO: 176, SEQ ID NO: 188, SEQ ID NO: 200, SEQ ID NO: 212, SEQ ID NO: 224, SEQ ID NO: 236, SEQ ID NO: 248, SEQ ID NO: 260, SEQ ID NO: 272, SEQ ID NO: 284, and SEQ ID NO: 296; and CDR3 comprising an amino acid sequence selected from the group consisting of SEQ ID NO: 9, SEQ ID NO: 21, SEQ ID NO: 33, SEQ ID NO: 45, SEQ ID NO: 57, SEQ ID NO: 69, SEQ ID NO: 81, SEQ ID NO: 93, SEQ ID NO: 105, SEQ ID NO: 117, SEQ ID NO: 129, SEQ ID NO: 141, SEQ ID NO: 153, SEQ ID NO: 165, SEQ ID NO: 177, SEQ ID NO: 189, SEQ ID NO: 201, SEQ ID NO: 213, SEQ ID NO: 225, SEQ ID NO: 237, SEQ ID NO: 249, SEQ ID NO: 261, SEQ ID NO: 273, SEQ ID NO: 285, and SEQ ID NO: 297; and (ii) a light chain variable region, comprising:

CDR1 comprising an amino acid sequence selected from the group consisting of SEQ ID NO: 10, SEQ ID NO: 22, SEQ ID NO: 34, SEQ ID NO: 46, SEQ ID NO: 58, SEQ ID NO: 70, SEQ ID NO: 82, SEQ ID NO: 94, SEQ ID NO: 106, SEQ ID NO: 118, SEQ ID NO: 130, SEQ ID NO: 142, SEQ ID NO: 154, SEQ ID NO: 166, SEQ ID NO: 178, SEQ ID NO: 190, SEQ ID NO: 202, SEQ ID NO: 214, SEQ ID NO: 226, SEQ ID NO: 238, SEQ ID NO: 250, SEQ ID NO: 262, SEQ ID NO: 274, SEQ ID NO: 286, and SEQ ID NO: 298;

CDR2 comprising an amino acid sequence selected from the group consisting of SEQ ID NO: 11, SEQ ID NO: 23, SEQ ID NO: 35, SEQ ID NO: 47, SEQ ID NO: 59, SEQ ID NO: 71, SEQ ID NO: 83, SEQ ID NO: 95, SEQ ID NO: 107, SEQ ID NO: 119, SEQ ID NO: 131, SEQ ID NO: 143, SEQ ID NO: 155, SEQ ID NO: 167, SEQ ID NO: 179, SEQ ID NO: 191, SEQ ID NO: 203, SEQ ID NO: 215, SEQ ID NO: 227, SEQ ID NO: 239, SEQ ID NO: 251, SEQ ID NO: 263, SEQ ID NO: 275, SEQ ID NO: 287, and SEQ ID NO: 299; and CDR3 comprising an amino acid sequence selected from the group consisting of SEQ ID NO: 12, SEQ ID NO: 24, SEQ ID NO: 36, SEQ ID NO: 48, SEQ ID NO: 60, SEQ ID NO: 72, SEQ ID NO: 84, SEQ ID NO: 96, SEQ ID NO: 108, SEQ ID NO: 120, SEQ ID NO: 132, SEQ ID NO: 144, SEQ ID NO: 156, SEQ ID NO: 168, SEQ ID NO: 180, SEQ ID NO: 192, SEQ ID NO: 204, SEQ ID NO: 216, SEQ ID NO: 228, SEQ ID NO: 240, SEQ ID NO: 252, SEQ ID NO: 264, SEQ ID NO: 276, SEQ ID NO: 288, and SEQ ID NO: 300, or wherein the binding domain comprises the amino acid sequence represented by SEQ ID NO: 402.

4. The chimeric antigen receptor of claim 3, wherein (i) the heavy chain variable region comprises:

CDR1 comprising or consisting of the amino acid sequence of SEQ ID NO: 7, SEQ ID NO: 67, SEQ ID NO: 79, SEQ ID NO: 115, or SEQ ID NO: 211;

CDR2 comprising or consisting of the amino acid sequence of SEQ ID NO: 8, SEQ ID NO: 68, SEQ ID NO: 80, SEQ ID NO: 116, or SEQ ID NO: 212; and CDR3 comprising or consisting of the amino acid sequence of SEQ ID NO: 9, SEQ ID NO: 69, SEQ ID NO: 81, SEQ ID NO: 117, or SEQ ID NO: 213, and (ii) the light chain variable region comprises:

CDR1 comprising or consisting of the amino acid sequence of SEQ ID NO: 10, SEQ ID NO: 70, SEQ ID NO: 82, SEQ ID NO: 118, or SEQ ID NO: 214;

CDR2 comprising or consisting of the amino acid sequence of SEQ ID NO: 11, SEQ ID NO: 71, SEQ ID NO: 83, SEQ ID NO: 119, or SEQ ID NO: 215; and CDR3 comprising or consisting of the amino acid sequence of SEQ ID NO: 12, SEQ ID NO: 72, SEQ ID NO: 84, SEQ ID NO: 120, or SEQ ID NO: ID NO: 216.

5. The chimeric antigen receptor of claim 1, further comprising a signal peptide, a GS linker, a transmembrane domain, and an intracytoplasmic domain.

6. The chimeric antigen receptor of claim 5, wherein the signal peptide comprises a CD8a signal peptide.

7. The chimeric antigen receptor of claim 5, wherein the transmembrane domain comprises a CD8 hinge (hinge of cluster of differentiation 8) and a CD28 transmembrane domain.

8. The chimeric antigen receptor of claim 5, wherein the intracytoplasmic domain comprises a CD28 intracellular domain and a CD32 intracellular domain.

9. A polynucleotide comprising a nucleic acid sequence encoding the chimeric antigen receptor of claim 1.

10. An expression vector comprising the polynucleotide of claim 9.

11. An immune cell comprising the chimeric antigen receptor of claim 1, a polynucleotide encoding the chimeric antigen receptor, or an expression vector comprising the polynucleotide.

12. The immune cell of claim 11, wherein the immune cell includes any one or more selected from the group consisting of a monocyte, a macrophage, a T cell, a natural killer cell (NK cell), and a dendritic cell.

13. A pharmaceutical composition for treatment of cancer expressing a CD300c antigen or a CD300c receptor, said pharmaceutical composition comprising the immune cell of claim 11 as an active ingredient.

14. The pharmaceutical composition of claim 13, wherein the cancer includes any one or more selected from the group consisting of colorectal cancer, rectal cancer, colon cancer, thyroid cancer, oral cancer, pharyngeal cancer, laryngeal cancer, cervical cancer, brain cancer, lung cancer, ovarian cancer, bladder cancer, kidney cancer, liver cancer, pancreatic cancer, prostate cancer, skin cancer, tongue cancer, breast cancer, uterine cancer, stomach cancer, bone cancer, and blood cancer.

15. The pharmaceutical composition of claim 13, further comprising another anticancer agent.

16. The pharmaceutical composition of claim 13, wherein the pharmaceutical composition inhibits the proliferation, survival, metastasis, recurrence, or anticancer agent resistance of cancer.

17. A method for treating cancer expressing a CD300c antigen or a CD300c receptor, the method comprising administering to a subject a composition comprising the immune cell of claim 11 as an active ingredient.

18. The method of claim 17, wherein the cancer includes any one or more selected from the group consisting of colorectal cancer, rectal cancer, colon cancer, thyroid cancer, oral cancer, pharyngeal cancer, laryngeal cancer, cervical cancer, brain cancer, lung cancer, ovarian cancer, bladder cancer, kidney cancer, liver cancer, pancreatic cancer, prostate cancer, skin cancer, tongue cancer, breast cancer, uterine cancer, stomach cancer, bone cancer, and blood cancer.

* * * * *